US008835107B2

(12) United States Patent
Van Der Hoek

(10) Patent No.: US 8,835,107 B2
(45) Date of Patent: Sep. 16, 2014

(54) CORONAVIRUS, NUCLEIC ACID, PROTEIN, AND METHODS FOR THE GENERATION OF VACCINE, MEDICAMENTS AND DIAGNOSTICS

(75) Inventor: Cornelia Maria Van Der Hoek, Diemen (NL)

(73) Assignee: Amsterdam Institute of Viral Genomics B.V., Amsterdam (NL)

( * ) Notice: Subject to any disclaimer, the term of this patent is extended or adjusted under 35 U.S.C. 154(b) by 0 days.

(21) Appl. No.: 12/843,359

(22) Filed: Jul. 26, 2010

(65) Prior Publication Data

US 2011/0065091 A1 Mar. 17, 2011

Related U.S. Application Data

(62) Division of application No. 10/922,232, filed on Aug. 18, 2004, now Pat. No. 7,803,918.

(60) Provisional application No. 60/535,002, filed on Jan. 7, 2004.

(30) Foreign Application Priority Data

Aug. 18, 2003 (EP) .................................... 03077602
Jan. 7, 2004 (EP) .................................... 04075050

(51) Int. Cl.

| | |
|---|---|
| ***C12Q 1/70*** | (2006.01) |
| ***A61K 39/215*** | (2006.01) |
| ***G01N 33/569*** | (2006.01) |
| ***C07K 14/005*** | (2006.01) |
| ***C07K 16/10*** | (2006.01) |
| ***C12N 7/00*** | (2006.01) |
| *A61K 39/00* | (2006.01) |
| *A61K 38/00* | (2006.01) |

(52) U.S. Cl.

CPC ............. *C07K 14/005* (2013.01); *A61K 39/215* (2013.01); *C12Q 1/701* (2013.01); *A61K 2039/525* (2013.01); *C12N 2770/20022* (2013.01); *C12N 2770/20034* (2013.01); *A61K 39/00* (2013.01); *G01N 33/56983* (2013.01); *C12Q 1/702* (2013.01); *G01N 2333/165* (2013.01); *A61K 38/00* (2013.01); *C12N 2770/20011* (2013.01); *C12Q 1/70* (2013.01); *C07K 16/10* (2013.01); *C12N 7/00* (2013.01); *C12N 2770/20021* (2013.01)

USPC ........................... 435/5; 536/24.3; 536/24.33

(58) Field of Classification Search
None
See application file for complete search history.

(56) References Cited

U.S. PATENT DOCUMENTS

2008/0044426 A1* 2/2008 De Jong et al. ............ 424/159.1

FOREIGN PATENT DOCUMENTS

WO WO0109290 2/2001
WO WO2005049814 6/2005

OTHER PUBLICATIONS

Vabret A. et al. “Direct diagnosis of human respiratory coronaviruses 229E and OC43 by the polymerase chain reaction” Journal of Virological Methods 97(2001) 59-66.*
Poon et al. (Journal of Virology. 2005; 79 (4): 2001-2009).*
Thiel et al., “Infectious RNA transcribed in vitro from a cDNA of the human coronavirus genome cloned in vaccinia virus,” Journal of General Virology, vol. 82, pp. 1273-1281, 2001.
NCBI Protein Accession No. AF304460; VRL Jul. 11, 2001.
NCBI Protein Accession No. Q05002; VRL Sep. 15, 2003.
NCBI Protein Accession No. P15423; VRL Jul. 15, 1999.
NCBI Protein Accession No. P15130; VRL Sep. 15, 2003.
Vabret et al., “Direct diagnosis of human respiratory coronaviruses 229E and O43 by the polymerase chain reaction,” Journal of Virological Methods, vol. 97, pp. 59-66, 2001.
NCBI Accession No. NC_001451; VRL Jun. 24, 2003.
Anand et al., “Coronavirus Main Proteinase (3CLpro) structure: Basis for Design of Anti-SARS Drugs,” Science, vol. 300, pp. 1763-1767, 2003.
Ziebuhr et al., “Biosynthesis, Purification, and Characterization of the Human Coronavirus 229E 3C-Like Proteinase,” Journal of Virology, vol. 71, No. 5, pp. 3992-3997, 1997.
van der Hoek et al., “Identification of a new human coronavirus,” Nature Medicine, vol. 10, No. 4, pp. 368-373, 2004.
Fouchier et al., “A previously undescribed coronavirus associated with respiratory disease in humans,” PNAS, vol. 101, No. 16, pp. 6212-6216, 2004.
Gerna G. et al., “Genetic variability of human coronavirus OC43-, 229E, and NL63-like strains and their association with lower respiratory tract infections of hospitalized infants and immunocompromised patients.” J. Med. Virol. 78:938-949 (2006).

* cited by examiner

*Primary Examiner* — Shanon A Foley
(74) *Attorney, Agent, or Firm* — Hoffmann & Baron, LLP

(57) ABSTRACT

A new coronavirus is disclosed herein with a tropism that includes humans. Means and methods are provided for diagnosing subjects (previously) infected with the virus. Also provided are among others vaccines, medicaments, nucleic acids and specific binding members.

9 Claims, 36 Drawing Sheets

Fig. 2
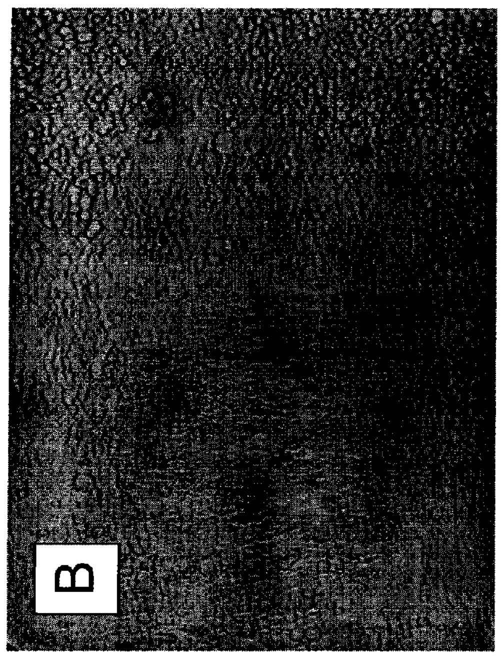
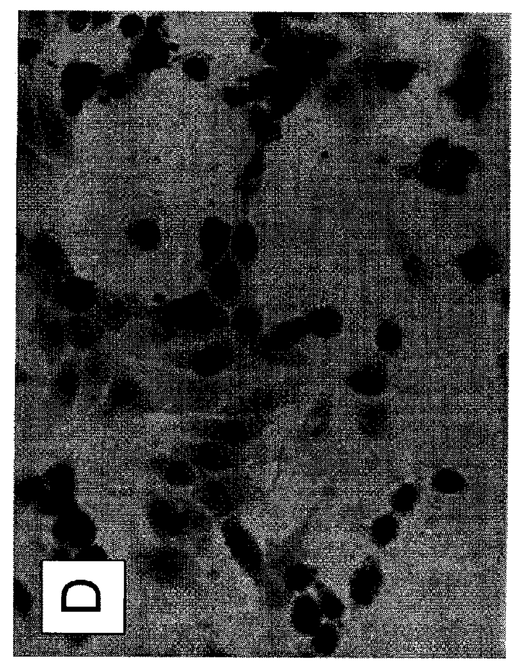
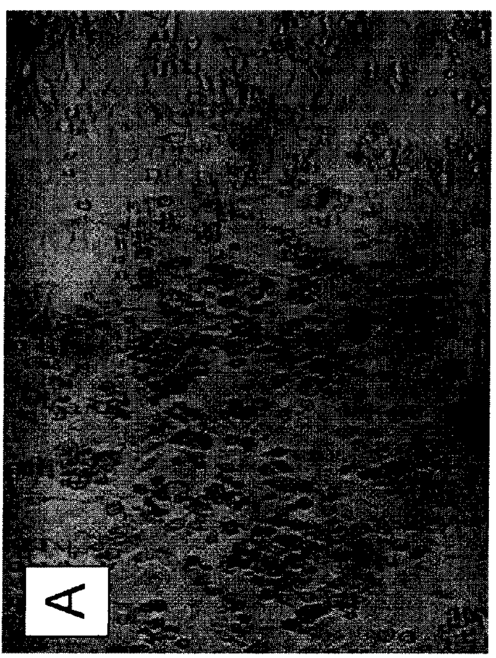
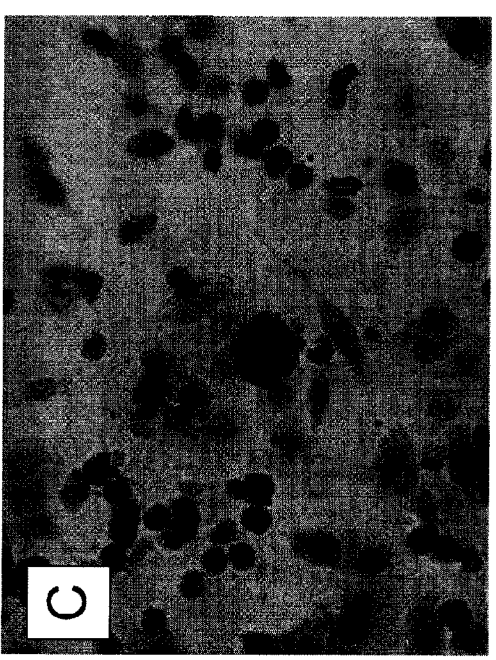

a schematic representation of the coronavirus genome organization (with HCoV-229E accession number AF304460 as an example). Red lines indicate the genome location of the sequence fragments of the new coronavirus HCoV-SLA163. UTR denotes unranslated region, orf: open reading frame, E: envelope protein, M: membrane protein, N: nucleocapsid protein.

HCoV-NL63

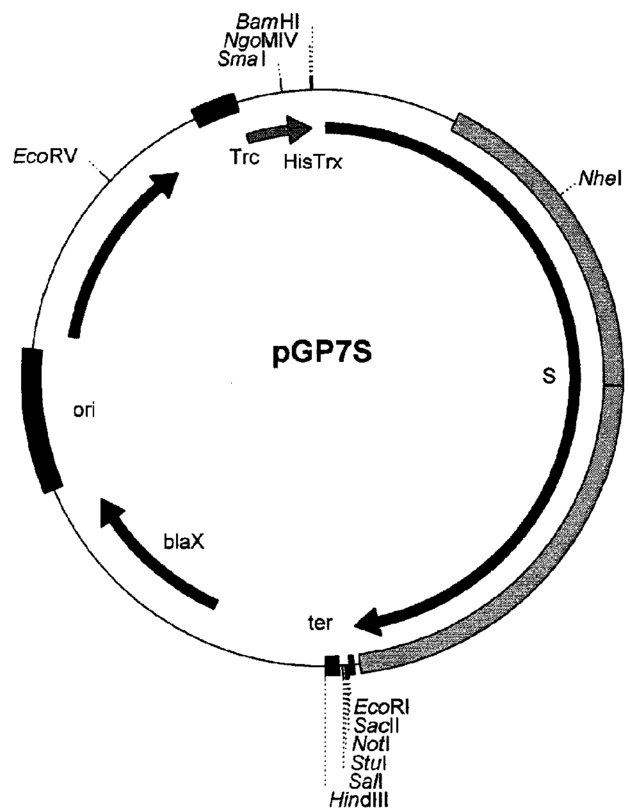
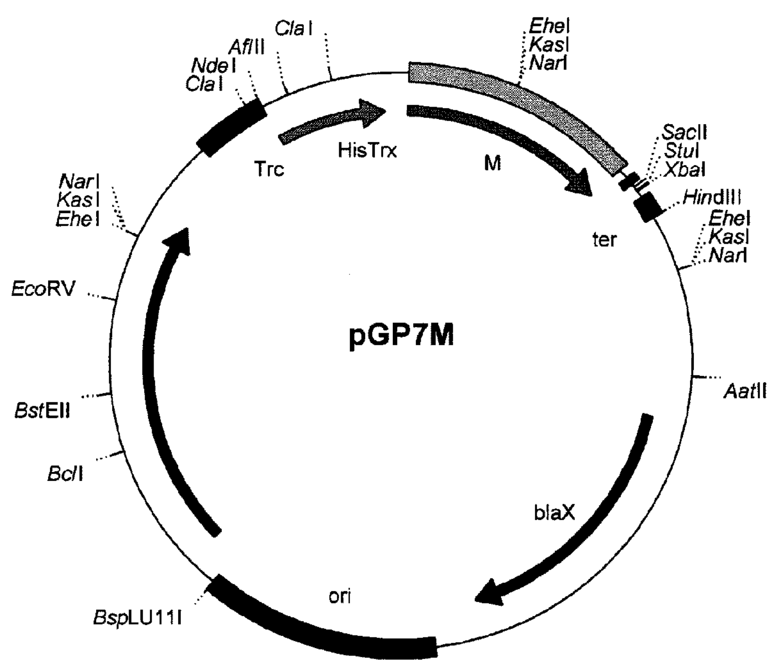
Fig. 8

TCATCCTAATTGTTGTGACTGTTATGATGATATGTGTGTTATACATTGTTCAAATTTTAACA
CACTCTT

Fig. 9

Chimera NL63/229E

CAACGTATGTGTTTGGAACCTTGTAATTTATATAATTATGGGAAGCCAGTTACTTTGCCT

Fig. 11

Chimera NL63/OC43

Sequence variation in HCoV-NL63 from additional patient samples

```
                   1                                                         60
  REF      (1)  TAATAATGCTGTCTATGATGGTGCTCGTTTATTTTCTTCAGATTTGTCTACTTTAGCTGT
223_B      (1)  TAATAATGCTGTCTATGATGGTGCTCGTTTATCTGCTTCAGATTTGTCTACTTTAGCTGT
246_B      (1)  TAATAATGCTGTCTATGATGGTGCTCGTTTATTTTCTTCAGATTTGTCTACTTTAGCTGT
248_B      (1)  TAATAATGCTGTCTATGATGGTGCTCGTTTATTTGCTTCAGATTTGTCTACTTTAGCTGT
251_B      (1)  TAATAATGCTGTCTATGATGGTGCTCGTTTATTTTCTTCAGATTTGTCTACTTTAGCTGT
466_B      (1)  TAATAATGCTGTCTATGATGGTGCTCGTTTATTTTCTTCAGATTTGTCTACTTTAGCTGT
496_B      (1)  TAATAATGCTGTCTATGATGGTGCTCGTTTATTTGCTTCAGATTTGTCTACTTTAGCTGT
                61                                                         120
  REF     (61)  TACAGCTATTGTTGTAGTAGGTGGTTGTGTAACATCTAATGTTCCAACAATTGTTAGTGA
223_B     (61)  TACAGCTATTGTTGTAGTAGGTGGTTGTGTAACATCTAATGTTCCACCAATTGTTAGTGA
246_B     (61)  TACAGCTATTGTTGTAGTAGGTGGTTGTGTAACATCTAATGTTCCACCAATTGTTAGTGA
248_B     (61)  TACAGCTATTGTTGTAGTAGGTGGTTGTGTAACATCTAATGTTCCACCAATTGTTAGTGA
251_B     (61)  TACAGCTATTGTTGTAGTAGGTGGTTGTGTAACATCTAATGTTCCACCAATTGTTAGTGA
466_B     (61)  TACAGCTATTGTTGTAGTAGGTGGTTGTGTAACATCTAATGTTCCAACAATTGTTAGTGA
496_B     (61)  TACAGCTATTGTTGTAGTAGGTGGTTGTGTAACATCTAATGTTCCATCAATTGTTAGTGA
                121                                                        180
  REF    (121)  GAAAATTTCTGTTATGGATAAACTTGATACTGGTGCACAAAAATTTTTCCAATTTGGTGA
223_B    (121)  GAAAATTTCTGTTATGGATAAACTTGATACTGGTGCACAAAAATTTTTCCAATTTGGTGA
246_B    (121)  GAAAATTTCTGTTATGGATAAACTTGATACTGGTGCACAAAAATTTTTCCAATTTGGTGA
248_B    (121)  GAAAATTTCTGTTATGGATAAACTTGATACTGGTGCACAAAAATTTTTCCAATTTGGTGA
251_B    (121)  GAAAATTTCTGTTATGGATAAACTTGATACTGGTGCACAAAAATTTTTCCAATTTGGTGA
466_B    (121)  GAAAATTTCTGTTATGGATAAACTTGATACTGGTGCACAAAAATTTTTCCAATTTGGTGA
496_B    (121)  GAAAATTTCTGTTATGGATAAACTTGATACTGGTGCACAAAAATTTTTCCAATTTGGTGA
                181                                                        240
  REF    (181)  TTTTGTTATGAATAACATTGTTCTGTTTTTAACTTGGTTGCTTAGTATGTTTAGTCTTTT
223_B    (181)  TTTTGTTATGAATAACATTGTTCTGTTTTTAACTTGGTTGCTTAGTATGTTTAGTCTTTT
246_B    (181)  TTTTGTTATGAATAACATTGTTCTGTTTTTAACTTGGTTGCTTAGTATGTTTAGTCTTTT
248_B    (181)  TTTTGTTATGAATAACATTGTTCTGTTTTTAACTTGGTTGCTTAGTATGTTTAGTCTTTT
251_B    (181)  TTTTGTTATGAATAACATTGTTCTGTTTTTAACTTGGTTGCTTAGTATGTTTAGTCTTTT
466_B    (181)  TTTTGTTATGAATAACATTGTTCTGTTTTTAACTTGGTTGCTTAGTATGTTTAGTCTTTT
496_B    (181)  TTTTGTTATGAATAACATTGTTCTGTTTTTAACTTGGTTGCTTAGTATGTTTAGTCTTTT
                241                                                        300
  REF    (241)  ACGTACTTCTATTATGAAGCATGATATTAAAGTTATTGCCAAGGCTCCTAAACGTACAGG
223_B    (241)  ACGTACTTCTATTATGAAGCATGATATTAAAGTTATTGCCAAGGCTCCTAAACGTACAGG
246_B    (241)  ACGTACTTCTATTATGAAGCATGATATTAAAGTTATTGCCAAGGCTCCTAAACGTACAGG
248_B    (241)  ACGTACTTCTATTATGAAGCATGATATTAAAGTTATTGCCAAGGCTCCTAAACGTACAGG
251_B    (241)  ACGTACTTCTATTATGAAGCATGATATTAAAGTTATTGCCAAGGCTCCTAAACGTACAGG
466_B    (241)  ACGTACTTCTATTATGAAGCATGATATTAAAGTTATTGCCAAGGCTCCTAAACGTACAGG
496_B    (241)  ACGTACTTCTATTATGAAGCATGATATTAAAGTTATTGCCAAGGCTCCTAAACGTACAGG
                301                                                        360
  REF    (301)  TGTTATTTTGACACGTAGTTTTAAGTATAACATTAGATCTGCTTTGTTTGTTATAAAGCA
223_B    (301)  TGTTATTTTGACACGTAGTTTTAAGTATAACATTAGATCTGCTTTGTTTGTTGTAAAGCA
246_B    (301)  TGTTATTTTGACACGTAGTTTTAAGTATAACATTAGATCTGCTTTGTTTGTTATAAAGCA
248_B    (301)  TGTTATTTTGACACGTAGTTTTAAGTATAACATTAGATCTGCTTTGTTTGTTGTAAAGCA
251_B    (301)  TGTTATTTTGACACGTAGTTTTAAGTATAACATTAGATCTGCTTTGTTTGTTATAAAGCA
466_B    (301)  TGTTATTTTGACACGTAGTTTTAAGTATAACATTAGATCTGCTTTGTTTGTTATAAAGCA
496_B    (301)  TGTTATTTTGACACGTAGTTTTAAGTATAACATTAGATCTGCTTTGTTTGTTATAAAGCA
                361                                                        420
  REF    (361)  GAAGTGGTGTGTTATTGTTACTTTGTTTAAGTTCTTATTATTATTATATGCTATTTATGC
223_B    (361)  GAAGTGGTGTGTTATTGTTACTTTGTTTAAGTTCTTATTGTTATTATATGCTATTTATGC
246_B    (361)  GAAGTGGTGTGTTATTGTTACTTTGTTTAAGTTCTTATTGTTATTATATGCTATTTATGC
248_B    (361)  GAAGTGGTGTGTTATTGTTACTTTGTTTAAGTTCTTATTGTTATTATATGCTATTTATGC
251_B    (361)  GAAGTGGTGTGTTATTGTTACTTTGTTTAAGTTCTTATTATTATTATATGCTATTTATGC
466_B    (361)  GAAGTGGTGTGTTATTGTTACTTTGTTTAAGTTCTTATTATTATTATATGCTATTTATGC
496_B    (361)  GAAGTGGTGTGTTATTGTTACTTTGTTTAAGTTCTTATTGTTATTATATGCTATTTATGC
                421                                          466
  REF    (421)  ACTTGTTTTTATGATTGTGCAATTTAGTCCTTTTAATAGTCTTTTA
223_B    (421)  ACTTGTTTTTATGATTGTGCAATTTAGTCCTTTTAATAGTCTTTTA
246_B    (421)  ACTTGTTTTTATGATTGTGCAATTTAGTCCTTTTAATAGTCTTTTA
248_B    (421)  ACTTGTTTTTATGATTGTGCAATTTAGTCCTTTTAATAGTCTTTTA
251_B    (421)  ACTTGTTTTTATGATTGTGCAATTTAGTCCTTTTAATAGTCTTTTA
466_B    (421)  ACTTGTTTTTATGATTGTGCAATTTAGTCCTTTTAATAGTCTTTTA
496_B    (421)  ACTTGTTTTTATGATTGTGCAATTTAGTCCTTTTAATAGTCTTTTA
```

Fig. 17

HCoV-NL63 Nucleocapsid (N) specific PCR primers

| Oligo | Sequence | $T_m$ | Amplicon |
|---|---|---|---|
| NL63NF1 | GCTAGTGTAAATTGGGCCGATG | 55.3 | 708 |
| NL63NR1 | CTTCCAACGAGGTTTCTTCAACTG | 56.0 | |
| NL63NF2 | TCCTCCTCCTTCATTTTACATGCC | 57.4 | 372 |
| NL63NR2 | AACTCAACAACAGAGAGCTCTGGAG | 55.1 | |

Fig. 18

Generic Coronavirus detection primers

| Oligo | Sequence | $T_m$ | Amplicon |
|---|---|---|---|
| COR1F | ATGGGWTGGGAYTATCCIAARTGTGA | 60.6 | 603 |
| COR1R | GYTGKGARCARAAYTCRTGWGGTCC | 60.7 | |
| COR2F | TATKTTAARCCWGGTGGIAC | 46.1 | 362 |
| COR2R | CATRAANACRYYATTYTGRTAATA | 46.7 | |

Fig. 19A

Nucleotide sequence HcoV_NL63

CTTAAAGAATTTTTCTATCTATAGATAGAGAATTTTCTTATTTAGACTTTGTGTCTACTC
TTCTCAACTAAACGAAATTTTTCTAGTGCTGTCATTTGTTATGGCAGTCCTAGTGTAATT
GAAATTTCGTCAAGTTTGTAAACTGGTTAGGCAAGTGTTGTATTTTCTGTGTCTAAGCAC
TGGTGATTCTGTTCACTAGTGCATACATTGATATTTAAGTGGTGTTCCGTCACTGCTTAT
TGTGGAAGCAACGTTCTGTCGTTGTGGAAACCAATAACTGCTAACCATGTTTTACAATCA
AGTGACACTTGCTGTTGCAAGTGATTCGGAAATTTCAGGTTTTGGTTTTGCCATTCCTTC
TGTAGCCGTTCGCACCTATAGCGAAGCCGCTGCACAAGGTTTTCAGGCATGCCGTTTTGT
TGCTTTTGGCTTACAGGATTGTGTAACCGGTATTAATGATGATGATTATGTCATTGCATT
GACTGGTACTAATCAGCTCTGTGCCAAAATTTTACCTTTTTCTGATAGACCCCTTAATTT
GCGAGGTTGGCTCATTTTTTCTAACAGCAATTATGTTCTTCAGGACTTTGATGTTGTTTT
TGGCCATGGTGCAGGAAGTGTGGTTTTTGTGGATAAGTACATGTGTGGTTTTGATGGTAA
ACCTGTGTTACCTAAAAACATGTGGGAATTTAGGGATTACTTTAATAATAATACTGATAG
TATTGTTATTGGTGGTGTCACTTATCAACTAGCATGGGATGTTATACGTAAAGACCTTTC
TTATGAACAGCAAAATGTTTTAGCCATTGAGAGCATTCATTACCTTGGTACTACAGGTCA
TACTTTGAAGTCTGGTTGCAAACTTACTAATGCTAAGCCGCCTAAATATTCTTCTAAGGT
TGTTTTGAGTGGTGAATGGAATGCTGTGTATAGGGCGTTTGGTTCACCATTTATTACAAA
TGGTATGTCATTGCTAGATATAATTGTTAAACCAGTTTTCTTTAATGCTTTTGTTAAATG
CAATTGTGGTTCTGAGAGTTGGAGTGTTGGTGCATGGGATGGTTACTTATCTTCTTGTTG
TGGCACACCTGCTAAGAAACTTTGTGTTGTTCCTGGTAATGTCGTTCCTGGTGATGTGAT
CATCACCTCAACTAGTGCTGGTTGTGGTGTTAAATACTATGCTGGCTTAGTTGTTAAACA
TATTACTAACATTACTGGTGTGTCTTTATGGCGTGTTACAGCTGTTCATTCTGATGGAAT
GTTTGTGGCATCATCTTCTTATGATGCACTCTTGCATAGAAATTCATTAGACCCTTTTTG
CTTTGATGTTAACACTTTACTTTCTAATCAATTACGTCTAGCTTTTCTTGGTGCTTCTGT
TACAGAAGATGTTAAATTTGCTGCTAGCACTGGTGTTATTGACATTAGTGCTGGTATGTT
TGGTCTTTACGATGACATATTGACAAACAATAAACCTTGGTTTGTACGCAAAGCTTCTGG
GCTTTTTGATGCAATCTGGGATGCTTTTGTTGCCGCTATTAAGCTTGTACCAACTACTAC
TGGTGTTTTGGTTAGGTTTGTTAAGTCTATTGCTTCAACTGTTTTAACTGTCTCTAATGG
TGTTATTATTATGTGTGCAGATGTTCCAGATGCTTTTCAATCAGTTTATCGCACATTTAC
ACAAGCTATTTGTGCTGCATTTGATTTTTCTTTAGATGTATTTAAAATTGGTGATGTTAA
ATTTAAACGACTTGGTGATTATGTTCTTACTGAAAACGCTCTTGTTCGTTTGACTACTGA
AGTTGTTCGTGGTGTTCGTGATGCTCGCATAAAGAAAGCCATGTTTACTAAAGTAGTTGT
AGGTCCTACAACTGAAGTTAAGTTTCTGTTATTGAACTTGCCACTGTTAATTTGCGTCT
TGTTGATTGTGCACCTGTAGTTTGCCCTAAAGGTAAGATTGTTGTTATTGCTGGACAAGC
TTTTTTCTATAGTGGTGGTTTTTATCGTTTTATGGTTGATCCTACAACTGTATTAAATGA
TCCTGTTTTTACTGGTGATTTATTCTACACTATTAAGTTTAGTGGTTTTAAGCTTGATGG
TTTTAACCATCAGTTTGTTACTGCTAGTTCTGCTACAGATGCCATTATTGCTGTTGAGCT
GTTGTTATTGGATTTTAAAACTGCAGTTTTTGTGTACACATGTGTGGTTGATGGCTGTAG
TGTCATTGTTAGACGTGATGCTACATTCGCTACACATGTGTGTTTTAAGGACTGTTATAA
TGTTTGGGAGCAATTCTGCATTGATAATTGTGGTGAGCCATGGTTTTTGACTGATTATAA
TGCTATCTTGCAGAGTAATAACCCTCAATGTGCTATTGTTCAAGCATCAGAGTCTAAAGT
TTTGCTTGAGAGGTTTTTACCTAAGTGTCCTGAAATACTGTTGAGTATTGATGATGGCCA
TTTATGGAATCTTTTTGTTGAAAAGTTTAATTTTGTTACAGATTGGTTAAAAACTCTTAA
GCTTACACTTACTTCTAATGGTCTTTTAGGTAATTGTGCCAAACGTTTTAGACGTGTTTT
GGTAAAATTGCTTGATGTCTATAATGGTTTTCTTGAAACTGTCTGTAGTGTCGCATACAC
TGCTGGTGTTTGCATCAAATATTATGCTGTTAATGTTCCATATGTAGTTATTAGTGGTTT
TGTAAGTCGTGTAATTCGTAGAGAAAGGTGTGACATGACTTTTCCTTGTGTTAGTTGTGT
CACCTTTTTCTATGAATTTTTAGACACTTGTTTTGGTGTTAGTAAACCTAATGCCATTGA
TGTTGAACATTTAGAGCTTAAAGAAACTGTTTTTGTTGAACCTAAGGATGGTGGTCAATT
TTTTGTTTCTGGTGATTATCTTTGGTATGTTGTAGATGACATTTATTATCCAGCTTCATG
TAATGGTGTATTGCCTGTTGCTTTTACAAAATTAGCTGGTGGTAAAATATCTTTTTCTGA
TGATGTTATAGTTCATGATGTTGAACCTACCCATAAAGTCAAGCTCATATTTGAGTTTGA
AGATGATGTTGTTACCAGTCTTTGTAAGAAGAGTTTTGGTAAGTCCATTATTTATACAGG

Fig. 19B

TGATTGGGAAGGTCTACATGAAGTTCTTACATCTGCAATGAATGTCATTGGGCAACATAT
TAAGTTGCCACAATTTTATATTTATGATGAAGAGGGTGGTTATGATGTTTCTAAACCAGT
TATGATTTCACAATGGCCTATTAGTAATGATAGTAATGGTTGTGTTGTTGAAGCGAGCAC
TGATTTTCATCAATTAGAATGTATTGTTGATGACTCTGTTAGAGAAGAGGTTGATATAAT
TGAACAACCTTTTGAAGAAGTTGAACATGTGCTCTCAATTAAGCAACCTTTTTCTTTTTC
TTTTAGAGATGAATTGGGTGTTCGTGTTTTAGATCAATCTGATAATAATTGTTGGATTAG
TACCACACTTGTACAGTTGCAACTTACAAAGCTTTTGGATGATTCTATTGAGATGCAATT
GTTTAAAGTTGGTAAAGTTGATTCAATTGTCCAAAAGTGTTATGAGTTGTCTCATTTAAT
TAGTGGTTCACTTGGTGATAGTGGTAAACTTCTTAGTGAACTTCTTAAAGAAAAATATAC
ATGTTCTATAACTTTTGAGATGTCTTGTGATTGTGGTAAAAAGTTTGATGATCAGGTTGG
TTGTTTGTTTTGGATTATGCCTTACACAAAACTTTTTCAAAAAGGTGAGTGTTGTATTTG
TCATAAAATGCAGACTTATAAGCTTGTTAGTATGAAAGGTACTGGTGTGTTTGTACAGGA
TCCAGCACCTATTGACATTGATGCTTTCCCTGTGAAACCTATATGTTCATCTGTATATTT
AGGTGTTAAGGGTTCTGGTCATTATCAAACAAATTTATACAGTTTTAACAAAGCTATTGA
TGGTTTTGGTGTCTTTGACATTAAAAATAGTAGTGTTAATACTGTTTGTTTTGTTGATGT
TGATTTTCATAGTGTAGAAATAGAAGCTGGTGAAGTTAAACCTTTTGCTGTATATAAAAA
TGTTAAATTTTATTTAGGTGATATTTCACACCTTGTAAACTGTGTTTCTTTTGACTTTGT
TGTCAATGCTGCTAATGAAAATCTCTTGCATGGAGGCGGTGTTGCACGTGCTATTGATAT
TTTGACTGAAGGTCAACTTCAGTCACTATCTAAAGATTACATTAGTAGTAATGGTCCACT
TAAGGTTGGAGCAGGTGTTATGTTGGAGTGTGAAAAATTCAACGTATTTAATGTTGTTGG
TCCGCGAACTGGTAAACATGAGCATTCATTACTTGTTGAAGCTTATAATTCTATTTTATT
TGAAAATGGTATTCCACTTATGCCTCTTCTTAGTTGTGGTATTTTTGGTGTAAGGATTGA
AAATTCTCTTAAAGCTTTGTTTAGTTGTGACATTAATAAACCATTGCAAGTTTTTGTTTA
TTCTTCAAATGAAGAACAAGCTGTTCTTAAGTTTTTAGATGGTTTAGATTTAACACCAGT
CATTGATGATGTTGATGTTGTTAAACCTTTTAGAGTTGAAGGTAATTTTTCATTCTTTGA
TTGTGGTGTCAATGCCTTGGATGGTGATATTTACTTATTATTTACTAACTCTATTTTAAT
GTTGGATAAACAAGGACAATTATTGGACACAAAACTTAATGGTATTTTGCAACAGGCAGC
TCTTGATTATCTTGCTACAGTTAAAACTGTACCAGCTGGTAATTTGGTTAAACTTTTTGT
TGAGAGTTGTACCATTTATATGTGTGTTGTACCATCGATAAATGATCTTTCTTTTGATAA
AAATCTTGGTCGTTGTGTGCGTAAACTTAATAGATTGAAAACTTGTGTTATTGCCAATGT
TCCTGCTATTGATGTTTTGAAAAAGCTTCTTTCAAGTTTGACTTTAACTGTTAAATTTGT
TGTAGAGAGTAATGTTATGGATGTTAACGACTGTTTTAAGAATGATAATGTAGTTTTGAA
AATTACTGAAGATGGTATTAATGTTAAAGATGTTGTTGTTGAGTCTTCTAAGTCACTTGG
TAAACAATTGGGTGTTGTGAGTGATGGTGTTGACTCTTTTGAAGGTGTTTTACCTATTAA
TACTGATACTGTCTTATCTGTAGCTCCAGAAGTTGACTGGGTTGCTTTTTACGGTTTTGA
AAAGGCAGCACTTTTTGCTTCTTTGGATGTAAAGCCATATGGTTACCCTAATGATTTTGT
TGGTGGTTTTAGAGTTCTTGGGACCACCGACAATAATTGTTGGGTTAATGCAACTTGTAT
AATTTTACAGTATCTTAAGCCTACTTTTAAATCTAAGGGTTTAAATGTTCTTTGGAACAA
ATTTGTTACAGGTGATGTTGGACCTTTTGTTAGTTTTATTTATTTTATAACTATGTCTTC
AAAGGGTCAAAAGGGTGATGCTGAAGAGGCATTATCTAAATTGTCAGAGTATTTGATTAG
TGATTCTATTGTTACTCTTGAACAATATTCAACTTGTGACATTTGTAAAAGTACTGTAGT
TGAAGTTAAAAGTGCTATTGTCTGTGCTAGTGTGCTTAAAGATGGTTGTGATGTTGGTTT
TTGTCCACACAGACATAAATTGCGTTCACGTGTTAAGTTTGTTAATGGACGTGTTGTTAT
TACCAATGTTGGTGAACCTATAATTTCACAACCTTCTAAGTTGCTTAATGGTATTGCTTA
TACAACATTTTCAGGTTCTTTTGATAACGGTCACTATGTAGTTTATGATGCTGCTAATAA
TGCTGTCTATGATGGTGCTCGTTTATTTTCTTCAGATTTGTCTACTTTAGCTGTTACAGC
TATTGTTGTAGTAGGTGGTTGTGTAACATCTAATGTTCCAACAATTGTTAGTGAGAAAAT
TTCTGTTATGGATAAACTTGATACTGGTGCACAAAAATTTTTCCAATTTGGTGATTTTGT
TATGAATAACATTGTTCTGTTTTTAACTTGGTTGCTTAGTATGTTTAGTCTTTTACGTAC
TTCTATTATGAAGCATGATATTAAAGTTATTGCCAAGGCTCCTAAACGTACAGGTGTTAT
TTTGACACGTAGTTTTAAGTATAACATTAGATCTGCTTTGTTTGTTATAAAGCAGAAGTG
GTGTGTTATTGTTACTTTGTTTAAGTTCTTATTATTATTATATGCTATTTATGCACTTGT
TTTTATGATTGTGCAATTTAGTCCTTTTAATAGTCTTTTATGTGGTGACATTGTAAGTGG
TTATGAAAAATCCACTTTTAATAAGGATATTTATTGTGGTAATTCTATGGTTTGTAAGAT
GTGTTTGTTCAGTTATCAAGAGTTTAATGATTTGGATCATACTAGTCTTGTTTGGAAGCA
CATTCGTGATCCTATATTAATCAGTTTACAACCATTTGTTATACTTGTTATTTGTTAAT

Fig. 19C

TTTTGGTAATATGTATTTGCGTTTTGGACTTTTATATTTTGTTGCACAATTTATTAGTAC
TTTTGGTTCTTTCTTAGGCTTTCATCAGAAACAGTGGTTTTTACATTTTGTGCCGTTTGA
TGTTTTATGTAATGAGTTTTTAGCTACATTTATTGTCTGCAAAATCGTTTTATTTGTTAG
ACATATTATTGTTGGCTGTAATAATGCTGACTGTGTAGCTTGTTCTAAAAGTGCTAGACT
TAAACGTGTACCACTTCAAACTATTATTAATGGTATGCATAAATCATTCTATGTTAATGC
TAATGGTGGTACTTGTTTCTGTAATAAACATAACTTCTTTTGTGTTAATTGTGATTCTTT
TGGGCCTGGTAATACTTTTATTAATGGTGATATTGCAAGAGAGCTTGGTAATGTTGTTAA
AACAGCTGTTCAACCCACAGCTCCTGCATATGTTATTATTGATAAGGTAGATTTTGTTAA
TGGATTTTATCGTCTTTATAGTGGTGACACTTTTTGGCGGTATGACTTTGACATTACTGA
ATCTAAGTATAGTTGTAAAGAGGTTCTGAAGAATTGTAATGTTTTAGAAAATTTTATTGT
TTACAATAATAGTGGTAGTAACATTACACAGATTAAAAATGCTTGTGTTTATTTTTCTCA
ATTGTTGTGTGAACCTATAAAGTTGGTAAATTCAGAGTTGTTGTCAACTTTATCTGTTGA
TTTTAATGGTGTTTTGCATAAGGCATATGTTGATGTTTTGTGTAATAGTTTTTTTAAGGA
GTTAACTGCTAACATGTCCATGGCTGAATGTAAAGCTACACTTGGTTTGACTGTTTCTGA
TGATGATTTTGTTTCAGCTGTTGCCAATGCACATAGGTATGACGTTTTGCTTTCAGATTT
GTCATTTAATAATTTTTTTATTTCTTATGCTAAACCTGAAGATAAGTTGTCCGTTTATGA
CATTGCTTGTTGTATGCGTGCCGGTTCTAAGGTTGTTAACCATAATGTTTTAATTAAAGA
GTCAATACCTATTGTTTGGGGTGTCAAGGACTTTAATACTCTTTCTCAAGAAGGTAAGAA
GTACCTTGTTAAAACAACTAAAGCAAAGGGTTTGACTTTTTTATTAACTTTTAATGATAA
CCAAGCAATTACACAAGTTCCTGCTACTAGTATAGTTGCAAAACAGGGTGCTGGTTTTAA
ACGTACTTATAATTTTCTGTGGTATGTATGTTTATTTGTTGTTGCATTGTTTATTGGTGT
CTCATTTATTGATTATACAACCACTGTAACTAGCTTTCATGGTTATGATTTTAAGTACAT
TGAGAATGGTCAGTTGAAGGTGTTTGAAGCACCTTTACACTGTGTTCGTAATGTTTTTGA
TAATTTTAATCAATGGCATGAGGCTAAGTTTGGTGTTGTTACTACTAATAGTGATAAATG
TCCTATAGTTGTTGGTGTTTCAGAGCGTATTAATGTTGTTCCTGGTGTTCCAACAAATGT
ATATTTGGTAGGAAAGACTCTTGTTTTTACATTACAGGCTGCTTTTGGAAACACAGGTGT
TTGTTATGACTTTGATGGTGTTACCACTAGTGATAAGTGTATTTTTAATTCTGCTTGTAC
TAGGTTGGAAGGTTTGGGTGGTGACAATGTTTATTGTTACAACACTGATCTTATTGAAGG
TTCTAAACCTTATAGTACTTTACAGCCCAATGCGTATTATAAGTATGATGCTAAAAATTA
TGTACGTTTTCCAGAAATTTTAGCTAGAGGTTTTGGCTTACGTACTATTAGAACTTTGGC
TACACGTTATTGTAGAGTTGGTGAATGCCGTGACTCACATAAAGGTGTTTGTTTTGGTTT
TGATAAATGGTATGTTAATGATGGACGTGTTGATGACGGTTACATTTGTGGTGATGGTCT
TATAGACCTTCTTGTTAATGTACTCTCAATCTTTAGTTCATCTTTTAGCGTTGTGGCTAT
GTCTGGACATATGTTGTTTAATTTTCTTTTTGCAGCATTTATTACATTTTTGTGCTTTTT
AGTTACTAAATTTAAACGTGTTTTTGGTGATCTTTCTTATGGTGTTTTTACTGTTGTTTG
TGCAACTTTGATTAATAACATTTCTTATGTTGTTACTCAAAATTTATTTTTTATGTTGCT
TTATGCTATTTTGTATTTTGTTTTTACTAGGACAGTGCGTTATGCTTGGATTTGGCATAT
TGCATACATTGTTGCATACTTCTTGTTAATACCATGGTGGCTTCTCACATGGTTTAGTTT
TGCTGCATTTTTAGAGCTTTTACCTAATGTTTTTAAGTTAAAAATCTCTACTCAATTGTT
TGAAGGTGATAAGTTTATAGGTACTTTTGAGAGTGCTGCTGCAGGTACATTTGTTCTTGA
CATGCGTTCTTATGAAAGGCTGATAAATACTATTTCACCTGAGAAACTTAAGAATTATGC
TGCAAGTTATAATAAATATAAATATTATAGTGGTAGTGCTAGTGAGGCTGATTATCGTTG
TGCTTGTTATGCTCATTTAGCCAAGGCTATGTTAGATTATGCAAAAGATCATAATGACAT
GTTATATTCTCCACCTACTATTAGCTACAATTCCACCTTACAATCTGGTCTTAAGAAGAT
GGCACAACCATCTGGTTGTGTTGAGAGATGTGTGGTTCGCGTCTGTTATGGTAGTACTGT
GCTTAATGGAGTTTGGTTAGGTGACACTGTTACTTGTCCTAGACATGTCATAGCACCATC
AACCACTGTTCTTATTGATTATGATCATGCATATAGTACTATGCGTTTGCATAATTTTTC
AGTGTCTCATAATGGTGTCTTCTTGGGAGTTGTCGGTGTTACAATGCATGGTTCTGTGTT
GCGTATTAAGGTTTCACAATCTAATGTACATACACCTAAACATGTTTTTAAAACGTTGAA
ACCTGGTGATTCTTTTAATATTTTAGCATGTTATGAAGGTATTGCATCTGGTGTTTTTGG
TGTTAATTTACGTACAAACTTTACTATTAAAGGTTCTTTTATAAATGGAGCTTGTGGTTC
TCCTGGTTATAATGTTAGAAATGATGGTACTGTTGAGTTTTGTTATTTACACCAAATTGA
GTTAGGTAGTGGTGCTCATGTTGGTTCTGATTTTACTGGTAGTGTTTATGGTAATTTTGA
TGACCAACCTAGTTTGCAAGTTGAGAGTGCCAACCTTATGCTATCAGATAATGTTGTTGC
CTTTTTGTATGCTGCTTTGTTGAATGGTTGTAGGTGGTGGTTGTGTTCAACTAGAGTTAA
TGTTGATGGTTTTAATGAATGGGCTATGGCTAATGGTTATACAAGTGTTTCTAGTGTTGA

Fig. 19D

GTGCTATTCTATTTTGGCAGCAAAAACTGGTGTTAGTGTTGAACAATTGTTAGCTTCCAT
TCAACATCTTCATGAAGGTTTTGGTGGTAAAAACATACTTGGTTATTCTAGTTTATGTGA
TGAGTTCACACTAGCTGAAGTTGTGAAGCAGATGTATGGTGTTAACTTGCAAAGTGGTAA
GGTTATTTTTGGTTTAAAAACAATGTTTTTATTTAGCGTTTTCTTCACAATGTTTTGGGC
AGAACTCTTTATTTATACAAACACTATATGGATAAACCCTGTGATACTTACACCTATATT
TTGTCTACTTTTGTTTTTGTCATTAGTTTTAACTATGTTTCTTAAACATAAGTTTTTGTT
TTTGCAAGTATTTTTATTACCTACTGTTATTGCAACTGCTTTATATAATTGTGTTTTGGA
TTATTACATAGTAAAATTTTTGGCTGACCATTTTAACTATAATGTTTCAGTATTACAAAT
GGATGTTCAGGGTTTAGTTAATGTTTTGGTCTGTTTATTTGTTGTATTTTTACACACATG
GCGCTTTTCTAAAGAACGTTTTACACATTGGTTTACATATGTGTGTTCTCTTATAGCAGT
TGCTTACACTTATTTTTATAGTGGTGACTTTTTGAGTTTGCTTGTTATGTTTTTATGTGC
TATATCTAGTGATTGGTACATTGGTGCCATTGTTTTTAGGTTGTCACGTTTGATTGTATT
TTTTTCACCTGAAAGTGTATTTAGTGTTTTTGGTGATGTGAAACTTACTTTAGTTGTTTA
TTTAATTTGTGGTTATTTAGTTTGTACTTATTGGGGCATTTTGTATTGGTTCAATAGGTT
TTTTAAATGTACTATGGGTGTTTATGATTTTAAGGTGAGTGCTGCTGAATTTAAATACAT
GGTTGCTAATGGACTTCATGCACCACATGGACCTTTTGATGCACTTTGGTTATCATTCAA
ACTACTTGGTATTGGTGGTGACCGTTGTATAAAAAATTTCAACTGTCCAATCCAAACTGAC
TGATTTGAAGTGTACTAATGTTGTGTTATTGGGTTGTTTGTCTAGTATGAACATTGCAGC
TAATTCTAGTGAATGGGCTTATTGTGTTGATTTACACAATAAGATTAATCTTTGTGATGA
CCCTGAAAAAGCTCAAAGTATGTTGTTAGCACTCCTTGCGTTCTTTCTAAGTAAACATAG
TGATTTTGGTCTTGATGGCCTTATTGATTCTTATTTTGATAATAGTAGCACCCCTTCAGAG
TGTTGCTTCATCATTTGTTAGTATGCCATCATATATTGCTTATGAAAATGCTAGACAAGC
TTATGAGGATGCTATTGCTAATGGATCTTCTTCTCAACTTATTAAACAATTGAAGCGTGC
CATGAATATCGCAAAGTCTGAATTTGATCATGAGATATCTGTTCAGAAGAAAATTAATAG
AATGGCTGAACAAGCTGCTACTCAGATGTATAAAGAAGCACGCTCTGTTAATAGAAAATC
TAAAGTTATTAGTGCTATGCACTCTTTACTTTTTGGAATGTTAAGACGTTTGGATATGTC
TAGTGTTGAAACTGTTTTGAATTTAGCACGTGATGGTGTTGTGCCATTGTCAGTTATACC
TGCAACTTCAGCTTCTAAACTAACTATTGTTAGTCCAGATCTTGAATCTTATTCTAAGAT
TGTTTGTGATGGTTCTGTTCATTATGCTGGAGTTGTTTGGACACTTAATGATGTTAAAGA
CAATGATGGTAGACCTGTTCATGTTAAAGAGATTACAAAGGAAAATGTTGAAACTTTGAC
ATGGCCTCTTATCCTTAATTGTGAACGTGTTGTTAAACTTCAAAATAATGAAATTATGCC
TGGTAAACTTAAGCAAAAACCTATGAAAGCTGAGGGTGATGGTGGTGTTTTAGGTGATGG
TAATGCCTTGTATAATACTGAGGGTGGTAAAACTTTTATGTACGCTTATATTTCTAATAA
AGCTGACCTTAAATTTGTTAAGTGGGAGTATGAGGGTGGTTGCAACACAATCGAGTTAGA
CTCTCCTTGTCGATTTATGGTCGAAACACCTAATGGTCCTCAAGTGAAGTATTTGTATTT
TGTTAAAAATTTAAATACCTTACGTAGAGGTGCCGTTCTTGGTTTTATAGGTGCCACAAT
TCGTCTACAAGCTGGTAAACAAACTGAATTGGCTGTTAATTCTGGACTTTTAACTGCTTG
TGCTTTTTCTGTTGATCCAGCAACTACTTACTTGGAAGCTGTTAAACATGGTGCAAAACC
TGTAAGTAATTGTATTAAGATGTTATCTAATGGTGCTGGTAATGGTCAAGCTATAACAAC
TAGTGTAGATGCTAACACCAATCAAGATTCTTATGGTGGAGCGTCTATTTGTTTGTATTG
TCGGGCCCACGTTCCTCACCCTAGTATGGATGGTTACTGTAAGTTTAAGGGTAAATGTGT
TCAGGTTCCTATTGGTTGTTTGGATCCTATTAGGTTTTGTTTAGAAAATAATGTGTGTAA
TGTTTGTGGTTGTTGGTTGGGACACGGGTGTGCTTGTGACCGTACAACTATTCAAAGTGT
TGACATTTCTTATTTAAACGAGCAAGGGGTTCTAGTGCAGCTCGACTAGAACCCTGCAAT
GGCACGGACATCGATAAGTGTGTTCGTGCTTTTGACATTTATAATAAAAATGTTTCATTC
TTGGGTAAGTGTTTGAAGATGAACTGTGTTCGTTTTAAAAATGCTGATCTTAAGGATGGT
TATTTTGTTATAAAGAGGTGTACTAAGTCGGTTATGGAACACGAGCAATCCATGTATAAC
CTACTTAACTTTTCTGGTGCTTTGGCTGAGCATGATTTCTTTACTTGGAAAGATGGCAGA
GTCATTTATGGTAATGTTAGTAGACATAATCTTACTAAATATACTATGATGGACTTGGTC
TATGCTATGCGTAACTTTGATGAACAAAATTGTGATGTTCTAAAAGAAGTATTAGTTTTA
ACTGGTTGTTGTGACAATTCTTATTTTGATAGTAAGGGTTGGTATGACCCAGTTGAAAAT
GAAGATATACATAGAGTTTATGCATCTCTTGGCAAAATTGTAGCTAGAGCTATGCTTAAA
TGCGTTGCTCTATGCGATGCGATGGTTGCTAAAGGTGTTGTTGGTGTTTTAACATTAGAT
AACCAAGATCTTAATGGTAACTTTTATGATTTTGGTGATTTTGTTGTTAGCTTACCTAAT
ATGGGTGTTCCCTGTTGTACATCATATTATTCTTATATGATGCCTATTATGGGTTTAACT
AATTGTTTAGCTAGTGAGTGTTTTGTCAAGAGTGATATTTTTGGTAGTGATTTTAAAACT

Fig. 19E

TTTGATTTGCTTAAGTATGATTTCACTGAACATAAAGAAAATTTATTCAATAAGTACTTT
AAGCATTGGAGTTTTGATTATCATCCTAATTGTTGTGACTGTTATGATGATATGTGTGTT
ATACATTGTGCTAATTTTAATACACTATTTGCCACAACTATACCAGGTACTGCTTTTGGT
CCACTATGTCGTAAAGTTTTTATAGATGGTGTTCCACTTGTTACAACTGCTGGTTATCAT
TTTAAGCAATTAGGTTTGGTTTGGAATAAAGATGTTAACACACACTCAGTTAGGTTGACA
ATTACTGAACTTTTGCAATTTGTCACCGACCCTTCCTTGATAATAGCTTCTTCCCCAGCA
CTCGTTGATCAACGCACTATTTGTTTTTCTGTTGCAGCATTGAGTACTGGTTTGACAAAT
CAAGTTGTTAAGCCAGGTCATTTTAATGAAGAGTTTTATAACTTTCTTCGTTTAAGAGGT
TTCTTTGATGAAGGTTCTGAACTTACATTAAAACATTTCTTCTTCGCACAGAATGGTGAT
GCTGCTGTTAAAGATTTTGACTTTTACCGTTATAATAAGCCTACCATTTTAGATATTTGT
CAAGCTAGAGTTACATATAAGATAGTCTCTCGTTATTTTGACATTTATGAAGGTGGCTGT
ATTAAGGCATGTGAAGTTGTTGTAACAAATCTTAATAAGAGTGCTGGTTGGCCATTAAAT
AAGTTTGGTAAAGCTAGTTTGTATTATGAATCTATATCTTATGAAGAACAGGATGCTTTG
TTTGCTTTGACAAAGCGTAATGTCCTCCCTACTATGACACAGCTGAATCTTAAGTATGCT
ATTAGTGGTAAAGAACGTGCTAGAACTGTTGGTGGTGTTTCTCTGTTGTCTACAATGACC
ACAAGACAATACCATCAAAAACATCTTAAATCCATTGTTAATACACGCAATGCCACTGTT
GTTATTGGTACTACCAAATTTTATGGTGGTTGGAATAATATGTTGCGTACTTTAATTGAT
GGTGTTGAAAACCCTATGCTTATGGGTTGGGATTATCCCAAATGTGATAGAGCTTTGCCT
AACATGATACGTATGATTTCAGCCATGGTGTTGGGCTCTAAGCATGTTAATTGTTGTACT
GCAACAGATAGGTTTTATAGGCTTGGTAATGAGTTGGCACAAGTTTTAACAGAAGTTGTT
TATTCTAATGGTGGTTTTTATTTTAAGCCAGGTGGTACGACTTCTGGTGACGCTAGTACA
GCTTATGCTAATTCTATTTTTAACATTTTTCAAGCCGTGAGTTCTAACATTAACAGGTTG
CTTAGTGTCCCATCAGATTCATGTAATAATGTTAATGTTAGGGATCTACAACGACGTCTG
TATGATAATTGTTATAGGTTAACTAGTGTTGAAGAGTCATTCATTGAAGATTATTATGGT
TATCTTAGGAAACATTTTTCAATGATGATTCTCTCTGATGACGGTGTTGTCTGTTATAAC
AAGGATTATGCTGAGTTAGGTTATATAGCAGACATTAGTGCTTTTAAAGCCACTTTGTAT
TACCAGAATAATGTCTTTATGAGTACTTCTAAATGTTGGGTTGAAGAAGATTTAACTAAG
GGACCACATGAGTTTTGTTCCCAGCATACTATGCAAATAGTTGACAAAGATGGTACCTAT
TATTTGCCTTACCCAGATCCTAGTAGGATCTTGTCAGCTGGTGTTTTTGTTGATGATGTT
GTTAAGACAGATGCTGTTGTTTTGTTAGAACGTTATGTGTCTTTAGCTATTGATGCATAC
CCTCTTTCAAAACACCCTAATTCCGAATATCGTAAGGTTTTTTACGTATTACTTGATTGG
GTTAAGCATCTTAACAAAAATTTGAATGAGGGTGTTCTTGAATCTTTTTCTGTTACACTT
CTTGATAATCAAGAAGATAAGTTTTGGTGTGAAGATTTTTATGCTAGTATGTATGAAAAT
TCTACAATATTGCAAGCTGCTGGTTTATGTGTTGTTTGTGGTTCACAAACTGTACTTCGT
TGTGGTGATTGTCTGCGTAAGCCTATGTTGTGCACTAAATGCGCATATGATCATGTATTT
GGTACCGACCACAAGTTTATTTTGGCTATAACACCGTATGTATGTAATGCATCAGGTTGT
GGTGTTAGTGATGTCAAAAAATTGTATCTTGGTGGTTTGAATTACTATTGTACAAATCAT
AAACCACAGTTGTCTTTTCCATTATGTTCAGCTGGTAATATATTTGGTTTATATAAAAAT
TCAGCAACTGGTTCCTTAGATGTTGAAGTTTTTAATAGGCTTGCAACGTCTGATTGGACT
GATGTTAGGGACTATAAACTTGCTAATGATGTTAAAGATACACTTAGACTCTTTGCGGCT
GAAACTATTAAAGCTAAAGAAGAGAGTGTTAAGTCTTCTTATGCTTTTGCAACTCTTAAA
GAGGTTGTTGGACCTAAAGAATTGCTTCTTAGTTGGGAAAGTGGTAAAGTTAAACCACCT
TTGAATCGTAATTCTGTTTTCACTTGTTTTCAAATAAGTAAGGACTCAAAATTCCAAATA
GGTGAGTTCATCTTTGAGAAGGTTGAATATGGTTCTGATACTGTTACGTATAAGTCTACT
GTAACTACTAAGTTAGTTCCTGGTATGATTTTTGTCTTAACATCTCACAATGTCCAACCT
TTACGTGCACCAACTATTGCAAACCAAGAGAAGTATTCTAGCATTTATAAATTGCACCCT
GCTTTTAATGTCAGTGATGCATATGCTAATTTGGTTCCATATTACCAACTTATTGGTAAA
CAAAAGATAACTACAATACAGGGTCCTCCTGGTAGTGGTAAGTCACATTGTTCCATTGGA
CTTGGATTGTACTACCCAGGTGCGCGTATTGTTTTTGTTGCTTGTGCCCATGCTGCTGTT
GATTCCTTATGTGCAAAAGCTATGACTGTTTATAGCATTGATAAGTGTACTAGGATTATA
CCTGCAAGAGCTCGGGTTGAGTGTTATAGTGGCTTTAAACCAAATAACACTAGTGCACAA
TACATATTTAGCACTGTTAACGCATTACCTGAGTGTAATGCTGATATCGTTGTTGTAGAT
GAAGTTTCAATGTGTACAAATTATGACCTTTCTGTTATTAACCAGCGTTTATCATATAAA
CATATTGTTTATGTTGGTGATCCACAACAACTTCCTGCACCTAGAGTAATGATTACTAAA
GGTGTTATGGAGCCTGTTGATTATAACGTTGTTACTCAACGTATGTGTGCTATAGGCCCT
GATGTTTTTCTTCATAAATGTTATAGATGTCCTGCTGAAATAGTAATACAGTTTCTGAAC

Fig. 19 F

TTGTTTATGAGAACAAGTTTGTCCCTGTTAAACCTGCTAGTAAACAGTGTTTTAAAGTCT
TTTTTAAGGGTAATGTACAAGGTTGACAATGGTTCTAGTATTAACAGAAAGCAGCTTGAA
ATAGTTAAGCTGTTTTTAGTTAAAAATCCAAGTTGGAGTAAGGCTGTGTTTATTTCTCCT
TATAATAGTCAGAATTATGTTGCTAGTAGATTTTTAGGACTTCAAATTCAAACTGTTGAT
TCTTCTCAAGGTAGTGAGTATGATTATGTAATCTATGCACAAACTTCTGACACTGCACAT
GCTTGCAATGTAAACCGTTTTAATGTTGCTATAACACGTGCTAAGAAGGGTATATTTTGT
GTAATGTGTGATAAAACTTTGTTTGATTCACTTAAGTTTTTTGAGATTAAACATGCAGAT
TTACACTCTAGCCAGGTTTGTGGCTTGTTTAAAAATTGTACACGCACTCCTCTTAATTTA
CCACCAACTCATGCACACACTTTCTTGTCGTTGTCAGATCAGTTTAAGACTACAGGTGAT
TTAGCTGTTCAAATAGGTTCAAATAACGTTTGTACTTATGAACATGTTATATCATTTATG
GGTTTAGGTTTGATATTAGTATTCCTGGTAGTCATAGTTTGTTTTGTACACGTGACTTT
GCTATTCGTAATGTGCGTGGTTGGTTGGGTATGGATGTTGAAAGTGCTCATGTTTGTGGC
GATAACATAGGTACTAATGTTCCTTTACAGGTTGGTTTTTCAAATGGTGTTAATTTTGTT
GTGCAAACTGAAGGTTGTGTGTCTACCAATTTTGGTGATGTTATTAAACCTGTTTGTGCA
AAATCTCCACCAGGTGAACAATTTAGACACCTTATTCCTCTTTTACGTAAAGGACAACCT
TGGTTAATTGTTCGTAGACGCATTGTGCAAATGATATCTGATTATTTGTCCAATTTGTCT
GACATTCTTGTCTTTGTTTTGTGGGCAGGTAGTTTGGAATTAACTACAATGCGTTACTTT
GTAAAAATAGGGCCAATTAAATATTGTTATTGTGGTAATTTTGCCACTTGTTATAATTCA
GTTAGTAATGAATATTGTTGTTTTAAACATGCATTGGGTTGTGATTATGTTTACAATCCG
TATGCTTTTGATATACAACAGTGGGGTTATGTTGGTTCCTTGAGCCAAAACCACCACACA
TTCTGTAACATTCATAGAAACGAGCATGATGCCTCTGGTGATGCTGTTATGACACGTTGT
TTGGCAGTACATGATTGTTTTGTCAAAAATGTTGATTGGACTGTAACGTACCCCTTTATT
GCAAATGAGAAATTTATCAATGGCTGTGGGCGTAATGTCCAGGGACATGTTGTTCGTGCA
GCCTTGAAATTGTATAAACCTAGTGTTATTCATGACATTGGTAATCCTAAAGGTGTACGT
TGTGCTGTTACTGATGCCAAATGGTACTGTTATGACAAGCAACCTGTTAATAGTAATGTC
AAGTTGTTGGATTATGATTATGCAACCCATGGTCAACTTGATGGTCTTTGTTTATTCTGG
AATTGTAATGTTGATATGTATCCAGAATTTTCAATTGTGTGTCGTTTTGACACACGTACT
CGTTCTGTTTTTAATTTAGAAGGTGTTAATGGTGGTTCTCTTTATGTTAACAAACATGCG
TTTCATACACCAGCATATGATAAACGTGCTTTTGTTAAATTAAAACCTATGCCCTTTTTT
TACTTTGATGACAGTGATTGTGATGTTGTGCAAGAACAAGTTAATTATGTACCCCTTCGC
GCTAGTAGTTGTGTTACTCGTTGTAATATAGGTGGTGCTGTTTGTTCAAAACATGCAAAT
TTGTATCAAAAATATGTTGAGGCATATAATACATTTACACAGGCAGGTTTTAACATTTGG
GTACCACATAGTTTTGATGTTTATAATTTGTGGCAAATTTTTATTGAAACTAATTTACAA
AGTCTTGAAAATATAGCATTTAATGTTGTAAAAAAAGGGTGTTTTACTGGTGTTGATGGT
GAGTTACCTGTTGCAGTTGTTAACGACAAAGTTTTTGTTCGCTATGGCGATGTTGACAAC
TTGGTTTTTACAAATAAAACAACATTGCCTACTAATGTTGCTTTTGAATTGTTTGCAAAA
CGAAAAATGGGTTTAACACCACCATTGTCTATTCTCAAAAATCTCGGTGTTGTTGCTACA
TATAAATTTGTTTTATGGGATTATGAAGCTGAAAGACCTTTTACCTCATATACTAAGAGT
GTATGTAAATACACTGATTTTAATGAGGATGTTTGTGTTTGTTTTGACAATAGTATTCAG
GGTTCGTATGAGCGTTTTACGCTTACTACGAACGCTGTTTTATTTTCTACTGTTGTCATT
AAAAATTTAACACCTATAAAGTTGAATTTTGGTATGTTGAATGGTATGCCAGTTTCTTCT
ATTAAGGGTGATAAAGGTGTTGAAAAATTAGTTAATTGGTACATATATGTTCGTAAAAAT
GGTCAATTTCAAGATCACTATGATGGTTTTTACACTCAAGGTAGGAATTTATCAGACTTT
ACACCAAGAAGTGATATGGAGTATGATTTTCTTAACATGGATATGGGTGTTTTTATTAAT
AAATATGGTCTTGAGGATTTTAATTTTGAACATGTTGTATATGGTGATGTTTCAAAAACT
ACATTAGGAGGTCTTCATTTGTTGATATCACAGTTTAGGCTTAGTAAAATGGGTGTTTTG
AAAGCTGATGATTTTGTCACTGCTTCTGACACAACTTTGAGGTGCTGTACTGTTACTTAT
CTTAATGAACTTAGTTCAAAAGTTGTTTGTACTTATATGGATTTGTTGTTGGACGACTTT
GTTACTATACTAAAGAGTTTAGATCTTGGTGTAATATCTAAAGTTCATGAAGTTATTATA
GATAATAAACCTTATAGGTGGATGTTGTGGTGTAAAGATAACCACTTGTCCACTTTTTAT
CCACAGTTGCAGTCTGCTGAATGGAAGTGTGGTTATGCTATGCCACAAATTTATAAGCTT
CAACGTATGTGTTTGGAACCTTGTAATTTATATAATTATGGTGCTGGTATTAAGTTGCCT
AGTGGTATAATGTTAAATGTTGTTAAATACACTCAGCTTTGTCAATACCTAAATAGCACT
ACAATGTGCGTACCTCATAATATGCGTGTTTTGCACTATGGTGCTGGTTCTGACAAAGGT
GTGGCACCTGGTACAACTGTTTTAAAACGTTGGCTACCACCCGATGCAATAATCATTGAT
AATGATATCAATGATTATGTTAGTGATGCAGATTTTAGCATTACAGGTGATTGTGCTACT

Fig. 19G

GTTTATCTTGAAGATAAGTTTGACTTACTTATTTCTGATATGTATGATGGTAGAATTAAA
TTTTGTGATGGTGAAAATGTCTCTAAAGATGGGTTTTTTACTTATCTTAATGGTGTTATT
AGAGAAAAATTAGCTATTGGTGGTAGTGTTGCCATTAAGATTACAGAATATAGTTGGAAT
AAGTATCTTTATGAATTAATACAAAGATTTGCTTTTTGGACTTTGTTTTGCACGTCTGTT
AATACATCCTCTTCAGAAGCTTTTCTTATTGGTATTAATTATTTAGGTGACTTTATTCAA
GGTCCTTTTATAGCTGGTAACACTGTTCATGCTAATTATATATTTTGGCGTAATTCTACT
ATTATGTCTTTGTCATACAATTCAGTTTTAGATTTAAGTAAGTTTGAATGTAAACATAAA
GCCACTGTTGTTGTTACACTTAAAGATAGTGATGTAAATGATATGGTTTTGAGTTTGATT
AAGAGTGGTAGGTTGTTGTTACGCAATAATGGTCGTTTTGGTGGTTTTAGTAATCATTTA
GTCTCAACTAAATGAAACTTTTCTTGATTTTGCTTGTTTTGCCCCTGGCCTCTTGCTTTT
TCACATGTAATAGTAATGCTAATCTCTCTATGTTACAATTAGGTGTTCCTGACAATTCTT
CAACTATTGTTACGGGTTTATTGCCAACTCATTGGTTTTGTGCTAATCAGAGTACATCTG
TTTACTCAGCCAATGGTTTCTTTTATATTGATGTTGGTAATCACCGTAGTGCTTTTGCGC
TCCATACTGGTTATTATGATGCTAATCAGTATTATATTTATGTTACTAATGAAATAGGCT
TAAATGCTTCTGTTACTCTTAAGATTTGTAAGTTTAGTAGAAACACTACTTTTGATTTTT
TAAGTAATGCTTCTAGTTCTTTTGACTGTATAGTTAATTTGTTATTTACAGAACAGTTAG
GTGCGCCTTTGGGCATAACTATATCTGGTGAAACTGTGCGTCTGCATTTATATAATGTAA
CTCGTACTTTTTATGTGCCAGCAGCTTATAAACTTACTAAACTTAGTGTTAAATGTTACT
TTAACTATTCCTGTGTTTTTAGTGTTGTCAACGCCACCGTTACTGTGAATGTCACCACAC
ATAATGGCCGTGTAGTTAACTACACTGTTTGTGATGATTGTAATGGTTATACTGATAACA
TATTTTCTGTTCAACAGGATGGCCGCATTCCTAATGGTTTCCCTTTTAATAATTGGTTTT
TGTTAACTAATGGTTCCACACTAGTGGACGGGGTCTCTAGACTTTATCAACCACTCCGTT
TAACTTGTTTATGGCCTGTACCTGGTCTTAAATCTTCAACTGGTTTTGTTTATTTTAATG
CCACTGGTTCTGATGTTAATTGTAACGGCTATCAACATAATTCTGTTGTTGATGTTATGC
GTTACAATCTTAACTTCAGTGCTAATTCTTTGGACAATCTCAAGAGTGGTGTTATAGTTT
TTAAAACTTTACAGTACGATGTTTTGTTTTATTGTAGTAATTCTTCCTCAGGTGTTCTTG
ACACCACAATACCTTTTGGCCCGTCCTCTCAACCTTATTACTGTTTTATAAACAGCACTA
TCAACACTACTCATGTTAGCACTTTTGTGGGTATTTTACCACCCACTGTGCGTGAAATTG
TTGTTGCTAGAACTGGCCAGTTTTATATTAATGGTTTTAAGTATTTCGATTTGGGTTTCA
TAGAAGCTGTCAATTTTAATGTCACGACTGCTAGCGCCACAGATTTTTGGACGGTTGCAT
TTGCTACTTTTGTTGATGTTTTGGTTAATGTTAGTGCAACTAACATTCAAAACTTACTTT
ATTGCGATTCTCCATTTGAAAAGTTGCAGTGTGAGCACTTGCAGTTTGGATTGCAGGATG
GTTTTTATTCTGCAAATTTTCTTGATGATAATGTTTTGCCTGAGACTTATGTTGCACTCC
CCATTTATTATCAACACACGGACATAAATTTTACTGCAACTGCATCTTTTGGTGGTTCTT
GTTATGTTTGTAAACCACACCAGGTTAATATATCTCTTAATGGTAACACTTCAGTGTGTG
TTAGAACATCTCATTTTTCAATTAGGTATATTTATAACCGCGTTAAGAGTGGTTCACCAG
GTGACTCTTCATGGCACATTTATTTAAAGAGTGGCACTTGTCCATTTTCTTTTTCTAAGT
TAAATAATTTTCAAAAGTTCAAGACTATTTGTTTCTCAACCGTCGAAGTGCCTGGTAGTT
GTAATTTTCCGCTTGAAGCCACCTGGCATTACACTTCTTATACTATTGTTGGTGCTTTGT
ATGTTACTTGGTCTGAAGGTAATTCTATTACTGGTGTACCTTATCCTGTCTCTGGTATTC
GTGAGTTTAGTAATTTAGTTTTAAATAATTGTACCAAATATAATATTTATGATTATGTTG
GTACTGGAATTATACGTTCTTCAAACCAGTCACTTGCTGGTGGTATTACATATGTTTCTA
ACTCTGGTAATTTACTTGGTTTTAAAAATGTTTCCACTGGTAACATTTTTATTGTGACAC
CATGTAACCAACCAGACCAAGTAGCTGTTTATCAACAAAGCATTATTGGTGCCATGACCG
CTGTTAATGAGTCTAGATATGGCTTGCAAAACTTACTACAGTTACCTAACTTTTATTATG
TTAGTAATGGTGGTAACAATTGCACTACGGCCGTTATGACTTATTCTAATTTTGGTATTT
GTGCTGATGGTTCTTTGATTCCTGTTCGTCCGCGTAATTCTAGTGATAATGGTATTTCAG
CCATAATCACTGCTAATTTATCCATTCCTTCTAACTGGACTACTTCAGTTCAAGTTGAGT
ACCTCCAAATTACTAGTACTCCAATAGTTGTTGATTGTGCTACTTATGTGTGTAATGGTA
ACCCTCGCTGTAAGAATCTACTTAAGCAGTATACTTCTGCTTGTAAAACTATTGAAGATG
CCTTACGACTTAGTGCTCATTTGGAAACTAATGATGTTAGTAGTATGCTAACTTTCGATA
GCAATGCTTTTAGTTTGGCTAATGTTACTAGTTTTGGAGATTATAACCTTTCTAGTGTTT
TACCTCAGAGAAACATTCGTTCAAGCCGTATAGCAGGACGTAGTGCTTTGGAAGATTTGT
TGTTTAGCAAAGTTGTTACATCTGGTTTGGGTACTGTTGATGTTGACTATAAGTCTTGTA
CTAAAGGTCTTTCTATTGCTGACCTTGCTTGTGCTCAGTACTACAATGGCATAATGGTTT
TGCCAGGTGTTGCTGATGCTGAACGTATGGCCATGTACACAGGTTCTCTTATAGGTGGCA

Fig. 19 H

TGGTGCTCGGAGGTCTTACATCAGCAGCCGCCATACCTTTTTCTTTGGCACTGCAAGCAC
GACTTAACTATGTTGCTTTACAAACTGATGTGCTTCAAGAAAATCAGAAAATTTTGGCTG
CATCATTTAATAAGGCTATTAATAATATTGTTGCTTCTTTTAGTAGCGTTAATGATGCTA
TTACACAAACTGCAGAGGCTATACATACTGTTACTATTGCACTTAATAAGATTCAGGATG
TTGTTAATCAACAGGGTAGTGCTCTTAACCATCTCACTTCACAATTGAGACATAATTTTC
AGGCCATTTCTAATTCAATTCAGGCTATTTATGACCGGCTTGATTCAATTCAAGCCGATC
AACAAGTTGACAGATTAATTACTGGACGGCTTGCAGCTTTGAATGCATTTGTTTCCCAAG
TTTTGAATAAATATACTGAAGTTCGTGGTTCAAGACGCTTAGCACAGCAGAAGATTAATG
AATGTGTCAAGTCACAATCTAATAGATATGGTTTTTGTGGCAATGGCACTCACATCTTTT
CAATCGTCAACTCTGCTCCAGATGGTTTGCTTTTTCTTCATACTGTTTTGCTGCCAACTG
ATTACAAGAATGTAAAGGCGTGGTCTGGTATCTGTGTTGATGGCATTTATGGCTATGTTC
TGCGTCAACCTAACTTGGTTCTTTATTCTGATAATGGTGTCTTTCGTGTAACTTCCAGGG
TCATGTTTCAACCTCGCTTACCTGTTTTGTCTGATTTTGTGCAAATATATAATTGTAATG
TTACTTTTGTTAACATATCTCGTGTTGAGTTACATACTGTCATACCTGACTACGTTGATG
TTAATAAAACATTACAAGAGTTTGCACAAAACTTACCAAAGTATGTTAAGCCTAATTTTG
ACTTGACTCCTTTTAATTTAACATATCTTAATTTGAGTTCTGAGTTGAAGCAACTCGAAG
CTAAAACTGCTAGTCTTTTTCAAACTACTGTTGAATTACAAGGTCTTATTGATCAGATTA
ACAGTACATATGTTGATTTGAAGTTGCTTAATAGGTTTGAAAATTATATCAAATGGCCTT
GGTGGGTTTGGCTCATTATTTCTGTTGTTTTTGTTGTATTGTTGAGTCTTCTTGTGTTTT
GTTGTCTTTCTACAGGTTGTTGTGGTTGTTGCAATTGTTTAACTTCATCAATGCGAGGCT
GTTGTGATTGTGGTTCAACTAAACTTCCTTATTACGAATTTGAAAAGGTCCACGTTCAAT
AATGCCTTTTGGTGGCCTATTTCAACTTACTCTTGAAAGTACTATTAATAAGAGTGTGGC
TAATCTCAAATTACCACCTCATGATGTTACTGTCTTGCGTGACAATCTTAAACCTGTTAC
TACACTTAGTACTATTACTGCTTATTTGTTAGTTAGTTTGTTTGTCACTTACTTTGCTTT
ATTCAAACCTCTTACTGCTAGAGGTCGTGTTGCTTGTTTTGTTTTAAAACTATTGACACT
ATTTGTCTATGTGCCTTTATTGGTTCTTTTTGGTATGTATCTTGACAGTTTTATAATTTT
TTCTACGCTGTTGTTTCGATTCATACATGTTGGCTATTATGCCTATCTCTATAAAAATTT
TTCATTTGTTTTGTTCAATGTTACTAAACTATGCTTCGTTTCAGGCAAGTGTTGGTATCT
TGAACAATCATTTTATGAAAATCGTTTTGCTGCTATTTATGGTGGTGACCACTATGTCGT
TTTAGGTGGTGAAACTATTACTTTTGTTTCTTTTGATGACCTTTATGTTGCTATTAGAGG
TTCTTGTGAAAAGAACCTACAACTTATGCGTAAGGTTGACTTGTATAATGGTGCTGTCAT
TTACATTTTTGCCGAAGAGCCTGTTGTTGGTATAGTCTACTCTTCTCAACTATACGAAGA
TGTTCCTTCGATTAATTGATGACAATGGTATTGTCCTCAATTCCATTTTATGGCTCCTTG
TTATGATATTTTTCTTTGTGTTGGCAATGACCTTTATTAAACTGATTCAATTGTGTTTTA
CTTGTCATTATTTTTTTAGTAGGACATTATATCAACCAGTTTATAAAATTTTTCTTGCTT
ACCAAGATTATATGCAAATAGCACCTGTTCCAGCTGAAGTACTAAATGTCTAAACTAAAC
GATGTCTAATAGTAGTGTGCCTCTTTTAGAGGTTTATGTCCATTTACGTAACTGGAACTT
TAGTTGGAATTTAATTCTAACGCTTTTTATAGTTGTGTTGCAGTATGGGCATTATAAGTA
TAGCAGACTTCTTTATGGTTTAAAGATGTCTGTTTTATGGTGTTTATGGCCACTTGTTCT
AGCTTTGTCTATTTTTGACTGTTTTGTCAATTTTAATGTGGACTGGGTCTTTTTTGGTTT
TAGTATTCTTATGTCTATTATTACACTTTGTTTATGGGTTATGTATTTTGTTAATAGTTT
CAGACTTTGGCGCCGTGTTAAAACTTTTTGGGCTTTTAATCCTGAAACTAATGCAATCAT
CTCTCTCCAGGTTTACGGACATAATTATTACTTACCGGTGATGGCTGCACCTACAGGTGT
TACATTAACACTTCTTAGTGGTGTACTTCTTGTTGATGGCCATAAGATTGCTACTCGTGT
TCAAGTGGGTCAGTTGCCTAAATATGTAATAGTTGCTACGCCTAGTACCACAATTGTTTG
TGACCGTGTTGGTCGCTCTGTTAATGAAACAAGCCAGACTGGTTGGGCATTCTACGTCCG
TGCTAAACATGGTGATTTTTCTGGTGTTGCCTCTCAGGAGGGTGTTTTGTCAGAAAGAGA
GAAGTTGCTTCATTTAATCTAAACTAAACAAAATGGCTAGTGTAAATTGGGCCGATGACA
GAGCTGCTAGGAAGAAATTTCCTCCTCCTTCATTTTACATGCCTCTTTTGGTTAGTTCTG
ATAAGGCACCATATAGGGTCATTCCCAGGAATCTTGTCCCTATTGGTAAGGGTAATAAAG
ATGAGCAGATTGGTTATTGGAATGTTCAAGAGCGTTGGCGTATGCGCAGGGGGCAACGTG
TTGATTTGCCTCCTAAAGTTCATTTTTATTACCTAGGTACTGGACCTCATAAGGACCTTA
AATTCAGACAACGTTCTGATGGTGTTGTTTGGGTTGCTAAGGAAGGTGCTAAAACTGTTA
ATACCAGTCTTGGTAATCGCAAACGTAATCAGAAACCTTTGGAACCAAAGTTCTCTATTG
CTTTGCCTCCAGAGCTCTCTGTTGTTGAGTTTGAGGATCGCTCTAATAACTCATCTCGTG
CTAGCAGTCGTTCTTCAACTCGTAACAACTCACGAGACTCTTCTCGTAGCACTTCAAGAC

Fig. 19I

AACAGTCTCGCACTCGTTCTGATTCTAACCAGTCTTCTTCAGATCTTGTTGCTGCTGTTA
CTTTGGCCTTAAAGAACTTAGGTTTTGATAACCAGTCGAAGTCACCTAGTTCTTCTGGTA
CTTCCACTCCTAAGAAACCTAATAAGCCTCTTTCTCAACCCAGGGCTGATAAGCCTTCTC
AGTTGAAGAAACCTCGTTGGAAGCGTGTTCCTACCAGAGAGGAAAATGTTATTCAGTGCT
TTGGTCCTCGTGATTTTAATCACAATATGGGGGATTCAGATCTTGTTCAGAATGGTGTTG
ATGCCAAAGGTTTTCCACAGCTTGCTGAATTGATTCCTAATCAGGCTGCGTTATTCTTTG
ATAGTGAGGTTAGCACTGATGAAGTGGGTGATAATGTTCAGATTACCTACACCTACAAAA
TGCTTGTAGCTAAGGATAATAAGAACCTTCCTAAGTTCATTGAGCAGATTAGTGCTTTTA
CTAAACCCAGTTCTATCAAAGAAATGCAGTCACAATCATCTCATGTTGCTCAGAACACAG
TACTTAATGCTTCTATTCCAGAATCTAAACCATTGGCTGATGATGATTCAGCCATTATAG
AAATTGTCAACGAGGTTTTGCATTAAATTGTTTTGTAATTCCAGTTGAATGTTTATTATT
ATTAGTTGCAACCCCATGCGTTTAGCGCATGATAAGGGTTTAGTCTTACACACAATGGTA
GGCCAGTGATAGTAAAGTGTAAGTAATTTGCTATCATATTAACATGTCTAGAGGAAAGTC
AGAACTTTTTCTGTTTGTGTTGTTGGAGTACTTAAAGATCGCATAGGCGCGCCAACAATG
GAAGAGCCAACAACATATCTAAAAATGTTTTGTCTGGTACTTGTTAATGATATTGTTTTT
GATATGGATACAC

Fig. 20 A

ORF 1a, replicase enzyme complex

MFYNQVTLAVASDSEISGFGFAIPSVAVRTYSEAAAQGFQACRFVAFGLQDCVTGINDDD
YVIALTGTNQLCAKILPFSDRPLNLRGWLIFSNSNYVLQDFDVVFGHGAGSVVFVDKYMC
GFDGKPVLPKNMWEFRDYFNNNTDSIVIGGVTYQLAWDVIRKDLSYEQQNVLAIESIHYL
GTTGHTLKSGCKLTNAKPPKYSSKVVLSGEWNAVYRAFGSPFITNGMSLLDIIVKPVFFN
AFVKCNCGSESWSVGAWDGYLSSCCGTPAKKLCVVPGNVVPGDVIITSTSAGCGVKYYAG
LVVKHITNITGVSLWRVTAVHSDGMFVASSSYDALLHRNSLDPFCFDVNTLLSNQLRLAF
LGASVTEDVKFAASTGVIDISAGMFGLYDDILTNNKPWFVRKASGLFDAIWDAFVAAIKL
VPTTTGVLVRFVKSIASTVLTVSNGVIIMCADVPDAFQSVYRTFTQAICAAFDFSLDVFK
IGDVKFKRLGDYVLTENALVRLTTEVVRGVRDARIKKAMFTKVVVGPTTEVKFSVIELAT
VNLRLVDCAPVVCPKGKIVVIAGQAFFYSGGFYRFMVDPTTVLNDPVFTGDLFYTIKFSG
FKLDGFNHQFVTASSATDAIIAVELLLLDFKTAVFVYTCVVDGCSVIVRRDATFATHVCF
KDCYNVWEQFCIDNCGEPWFLTDYNAILQSNNPQCAIVQASESKVLLERFLPKCPEILLS
IDDGHLWNLFVEKFNFVTDWLKTLKLTLTSNGLLGNCAKRFRRVLVKLLDVYNGFLETVC
SVAYTAGVCIKYYAVNVPYVVISGFVSRVIRRERCDMTFPCVSCVTFFYEFLDTCFGVSK
PNAIDVEHLELKETVFVEPKDGGQFFVSGDYLWYVVDDIYYPASCNGVLPVAFTKLAGGK
ISFSDDVIVHDVEPTHKVKLIFEFEDDVVTSLCKKSFGKSIIYTGDWEGLHEVLTSAMNV
IGQHIKLPQFYIYDEEGGYDVSKPVMISQWPISNDSNGCVVEASTDFHQLECIVDDSVRE
EVDIIEQPFEEVEHVLSIKQPFSFSFRDELGVRVLDQSDNNCWISTTLVQLQLTKLLDDS
IEMQLFKVGKVDSIVQKCYELSHLISGSLGDSGKLLSELLKEKYTCSITFEMSCDCGKKF
DDQVGCLFWIMPYTKLFQKGECCICHKMQTYKLVSMKGTGVFVQDPAPIDIDAFPVKPIC
SSVYLGVKGSGHYQTNLYSFNKAIDGFGVFDIKNSSVNTVCFVDVDFHSVEIEAGEVKPF
AVYKNVKFYLGDISHLVNCVSFDFVVNAANENLLHGGGVARAIDILTEGQLQSLSKDYIS
SNGPLKVGAGVMLECEKFNVFNVVGPRTGKHEHSLLVEAYNSILFENGIPLMPLLSCGIF
GVRIENSLKALFSCDINKPLQVFVYSSNEEQAVLKFLDGLDLTPVIDDVDVVKPFRVEGN
FSFFDCGVNALDGDIYLLFTNSILMLDKQGQLLDTKLNGILQQAALDYLATVKTVPAGNL
VKLFVESCTIYMCVVPSINDLSFDKNLGRCVRKLNRLKTCVIANVPAIDVLKKLLSSLTL
TVKFVVESNVMDVNDCFKNDNVVLKITEDGINVKDVVVESSKSLGKQLGVVSDGVDSFEG
VLPINTDTVLSVAPEVDWVAFYGFEKAALFASLDVKPYGYPNDFVGGFRVLGTTDNNCWV
NATCIILQYLKPTFKSKGLNVLWNKFVTGDVGPFVSFIYFITMSSKGQKGDAEEALSKLS
EYLISDSIVTLEQYSTCDICKSTVVEVKSAIVCASVLKDGCDVGFCPHRHKLRSRVKFVN
GRVVITNVGEPIISQPSKLLNGIAYTTFSGSFDNGHYVVYDAANNAVYDGARLFSSDLST
LAVTAIVVVGGCVTSNVPTIVSEKISVMDKLDTGAQKFFQFGDFVMNNIVLFLTWLLSMF
SLLRTSIMKHDIKVIAKAPKRTGVILTRSFKYNIRSALFVIKQKWCVIVTLFKFLLLLYA
IYALVFMIVQFSPFNSLLCGDIVSGYEKSTFNKDIYCGNSMVCKMCLFSYQEFNDLDHTS
LVWKHIRDPILISLQPFVILVILLIFGNMYLRFGLLYFVAQFISTFGSFLGFHQKQWFLH
FVPFDVLCNEFLATFIVCKIVLFVRHIIVGCNNADCVACSKSARLKRVPLQTIINGMHKS
FYVNANGGTCFCNKHNFFCVNCDSFGPGNTFINGDIARELGNVVKTAVQPTAPAYVIIDK
VDFVNGFYRLYSGDTFWRYDFDITESKYSCKEVLKNCNVLENFIVYNNSGSNITQIKNAC
VYFSQLLCEPIKLVNSELLSTLSVDFNGVLHKAYVDVLCNSFFKELTANMSMAECKATLG
LTVSDDDFVSAVANAHRYDVLLSDLSFNNFFISYAKPEDKLSVYDIACCMRAGSKVVNHN
VLIKESIPIVWGVKDFNTLSQEGKKYLVKTTKAKGLTFLLTFNDNQAITQVPATSIVAKQ
GAGFKRTYNFLWYVCLFVVALFIGVSFIDYTTTVTSFHGYDFKYIENGQLKVFEAPLHCV
RNVFDNFNQWHEAKFGVVTTNSDKCPIVVGVSERINVVPGVPTNVYLVGKTLVFTLQAAF
GNTGVCYDFDGVTTSDKCIFNSACTRLEGLGGDNVYCYNTDLIEGSKPYSTLQPNAYYKY
DAKNYVRFPEILARGFGLRTIRTLATRYCRVGECRDSHKGVCFGFDKWYVNDGRVDDGYI
CGDGLIDLLVNVLSIFSSSFSVVAMSGHMLFNFLFAAFITFLCFLVTKFKRVFGDLSYGV
FTVVCATLINNISYVVTQNLFFMLLYAILYFVFTRTVRYAWIWHIAYIVAYFLLIPWWLL
TWFSFAAFLELLPNVFKLKISTQLFEGDKFIGTFESAAAGTFVLDMRSYERLINTISPEK
LKNYAASYNKYKYYSGSASEADYRCACYAHLAKAMLDYAKDHNDMLYSPPTISYNSTLQS
GLKKMAQPSGCVERCVVRVCYGSTVLNGVWLGDTVTCPRHVIAPSTTVLIDYDHAYSTMR
LHNFSVSHNGVFLGVVGVTMHGSVLRIKVSQSNVHTPKHVFKTLKPGDSFNILACYEGIA
SGVFGVNLRTNFTIKGSFINGACGSPGYNVRNDGTVEFCYLHQIELGSGAHVGSDFTGSV

Fig. 20B

YGNFDDQPSLQVESANLMLSDNVVAFLYAALLNGCRWWLCSTRVNVDGFNEWAMANGYTS
VSSVECYSILAAKTGVSVEQLLASIQHLHEGFGGKNILGYSSLCDEFTLAEVVKQMYGVN
LQSGKVIFGLKTMFLFSVFFTMFWAELFIYTNTIWINPVILTPIFCLLLFLSLVLTMFLK
HKFLFLQVFLLPTVIATALYNCVLDYYIVKFLADHFNYNVSVLQMDVQGLVNVLVCLFVV
FLHTWRFSKERFTHWFTYVCSLIAVAYTYFYSGDFLSLLVMFLCAISSDWYIGAIVFRLS
RLIVFFSPESVFSVFGDVKLTLVVYLICGYLVCTYWGILYWFNRFFKCTMGVYDFKVSAA
EFKYMVANGLHAPHGPFDALWLSFKLLGIGGDRCIKISTVQSKLTDLKCTNVVLLGCLSS
MNIAANSSEWAYCVDLHNKINLCDDPEKAQSMLLALLAFFLSKHSDFGLDGLIDSYFDNS
STLQSVASSFVSMPSYIAYENARQAYEDAIANGSSSQLIKQLKRAMNIAKSEFDHEISVQ
KKINRMAEQAATQMYKEARSVNRKSKVISAMHSLLFGMLRRLDMSSVETVLNLARDGVVP
LSVIPATSASKLTIVSPDLESYSKIVCDGSVHYAGVVWTLNDVKDNDGRPVHVKEITKEN
VETLTWPLILNCERVVKLQNNEIMPGKLKQKPMKAEGDGGVLGDGNALYNTEGGKTFMYA
YISNKADLKFVKWEYEGGCNTIELDSPCRFMVETPNGPQVKYLYFVKNLNTLRRGAVLGF
IGATIRLQAGKQTELAVNSGLLTACAFSVDPATTYLEAVKHGAKPVSNCIKMLSNGAGNG
QAITTSVDANTNQDSYGGASICLYCRAHVPHPSMDGYCKFKGKCVQVPIGCLDPIRFCLE
NNVCNVCGCWLGHGCACDRTTIQSVDISYLNEQGVLVQLD

Fig. 21A

ORF 1ab replicase polyprotein

MFYNQVTLAVASDSEISGFGFAIPSVAVRTYSEAAAQGFQACRFVAFGLQDCVTGINDDD
YVIALTGTNQLCAKILPFSDRPLNLRGWLIFSNSNYVLQDFDVVFGHGAGSVVFVDKYMC
GFDGKPVLPKNMWEFRDYFNNNTDSIVIGGVTYQLAWDVIRKDLSYEQQNVLAIESIHYL
GTTGHTLKSGCKLTNAKPPKYSSKVVLSGEWNAVYRAFGSPFITNGMSLLDIIVKPVFFN
AFVKCNCGSESWSVGAWDGYLSSCCGTPAKKLCVVPGNVVPGDVIITSTSAGCGVKYYAG
LVVKHITNITGVSLWRVTAVHSDGMFVASSSYDALLHRNSLDPFCFDVNTLLSNQLRLAF
LGASVTEDVKFAASTGVIDISAGMFGLYDDILTNNKPWFVRKASGLFDAIWDAFVAAIKL
VPTTTGVLVRFVKSIASTVLTVSNGVIIMCADVPDAFQSVYRTFTQAICAAFDFSLDVFK
IGDVKFKRLGDYVLTENALVRLTTEVVRGVRDARIKKAMFTKVVVGPTTEVKFSVIELAT
VNLRLVDCAPVVCPKGKIVVIAGQAFFYSGGFYRFMVDPTTVLNDPVFTGDLFYTIKFSG
FKLDGFNHQFVTASSATDAIIAVELLLLDFKTAVFVYTCVVDGCSVIVRRDATFATHVCF
KDCYNVWEQFCIDNCGEPWFLTDYNAILQSNNPQCAIVQASESKVLLERFLPKCPEILLS
IDDGHLWNLFVEKFNFVTDWLKTLKLTLTSNGLLGNCAKRFRRVLVKLLDVYNGFLETVC
SVAYTAGVCIKYYAVNVPYVVISGFVSRVIRRERCDMTFPCVSCVTFFYEFLDTCFGVSK
PNAIDVEHLELKETVFVEPKDGGQFFVSGDYLWYVVDDIYYPASCNGVLPVAFTKLAGGK
ISFSDDVIVHDVEPTHKVKLIFEFEDDVVTSLCKKSFGKSIIYTGDWEGLHEVLTSAMNV
IGQHIKLPQFYIYDEEGGYDVSKPVMISQWPISNDSNGCVVEASTDFHQLECIVDDSVRE
EVDIIEQPFEEVEHVLSIKQPFSFSFRDELGVRVLDQSDNNCWISTTLVQLQLTKLLDDS
IEMQLFKVGKVDSIVQKCYELSHLISGSLGDSGKLLSELLKEKYTCSITFEMSCDCGKKF
DDQVGCLFWIMPYTKLFQKGECCICHKMQTYKLVSMKGTGVFVQDPAPIDIDAFPVKPIC
SSVYLGVKGSGHYQTNLYSFNKAIDGFGVFDIKNSSVNTVCFVDVDFHSVEIEAGEVKPF
AVYKNVKFYLGDISHLVNCVSFDFVVNAANENLLHGGGVARAIDILTEGQLQSLSKDYIS
SNGPLKVGAGVMLECEKFNVFNVVGPRTGKHEHSLLVEAYNSILFENGIPLMPLLSCGIF
GVRIENSLKALFSCDINKPLQVFVYSSNEEQAVLKFLDGLDLTPVIDDVDVVKPFRVEGN
FSFFDCGVNALDGDIYLLFTNSILMLDKQGQLLDTKLNGILQQAALDYLATVKTVPAGNL
VKLFVESCTIYMCVVPSINDLSFDKNLGRCVRKLNRLKTCVIANVPAIDVLKKLLSSLTL
TVKFVVESNVMDVNDCFKNDNVVLKITEDGINVKDVVVESSKSLGKQLGVVSDGVDSFEG
VLPINTDTVLSVAPEVDWVAFYGFEKAALFASLDVKPYGYPNDFVGGFRVLGTTDNNCWV
NATCIILQYLKPTFKSKGLNVLWNKFVTGDVGPFVSFIYFITMSSKGQKGDAEEALSKLS
EYLISDSIVTLEQYSTCDICKSTVVEVKSAIVCASVLKDGCDVGFCPHRHKLRSRVKFVN
GRVVITNVGEPIISQPSKLLNGIAYTTFSGSFDNGHYVVYDAANNAVYDGARLFSSDLST
LAVTAIVVVGGCVTSNVPTIVSEKISVMDKLDTGAQKFFQFGDFVMNNIVLFLTWLLSMF
SLLRTSIMKHDIKVIAKAPKRTGVILTRSFKYNIRSALFVIKQKWCVIVTLFKFLLLLYA
IYALVFMIVQFSPFNSLLCGDIVSGYEKSTFNKDIYCGNSMVCKMCLFSYQEFNDLDHTS
LVWKHIRDPILISLQPFVILVILLIFGNMYLRFGLLYFVAQFISTFGSFLGFHQKQWFLH
FVPFDVLCNEFLATFIVCKIVLFVRHIIVGCNNADCVACSKSARLKRVPLQTIINGMHKS
FYVNANGGTCFCNKHNFFCVNCDSFGPGNTFINGDIARELGNVVKTAVQPTAPAYVIIDK
VDFVNGFYRLYSGDTFWRYDFDITESKYSCKEVLKNCNVLENFIVYNNSGSNITQIKNAC
VYFSQLLCEPIKLVNSELLSTLSVDFNGVLHKAYVDVLCNSFFKELTANMSMAECKATLG
LTVSDDDFVSAVANAHRYDVLLSDLSFNNFFISYAKPEDKLSVYDIACCMRAGSKVVNHN
VLIKESIPIVWGVKDFNTLSQEGKKYLVKTTKAKGLTFLLTFNDNQAITQVPATSIVAKQ
GAGFKRTYNFLWYVCLFVVALFIGVSFIDYTTTVTSFHGYDFKYIENGQLKVFEAPLHCV
RNVFDNFNQWHEAKFGVVTTNSDKCPIVVGVSERINVVPGVPTNVYLVGKTLVFTLQAAF
GNTGVCYDFDGVTTSDKCIFNSACTRLEGLGGDNVYCYNTDLIEGSKPYSTLQPNAYYKY
DAKNYVRFPEILARGFGLRTIRTLATRYCRVGECRDSHKGVCFGFDKWYVNDGRVDDGYI
CGDGLIDLLVNVLSIFSSSFSVVAMSGHMLFNFLFAAFITFLCFLVTKFKRVFGDLSYGV
FTVVCATLINNISYVVTQNLFFMLLYAILYFVFTRTVRYAWIWHIAYIVAYFLLIPWWLL
TWFSFAAFLELLPNVFKLKISTQLFEGDKFIGTFESAAAGTFVLDMRSYERLINTISPEK
LKNYAASYNKYKYYSGSASEADYRCACYAHLAKAMLDYAKDHNDMLYSPPTISYNSTLQS
GLKKMAQPSGCVERCVVRVCYGSTVLNGVWLGDTVTCPRHVIAPSTTVLIDYDHAYSTMR
LHNFSVSHNGVFLGVVGVTMHGSVLRIKVSQSNVHTPKHVFKTLKPGDSFNILACYEGIA
SGVFGVNLRTNFTIKGSFINGACGSPGYNVRNDGTVEFCYLHQIELGSGAHVGSDFTGSV

Fig. 21B

YGNFDDQPSLQVESANLMLSDNVVAFLYAALLNGCRWWLCSTRVNVDGFNEWAMANGYTS
VSSVECYSILAAKTGVSVEQLLASIQHLHEGFGGKNILGYSSLCDEFTLAEVVKQMYGVN
LQSGKVIFGLKTMFLFSVFFTMFWAELFIYTNTIWINPVILTPIFCLLLFLSLVLTMFLK
HKFLFLQVFLLPTVIATALYNCVLDYYIVKFLADHFNYNVSVLQMDVQGLVNVLVCLFVV
FLHTWRFSKERFTHWFTYVCSLIAVAYTYFYSGDFLSLLVMFLCAISSDWYIGAIVFRLS
RLIVFFSPESVFSVFGDVKLTLVVYLICGYLVCTYWGILYWFNRFFKCTMGVYDFKVSAA
EFKYMVANGLHAPHGPFDALWLSFKLLGIGGDRCIKISTVQSKLTDLKCTNVVLLGCLSS
MNIAANSSEWAYCVDLHNKINLCDDPEKAQSMLLALLAFFLSKHSDFGLDGLIDSYFDNS
STLQSVASSFVSMPSYIAYENARQAYEDAIANGSSSQLIKQLKRAMNIAKSEFDHEISVQ
KKINRMAEQAATQMYKEARSVNRKSKVISAMHSLLFGMLRRLDMSSVETVLNLARDGVVP
LSVIPATSASKLTIVSPDLESYSKIVCDGSVHYAGVVWTLNDVKDNDGRPVHVKEITKEN
VETLTWPLILNCERVVKLQNNEIMPGKLKQKPMKAEGDGGVLGDGNALYNTEGGKTFMYA
YISNKADLKFVKWEYEGGCNTIELDSPCRFMVETPNGPQVKYLYFVKNLNTLRRGAVLGF
IGATIRLQAGKQTELAVNSGLLTACAFSVDPATTYLEAVKHGAKPVSNCIKMLSNGAGNG
QAITTSVDANTNQDSYGGASICLYCRAHVPHPSMDGYCKFKGKCVQVPIGCLDPIRFCLE
NNVCNVCGCWLGHGCACDRTTIQSVDISYLNEQGVLVQLDRARGSSAARLEPCNGTDIDK
CVRAFDIYNKNVSFLGKCLKMNCVRFKNADLKDGYFVIKRCTKSVMEHEQSMYNLLNFSG
ALAEHDFFTWKDGRVIYGNVSRHNLTKYTMMDLVYAMRNFDEQNCDVLKEVLVLTGCCDN
SYFDSKGWYDPVENEDIHRVYASLGKIVARAMLKCVALCDAMVAKGVVGVLTLDNQDLNG
NFYDFGDFVVSLPNMGVPCCTSYYSYMMPIMGLTNCLASECFVKSDIFGSDFKTFDLLKY
DFTEHKENLFNKYFKHWSFDYHPNCCDCYDDMCVIHCANFNTLFATTIPGTAFGPLCRKV
FIDGVPLVTTAGYHFKQLGLVWNKDVNTHSVRLTITELLQFVTDPSLIIASSPALVDQRT
ICFSVAALSTGLTNQVVKPGHFNEEFYNFLRLRGFFDEGSELTLKHFFFAQNGDAAVKDF
DFYRYNKPTILDICQARVTYKIVSRYFDIYEGGCIKACEVVVTNLNKSAGWPLNKFGKAS
LYYESISYEEQDALFALTKRNVLPTMTQLNLKYAISGKERARTVGGVSLLSTMTTRQYHQ
KHLKSIVNTRNATVVIGTTKFYGGWNNMLRTLIDGVENPMLMGWDYPKCDRALPNMIRMI
SAMVLGSKHVNCCTATDRFYRLGNELAQVLTEVVYSNGGFYFKPGGTTSGDASTAYANSI
FNIFQAVSSNINRLLSVPSDSCNNVNVRDLQRRLYDNCYRLTSVEESFIEDYYGYLRKHF
SMMILSDDGVVCYNKDYAELGYIADISAFKATLYYQNNVFMSTSKCWVEEDLTKGPHEFC
SQHTMQIVDKDGTYYLPYPDPSRILSAGVFVDDVVKTDAVVLLERYVSLAIDAYPLSKHP
NSEYRKVFYVLLDWVKHLNKNLNEGVLESFSVTLLDNQEDKFWCEDFYASMYENSTILQA
AGLCVVCGSQTVLRCGDCLRKPMLCTKCAYDHVFGTDHKFILAITPYVCNASGCGVSDVK
KLYLGGLNYYCTNHKPQLSFPLCSAGNIFGLYKNSATGSLDVEVFNRLATSDWTDVRDYK
LANDVKDTLRLFAAETIKAKEESVKSSYAFATLKEVVGPKELLLSWESGKVKPPLNRNSV
FTCFQISKDSKFQIGEFIFEKVEYGSDTVTYKSTVTTKLVPGMIFVLTSHNVQPLRAPTI
ANQEKYSSIYKLHPAFNVSDAYANLVPYYQLIGKQKITTIQGPPGSGKSHCSIGLGLYYP
GARIVFVACAHAAVDSLCAKAMTVYSIDKCTRIIPARARVECYSGFKPNNTSAQYIFSTV
NALPECNADIVVVDEVSMCTNYDLSVINQRLSYKHIVYVGDPQQLPAPRVMITKGVMEPV
DYNVVTQRMCAIGPDVFLHKCYRCPAEIVIQFLNLFMRTSLSLLNLLVNSVLKSFLRVMY
KVDNGSSINRKQLEIVKLFLVKNPSWSKAVFISPYNSQNYVASRFLGLQIQTVDSSQGSE
YDYVIYAQTSDTAHACNVNRFNVAITRAKKGIFCVMCDKTLFDSLKFFEIKHADLHSSQV
CGLFKNCTRTPLNLPPTHAHTFLSLSDQFKTTGDLAVQIGSNNVCTYEHVISFMGFRFDI
SIPGSHSLFCTRDFAIRNVRGWLGMDVESAHVCGDNIGTNVPLQVGFSNGVNFVVQTEGC
VSTNFGDVIKPVCAKSPPGEQFRHLIPLLRKGQPWLIVRRRIVQMISDYLSNLSDILVFV
LWAGSLELTTMRYFVKIGPIKYCYCGNFATCYNSVSNEYCCFKHALGCDYVYNPYAFDIQ
QWGYVGSLSQNHHTFCNIHRNEHDASGDAVMTRCLAVHDCFVKNVDWTVTYPFIANEKFI
NGCGRNVQGHVVRAALKLYKPSVIHDIGNPKGVRCAVTDAKWYCYDKQPVNSNVKLLDYD
YATHGQLDGLCLFWNCNVDMYPEFSIVCRFDTRTRSVFNLEGVNGGSLYVNKHAFHTPAY
DKRAFVKLKPMPFFYFDDSDCDVVQEQVNYVPLRASSCVTRCNIGGAVCSKHANLYQKYV
EAYNTFTQAGFNIWVPHSFDVYNLWQIFIETNLQSLENIAFNVVKKGCFTGVDGELPVAV
VNDKVFVRYGDVDNLVFTNKTTLPTNVAFELFAKRKMGLTPPLSILKNLGVVATYKFVLW
DYEAERPFTSYTKSVCKYTDFNEDVCVCFDNSIQGSYERFTLTTNAVLFSTVVIKNLTPI
KLNFGMLNGMPVSSIKGDKGVEKLVNWYIYVRKNGQFQDHYDGFYTQGRNLSDFTPRSDM
EYDFLNMDMGVFINKYGLEDFNFEHVVYGDVSKTTLGGLHLLISQFRLSKMGVLKADDFV
TASDTTLRCCTVTYLNELSSKVVCTYMDLLLDDFVTILKSLDLGVISKVHEVIIDNKPYR
WMLWCKDNHLSTFYPQLQSAEWKCGYAMPQIYKLQRMCLEPCNLYNYGAGIKLPSGIMLN

Fig. 21C

VVKYTQLCQYLNSTTMCVPHNMRVLHYGAGSDKGVAPGTTVLKRWLPPDAIIIDNDINDY
VSDADFSITGDCATVYLEDKFDLLISDMYDGRIKFCDGENVSKDGFFTYLNGVIREKLAI
GGSVAIKITEYSWNKYLYELIQRFAFWTLFCTSVNTSSSEAFLIGINYLGDFIQGPFIAG
NTVHANYIFWRNSTIMSLSYNSVLDLSKFECKHKATVVVTLKDSDVNDMVLSLIKSGRLL
LRNNGRFGGFSNHLVSTK

Like the ORF 1a gene product, this polyprotein is proteolytically cleaved at sites corresponding to the consensus LQ?(S, G or A)[1] by action of the $3CI^{pro}$ protease. Potential proteolytic cleavage sites are indicated in bold print in grey background. The $3CI^{pro}$-encoding domain is boldly underlined and is also shown as separate protein below. The remaining proteolysis products perform functions in the replication and processing of the viral RNA. Normal blast searches are not sensitive enough to detect this kind of dispersed homology. However, using PFAM (Protein Family) domains tentative functions can be attributed to the proteolysis products.

MFYNQVTLAVASDSEISGFGFAIPSVAVRTYSEAAAQGFQACRFVAFGLQDCVTGINDDDYVIALTGT
NQLCAKILPFSDRPLNLRGWLIFSNSNYVLQDFDVVFGHGAGSVVFVDKYMCGFDGKPVLPKNMWEFR
DYFNNNTDSIVIGGVTYQLAWDVIRKDLSYEQQNVLAIESIHYLGTTGHTLKSGCKLTNAKPPKYSSK
VVLSGEWNAVYRAFGSPFITNGMSLLDIIVKPVFFNAFVKCNCGSESWSVGAWDGYLSSCCGTPAKKL
CVVPGNVVPGDVIITSTSAGCGVKYYAGLVVKHITNITGVSLWRVTAVHSDGMFVASSSYDALLHRNS
LDPFCFDVNTLLSNQLRLAFLGASVTEDVKFAASTGVIDISAGMFGLYDDILTNNKPWFVRKASGLFD
AIWDAFVAAIKLVPTTTGVLVRFVKSIASTVLTVSNGVIIMCADVPDAFQSVYRTFTQAICAAFDFSL
DVFKIGDVKFKRLGDYVLTENALVRLTTEVVRGVRDARIKKAMFTKVVVGPTTEVKFSVIELATVNLR
LVDCAPVVCPKGKIVVIAGQAFFYSGGFYRFMVDPTTVLNDPVFTGDLFYTIKFSGFKLDGFNHQFVT
ASSATDAIIAVELLLLDFKTAVFVYTCVVDGCSVIVRRDATFATHVCFKDCYNVWEQFCIDNCGEPWF
LTDYNAILQSNNPQCAIVQASESKVLLERFLPKCPEILLSIDDGHLWNLFVEKFNFVTDWLKTLKLTL
TSNGLLGNCAKRFRRVLVKLLDVYNGFLETVCSVAYTAGVCIKYYAVNVPYVVISGFVSRVIRRERCD
MTFPCVSCVTFFYEFLDTCFGVSKPNAIDVEHLELKETVFVEPKDGGQFFVSGDYLWYVVDDIYYPAS
CNGVLPVAFTKLAGGKISFSDDVIVHDVEPTHKVKLIFEFEDDVVTSLCKKSFGKSIIYTGDWEGLHE
VLTSAMNVIGQHIKLPQFYIYDEEGGYDVSKPVMISQWPISNDSNGCVVEASTDFHQLECIVDDSVRE
EVDIIEQPFEEVEHVLSIKQPFSFSFRDELGVRVLDQSDNNCWISTTLVQLQLTKLLDDSIEMQLFKV
GKVDSIVQKCYELSHLISGSLGDSGKLLSELLKEKYTCSITFEMSCDCGKKFDDQVGCLFWIMPYTKL
FQKGECCICHKMQTYKLVSMKGTGVFVQDPAPIDIDAFPVKPICSSVYLGVKGSGHYQTNLYSFNKAI
DGFGVFDIKNSSVNTVCFVDVDFHSVEIEAGEVKPFAVYKNVKFYLGDISHLVNCVSFDFVVNAANEN
LLHGGGVARAIDILTEGQLQSLSKDYISSNGPLKVGAGVMLECEKFNVFNVVGPRTGKHEHSLLVEAY
NSILFENGIPLMPLLSCGIFGVRIENSLKALFSCDINKPLQVFVYSSNEEQAVLKFLDGLDLTPVIDD
VDVVKPFRVEGNFSFFDCGVNALDGDIYLLFTNSILMLDKQGQLLDTKLNGILQQAALDYLATVKTVP
AGNLVKLFVESCTIYMCVVPSINDLSFDKNLGRCVRKLNRLKTCVIANVPAIDVLKKLLSSLTLTVKF
VVESNVMDVNDCFKNDNVVLKITEDGINVKDVVVESSKSLGKQLGVVSDGVDSFEGVLPINTDTVLSV
APEVDWVAFYGFEKAALFASLDVKPYGYPNDFVGGFRVLGTTDNNCWVNATCIILQYLKPTFKSKGLN
VLWNKFVTGDVGPFVSFIYFITMSSKGQKGDAEEALSKLSEYLISDSIVTLEQYSTCDICKSTVVEVK
SAIVCASVLKDGCDVGFCPHRHKLRSRVKFVNGRVVITNVGEPIISQPSKLLNGIAYTTFSGSFDNGH
YVVYDAANNAVYDGARLFSSDLSTLAVTAIVVVGGCVTSNVPTIVSEKISVMDKLDTGAQKFFQFGDF
VMNNIVLFLTWLLSMFSLLRTSIMKHDIKVIAKAPKRTGVILTRSFKYNIRSALFVIKQKWCVIVTLF
KFLLLLYAIYALVFMIVQFSPFNSLLCGDIVSGYEKSTFNKDIYCGNSMVCKMCLFSYQEFNDLDHTS
LVWKHIRDPILISLQPFVILVILLIFGNMYLRFGLLYFVAQFISTFGSFLGFHQKQWFLHFVPFDVLC
NEFLATFIVCKIVLFVRHIIVGCNNADCVACSKSARLKRVPLQTIINGMHKSFYVNANGGTCFCNKHN
FFCVNCDSFGPGNTFINGDIARELGNVVKTAVQPTAPAYVIIDKVDFVNGFYRLYSGDTFWRYDFDIT
ESKYSCKEVLKNCNVLENFIVYNNSGSNITQIKNACVYFSQLLCEPIKLVNSELLSTLSVDFNGVLHK
AYVDVLCNSFFKELTANMSMAECKATLGLTVSDDDFVSAVANAHRYDVLLSDLSFNNFFISYAKPEDK
LSVYDIACCMRAGSKVVNHNVLIKESIPIVWGVKDFNTLSQEGKKYLVKTTKAKGLTFLLTFNDNQAI
TQVPATSIVAKQGAGFKRTYNFLWYVCLFVVALFIGVSFIDYTTTVTSFHGYDFKYIENGQLKVFEAP
LHCVRNVFDNFNQWHEAKFGVVTTNSDKCPIVVGVSERINVVPGVPTNVYLVGKTLVFTLQAAFGNTG
VCYDFDGVTTSDKCIFNSACTRLEGLGGDNVYCYNTDLIEGSKPYSTLQPNAYYKYDAKNYVRFPEIL
ARGFGLRTIRTLATRYCRVGECRDSHKGVCFGFDKWYVNDGRVDDGYICGDGLIDLLVNVLSIFSSSF
SVVAMSGHMLFNFLFAAFITFLCFLVTKFKRVFGDLSYGVFTVVCATLINNISYVVTQNLFFMLLYAI

Fig. 21D

LYFVFTRTVRYAWIWHIAYIVAYFLLIPWWLLTWFSFAAFLELLPNVFKLKISTQLFEGDKFIGTFES
AAAGTFVLDMRSYERLINTISPEKLKNYAASYNKYKYYSGSASEADYRCACYAHLAKAMLDYAKDHND
MLYSPPTISYNSTLQSGLKKMAQPSGCVERCVVRVCYGSTVLNGVWLGDTVTCPRHVIAPSTTVLIDY
DHAYSTMRLHNFSVSHNGVFLGVVGVTMHGSVLRIKVSQSNVHTPKHVFKTLKPGDSFNILACYEGIA
SGVFGVNLRTNFTIKGSFINGACGSPGYNVRNDGTVEFCYLHQIELGSGAHVGSDFTGSVYGNFDDQP
SLQVESANLMLSDNVVAFLYAALLNGCRWWLCSTRVNVDGFNEWAMANGYTSVSSVECYSILAAKTGV
SVEQLLASIQHLHEGFGGKNILGYSSLCDEFTLAEVVKQMYGVNLQSGKVIFGLKTMFLFSVFFTMFW
AELFIYTNTIWINPVILTPIFCLLLFLSLVLTMFLKHKFLFLQVFLLPTVIATALYNCVLDYYIVKFL
ADHFNYNVSVLQMDVQGLVNVLVCLFVVFLHTWRFSKERFTHWFTYVCSLIAVAYTYFYSGDFLSLLV
MFLCAISSDWYIGAIVFRLSRLIVFFSPESVFSVFGDVKLTLVVYLICGYLVCTYWGILYWFNRFFKC
TMGVYDFKVSAAEFKYMVANGLHAPHGPFDALWLSFKLLGIGGDRCIKISTVQSKLTDLKCTNVVLLG
CLSSMNIAANSSEWAYCVDLHNKINLCDDPEKAQSMLLALLAFFLSKHSDFGLDGLIDSYFDNSSTLQ
SVASSFVSMPSYIAYENARQAYEDAIANGSSSQLIKQLKRAMNIAKSEFDHEISVQKKINRMAEQAAT
QMYKEARSVNRKSKVISAMHSLLFGMLRRLDMSSVETVLNLARDGVVPLSVIPATSASKLTIVSPDLE
SYSKIVCDGSVHYAGVVWTLNDVKDNDGRPVHVKEITKENVETLTWPLILNCERVVKLQNNEIMPGKL
KQKPMKAEGDGGVLGDGNALYNTEGGKTFMYAYISNKADLKFVKWEYEGGCNTIELDSPCRFMVETPN
GPQVKYLYFVKNLNTLRRGAVLGFIGATIRLQAGKQTELAVNSGLLTACAFSVDPATTYLEAVKHGAK
PVSNCIKMLSNGAGNGQAITTSVDANTNQDSYGGASICLYCRAHVPHPSMDGYCKFKGKCVQVPIGCL
DPIRFCLENNVCNVCGCWLGHGCACDRTTIQSVDISYLNEQGVLVQLDRARGSSAARLEPCNGTDIDK
CVRAFDIYNKNVSFLGKCLKMNCVRFKNADLKDGYFVIKRCTKSVMEHEQSMYNLLNFSGALAEHDFF
TWKDGRVIYGNVSRHNLTKYTMMDLVYAMRNFDEQNCDVLKEVLVLTGCCDNSYFDSKGWYDPVENED
IHRVYASLGKIVARAMLKCVALCDAMVAKGVVGVLTLDNQDLNGNFYDFGDFVVSLPNMGVPCCTSYY
SYMMPIMGLTNCLASECFVKSDIFGSDFKTFDLLKYDFTEHKENLFNKYFKHWSFDYHPNCCDCYDDM
CVIHCANFNTLFATTIPGTAFGPLCRKVFIDGVPLVTTAGYHFKQLGLVWNKDVNTHSVRLTITELLQ
FVTDPSLIIASSPALVDQRTICFSVAALSTGLTNQVVKPGHFNEEFYNFLRLRGFFDEGSELTLKHFF
FAQNGDAAVKDFDFYRYNKPTILDICQARVTYKIVSRYFDIYEGGCIKACEVVVTNLNKSAGWPLNKF
GKASLYYESISYEEQDALFALTKRNVLPTMTQLNLKYAISGKERARTVGGVSLLSTMTTRQYHQKHLK
SIVNTRNATVVIGTTKFYGGWNNMLRTLIDGVENPMLMGWDYPKCDRALPNMIRMISAMVLGSKHVNC
CTATDRFYRLGNELAQVLTEVVYSNGGFYFKPGGTTSGDASTAYANSIFNIFQAVSSNINRLLSVPSD
SCNNVNVRDLQRRLYDNCYRLTSVEESFIEDYYGYLRKHFSMMILSDDGVVCYNKDYAELGYIADISA
FKATLYYQNNVFMSTSKCWVEEDLTKGPHEFCSQHTMQIVDKDGTYYLPYPDPSRILSAGVFVDDVVK
TDAVVLLERYVSLAIDAYPLSKHPNSEYRKVFYVLLDWVKHLNKNLNEGVLESFSVTLLDNQEDKFWC
EDFYASMYENSTILQAAGLCVVCGSQTVLRCGDCLRKPMLCTKCAYDHVFGTDHKFILAITPYVCNAS
GCGVSDVKKLYLGGLNYYCTNHKPQLSFPLCSAGNIFGLYKNSATGSLDVEVFNRLATSDWTDVRDYK
LANDVKDTLRLFAAETIKAKEESVKSSYAFATLKEVVGPKELLLSWESGKVKPPLNRNSVFTCFQISK
DSKFQIGEFIFEKVEYGSDTVTYKSTVTTKLVPGMIFVLTSHNVQPLRAPTIANQEKYSSIYKLHPAF
NVSDAYANLVPYYQLIGKQKITTIQGPPGSGKSHCSIGLGLYYPGARIVFVACAHAAVDSLCAKAMTV
YSIDKCTRIIPARARVECYSGFKPNNTSAQYIFSTVNALPECNADIVVVDEVSMCTNYDLSVINQRLS
YKHIVYVGDPQQLPAPRVMITKGVMEPVDYNVVTQRMCAIGPDVFLHKCYRCPAEIVIQFLNLFMRTS
LSLLNLLVNSVLKSFLRVMYKVDNGSSINRKQLEIVKLFLVKNPSWSKAVFISPYNSQNYVASRFLGL
QIQTVDSSQGSEYDYVIYAQTSDTAHACNVNRFNVAITRAKKGIFCVMCDKTLFDSLKFFEIKHADLH
SSQVCGLFKNCTRTPLNLPPTHAHTFLSLSDQFKTTGDLAVQIGSNNVCTYEHVISFMGFRFDISIPG
SHSLFCTRDFAIRNVRGWLGMDVESAHVCGDNIGTNVPLQVGFSNGVNFVVQTEGCVSTNFGDVIKPV
CAKSPPGEQFRHLIPLLRKGQPWLIVRRRIVQMISDYLSNLSDILVFVLWAGSLELTTMRYFVKIGPI
KYCYCGNFATCYNSVSNEYCCFKHALGCDYVYNPYAFDIQQWGYVGSLSQNHHTFCNIHRNEHDASGD
AVMTRCLAVHDCFVKNVDWTVTYPFIANEKFINGCGRNVQGHVVRAALKLYKPSVIHDIGNPKGVRCA
VTDAKWYCYDKQPVNSNVKLLDYDYATHGQLDGLCLFWNCNVDMYPEFSIVCRFDTRTRSVFNLEGVN
GGSLYVNKHAFHTPAYDKRAFVKLKPMPFFYFDDSDCDVVQEQVNYVPLRASSCVTRCNIGGAVCSKH
ANLYQKYVEAYNTFTQAGFNIWVPHSFDVYNLWQIFIETNLQSLENIAFNVVKKGCFTGVDGELPVAV
VNDKVFVRYGDVDNLVFTNKTTLPTNVAFELFAKRKMGLTPPLSILKNLGVVATYKFVLWDYEAERPF
TSYTKSVCKYTDFNEDVCVCFDNSIQGSYERFTLTTNAVLFSTVVIKNLTPIKLNFGMLNGMPVSSIK
GDKGVEKLVNWYIYVRKNGQFQDHYDGFYTQGRNLSDFTPRSDMEYDFLNMDMGVFINKYGLEDFNFE
HVVYGDVSKTTLGGLHLLISQFRLSKMGVLKADDFVTASDTTLRCCTVTYLNELSSKVVCTYMDLLLD
DFVTILKSLDLGVISKVHEVIIDNKPYRWMLWCKDNHLSTFYPQLQSAEWKCGYAMPQIYKLQRMCLE
PCNLYNYGAGIKLPSGIMLNVVKYTQLCQYLNSTTMCVPHNMRVLHYGAGSDKGVAPGTTVLKRWLPP
DAIIIDNDINDYVSDADFSITGDCATVYLEDKFDLLISDMYDGRIKFCDGENVSKDGFFTYLNGVIRE

Fig. 21 E

KLAIGGSVAIKITEYSWNKYLYELIQRFAFWTLFCTSVNTSSSEAFLIGINYLGDFIQGPFIAGNTVH
ANYIFWRNSTIMSLSYNSVLDLSKFECKHKATVVVTLKDSDVNDMVLSLIKSGRLLLRNNGRFGGFSN
HLVSTK

Fig. 21 F

Annotated putative proteolytic cleavage products ORF 1ab

Adenosine diphosphate-ribose 1'- phosphatase

SNNPQCAIVQASESKVLLERFLPKCPEILLSIDDGHLWNLFVEKFNFVTDWLKTLKLTLTSNGLLGNC
AKRFRRVLVKLLDVYNGFLETVCSVAYTAGVCIKYYAVNVPYVVISGFVSRVIRRERCDMTFPCVSCV
TFFYEFLDTCFGVSKPNAIDVEHLELKETVFVEPKDGGQFFVSGDYLWYVVDDIYYPASCNGVLPVAF
TKLAGGKISFSDDVIVHDVEPTHKVKLIFEFEDDVVTSLCKKSFGKSIIYTGDWEGLHEVLTSAMNVI
GQHIKLPQFYIYDEEGGYDVSKPVMISQWPISNDSNGCVVEASTDFHQLECIVDDSVREEVDIIEQPF
EEVEHVLSIKQPFSFSFRDELGVRVLDQSDNNCWISTTLVQLQLTKLLDDSIEMQLFKVGKVDSIVQK
CYELSHLISGSLGDSGKLLSELLKEKYTCSITFEMSCDCGKKFDDQVGCLFWIMPYTKLFQKGECCIC
HKMQTYKLVSMKGTGVFVQDPAPIDIDAFPVKPICSSVYLGVKGSGHYQTNLYSFNKAIDGFGVFDIK
NSSVNTVCFVDVDFHSVEIEAGEVKPFAVYKNVKFYLGDISHLVNCVSFDFVVNAANENLLHGGGVAR
AIDILTEGQLQSLSKDYISSNGPLKVGAGVMLECEKFNVFNVVGPRTGKHEHSLLVEAYNSILFENGI
PLMPLLSCGIFGVRIENSLKALFSCDINKPLQVFVYSSNEEQAVLKFLDGLDLTPVIDDVDVVKPFRV
EGNFSFFDCGVNALDGDIYLLFTNSILMLDKQGQLLDTKLNGILQQAALDYLATVKTVPAGNLVKLFV
ESCTIYMCVVPSINDLSFDKNLGRCVRKLNRLKTCVIANVPAIDVLKKLLSSLTLTVKFVVESNVMDV
NDCFKNDNVVLKITEDGINVKDVVVESSKSLGKQLGVVSDGVDSFEGVLPINTDTVLSVAPEVDWVAF
YGFEKAALFASLDVKPYGYPNDFVGGFRVLGTTDNNCWVNATCIILQYLKPTFKSKGLNVLWNKFVTG
DVGPFVSFIYFITMSSKGQKGDAEEALSKLSEYLISDSIVTLEQYSTCDICKSTVVEVKSAIVCASVL
KDGCDVGFCPHRHKLRSRVKFVNGRVVITNVGEPIISQPSKLLNGIAYTTFSGSFDNGHYVVYDAANN
AVYDGARLFSSDLSTLAVTAIVVVGGCVTSNVPTIVSEKISVMDKLDTGAQKFFQFGDFVMNNIVLFL
TWLLSMFSLLRTSIMKHDIKVIAKAPKRTGVILTRSFKYNIRSALFVIKQKWCVIVTLFKFLLLLYAI
YALVFMIVQFSPFNSLLCGDIVSGYEKSTFNKDIYCGNSMVCKMCLFSYQEFNDLDHTSLVWKHIRDP
ILISLQPFVILVILLIFGNMYLRFGLLYFVAQFISTFGSFLGFHQKQWFLHFVPFDVLCNEFLATFIV
CKIVLFVRHIIVGCNNADCVACSKSARLKRVPLQTIINGMHKSFYVNANGGTCFCNKHNFFCVNCDSF
GPGNTFINGDIARELGNVVKTAVQPTAPAYVIIDKVDFVNGFYRLYSGDTFWRYDFDITESKYSCKEV
LKNCNVLENFIVYNNSGSNITQIKNACVYFSQLLCEPIKLVNSELLSTLSVDFNGVLHKAYVDVLCNS
FFKELTANMSMAECKATLGLTVSDDDFVSAVANAHRYDVLLSDLSFNNFFISYAKPEDKLSVYDIACC
MRAGSKVVNHNVLIKESIPIVWGVKDFNTLSQEGKKYLVKTTKAKGLTFLLTFNDNQAITQVPATSIV
AKQGAGFKRTYNFLWYVCLFVVALFIGVSFIDYTTTVTSFHGYDFKYIENGQLKVFEAPLHCVRNVFD
NFNQWHEAKFGVVTTNSDKCPIVVGVSERINVVPGVPTNVYLVGKTLVFTLQAAFGNTGVCYDFDGVT
TSDKCIFNSACTRLEGLGGDNVYCYNTDLIEGSKPYSTLQPNAYYKYDAKNYVRFPEILARGFGLRTI
RTLATRYCRVGECRDSHKGVCFGFDKWYVNDGRVDDGYICGDGLIDLLVNVLSIFSSSFSVVAMSGHM
LFNFLFAAFITFLCFLVTKFKRVFGDLSYGVFTVVCATLINNISYVVTQNLFFMLLYAILYFVFTRTV
RYAWIWHIAYIVAYFLLIPWWLLTWFSFAAFLELLPNVFKLKISTQLFEGDKFIGTFESAAAGTFVLD
MRSYERLINTISPEKLKNYAASYNKYKYYSGSASEADYRCACYAHLAKAMLDYAKDHNDMLYSPPTIS
YNSTLQ

3CI^pro Coronavirus polyprotein processing endoprotease

SGLKKMAQPSGCVERCVVRVCYGSTVLNGVWLGDTVTCPRHVIAPSTTVLIDYDHAYSTMRLHNFSVS
HNGVFLGVVGVTMHGSVLRIKVSQSNVHTPKHVFKTLKPGDSFNILACYEGIASGVFGVNLRTNFTIK
GSFINGACGSPGYNVRNDGTVEFCYLHQIELGSGAHVGSDFTGSVYGNFDDQPSLQVESANLMLSDNV
VAFLYAALLNGCRWWLCSTRVNVDGFNEWAMANGYTSVSSVECYSILAAKTGVSVEQLLASIQHLHEG
FGGKNILGYSSLCDEFTLAEVVKQMYGVNLQ

RNA dependant RNA polymerase (pfam00680)

AGKQTELAVNSGLLTACAFSVDPATTYLEAVKHGAKPVSNCIKMLSNGAGNGQAITTSVDANTNQDSY
GGASICLYCRAHVPHPSMDGYCKFKGKCVQVPIGCLDPIRFCLENNVCNVCGCWLGHGCACDRTTIQS
VDISYLNEQGVLVQLDRARGSSAARLEPCNGTDIDKCVRAFDIYNKNVSFLGKCLKMNCVRFKNADLK
DGYFVIKRCTKSVMEHEQSMYNLLNFSGALAEHDFFTWKDGRVIYGNVSRHNLTKYTMMDLVYAMRNF
DEQNCDVLKEVLVLTGCCDNSYFDSKGWYDPVENEDIHRVYASLGKIVARAMLKCVALCDAMVAKGVV
GVLTLDNQDLNGNFYDFGDFVVSLPNMGVPCCTSYYSYMMPIMGLTNCLASECFVKSDIFGSDFKTFD
LLKYDFTEHKENLFNKYFKHWSFDYHPNCCDCYDDMCVIHCANFNTLFATTIPGTAFGPLCRKVFIDG
VPLVTTAGYHFKQLGLVWNKDVNTHSVRLTITELLQFVTDPSLIIASSPALVDQRTICFSVAALSTGL

Fig. 21G

TNQVVKPGHFNEEFYNFLRLRGFFDEGSELTLKHFFFAQNGDAAVKDFDFYRYNKPTILDICQARVTY
KIVSRYFDIYEGGCIKACEVVVTNLNKSAGWPLNKFGKASLYYESISYEEQDALFALTKRNVLPTMTQ
LNLKYAISGKERARTVGGVSLLSTMTTRQYHQKHLKSIVNTRNATVVIGTTKFYGGWNNMLRTLIDGV
ENPMLMGWDYPKCDRALPNMIRMISAMVLGSKHVNCCTATDRFYRLGNELAQVLTEVVYSNGGFYFKP
GGTTSGDASTAYANSIFNIFQAVSSNINRLLSVPSDSCNNVNVRDLQRRLYDNCYRLTSVEESFIEDY
YGYLRKHFSMMILSDDGVVCYNKDYAELGYIADISAFKATLYYQNNVFMSTSKCWVEEDLTKGPHEFC
SQHTMQIVDKDGTYYLPYPDPSRILSAGVFVDDVVKTDAVVLLERYVSLAIDAYPLSKHPNSEYRKVF
YVLLDWVKHLNKNLNEGVLESFSVTLLDNQEDKFWCEDFYASMYENSTILQ

ExoN 3'to 5' Exonuclease and helicase

The bold underlined amino acid residues are conserved in orthologous cellular and viral enzymes.

AAGLCVVCGSQTVLRCGDCLRKPMLCTKCAYDHVFGTDHKFILAITPYVCNASGCGVSDVKKLYLGGL
NYYCTNHKPQLSFPLCSAGNIFGLYKNSATGSLDVEVFNRLATSDWTDVRDYKLANDVKDTLRLFAAE
TIKAKEESVKSSYAFATLKEVVGPKELLLSWESGKVKPPLNRNSVFTCFQISKDSKFQIGEFIFEKVE
YGSDTVTYKSTVTTKLVPGMIFVLTSHNVQPLRAPTIANQEKYSSIYKLHPAFNVSDAYANLVPYYQL
IGKQKITTIQGPPGSGKSHCSIGLGLYYPGARIVFVACAHAAVDSLCAKAMTVYSIDKCTRIIPARAR
VECYSGFKPNNTSAQYIFSTVNALPECNADIVVVDEVSMCTNYDLSVINQRLSYKHIVYVGDPQQLPA
PRVMITKGVMEPVDYNVVTQRMCAIGPDVFLHKCYRCPAEIVIQFLNLFMRTSLSLLNLLVNSVLKSF
LRVMYKVDNGSSINRKQLEIVKLFLVKNPSWSKAVFISPYNSQNYVASRFLGLQIQTVDSSQGSEYDY
VIYAQTSDTAHACNVNRFNVAITRAKKGIFCVMCDKTLFDSLKFFEIKHADLHSSQVCGLFKNCTRTP
LNLPPTHAHTFLSLSDQFKTTGDLAVQIGSNNVCTYEHVISFMGFRFDISIPGSHSLFCTRDFAIRNV
RGWLGMDVESAHVCGDNIGTNVPLQVGFSNGVNFVVQTEGCVSTNFGDVIKPVCAKSPPGEQFRHLIP
LLRKGQPWLIVRRRIVQMISDYLSNLSDILVFVLWAGSLELTTMRYFVKIGPIKYCYCGNFATCYNSV
SNEYCCFKHALGCDYVYNPYAFDIQQWGYVGSLSQNHHTFCNIHRNEHDASGDAVMTRCLA**VHDCFVK
NVDWTVTYPFIANEKFINGCGRNVQGHVVRAALKLYKPSVIHDIGNPKGVRCAVTDAKWYCYDKQPVN
SNVKLLDYDYATHGQLDGLCLFWNCNVDMYPEFSIVCRFDTRTRSVFNLEGVNGGSLYVNKHAFHTPA
YDKRAFVKLKPMPFFYFDDSDCDVVQEQVNYVPLRASSCVTRCNIGGAVCSKHANLYQKYVEAYNTFT
QAGFNIWVPHSFDVYNLWQIFIETNLQ

XendoU (homolog of) polyU-specific endoribonuclease

SLENIAFNVVKKGCFTGVDGELPVAVVNDKVFVRYGDVDNLVFTNKTTLPTNVAFELFAKRKMGLTPP
LSILKNLGVVATYKFVLWDYEAERPFTSYTKSVCKYTDFNEDVCVCFDNSIQGSYERFTLTTNAVLFS
TVVIKNLTPIKLNFGMLNGMPVSSIKGDKGVEKLVNWYIYVRKNGQFQDHYDGFYTQGRNLSDFTPRS
DMEYDFLNMDMGVFINKYGLEDFNFEHVVYGDVSKTTLGGLHLLISQFRLSKMGVLKADDFVTASDTT
LRCCTVTYLNELSSKVVCTYMDLLLDDFVTILKSLDLGVISKVHEVIIDNKPYRWMLWCKDNHLSTFY
PQLQ

2'-O-MT 2: S-adenosylmethionine-dependant ribose 2'-orthomethyltransferase

Plays a role in the methylation of cap structure (GpppNm) at the 5'end of the viral RNA. Antiviral compounds inhibiting this transfer of methyl groups to reaction (carboxylic adenosine analogs *e.g.* Neoplanocin A and 3-deazaneoplancin A) interfere with expression of viral proteins. Again the underlined residues in bold print are conserved

SAEWKCGYAMPQIYKLQRMCLEPCNLYNYGAGIKLPSGIMLNVVKYTQLCQYLNSTTMCVPHNMRVLH
YGAGSDKGVAPGTTVLKRWLPPDAIIIDNDINDYVSDADFSITGDCATVYLEDKFDLLISDMYDGRIK
FCDGENVSKDGFFTYLNGVIREKLAIGGSVAIKITEYSWNKYLYELIQRFAFWTLFCTSVNTSSSEAF
LIGINYLGDFIQGPFIAGNTVHANYIFWRNSTIMSLSYNSVLDLSKFECKHKATVVVTLKDSDVNDMV
LSLIKSGRLLLRNNGRFGGFSNHLVSTK

CORONAVIRUS, NUCLEIC ACID, PROTEIN, AND METHODS FOR THE GENERATION OF VACCINE, MEDICAMENTS AND DIAGNOSTICS

The invention relates to the fields of virology and medicine. More in particular the invention relates to the identification of a new coronavirus and to means and methods associated with a virus such as means and methods for typing the virus in various samples and diagnosing of disease, means and methods for developing vaccines and medicaments for the treatment of infected subjects or of subjects at risk thereof.

Coronaviruses, a genus in the family of Coronaviridae, are large enveloped plus strand RNA viruses. The genomic RNA is 27 to 32 kb in size, capped and polyadenylated. Three serologically distinct groups of coronaviruses have been identified. Within each group, viruses are identified by hosts range and genome sequence. Coronaviruses have been identified in mice, rats, chickens, turkeys, swine, dogs, cats, rabbits, horses, cattle and humans (39, 40). Most coronaviruses infect only one host species and can cause severe disease including gastroenteritis, and respiratory tract diseases. In humans, 3 coronaviruses have been studied in detail. HCoV-229E and HCoV-OC43 have been identified in the mid sixties and are known to cause common cold (13-17, 19, 41, 42). Besides common cold it has been suggested that the HCoV-229E may cause a more serious disease in infants as HCoV-229E virus has been isolated from infants suffering from lower respiratory tract disease(28). The third and most recently identified coronavirus: SARS-CoV, is, with its ability to cause a life threatening pneumonia (43), the most pathogenic human coronavirus identified thus far. It has been suggested that SARS-CoV is the first member of a fourth group of coronaviruses, or that the virus is an outlier of the group 2 coronaviruses (27, 44).

The genome of coronaviruses encodes four structural proteins: the spike protein, the membrane protein, the envelope protein and the nucleocapsid protein. Several non-structural proteins are involved in replication and transcription, which are encoded by two long overlapping open reading frames (ORFs) at the 5' end of the genome (1A and 1B). These 2 ORFs are connected via a ribosomal frame shift. The polypeptides encoded by ORF 1A and 1B are post-translationally processed by viral encoded proteases. Furthermore, additional non-structural proteins are encoded between the S and E gene, or between the M and N gene or downstream of the N gene. Some of these "accessory non-structural protein genes" have been found to be not essential for virus reproduction(45, 46). The coronavirus gene products of 1A and 1B are translated from the genomic RNA but the remaining viral proteins are translated from subgenomic mRNAs (sg mRNA), each with a 5' end derived from the 5' part of the genome. The sg mRNA are derived via a discontinuous transcription process that most probably occurs during negative strand synthesis (47). Discontinuous transcription requires base-pairing between cis-acting elements, the transcription associated sequences (TRSs), one located at the 5' part of the genome (the leader TRS) and others located upstream of the ORFs (the body TRSs)(48)).

The novel coronavirus that we present here was isolated from a child suffering from bronchiolitis. Infection by this virus was not an isolated case since we found 7 more persons suffering from respiratory tract disease carrying the virus. In addition, we show here the complete genome sequence providing critical information concerning the genome structure of the new coronavirus.

To date there is a range of human diseases with unknown etiology. For many of these a viral origin has been suggested, emphasizing the importance of a continuous search for new viruses[22, 23, 24]. Major difficulties are encountered when searching for new viruses. First, some viruses do not replicate in vitro, at least not in the cells that are commonly used in viral diagnostics. Second, for those viruses that do replicate in vitro and that cause a cytopathic effect (CPE), the subsequent virus-identification methods may fail. Antibodies raised against known viruses may not recognize the cultured virus and virus specific PCR methods may not amplify the new viral genome. We have developed a method for virus discovery based on the cDNA amplified restriction fragment length polymorphism technique (cDNA-AFLP). With this technique, RNA or DNA is reproducibly amplified. There is no need to have prior knowledge of the sequence of the target gene[1]. Generally the cDNA-AFLP method is used to monitor differential gene expression, however, we modified this method such that it can amplify viral sequences either directly from patient blood-plasma/serum samples or indirectly from CPE-positive virus culture (FIG. 1). In the modified Virus-Discovery-cDNA-AFLP (VIDISCA) method the mRNA isolation step prior to amplification is replaced by a treatment to selectively enrich for viral nucleic acid. Of relevance to the purification is a centrifugation step to remove residual cells and mitochondria. In addition, a DNAse treatment can be used to remove interfering chromosomal and mitochondrial DNA from degraded cells whereas viral nucleic acid is protected within the viral particle. Finally, by choosing frequently cutting restriction enzymes, the method can be fine-tuned such that most viruses will be amplified.

In January 2003 a 7-month-old child appeared in the hospital with coryza, conjunctivitis and fever. Chest radiography showed typical features of bronchiolitis and a nasopharyngeal aspirate specimen was collected (sample nr: NL63) five days after the onset of disease. All diagnostic tests on this sample for respiratory syncytial virus (RSV), adenovirus, influenza A and B virus, parainfluenza virus type 1, 2 and 3, rhinovirus, enterovirus, HCoV-229E and HCoV-OC43 were negative. Immunofluorescent assays to detect RSV, adenovirus, influenza A and B virus, and parainfluenza virus type 1, 2 and 3 in cultures of the virus remained negative. Acid lability and chloroform sensitivity tests demonstrated that the virus was most likely enveloped and not a member of the Picornavirus group. In fact it was a new coronavirus.

In the present invention we present a detailed description of a novel human coronavirus. Coronaviruses are characterized by a very long non-segmented, single-stranded, (+) sense RNA of approximately 27-31 kb. This is the longest genome of any known RNA virus. The genome has a 5' methylated cap and 3' poly-A and functions directly as mRNA. Thus far only 3 human coronaviruses have been characterized, therefore sorting out the characteristics of a fourth human coronavirus supplies attractive information on the variation among the human coronaviruses. The novel virus is a member of the group 1 coronaviruses and is most related to HCoV-229E, yet the differences are prominent. The similarity is not larger than 85% at the nucleotide level, at the position of the 4A and 4B gene of HCoV-229E only one ORF is present in HCoV-NL63 (ORF 3), and the 5' region of the S gene of HCoV-NL63 contains a unique in frame insertion of 537 nucleotides. Since binding of the receptor has been mapped to the N-terminal part of the protein, the 179 amino acids encoded by the insertion are most likely involved in receptor binding. This unique part at the N-terminus of the spike protein might explain the expanded host range of the virus in cell culture. Where HCoV-229E is fastidious in cell culture with a narrow host range, HCoV-NL63 replicates efficiently in monkey kidney cells. Besides HCoV-NL63 also SARS-CoV is able to replicate in monkey kidney cells (Vero-E6 cells and NCI-H292 cells for SARS-CoV (21)). Yet, comparing the predicted Spike genes did not identify a protein region that is shared by both viruses to clarify the common host range of the viruses in vitro. Also the insertion in the S gene of HCoV-NL63 was not present in the SARS S gene. Alternatively, other viral proteins may be involved in the cell tropism of a virus, however we did not identify any gene of HCoV-NL63 that had more similarity at the protein level to the SARS-CoV than to the similarity to HCoV-229E.

The 2 major differences between HCoV-229E and HCoV-NL63: the insertion in the S gene and the altered non-structural accessory proteins genes, are comparably to the differences that are noted between the porcine coronaviruses PRCoV and TGEV. Although these 2 porcine viruses are antigenically and genetically related their pathogenicity is very different. TGEV causes severe diarrhea with a high mortality in neonatal swine. It replicates and destroys the enterocytes in the small intestine whereas PRCoV has a selective tropism for respiratory tissue with very little to no replication in intestinal tissue. The genome differences in the S, 3A and 3B genes between TGEV and PRCoV are comparable with the differences between HCoV-NL63 and HCoV-229E. Alike HCoV-NL63, TGEV has a unique in frame insertion at the 5' part of the S gene ranging from 672 to 681nt (53). Furthermore, the accessory protein genes 3A and 3B that are intact in TGEV, are often mutated or inactive in the PRCoV. Extrapolating these data to the human coronaviruses one can speculate that HCoV-NL63 might be a more pathogenic human virus in comparison with HCoV-229E. However there are no epidemiological data supporting this. Based on our data it seems likely that HCoV-NL63 and HCoV-229E share the same pathogenicity. The common cold virus HCoV-229E can cause a more serious disease in infants (28), comparable to our data that suggest that HCoV-NL63 is causing a respiratory disease only in infants and immuno-compromised patients.

To date, a viral pathogen cannot be identified in a substantial portion of respiratory disease cases in humans (on average 20%[59]), our data indicate that in a part of these cases HCoV-NL63 is involved. The frequency with which HCoV-NL63 was detected in patients suffering from respiratory disease was up to 5% in January 2003. The virus was not detected in any of the samples collected in the spring or summer of 2003, which is in harmony with the epidemiology of human coronaviruses that have a tendency to spread predominantly in the winter season (15). The primers for our diagnostic PCR were located in the 1B gene and the genomic RNA can be used as template. Using primers that anneal in the nucleocapsid gene or 3'UTR supplies more template in the PCR because besides the genomic RNA also all sg mRNA in infected cells are template for amplification. It might be that the number of persons that we found positive for HCoV-NL63 is an under-estimation of the correct number of persons carrying HCoV-NL63.

The newly found coronavirus, (designated HCoV-NL63) was characterized and sequenced. A sequence of a prototype HCoV-NL63 is provided in FIG. 19 and parts thereof in table 3. In one aspect the invention therefore provides an isolated and/or recombinant nucleic acid comprising a sequence as depicted in FIG. 19 and/or table 3, or a functional part, derivative and/or analogue thereof. The virus HCoV-NL63 is characterized by the prototype, however, many natural variants exist as for instance shown in FIG. 16 for polymorphisms in the ORF 1a region. The existence of such natural variants is normal for RNA viruses that undergo frequent mutation through for instance the introduction of mistakes by the polymerases that copy the genome. HCoV-NL63 viruses that have a slightly divergent nucleic acid sequence are thus also provided by the present invention. Such viruses are considered to be a derivative of the nucleic acid having the prototype nucleic acid sequence. The variant does not necessarily have to be a natural variant. It is very well possible to generate variants through recombinant means. For instance many parts of the virus can be altered through nucleotide substitution to make use of the redundancy in the triplet genetic code for particular amino acids. Thus without altering the amino acid sequence of the encoded proteins. However, even amino acid alterations can typically be introduced without affecting the replicating and coding potential of the viruses. For instance conservative amino acid substitutions are often tolerated. Alterations in the prototype virus may be up to 70% of the nucleic acid sequence without altering the replicating potential of the virus. Thus in one embodiment the invention provides an isolated and/or recombinant nucleic acid that is at least 70% homologous to a nucleic acid of the prototype HCoV-NL63. Most of the viable variants however are at least 95% homologous and more preferably at least 99% to a nucleic acid according to the prototype HCoV-NL63. The homology between different coronaviruses in the UTR regions is typically high, for this reason the homology in this application is measured in a region outside the UTR regions, preferably in a protein coding region. Thus the invention provides a derivative of HCoV-NL63 virus comprising at least 95% homology and preferably at least 99% homology (on the nucleic acid level) in at least one protein coding region depicted FIG. 20, 21, 22, 23, or table 3. The nucleic acid of the virus or parts thereof can be cloned and used as a probe to detect the virus in samples. Thus the present invention further provides an isolated and/or recombinant nucleic acid comprising a stretch of 100 consecutive nucleotides of a nucleic acid of the prototype virus, or a region that is at least 95% and preferably at least 99% homologous to said 100 consecutive nucleotides (when measured on the nucleic acid level outside a UTR region). A stretch of 100 consecutive nucleotides is considered to be a functional part of the virus of the present invention. Further provided is a bacterial vector comprising a nucleic acid of HCoV-NL63 or a functional part, derivative and/or analogue thereof. Further provided is a bacterium comprising said bacterial vector. The sequence of HCoV-NL63 or a part thereof can be used to generate a primer that is specific for HCoV-NL63 and thus capable of specifically replicating HCoV-NL63 nucleic acid. Similarly, a probe can be generated that specifically hybridizes to HCoV-NL63 nucleic acid under stringent conditions. Thus the invention further provides a primer and/or probe, capable of specifically hybridizing to a nucleic acid of a HCoV-NL63 virus or functional part, derivative or analogue thereof. Preferably, said primer or probe is capable of hybridizing to said nucleic acid under stringent conditions. In a particularly preferred embodiment said primer and/or probe comprises a sequence as depicted in table 3, table 7, table 10 or FIGS. 16 to 18.

The nucleic acid of the prototype virus encodes various proteins and polyproteins. These proteins are expressed for instance in cells producing the virus or transformed with a nucleic acid encoding the (poly)protein. The invention thus further provides an isolated and/or recombinant proteinaceous molecule comprising a sequence as depicted in FIG. 20, 21, 22, 23 or table 3, or a functional part, derivative and/or analogue thereof. Many different variants of the proteins having the same function in kind, not necessarily in amount are, as mentioned above, present in nature and can be generated artificially, thus the invention further provides an isolated and/or recombinant proteinaceous molecule that is at least 70% homologues to a proteinaceous molecule mentioned above. Such homologous proteins are considered derivatives of a protein encoded by the prototype. Preferably, a derivative protein comprises at least 95% and more preferably at least 99% homology with a protein encoded by the prototype HCoV-NL63. Fragments and parts of a proteinaceous molecule encoded by the prototype virus can be generated, such parts are therefore also provided by the present invention. In a preferred embodiment is provided an isolated and/or recombinant proteinaceous molecule comprising a stretch of at least 30 consecutive amino acids of a proteinaceous molecule encoded by the prototype virus. A protein encoded by the prototype virus can be encoded through a variety of different nucleic acid sequences using the redundancy of the genetic code. Thus the invention further provides a nucleic acid encoding a protein depicted in FIG. 20, 21, 22, 23 or table 3. The HCoV-NL63 virus can be replicated using in vitro growing cell lines. The virus can be harvested from such cultures and used in a variety of different application including but not limited to the generation of an immune response in a subject. The invention thus further provides an isolated or recombinant virus comprising a HCoV-NL63 nucleic acid sequence or a functional part, derivative and/or analogue thereof. Also provided is an isolated or recombinant virus comprising a proteinaceous molecule as depicted in FIG. 20, 21, 22, 23 or table 3, or a functional part, derivative and/or analogue thereof. Subjects that have become infected with HCoV-NL63 can display a number of different clinical and/or subclinical symptoms. Thus further provided is an isolated or recombinant virus or a functional part, derivative or analogue thereof capable of inducing a HCoV-NL63-related disease.

The virus comprises substances that can be used to generate specific binding partners that are able to specifically bind the substance of the virus. Binding partners can be generated by means of injection of the virus into in an immuno-competent subject. As a result of the immunization the serum obtained from the subject will typically contain a number of different antibodies specific for the virus or an immunogenic part, derivative and/or analogue thereof. Specific binding partners can of course be generated through a large variety of different technologies. For instance phage display technologies. The method of producing the specific binding partner is not limited herein. The binding is typically specific for a proteinaceous part of the virus. But can of course also be specific for a virus specific post translation modification of a protein contained in the virus. Thus the present invention further provides an isolated binding molecule capable of specifically binding a proteinaceous molecule of a HCoV-NL63 virus, preferably against encoded by a nucleic acid of the prototype HCoV-NL63. Preferably, a proteinaceous molecule as depicted in FIG. 20, 21, 22, 23 or table 3, or a functional part, derivative and/or analogue thereof. The binding molecule can be capable of specifically binding a nucleic acid sequence of a HCoV-NL63, preferably of FIG. 19 or table 3. The binding molecule is preferably a proteinaceous molecule. However, other binding molecules are also within the scope of the present invention. For instance, it is possible to generate protein mimetics or analogues having the same binding quality as a protein in kind not necessarily in amount. Provided is further a method for producing a binding molecule according to the invention comprising producing molecules capable of binding a HCoV-NL63 virus or functional part, derivative or analogue thereof or an isolated and/or recombinant proteinaceous molecule encoded by a prototype nucleic acid of HCoV-NL63, and selecting a proteinaceous binding molecule that is specific for said virus and/or said proteinaceous molecule.

The overall homology of HCoV-NL63 virus with other human coronaviruses is not very high. Thus many different binding molecules capable of specifically binding to HCoV-NL63 virus can be generated. Such binding molecules can be used to detect HCoV-NL63 virus in a sample. The invention thus further provides an isolated or recombinant virus which is immunoreactive with a binding molecule capable of specifically binding HCoV-NL63 virus. Similarly, the invention provides the use of an isolated and/or recombinant proteinaceous molecule as depicted in FIG. 20, 21, 22, 23 or table 3, or a functional part, derivative and/or analogue thereof, for detecting a binding molecule capable of specifically binding HCoV-NL63 virus, or functional part, derivative and/or analogue of said virus in a sample Vise versa, HCoV-NL63 virus can be used to detect a molecule capable of specifically binding said virus in a sample. Binding of HCoV-NL63 virus to a susceptible target cell occurs via a specific receptor. This receptor can be used as a binding molecule of the invention. Preferably, the binding molecule comprises an antibody or functional equivalent thereof. The detection methods can be used to diagnose HCoV-NL63 related disease in a subject. Thus provided is a method for detecting a HCoV-NL63 virus or functional part, derivative or analogue thereof in a sample, comprising hybridizing and/or amplifying a nucleic acid of said virus or functional part, derivative or analogue with a HCoV-NL63 specific primer and/or probe and detecting hybridized and/or amplified product. Further provided is a kit, preferably a diagnostic kit comprising a HCoV-NL63 virus or functional part, derivative or analogue thereof, a binding molecule according to the invention, and/or a HCoV-NL63 virus specific primer/probe according to invention.

In a particular preferred embodiment is provided the use of a primer or probe capable of specifically hybridizing to a nucleic acid of a HCoV-NL63 virus or functional part, derivative or analogue thereof or a binding molecule capable of specifically binding a proteinaceous molecule depicted in FIG. 20, 21, 22, 23 or table 3 or an HCoV-NL63 virus and/or a nucleic acid or functional part, derivative or analogue of a prototype HCoV-NL63 for detecting and/or identifying a HCoV-NL63 coronavirus in a sample. Preferably said nucleic acid comprises a sequence as depicted in table 3.

The invention further provides a vaccine comprising HCoV-NL63 virus or functional part, derivative or analogue thereof. Further provided is a vaccine comprising a proteinaceous molecule depicted in FIG. 20, 21, 22, 23 or table 3 or functional part, derivative and/or analogue of such a proteinaceous molecule. A proteinaceous molecule of the invention may be provided as a vaccine by itself or as a part of the protein or as derivatives or analogues thereof. A suitable analogue is a nucleic acid encoding a HCoV-NL63 virus proteinaceous molecule or a functional part or derivative thereof. The nucleic acid may be used in a DNA vaccine approach which is also provided in the present invention. As carrier for the DNA vaccine it is often suitable to incorporate an expressible HCoV-NL63 virus nucleic acid in a viral replicon allowing replication of the HCoV-NL63 virus nucleic acid in the target cell and thereby allowing boosting of the provided immune response. A HCoV-NL63 virus encoded protein that is suited for such a DNA vaccine approach is the S protein depicted in FIG. 22 or a functional part, derivative and/or analogue thereof. A part of an S protein preferably comprises an immunogenic part of the 537 in frame insertion as compared with HCoV-229E virus. Preferably said part comprises essentially said 537 insertion. With the 537 insertion is meant a sequence corresponding to sequences 20472 to 21009 of FIG. 19. Other suitable candidates are the M and or the N protein or a functional part, derivative and/or analogue thereof. Typically a vaccine includes an appropriate adjuvant. Apart from the use in a vaccine the mentioned virus and/or proteinaceous molecules can also be used to generate and/or boost a HCoV-NL63 virus specific immune response in a subject. The immune response can be both cellular or humoral. Thus further provided is an isolated T-cell comprising a T-cell receptor that is specific for HCoV-NL63 virus or a proteinaceous molecule encoded by a prototype HCoV-NL63 virus. Further provided is an isolated B-cell producing an antibody specific for HCoV-NL63 virus or a proteinaceous molecule encoded by a HCoV-NL63 virus. The antibody or T-cell receptor can be cloned whereupon a cell line can be provided with an expression cassette comprising the cloned receptor or antibody. Thus the invention further provides a cell producing such a receptor or antibody. Such a cell is preferably a cell that is suitable for large scale production of the mentioned proteins such as CHO cells.

It is also possible to provide a subject with passive immunity to HCoV-NL63 virus. To this end the subject can be provided with a HCoV-NL63 specific binding molecule of the invention. Such immunity can be used to provide a barrier for (further) infection with HCoV-NL63 virus in the subject, thus further provided is a vaccine comprising a HCoV-NL63 virus specific binding molecule according to the invention. In a preferred embodiment, passive immunity is provided by a human or humanized antibody capable of specifically binding a HCoV-NL63 virus of the invention. The barrier does not have to be perfect. The presence of a binding molecule at least reduces the spread of the virus to other target cells in the subject. The passive immunity may be administered to a subject as prophylactic to at least reduce the spread of HCoV-NL63 virus in the subject when exposed to the virus. Alternatively, the passive immunity may be provided to a subject already infected with the virus. In the latter case one or more HCoV-NL63 virus specific binding molecules of the invention are used as a medicament to at least reduce the spread of the virus in the subject and thereby at least in part combat the virus infection. The invention thus further provides a medicament comprising a HCoV-NL63 virus specific binding molecule according to the invention. Further provided is the use of a virus of the invention or functional part, derivative or analogue thereof or a proteinaceous molecule of the invention or a HCoV-NL63 virus specific binding molecule of the invention, for the preparation of a vaccine against a coronaviral genus related disease. Further provided is a method for treating an individual suffering from, or at risk of suffering from, an HCoV-NL63 related disease, comprising administering to said individual a vaccine or medicament according to the invention. In yet another embodiment is provided a method for determining whether an individual suffers from an HCoV-NL63 related disease, comprising obtaining a sample from said individual and detecting a HCoV-NL63 virus or functional part, derivative or analogue thereof in said sample.

In yet another embodiment is provided an isolated cell, or recombinant or cell line comprising HCoV-NL63 virus, or a functional part, derivative and/or analogue thereof. Preferably said cell is a primate cell, preferably a monkey cell. In a preferred embodiment, said cell is a cell that replicates the HCoV-NL63 virus of the invention. In a particular embodiment the cell is a kidney cell. The cell can be used to produce the HCoV-NL63 virus of the invention or to attenuate HCoV-NL63 such that it becomes less pathogenic. Virus attenuation is spontaneous upon continued culture of the virus on the mentioned preferred cell lines. Attenuated HCoV-NL63 virus can be used as a vaccine.

HCoV-NL63 virus encodes an endoprotease. A sequence for the protease in the prototype HCoV-NL63 virus is depicted in FIG. 21). The protease is important for the processing of the polyproteins encoded by HCoV-NL63. The action of the protease is at least in part inhibited by a viral protease inhibitor as further described herein. Thus the invention further provides a compound for at least in part inhibiting HCoV-NL63 virus replication. Preferred compounds are inhibitors of inosine monophosphate dehydrogenase (55) (e.g. Ribavirin(54) and mycophenolic acid), orotidine-5'-phosphate decarboxylase inhibitors (e.g. 6-azauridine and pyrazofurin), 3CL-protease inhibitors(56) (e.g. the VNSTLQ-AG7088 ester, see below), cap-methylase inhibitors(58) (carboxylic adenosine analogs e.g. Neoplanocin A and 3-deazaneoplancin A), nitrous oxide synthase inducing compounds (e.g. glycyrrhizin) and Interferons (57). Of these the protease inhibitors are particularly preferred. The sequence VNSTLQ is the N-terminal proteolytic processing site of SARS-3CLpro that is used in the 3Clpro inhibitor VNSTLQ-AG7088 (56). In this compound the hexapeptide VNSTLQ is C-terminally linked to the vinylogous ethyl ester (AG7088, see structural formula I depicted below,) that inhibits SARS 3CLpro activity.

Structure of formula I

P2 = p-fluoro-benzyl: AG7088

The hexapeptide VNSTLQ corresponds to YNSTLQ in HCoV-NL63. Therefore YNSTLQ-AG7088 inhibits the HCoV-NL63 3CLpro orthologs. Thus in a preferred embodiment the protease inhibitor comprises the amino acid sequence VNSTLQ more preferably YNSTLQ. Analogues of such protease inhibitors that comprise the same activity in kind not necessarily in amount are also provided by the present invention. Such analogues include, compounds comprising a peptide with the preferred sequence, wherein the peptide comprises a modification. Other analogues include compounds having protein mimetic activity that mimic the preferred amino-acid sequence.

S-adenosylmethionine-dependant ribose 2'-orthomethyltransferase Plays a role in the methylation of cap structure (GpppNm) at the 5' end of the viral RNA. Antiviral compounds inhibiting this transfer of methyl groups to reaction (carboxylic adenosine analogs e.g. Neoplanocin A and 3-deazaneoplancin A) interfere with expression of viral proteins.

The invention further provides a proteinaceous molecule encoded by HCoV-NL63 nucleic acid, wherein said proteinaceous molecule is a 3CL protease or a functional equivalent thereof. Functional equivalents include an proteolytically active part and/or derivative having one or more conservative amino acid substitutions. There are many methods known in the art to determine whether a compound has anticoronaviral activity, preferably antiproteolytic activity of a coronavirus. The invention thus further provides a method for determining whether a compound comprises anticoronavirus replication activity characterized in that said method utilizes HCoV-NL63-virus or a HCoV-NL63 protein involved in replication of HCoV-NL63 or a functional part, derivative and/or analogue thereof. Preferably, the invention provides a method for determining whether a compound is capable of at least in part inhibiting a viral protease characterized in that said protease is a 3CL protease of HCoV-NL63 or a functional part, derivative and/or analogue thereof. Preferred compounds that can be tested for 3CL inhibiting quality are hexapeptides located N-terminally of 3Clpro cleavage sites. Compounds effective in at least in part inhibiting 3Cl proteolytic activity can be used for the preparation of a medicament for the treatment of an individual suffering or at risk of suffering from a HCoV-NL63 virus infection.

One or more of the preferred anticoronaviral replication compounds can be used as a medicament for the treatment of a subject suffering from or at risk of suffering from a HCoV-NL63 virus infection. The invention thus further provides a medicament for the treatment of an individual suffering from an coronavirus infection or an individual at risk of suffering there from comprising wherein said coronavirus comprises a nucleic acid sequence of a HCoV-NL63 prototype virus or a functional part, derivative and/or analogue thereof.

In the present invention several different recombinant viruses are produced using HCoV-NL63 virus nucleic acid as a backbone. Such replication competent or replication defective recombinant virus can be used for instance as gene delivery vehicles. On the other hand parts of a HCoV-NL63 virus can be used in gene delivery vehicles that are based on other means for delivering genetic material to a cell. Thus the invention further provides a gene delivery vehicle comprising at least part of a HCoV-NL63 virus nucleic acid. Preferably of the prototype virus. Preferably comprising a nucleic acid encoding a protein of HCoV-NL63 virus or a functional part, derivative and/or analogue thereof. The invention also shows chimearic coronaviruses comprising nucleic acid derived from at least two coronaviruses wherein at least one of said parts is derived from a HCoV-NL63 virus. Said HCoV-NL63 virus derived part comprises preferably at least 50 nucleotides of a protein coding domain. More preferably said HCoV-NL63 derived part comprises at least 500 and more preferably at least 1000 nucleotides of the sequence as depicted in FIG. 19 or a functional derivative thereof. In a preferred embodiment the invention provides a chimearic coronavirus comprising at least 1000 nucleotides of a sequence as depicted in FIG. 19 and at least 1000 nucleotides of another coronavirus wherein said latter 1000 nucleotides comprise a sequence that is more than 5% sequence divergent with a sequence as depicted in FIG. 19. The sequences of a number of HCoV-NL63 virus fragments are depicted in table 3. The location of the fragments in the large genomic RNA is depicted in FIG. 5. The invention therefore, in one aspect, provides an isolated or recombinant virus comprising a nucleic acid sequence as depicted in table 3, or a functional part, derivative or analogue of said virus. With the aid of the identifying prototype fragments it is possible to further sequence the genome. One way of doing this by primer walking on the genome. A primer is directed to a region of which the sequence is known and this primer is used to sequence a flanking region that is as yet unknown. A subsequent primer can be generated against the newly identified sequence and a further region can be sequenced. This procedure can be repeated until the entire sequence of the virus is elucidated. As a source of the virus one may turn to Dr. C. van der Hoek, Department of Human Retrovirology, Academic Medical Center, University of Amsterdam, Amsterdam, The Netherlands.

Alignments of the determined nucleic acid sequences revealed the reading frame used in the sequences found, accordingly the invention further provides an isolated or recombinant virus comprising an amino acid sequence as depicted in (table 3). or a functional part, derivative or analogue of said virus. A particular amino acid sequence can be produced from a variety of nucleic acids depending on the codons used. Thus the invention further provides a nucleic acid encoding an amino acid sequence as depicted in (table 3). Further provided is an isolated or recombinant virus comprising a nucleic acid sequence encoding an amino acid sequence as depicted in (table 3), or a functional part, derivative or analogue of said virus.

Coronaviruses as many other types of viruses acquire a plurality of spontaneous and selected mutations upon spreading of the virus through the subject population and/or during culturing ex vivo. Moreover, artificial mutations having no recognized counterpart in nature can be introduced into the sequence of the prototype virus or a derivative thereof, without altering the viral- and/or disease causing properties of the virus. Having characterized the prototype of the newly discovered subtype gives access to this group of viruses belonging to the same subtype. Thus the invention further provides an isolated or recombinant virus comprising a nucleic acid sequence that is approximately 80% homologous to a sequence as depicted in table 3, or 80% homologous to an amino acid sequence depicted in Table 3 (. Preferably the homology is at least 90%, more preferably at least 95% and even more preferably at least 99%.

The respective prototype fragments were compared with a database of viral sequences and hits having a particularly high homology are mentioned in the tables 5 and 6. It may be noted that the compared fragments do not share extensive homology with any of the currently known Coronaviruses. The invention thus provides an isolated and/or recombinant virus comprising an amino acid sequence which is more than 89% homologous to 163-2 amino acid sequence as depicted in Table 3. Preferably said homology is at least 90%, more preferably at least 95% and even more preferably at least 99%. Further provided is an isolated or recombinant virus comprising an amino acid sequence which is more than 60% homologous to 163-4 amino acid sequence as depicted in Table 3. Preferably said homology is at least 90%, more preferably at least 95% and even more preferably at least 99%. Further provided is an isolated or recombinant virus comprising a nucleic acid sequence which is more than 85% homologous to 163-9 nucleic acid sequence as depicted in Table 3. Preferably said homology is at least 90%, more preferably at least 95% and even more preferably at least 99%. Further provided is an isolated or recombinant virus comprising an amino acid sequence which is more than 94% homologous to 163-10 amino acid sequence as depicted in Table 3. Preferably said homology is at least 90%, more preferably at least 95% and even more preferably at least 99%. Further provided is an isolated or recombinant virus comprising an amino acid sequence which is more than 50% homologous to 163-11 amino acid sequence as depicted in Table 3. Preferably said homology is at least 90%, more preferably at least 95% and even more preferably at least 99%.

Further provided is an isolated or recombinant virus comprising an amino acid sequence which is more than 87% homologous to 163-14 amino acid sequence as depicted in Table 3. Preferably said homology is at least 90%, more preferably at least 95% and even more preferably at least 99%. Further provided is an isolated or recombinant virus comprising an amino acid sequence which is more than 83% homologous to 163-15 amino acid sequence as depicted in Table 3. Preferably said homology is at least 90%, more preferably at least 95% and even more preferably at least 99%. Further provided is an isolated or recombinant virus comprising an amino acid sequence which is more than 78% homologous to 163-18 amino acid sequence as depicted in Table 3. Preferably said homology is at least 90%, more preferably at least 95% and even more preferably at least 99%. Further provided is an isolated or recombinant virus comprising a nucleic acid sequence which is at least 50% homologous to a nucleic acid sequence as depicted in Table 3. Preferably said homology is at least 80%, more preferably at least 90%, more preferably at least 95% and even more preferably at least 99%.

The invention also provides a functional part, derivative and/or analogue of an isolated and/or recombinant HCoV-NL63 virus. A part of a virus can be a membrane containing part, a nucleocapsid containing part, a proteinaceous fragment and/or a nucleic acid containing part. The functionality of the part varies with the application chosen for the part, for instance, part of the virus may be used for immunization purposes. In this embodiment the functionality comprises similar immunogenic properties in kind as the entire virus not necessarily in amount. Another use of the virus is the infectivity of the virus, for instance, for in vitro (or in vivo) culture, in this embodiment the functionality comprises a similar infectivity in kind not necessarily in amount. Many other functionalities may be defined, as there are many different uses for viruses, non-limiting examples are the generation of chimeric viruses, (i.e. with one or more other (corona) viruses, and the generation of viral vectors for vaccination and/or gene therapeutic purposes. Such viruses and/or vectors also contain a functional part of HCoV-NL63 and are thus also encompassed in the present invention. A functional derivative of a virus of the invention is defined as a virus that has been altered such that the properties of said compound are essentially the same in kind, not necessarily in amount. A derivative can be provided in many ways, for instance through nucleotide substitution (preferably "wobble" based), through (conservative) amino acid substitution, subsequent modification, etcetera.

Analogous compounds of a virus can also be generated using methods in the art. For instance, a chimeric virus can be produced, or an HCoV-NL63 virus having a chimeric protein. For instance, HCoV-NL63 can be rendered more immunogenic by generating a cell surface associated fusion protein comprising at least part of an HCoV-NL63 surface protein and a non-HCoV-NL63 immunogenic part. HCoV-NL63 virus comprising such chimeric protein can be used for inducing an enhanced immune response in a host, for instance for vaccination purposes.

As used herein, the term "a virus of the invention" is meant to also comprise a functional part, derivative and/or analogue of said virus.

The three groups of coronaviruses are associated with a variety of diseases of humans and domestic animals, including gastroenteritis and upper and lower respiratory tract disease. The human coronaviruses HCoV-229E and HCoV-OC43 are associated with mild disease (the common cold) but more severe disease is observed in children[16], albeit at a very low incidence. Several coronaviruses cause a severe disease in animals and SARS-CoV is the first example of a coronavirus that causes severe disease in humans. However, it should be emphasized that a substantial part of respiratory disease cases in humans remains undiagnosed. For instance, a recent survey of respiratory viruses in hospitalized children with bronchiolitis in Canada could not reveal a viral pathogen in about 20% of the patients[17]. The fact that we identified the new coronavirus in a child with bronchiolitis shows that HCoV-NL63 is a pathogenic respiratory virus.

When considering that the HCoV-NL63 is a pathogenic respiratory virus able to cause bronchiolitis in infected children, the interesting question remains why HCoV-NL63 was not recognized previously by cell culture. We found that the virus can be cultured in monkey kidney cells (tMK or LLC-MK2 cells), cells that are often used in a routine diagnostic setting and one might therefore speculate that HCoV-NL63, like SARS-CoV, was newly introduced from an animal reservoir into the human population or that this is a human virus that recently broadened its host cell range. Clearly it is of importance to study the prevalence of HCoV-NL63 infection, and screening specimens from patients with respiratory tract disease using the HCoV-NL63 diagnostic RT-PCR will shed light on this issue.

It is remarkable that the new human coronavirus was harvested from tMK cells and LLC-MK2 cells since coronaviruses are typically fastidious in cell culture with a narrow host range. However, both SARS-CoV and HCoV-NL63 seem to replicate efficiently in monkey kidney cells (Vero-E6 cells and NCI-H292 cells for SARS-CoV). The recently described genome of SARS-CoV has several exclusive features, including some unique open reading frames that are probably of biological significance[15, 18]. We will therefore analyze the complete genome sequence of HCoV-NL63 to screen for similarities and differences with SARS-CoV that may determine the expanded host cell range and enhanced pathogenicity of these viruses.

HCoV-NL63 is associated with a particular phenotype in infected subjects. The phenotype can encompass bronchiolitis, coryza, conjunctivitis and fever and may further encompass other respiratory problems and diarrhea. In one embodiment the invention thus further provides an isolated and or recombinant virus of the invention (having one or more of the above mentioned homology) wherein said virus or functional part, derivative and/or analogue further comprises the capability to induce an HCoV-NL63 related disease or symptom in a subject. In another embodiment the invention provides an isolated and/or recombinant virus of the invention further comprising the property to cause CPE in tertiary monkey kidney cells (tMK; Cynomolgus monkey[37]) and/or upon passage onto the monkey cell line LLC-MK2 (ECCAC 85062804, ATCC CCL-7). In a preferred embodiment said virus does not produce CPE in Vero-cells (ATCC CRL-1586)[34].

The invention further provides a nucleic acid as depicted in table 3, and an amino acid sequence as depicted in Table 3, or a functional part and/or equivalent of such a nucleic acid and/or amino acid sequence. A functional equivalent of said nucleic acid comprises the same hybridization properties in kind, not necessarily in amount, as said nucleic acid (or part thereof). A functional equivalent of an amino acid sequence of the invention comprises the same immunogenic properties in kind, not necessarily in amount, as said amino acid sequence (or part thereof). A part of a nucleic acid of the invention comprises at least 15 nucleotides, preferably at least 20, more preferably at least 30 nucleotides. A part of an amino acid sequence comprises at least 5 amino acids in peptidic linkage with each other, more preferably at least 8, and more preferably at least 12, more preferably at least 16 amino acids. In a preferred embodiment said nucleotides and/or amino acids are at least semi-consecutive, more preferably, said nucleotides and/or amino acids are consecutive. An equivalent of a nucleic acid and/or amino acid sequence of the invention or part thereof comprises at least 80% homology to a nucleic acid and/or amino acid sequence of the invention, preferably at least 90% homology, more preferably at least 95% and even more preferably at least 99% homology to a nucleic acid and/or amino acid sequence of the invention or a part thereof.

The invention further provides a primer and/or probe, capable of specifically hybridizing to a nucleic acid of a virus or functional part, derivative or analogue according to the invention, preferably a primer and/or probe, capable of specifically hybridizing to a nucleic acid sequence as depicted in Table 3. More preferably, a primer and/or probe, which is capable of hybridizing to said nucleic acid under stringent conditions. In a particular preferred embodiment is provided a primer and/or probe, comprising a sequence as depicted in Table 7.

The art knows many ways in which a specific binding member can be generated against an identified nucleic acid, lipid and/or amino acid sequence. Such specific binding members may be of any nature but are typically of a nucleic acid and/or proteinaceous nature. The invention thus further provides an isolated molecule capable of specifically binding a virus, nucleic acid and/or amino acid or functional part, derivative or analogue thereof according to the invention. Said isolated molecule is also referred to as specific binding member. Preferably said specific binding member is capable of specifically binding at least part of a nucleic acid sequence as depicted in table 3 and/or at least part of an amino acid sequence as depicted in Table 3. In a preferred embodiment said binding member is a proteinaceous molecule. Preferably an antibody or a functional part, derivative and/or analogue thereof. A specific binding member preferably comprises a significantly better binding property for the HCoV-NL63 virus compared to unrelated control. However, for instance for antibodies, it is possible that the epitope specifically recognized in HCoV-NL63 is also present in a limited number of other molecules. Thus though the binding of the binding member may be specific, it may recognize also other molecules than those present in HCoV-NL63. This cross-reactivity is to be separated from a-specific binding and is a general property of antibodies. Cross-reactivity does not usually hinder the selection of suitable specific binding members for particular purposes. For instance a specific binding member that also recognized a protein in liver cells can be used in many applications even in the presence of liver cells, where additional information such as location in the cell can often be used to discriminate.

One source of an antibody of the invention is the blood of the infected subjects screened for the virus of the present invention. One may further characterize B-cells obtained from said subject. A suitable B-cell may be cultured and the antibody collected. Alternatively, the antibody may be sequenced from this B-cell and generated artificially. Another source of an antibody of the invention can be generated by immunisation of test animals or using artificial libraries to screen a purified fraction of virus. A functional part of an antibody has essentially the same properties of said antibody in kind, not necessarily in amount. Said functional part is preferably capable of specifically binding an antigen of HCoV-NL63. However, said functional part may bind such antigen to a different extend as compared to said whole antibody. A functional part or derivative of an antibody for instance comprises a FAB fragment or a single chain antibody. An analogue of an antibody for instance comprises a chimeric antibody. As used herein, the term "antibody" is also meant to comprise a functional part, derivative and/or analogue of said antibody.

Once antibody of the invention is obtained, a desired property, such as its binding capacity, can be improved. This can for instance be done by an Ala-scan and/or replacement net mapping method. With these methods, many different proteinaceous molecules are generated, based on an original amino acid sequence but each molecule containing a substitution of at least one amino acid residue. Said amino acid residue may either be replaced by Alanine (Ala-scan) or by any other amino acid residue (replacement net mapping). Each variant is subsequently screened for said desired property. Generated data are used to design an improved proteinaceous molecule.

There are many different ways in which a specific binding member can be generated. In a preferred embodiment the invention provides a method for producing a specific proteinaceous binding member comprising producing proteinaceous molecules capable of binding a virus according to the invention or to a functional part, derivative or analogue, and selecting a proteinaceous molecule that is specific for said virus. If need be, the method may be used to generate a collection of proteinaceous molecules capable of binding to said virus or functional part, derivative and/or analogue thereof and selecting from said collection one or more binding members capable of specifically binding said virus or functional part, derivative and/or analogue thereof.

Any specific binding member is characteristic for the HCoV-NL63virus of the invention. Thus a virus that is specifically reactive with such binding member is an HCoV-NL63 virus and thus provided by the invention. Thus the invention provides an isolated and/or recombinant virus that is immunoreactive with specific binding member of the invention, preferably a proteinaceous binding member. The invention further provides a composition of matter comprising isolated HCoV-NL63 virus, and/or a virus essentially corresponding to HCoV-NL63. The term, a virus "essentially corresponding to HCoV-NL63" refers to HCoV-NL63 viruses which are either identical to the HCoV-NL63 strain described hereinabove, or which comprises one or more mutations compared to the said HCoV-NL63strain. These mutations may include natural mutations or artificial mutations. Said mutations of course should allow detection with a specific binding member of HCoV-NL63, not necessarily with all of the specific binding members). Said mutations should allow the detection of the variants using common detection methods such as antibody interaction, amplification and/or hybridization.

Considering that specific binding members are important molecules for instance for diagnostic purposes, the invention further provides the use of a virus of the invention or functional part, derivative and/or analogue thereof, for detecting a molecule capable of specifically binding said virus in a sample. Further provided is the use of a nucleic acid and/or amino acid sequence of a virus or functional part, derivative or analogue as defined by the invention, for detecting a molecule capable of specifically binding said virus or functional part, derivative and/or analogue in a sample. Preferably said nucleic acid and/or amino acid sequence comprises a sequence as depicted in table 3 or Table 3 or a functional part, derivative or analogue thereof. Preferably said part is at least 30 nucleotides and/or amino acids long wherein said part preferably comprises more than 95% sequence identity, preferably more than 99%. In a preferred aspect said specific binding member comprises a specific ligand and/or antibody of said virus.

Further provided is a primer and/or probe according to the invention, a specific binding member of the invention, and/or a nucleic acid of a virus or functional part, derivative or analogue according to the invention, for detecting and/or identifying a HCoV-NL63 coronavirus or part thereof in a sample. Preferably, said nucleic acid comprises a sequence as depicted in table 3.

HCoV-NL63 virus may be used to generate an immune response in a subject. This can be useful for instance in vaccination strategies. Thus the invention further HCoV-NL63 provides HCoV-NL63 virus or functional part, derivative or analogue thereof for use as a vaccine or medicament. The medicament use is typically when the subject is already infected with the virus and the immunogen is used to augment the immune response against the virus. The invention further provides a specific binding member of the invention for use as a vaccine or medicament. This use is particularly favorable for when the specific binding member comprises a proteinaceous molecule, preferably an antibody or functional part, derivative and/or analogue thereof. Such an antibody can provide passive immunity but may also have active components such as proteases attached to it. The medicament use may again be the case wherein a subject infected with an HCoV-NL63 virus is treated with the specific binding member.

Vaccines may be generated in a variety of ways. One way is to culture the HCoV-NL63 virus for example on the mentioned monkey cell line(s) and to use inactivated virus harvested from the culture. Alternatively, attenuated virus may be used either inactivated or as a live vaccine. Methods for the generation of coronavirus vaccines may be adapted to produce vaccines for the HCoV-NL63 of the invention. The invention thus further provides the use of an HCoV-NL63 virus or functional part, derivative or analogue thereof for the preparation of a vaccine against a coronaviral genus related disease. The invention further provides the use of a specific binding member of the invention for the preparation of a vaccine or medicament against a coronaviral genus related disease. Further provided is the use of an HCoV-NL63 virus or functional part, derivative or analogue thereof, a specific binding member of the invention, a nucleic acid of the invention or a primer and/or probe of the invention for diagnosis of a coronaviral genus related disease. Preferably said coronaviral genus related disease comprises a HCoV-NL63coronavirus related disease.

Further provided is a vaccine comprising an HCoV-NL63 virus or functional part, derivative or analogue thereof and/or a specific binding member of the invention. Also provided is a medicament comprising an HCoV-NL63virus or functional part, derivative or analogue thereof and/or a specific binding member of the invention. Preferably said vaccine or medicament is used for at least in part preventing and/or treating a HCoV-NL63 related disease.

An important use of the present invention is the generation of a diagnostic tool for determining whether a subject is suffering from an HCoV-NL63 virus infection or has been exposed to an HCoV-NL63 virus infection. Many different diagnostic applications can be envisioned. They typically contain an identifying component allowing the typing of the virus that is or was present in the subject. One diagnostic tool for HCoV-NL63 makes use of the particular proliferation characteristics of the virus in various cell lines. It replicates in the mentioned preferred monkey cell lines but does not replicate in Vero-cells. This property can be used to discriminate HCoV-NL63 from other known coronaviruses. Thus in one aspect the invention provides a diagnostic kit comprising at least one of the preferred monkey cell lines, preferably the tertiary monkey kidney cells (tMK; Cynomolgus monkey or the monkey cell line LLC-MK2.

Many modern diagnostic kits comprise a specific binding member (to detect the virus or virus infected cells) and/or an HCoV-NL63 virus or a functional part, derivative and/or analogue thereof and/or amino acid of the invention or a functional part, derivative and/or analogue thereof (for detecting antibodies in blood components of the diagnosed subject). Many other current diagnostic kits rely on identification of HCoV-NL63 virus specific nucleic acid in a sample. There are various ways in which such an assay may be implemented one is a method for detecting an HCoV-NL63 virus or functional part, derivative or analogue thereof in a sample, comprising hybridizing and/or amplifying a nucleic acid of said virus or functional part, derivative or analogue with a primer and/or probe according to the invention and detecting hybridized and/or amplified product. The invention thus also provides a diagnostic kit comprising an HCoV-NL63 virus or functional part, derivative or analogue thereof, a specific binding member according to the invention and/or a primer/probe according to the invention.

Further provided is a method for treating an individual suffering from, or at risk of suffering from, a HCoV-NL63 related disease, comprising administering to said individual a vaccine or medicament according to the invention. Also provided is a method for determining whether an individual suffers from a HCoV-NL63 related disease, comprising obtaining a sample from said individual and detecting a HCoV-NL63 virus or functional part, derivative or analogue thereof in said sample with a method and/or diagnostic kit of the invention.

Further provided is an isolated or recombinant nucleic acid encoding a virus or functional part, derivative and/or analogue according to the invention and a nucleic acid according to the invention, comprising at least a functional part of a sequence as depicted in Table 3. Further provided is an amino acid sequence encoded by a nucleic acid according to the invention, and an amino acid sequence according to the invention, comprising at least a functional part of a sequence as depicted in Table 3. Further provided is a proteinaceous molecule capable of specifically binding HCoV-NL63, obtainable by a method according to the invention and, the use of such a proteinaceous molecule in a vaccine or a diagnostic method for the detection of HCoV-NL63.

EXAMPLES

Example 1 cDNA-AFLP for Virus Discovery

We modified the cDNA-AFLP technique such that it can amplify viral sequences from blood-plasma/serum samples or from CPE-positive culture supernatants (FIG. 1). In the adjusted method the mRNA isolation step prior to amplification is replaced by a treatment to purify viral nucleic acid. Of importance to the purification is a centrifugation step to remove residual cells and mitochondria. In addition, a single DNAse treatment is sufficient to get rid of interfering chromosomal DNA and mitochondrial DNA from broken down cells and finally, by choosing frequent cutting restriction enzymes, the method is fine-tuned such that the majority of viruses will be amplified. With this so-called Virus Discovery cDNA-AFLP (VIDISCA) we were able to amplify viral nucleic acids from EDTA-plasma of a person with hepatitis B virus infection and a person with an acute Parvo B19 infection (results not shown). The technique can also detect HIV-1 in a positive culture supernatant demonstrating its capacity to identify both RNA and DNA viruses (results not shown).

To eliminate residual cells, 110 μl of virus culture supernatant was spun down for 10 min at maximum speed in an Eppendorf microcentrifuge (13500 rpm). One hundred μl was transferred to a fresh tube and DNAse treated for 45 minutes at 37° C. using 15 μl of DNAse buffer and 20 Units of DNAse I (Ambion). The DNAse treatment was included to get rid of chromosomal DNA from broken down cells. After this 900 μl of L6 lysis buffer and 40 μl of silica suspension was added and nucleic acids were extracted as described by Boom[4]. The viral nucleic acids were eluted in 40 μl $H_2O$. With 20 μl eluate the reverse transcription was performed using 2.5 μg random hexamers (Amersham Bioscience), 200 U MMLV-RT (InVitrogen) in a buffer containing 10 mM Tris-HCl pH 8.3, 50 mM KCl, 0.1% Triton X-100, 4.8 mM MgCl2, and 0.4 mM of each dNTP. The sample was incubated at 37° C. for 90 minutes. Subsequently the second strand DNA synthesis was performed using 26 U Sequenase II (Amersham Bioscience), 7.5 U RNAse H (Amersham Bioscience) in 0.25 mM dNTPs each, 17.5 mM MgCl2 and 35 mM Tris-HCl pH 7.5. After the incubation at 37° C. for 90 minutes a phenol/chloroform extraction was performed followed by an ethanol precipitation. The pellet was dissolved in 30 μl of $H_2O$. The cDNA-AFLP was performed essentially as described by Bachem[1] with some modifications. The dsDNA was digested with the HinP I and MseI restriction enzymes (New England Biolabs) according to the manufacturers protocol. After the digestion, MseI adaptor and HinP I adaptor (see below) are added together with 5U ligase enzyme (InVitrogen) and ligase buffer, followed by an additional incubation of 2 hrs at 37° C. The MseI adaptor and HinP I adaptor were prepared previously by mixing a top strand oligo for the MSE and the HinPI adaptors (Table 1) with a bottom strand oligo for the MSE adaptor and for the HinPI adaptor, incubate at 65° C. followed by cooling down to room temperature in the presence of a 1:40 dilution of ligase buffer.

The first PCR was performed with 10 μl of ligation mixture as input, 2.5 U of AmpliTaq polymerase (Perkin-Elmer), 100 ng of HinPI standard primer and 100 ng of MseI standard primer. The PCR reaction was performed according to the profile 5 min 95 C; 20 cycles of: 1 min 95° C.-1 min 55° C.-2 min 72° C.; 10 min 72° C. Five μl of first PCR product was used as input in the second "selective" amplification step containing 100 ng of HinPI-N primer and 100 ng MseI-N (sequence of the standard primers extended with one nucleotide) and 2 U AmpliTaq polymerase. The selective PCRs were amplified according to the profile of the "touch down PCR": 10 cycles of 60 sec 94° C.-30 sec 65° C.-1 min 72° C. over which the annealing temperature was reduced from 65° C. with 1° C. with each cycle, followed by 23 cycles: 30 sec 94° C.-30 sec 56° C.-1 min 72° C. Finally the sample was incubated for 10 min at 72° C. The PCR products were evaluated on 4% Metaphor® gels (Cambrex, Rockland, USA). If the bands on the gel were very faint the PCR products were concentrated by vacuum drying using 60 μl of the PCR product. The PCR fragments of interest were cut out of gel and DNA was eluted from the gel using the Qiagen gel purification kit according to the manufacturer's protocol. The PCR products were cloned using pCR® 2.1-TOPO plasmid (InVitrogen) and chemically competent One Shot *E. coli* (InVitrogen). A PCR on the colony was performed and this PCR product was input for sequencing the insert using Big Dye terminator chemistry (Applied Biosystems). The reverse transcription step was excluded, only HinP I digestion and adaptor ligation was performed, the first PCR was performed with 35 cycles instead of 20 and those first PCR fragments were visualized on agarose gel electrophoresis.

DNA Sequencing and Analysis.

Coronavirus-PCR product containing plasmids were sequenced with the BigDye™ Terminator Cycle Sequencing Kit (Applied Biosystems, Foster City, Calif.), using the −21 M13RP and T7 primers. Electrophoresis of sequencing reaction mixtures was performed with an Applied Biosystems 377 automated sequencer, following the manufacturer's protocols. The Sequence Navigator (version 1.01) and Auto Assembler (version 2.1) software packages (ABI, California, USA) were used to analyze all sequencing data. Sequences were compared to all sequences in the Genbank database using the BLAST tool of the NCBI. For phylogenetic analysis the sequences were aligned using the ClustalX software package[34] with the following settings: Gap opening penalties: 10.00; Gap extension penalty 0.20, Delay divergent sequences switch at 30% and transition weight 0.59. Phylogenetic analysis was carried out using the neighbor-joining method of the MEGA program (9). The nucleotide distance matrix was generated either by Kimura's 2-parameter estimation or by the p-distance estimation (5). Bootstrap resampling (500 replications) was employed to place approximate confidence limits on individual branches.

Determining the Nucleotide Sequence of the Complete HCoV-NL63 Genome.

Using a combination of specific primers, located in the already sequenced domains of the HCoV-NL63 genome, and the proprietary PALM-method (WO 0151661) we are in the process of cloning and determining the full-length genomic sequence for this new coronavirus. Using a combination of 5'-oligonucleotides located in the analyzed part of the HCoV-NL63 genome and a 3' tagged random primer (JZH2R) additional fragments were amplified using a nested RT-PCR protocol similar to the one mentioned previously.

Isolation of SZ 163

In January 2003 a 7-month-old child appeared in hospital with coryza, conjunctivitis and fever. Chest radiography showed typical features of bronchiolitis and four days after the onset of disease a nasopharyngeal aspirate specimen was collected (sample nr: HCoV-NL63). All routinely used tests on this sample for adenovirus, respiratory syncytial virus (RSV), influenza A and B, parainfluenza 1, 2 and 3, rhinovirus, HCoV-229E and HCoV-OC43 were negative. The clinical sample was subsequently inoculated onto a variety of cells including human fibroblast lung (HFL) cells, tertiary monkey kidney cells (tMK; Cynomolgus) and R-HeLa cells. A CPE was detected exclusively on tMK cells and first noted at eight days post-inoculation. The CPE was diffuse with a refractive appearance in the affected cells followed by cell detachment after 7 days. More pronounced CPE was observed upon passage onto LLC-MK2 cells. Besides overall cell rounding, moderate cell enlargement was observed. Additional subculturing on human endothelial lung cells, HFL, Rhabdomyosarcoma cells and Vero cells remained negative for CPE. Immunofluorescent assays to detect influenzavirus A and B, RSV, adenoviruses or parainfluenza virus types 1, 2 or 3 in the culture remained negative The culture supernatant of infected LLC-MK2 cells was subsequently analyzed by VIDISCA. As control we used the supernatant of uninfected LLC-MK2 cells. After the second PCR amplification step, several DNA fragments were present in the test sample but not in the control. These fragments were cloned and sequenced. A Blast search in GenBank revealed that 8 of 16 fragments had sequence similarity to the family of corona viruses with the highest homology the human corona virus 229E (Tables 4 and 5).

Phylogenetic analysis of a 270 nt fragment of the replicase 1B region indicated that we identified a distinct new member of the coronavirus group 1. With the VIDISCA technique, 8 HCOV-163-specific fragments, named 163-2, 163-4, 163-9, 163-10, 163-11, 163-14, 163-15 and 163-18 were isolated, cloned, sequenced and aligned with the relevant sequences from GenBank. The Genbank accession number of the used sequences are: MHV (mouse hepatitis virus): AF201929; HCoV-229E: AF304460; PEDV (porcine epidemic diarrhea virus): AF353511; TGEV (transmissible gastroenteritis virus): AJ271965; SARS-CoV: AY278554; IBV (avian infectious bronchitis virus): NC__001451; BCoV (bovine coronavirus): NC__003045; FCoV (feline coronavirus): Y13921 and X80799; CCoV (canine coronavirus): AB105373 and A22732; PRCoV (porcine respiratory coronavirus): M94097; FIPV (feline infectious peritonitis virus): D32044. Position of the HCoV-NL63 fragments compared to HCoV-229E (AF304460): Replicase 1AB gene: 15155-15361, 16049-16182, 16190-16315, 18444-18550, Spike gene: 22124-22266; Nucleocapsid gene: 25667-25882 and 25887-25957; 3'UTR: 27052-27123. Branch lengths indicate the number of substitutions per sequence. From the most closely related species sequence identity scores were calculated (Tables 5 and 6).

Also the deduced amino acid sequence were aligned to the corresponding domains in the open reading frames of related corona (-like) viruses (Table 6).

The human corona viruses account for 10 to 30% of the common colds in man[7], and it is not unusual to find a coronavirus in a child with a respiratory illness. However, it is striking that the virus HCoV-NL63 was harvested from LLC-MK cells. Human Corona virus 229E and OC-43 are known for there inability to replicate on monkey kidney cells. Intriguingly, the newly identified human corona virus that is responsible for SARS is also able to replicate in monkey kidney cells[30].

Propagation of HCoV-NL63 in Cell Culture

A nasopharyngeal aspirate was collected 4 days after the onset of symptoms. The specimen was tested for the presence of adenovirus, RSV, influenza A, influenza B, and parainfluenza type 1, 2 an 3 using the Virus Respiratory Kit (Bartels: Trinity Biotech plc, Wicklow Ireland). In addition, PCR diagnosis for rhinoviruses, meta-pneumovirus and HCoV-OC43 and HCoV-229E were performed[2, 10]. The original nasopharyngeal aspirate was subsequently inoculated onto a variety of cell cultures including HFL cells, tMK cells and R-HeLa cells. The tubes were kept in a roller drum at 34° C. and observed every 3 to 4 days. Maintenance medium was replenished every 3 to 4 days. Two different types of medium were implemented: Optimem 1 (Gibco) without bovine fetal serum was used for the tMK cells and MEM Hanks'/Earle's medium (Gibco) with 3% bovine fetal serum was used for the remaining cell types. On the virus culture direct staining was performed with pools of fluorescent-labeled mouse antibodies against influenzavirus A and B, RSV and adenoviruses (Imagen, DAKO). Indirect staining was performed for parainfluenza virus types 1, 2 or 3 with mouse antibodies (Chemicon, Brunschwig, Amsterdam Netherlands) and subsequent staining with labeled rabbit anti-mouse antibodies (Imagen, DAKO).

Method to Detect HCoV-NL63 in Nasopharyngeal Swabs.

For the diagnostic RT-PCR, nucleic acids were extracted by the Boom method[4] 4 from 50 μl virus supernatant or 50 μl suspended nasopharyngeal swab. The reverse transcription was performed as described above with the exception that 10 ng of reverse transcription primer repSZ-RT (Table 7) was used. The entire RT mixture was added to the first PCR mixture containing 100 ng of primer repSZ-1 and 100 ng of primer repSZ-3. The PCR reaction was performed according to the profile 5 min 95° C.; 20 cycles of: 1 min 95° C.-1 min 55° C.-2 min 72° C.; 10 min 72° C. A nested PCR was started using 5 μl of the first PCR with 100 ng of primer repSZ-2 and 100 ng of primer repSZ-4. Twenty-five PCR cycles were performed of the same profile as the first PCR.

Ten μl of the first and 10 μl of the nested PCR was analyzed by agarose gel electrophoresis (FIG. 2). Cloning and sequencing of the fragments was performed essentially as described above.

Method of Raising Polyclonal Antibodies

Appropriate domains within the HCoV-NL63 surface proteins (e.g. S-glycoprotein or HE-glycoprotein) can be selected and amplified with suitable oligonucleotides and RT-PCR. The corresponding purified viral antigens can be obtained by expression in a suitable host (e.g. *Yarrowia lipolytica* as previously described[38]). Female NZW rabbits (approx 4 kg) are primed with 0.5 to 5.0 mg of viral protein antigen preparation. The antigen is suspended in 0.5 ml. of phosphate buffered saline (pH 7.3) and emulsified in an equal volume of complete Freund's adjuvant (CFA). Freund's Adjuvant is a well-established adjuvant system that is appropriate for use in these experiments where small amounts of antigen are used, and where immunogenicity of the antigen (although likely) is unknown. Published guidelines for use will be followed, including limiting injection to 0.1 ml at each site, using CFA only for initial immunization dose. This antigen preparation (1 ml total volume) is injected subdermally in the loose skin on the backside of the rabbit's neck. This injection route is immunologically effective and minimizes the possibility of local inflammation associated with unilateral or bilateral flank injection (such ensuing flank inflammation can impair animal mobility). After resting for 3 weeks, one ml of blood will be removed from the ear artery for a test bleed. Antibodies will be boosted if titers of the desirable antibodies are judged to be too low. Rabbits with adequate antibody levels will be boosted subdermally 1.0 mg of antigen contained in CFA. Boosted animals will be bled after two weeks; i.e., 15 ml of blood will be taken from the ear artery using a heat lamp to dilate the blood vessel. The rabbit will be placed in a commercial restraint, tranquillized with xylazine not more than seven times in total after which the rabbit will be exsanguinated by cardiac puncture following anesthesia using xylazine/ketamine.

Method for Vaccine Production

For the production of a subunit vaccine the S-glycoprotein perhaps combined with the HE, M and N proteins, could be expressed in a suitable eukaryotic host (e.g. *Y. lipolytica* or LLC-MK2 cells) and purified using preferentially two small affinity tags (e.g. His-tag or the StrepII tag). After appropriate purification, the resulting viral proteins can be used as a subunit vaccine.

Alternatively the HCoV-NL63 virus can be propagated in a suitable cell line as described above and subsequently treated as described by Wu[11]. Briefly the virus is precipitated from culture medium with 20% polyethylene glycol 6000 and purified by ultracentrifugation at 80.000×g for 4 hours through a discontinuous 40-65% sucrose gradient followed by a linear 5 to 40% CsCl gradient for 4 hours at 120.000×g. The resulting virus preparation can be inactivated by heating for 30 minutes at 65° C. as described by Blondel[3].

Analysis of S Glycoprotein or any of the HCOV-NL63 Viral Proteins Binding to an Immobilized Ligand (e.g. Antibody) in an Optical Biosensor.

Binding reactions were carried out in an IAsys two-channel resonant mirror biosensor at 20° C. (Affinity Sensors, Saxon Hill, Cambridge, United Kingdom) with minor modifications. Planar biotin surfaces, with which a signal of 600 arc s corresponds to 1 ng of bound protein/mm2, were derivatized with streptavidin according to the manufacturer's instructions. Controls showed that the viral proteins did not bind to streptavidin-derivatized biotin surfaces (result not shown). Biotinylated antibody was immobilized on planar streptavidin-derivatized surfaces, which were then washed with PBS. The distribution of the immobilized ligand and of the bound S-glycoprotein on the surface of the biosensor cuvette was inspected by the resonance scan, which showed that at all times these molecules were distributed uniformly on the sensor surface and therefore were not micro-aggregated. Binding assays were conducted in a final volume of 30 μl of PBS at 20±0.1° C. The ligate was added at a known concentration in 1 μl to 5 μl of PBS to the cuvette to give a final concentration of S-glycoprotein ranging from 14 to 70 nM. To remove residual bound ligate after the dissociation phase, and thus regenerate the immobilized ligand, the cuvette was washed three times with 50 μl of 2 M NaCl-10 mM Na2HPO4, pH 7.2, and three times with 50 μl of 20 mM HCl. Data were pooled from experiments carried out with different amounts of immobilized antibody (0.2, 0.6, and 1.2 ng/mm2). For the calculation of $k_{on}$, low concentrations of ligate (S-glycoprotein) were used, whereas for the measurement of $k_{off}$, higher concentrations of ligate were employed (1 μM) to avoid any rebinding artefacts. The binding parameters $k_{on}$ and $k_{off}$ were calculated from the association and dissociation phases of the binding reactions, respectively, using the non-linear curve-fitting FastFit software (Affinity Sensors) provided with the instrument. The dissociation constant ($K_d$) was calculated from the association and dissociation rate constants and from the extent of binding observed near equilibrium.

Example 2

Methods

Virus Isolation

The child, who was living in Amsterdam, was admitted to the hospital with complaints of coryza and conjunctivitis since 3 days. At admission she had shortness of breath and refused to drink. The patient's temperature was 39° C., the respiratory rate was 50 breaths/min with oxygen saturation of 96% and her pulse was 177 beats/min. Upon auscultation bilateral prolonged expirium and end-expiratory wheezing was found. A chest radiograph showed the typical features of bronchiolitis. The child was treated with salbutamol and ipratropium at the first day, followed by the use of salbutamol only for 5 days. The child was seen daily at the out patient clinic and the symptoms gradually decreased. A nasopharyngeal aspirate was collected 5 days after the onset of symptoms. The specimen was tested for the presence of RSV, adenovirus, influenza A and B virus, and parainfluenza virus type 1, 2 and 3 using the Virus Respiratory Kit (Bartels: Trinity Biotech plc, Wicklow Ireland). In addition, PCR tests for rhinoviruses, enterovirus, meta-pneumovirus and HCoV-OC43 and HCoV-229E were performed (2, 10). The original nasopharyngeal aspirate was inoculated onto a variety of cells. The cultures were kept in a roller drum at 34° C. and observed every 3 to 4 days. Maintenance medium was replenished every 3 to 4 days. Two different types of medium were implemented: Optimem 1 (InVitrogen, Breda, The Netherlands) without bovine fetal serum was used for the tMK cells and MEM Hanks'/Earle's medium (InVitrogen, Breda, The Netherlands) with 3% bovine fetal serum was used for the remaining cell types. Cell cultures that were infected with the aspirate specimen were stained for the presence of respiratory viruses after one week of incubation. Direct staining was performed with pools of fluorescent-labeled mouse antibodies against RSV and influenza A and B virus (Imagen, DakoCytomation Ltd, Cambridge, UK). Indirect staining was performed for adenoviruses and parainfluenza virus type 1, 2 or 3 with mouse antibodies (Chemicon International, Temecula, Calif.) and subsequent staining with FITC-labeled rabbit anti-mouse antibodies (Imagen, DakoCytomation Ltd, Cambridge, UK).

VIDISCA Method

To remove residual cells and mitochondria, 110 ill of virus culture supernatant was spun down for 10 min at maximum speed in an eppendorf microcentrifuge (13500 rpm). To remove chromosomal DNA and mitochondrial DNA from the lysed cells, 100 μl was transferred to a fresh tube and treated with DNAse I for 45 min at 37° C. (Ambion, Huntingdon, UK). Nucleic acids were extracted as described by Boom et al. (4). A reverse transcription reaction was performed with random hexamer primers (Amersham Bioscience, Roosendaal, The Netherlands) and MMLV-RT (InVitrogen, Breda The Netherlands) while second strand DNA synthesis was carried out with Sequenase II (Amersham Bioscience, Roosendaal, The Netherlands). A phenol/chloroform extraction was followed by an ethanol precipitation. The cDNA-AFLP was performed essentially as described by Bachem et al (1) with some modifications. The dsDNA was digested with the HinP I and Mse I restriction enzymes (New England Biolabs, Beverly, Mass.). Mse I- and HinP I-anchors (see below) were subsequently added with 5U ligase enzyme (InVitrogen, Breda, The Netherlands) in the supplied ligase buffer for 2 hrs at 37° C. The Mse I- and HinP I-anchors were prepared by mixing a top strand oligo (5'-CTCGTAGACTGCGTACC-3' (SEQ. ID. NO: 3) for the Mse I anchor and 5'-GACGATGAGTCCTGAC-3' (SEQ. ID. NO: 4) for the HinP I anchor) with a bottom strand oligo (5'-TAGGTACGCAGTC-3' (SEQ. ID. NO: 5) for the Mse I anchor and 5'-CGGTCAGGACTCAT-3' (SEQ. ID. NO: 6) for the HinP I anchor) in a 1:40 dilution of ligase buffer. A 20 cycle PCR was performed with 10 I of the ligation mixture, 100 ng HinP I standard primer (5'-GACGATGAGTCCTGACCGC-3' (SEQ. ID. NO: 7)) and 100 ng Mse I standard primer (5'-CTCGTAGACTGCGTACCTAA-3' (SEQ. ID. NO: 1)). Five I of this PCR product was used as input in the second "selective" amplification step with 100 ng HinPI-N primer and 100 ng MseI-N (the "N" denotes that the standard primers are extended with one nucleotide: G, A, T or C). The selective rounds of amplification were done with a "touch down PCR": 10 cycles of [60 sec 94° C.-30 sec 65° C.-1 min 72° C.] and the annealing temperature was reduced with 1° C. each cycle, followed by 23 cycles: [30 sec 94° C.-30 sec 56° C.-1 min 72° C.] and 1 cycle 10 min 72° C. The PCR products were analyzed on 4% Metaphor® agarose gels (Cambrex, Rockland, Me.) and the fragments of interest were cloned and sequenced using BigDye terminator reagents. Electrophoresis and data collection was performed on an ABI 377 instrument.

cDNA Library Construction and Full Genome Sequencing

The cDNA library was produced as described by Marra et al[17], with minor modifications. During reverse transcription only random hexamer primers were used and no oligo-dT primer, and the amplified cDNA was cloned into PCR2.1-TOPO TA cloning vector. Colonies were picked and suspended in BHI media. The *E. coli* suspension was used as input in a PCR amplification using T7 and M13 RP for amplification. The PCR products were subsequently sequenced with the same primers that were used in the PCR-amplification and the BigDye terminator reagent. Electrophoresis and data collection was performed on an ABI 377 instrument. Sequences were assembled using the AutoAssembler DNA sequence Assembly software version 2.0.

Diagnostic RT-PCR

From 492 persons a total of 600 respiratory samples collected between December 2002 and August 2002. The kind of material ranged from oral/nasopharyngeal aspirate, throat swabs, bronchioalveolary lavages and sputum. The samples were collected for routine virus diagnostic screening of persons suffering from upper and lower respiratory tract disease. One hundred 1 of the sample was used in a Boom extraction (4). The reverse transcription was performed with MMLV-RT (InVitrogen) using 10 ng or reverse transcription primer (repSZ-RT: 5'-CCACTATAAC-3' (SEQ. ID. NO: 9)). The entire RT mixture was added to the first PCR mixture containing 100 ng of primer repSZ-1 (5'-GTGATGCATATGCTAATTTG-3' (SEQ. ID. NO: 10)) and 100 ng of primer repSZ-3 (5'-CTCTTGCAGGTATAATCCTA-3' (SEQ. ID. NO: 11)). The PCR reaction was performed according to the profile 5 min 95 C; 20 cycles of: 1min 95° C.-1min 55° C.-2 min 72° C.; 10 min 72° C. A nested PCR was started using 5 S1 of the first PCR with 100 ng of primer repSZ-2 (5'-TTGGTAAACAAAAGATAACT-3' (SEQ. ID. NO: 12)) and 100 ng of primer repSZ-4 (5'-TCAATGCTATAAACAGTCAT-3' (SEQ. ID. NO: 13)). Twenty-five PCR cycles were performed of the same profile as the first PCR. Ten µl of the PCR products was analyzed by agarose gel electrophoresis. All positive samples were sequenced to confirm the presence of HCoV-NL63 in the sample.

Sequence Analysis

Sequences were compared to all sequences in the Genbank database using the BLAST tool of the NCBI. For phylogenetic analysis the sequences were aligned using the ClustalX software package with the following settings: Gap opening penalties: 10.00; Gap extension penalty 0.20; Delay divergent sequences switch at 30% and transition weight 0.5 (9). Phylogenetic analysis was carried out using the neighbor-joining method of the MEGA program (5) using the information of all fragments within one gene. The nucleotide distance matrix was generated either by Kimura's 2 parameter estimation or by the p-distance estimation (6). Bootstrap resampling (500 replicates) was employed to place approximate confidence limits on individual branches.

Results

Virus Isolation from a Child with Acute Respiratory Disease

In January 2003 a 7-month-old child appeared in the hospital with coryza, conjunctivitis and fever. Chest radiography showed typical features of bronchiolitis and a nasopharyngeal aspirate specimen was collected five days after the onset of disease (sample NL63). Diagnostic tests for respiratory syncytial virus (RSV), adenovirus, influenza A and B virus, parainfluenza virus type 1, 2 and 3, rhinovirus, enterovirus, HCoV-229E and HCoV-OC43 remained negative. The clinical sample was subsequently inoculated onto human fetal lung fibroblasts (HFL), tertiary monkey kidney cells (tMK; Cynomolgus monkey) and HeLa cells. CPE was detected exclusively on tMK cells and first noted at eight days post-inoculation. The CPE was diffuse with a refractive appearance in the affected cells followed by cell detachment after 7 days. More pronounced CPE was observed upon passage onto the monkey kidney cell line LLC-MK2 with overall cell rounding and moderate cell enlargement (FIG. 1). Additional subcultures on HFL, rhabdomyosarcoma cells and Vero cells remained negative for CPE. Immunofluorescent assays to detect RSV, adenovirus, influenza A and B virus, or parainfluenza virus type 1, 2 and 3 in the culture remained negative. Acid lability and chloroform sensitivity tests demonstrated that the virus is most likely enveloped and not a member of the picornavirus group[24].

Virus Discovery by the VIDISCA Method

Identification of unknown pathogens by molecular biology tools encounters the problem that the target sequence is not known and that genome specific PCR-primers cannot be designed. To overcome this problem we developed the VIDISCA method that is based on the cDNA-AFLP technique[4]. The advantage of VIDISCA is that prior knowledge of the sequence is not required as the presence of restriction enzyme sites is sufficient to guarantee amplification. The input sample can be either blood plasma/serum or culture supernatant. Whereas cDNA-AFLP starts with isolated mRNA, the VIDISCA technique begins with a treatment to selectively enrich for viral nucleic acid, which includes a centrifugation step to remove residual cells and mitochondria. In addition, a DNAse treatment is used to remove interfering chromosomal DNA and mitochondrial DNA from degraded cells, whereas viral nucleic acid is protected within the viral particle. Finally, by choosing frequently cutting restriction enzymes, the method is fine-tuned such that most viruses will be amplified. Using VIDISCA we were able to amplify viral nucleic acids from EDTA-plasma of a person with hepatitis B virus infection and a person with an acute parvovirus B19 infection. The technique can also detect HIV-1 in cell culture, demonstrating its capacity to identify both RNA and DNA viruses.

The supernatant of the CPE-positive culture NL63 was analyzed by VIDISCA. We used the supernatant of uninfected cells as a control. After the second PCR amplification step, unique and prominent DNA fragments were present in the test sample but not in the control. These fragments were cloned and sequenced. Twelve out of 16 fragments showed sequence similarity to members of the family of coronaviruses, but significant sequence divergence was apparent in all fragments. These results indicate that we identified a novel coronavirus (HCoV-NL63).

Detection of HCoV-NL63 in Patient Specimens

To demonstrate that HCoV-NL63 originated from the nasopharyngeal aspirate of the child, we designed a diagnostic RT-PCR that specifically detects HCoV-NL63. This test, based on unique sequences within the 1b gene, confirmed the presence of HCoV-NL63 in the clinical sample. The sequence of this PCR product was identical to that of the virus identified upon in vitro passage in LLC-MK2 cells (results not shown).

Having confirmed that the cultured coronavirus originated from the child, the question remains whether this is an isolated clinical case or whether HCoV-NL63 is circulating in humans. To address this question, we examined respiratory specimens of hospitalized persons and individuals visiting the outpatient clinic between December 2002 and August 2003 for the presence of HCoV-NL63. We identified 7 additional persons that carried HCoV-NL63. Sequence analysis of the PCR products indicated the presence of a few characteristic (and reproducible) point mutations in several samples, suggesting that several subgroups of NL63 may co-circulate. At least 5 of the HCoV-NL63-positive individuals suffered from a respiratory tract illness, the clinical data of 2 persons were not available. Including the index case, five patients were children less than 1 year old and 3 patients were adults. Two adults are likely to be immuno-suppressed, as one of them is a bone marrow transplant recipient, and the other is an HIV positive patient suffering from AIDS with very low CD4 cell counts. No clinical data of the third adult was available. Only 1 patient had a co-infection with RSV (nr 72), and the HIV-infected patient (nr 466) carried *Pneumocystis carinii*.

No other respiratory agent was found in the other HCoV-NL63-positive patients, suggesting that the respiratory symptoms were caused by HCoV-NL63. All HCoV-NL63 positive samples were collected during the last winter season, with a detection frequency of 7% in January 2003. None of the 306 samples collected in the spring and summer of 2003 contained the virus (P<0.01, 2-tailed t-test).

Complete Genome Analysis of HCoV-NL63

The genomes of coronaviruses have a characteristic, genome organization. The 5' half contains the large 1a and 1b genes, encoding the non-structural polyproteins, followed by the genes coding for four structural proteins: spike (S), membrane (M), envelope (E) and the nucleocapsid (N) protein. Additional non-structural proteins are encoded either between 1b and the S gene, between the S and E gene, between the M and N gene or downstream of the N gene.

To determine whether the HCoV-NL63 genome organization shares these characteristics, we constructed a cDNA library with a purified virus stock as input material. A total of 475 genome fragments were analyzed, with an average coverage of 7 sequences per nucleotide. Specific PCRs were designed to fill in gaps and to sequence regions with low quality sequence data. Combined with 5'RACE (Rapid Amplification of cDNA Ends) and 3'RACE experiments the complete HCoV-NL63 genome sequence was resolved.

The genome of HCoV-NL63 is a 27,553-nucleotide RNA with a poly A tail. With a G-C content of 34% it has the lowest G-C content among the coronaviridae, which range from 37%-42%[25]. ZCurve software was used to identify ORFs[26] and the genome configuration is portrayed using the similarity with known coronaviruses (FIG. 6). The 1a and 1b genes encode the RNA polymerase and proteases that are essential for virus replication. A potential pseudoknot structure is present at position 12439, which may provide the −1 frameshift signal to translate the 1b polyprotein. Genes predicted to encode the S, E, M and N proteins are found in the 3' part of the genome. Short untranslated regions (UTRs) of 286 and 287 nucleotides are present at the 5' and 3' termini, respectively. The hemagglutinin-esterase gene, which is present in some group 2 and group 3 coronaviruses, was not present. ORF 3 between the S and E gene probably encodes a single accessory non-structural protein.

The 1a and 1ab polyproteins are translated from the genomic RNA, but the remaining viral proteins are translated from subgenomic mRNAs (sg mRNA), each with a common 5' end derived from the 5' part of the genome (the 5' leader sequence) and 3' coterminal parts. The sg mRNA are made by discontinuous transcription during negative strand synthesis[27]. Discontinuous transcription requires base-pairing between cis-acting transcription regulatory sequences (TRSs), one located near the 5' part of the genome (the leader TRS) and others located upstream of the respective ORFs (the body TRSs)[28]. The cDNA bank that we used for sequencing contained copies of sg mRNA of the N protein, thus providing the opportunity to exactly map the leader sequence that is fused to all sg mRNAs. A leader of 72 nucleotides was identified at the 5' UTR. The leader TRS (5'-UCUCAACUAAAC-3' (SEQ. ID. NO: 14)) showed 11/12-nucleotide similarity with the body TRS upstream of the N gene. A putative TRS was also identified upstream of the S, ORF 3, E and M gene.

The sequence of HCoV-NL63 was aligned with the complete genomes of other coronaviruses. The percentage nucleotide identity was determined for each gene. For all genes except the M gene, the percentage identity was the highest with HCoV-229E. To confirm that HCoV-NL63 is a new member of the group 1 coronaviruses, phylogenetic analysis was performed using the nucleotide sequence of the 1A, 1B, S, M and N gene. For each gene analyzed, HCoV-NL63 clustered with the group 1 coronaviruses. The bootstrap values of the subgroup HCoV-NL63/HCoV-229E were 100 for the 1a, 1b and S gene. However, for the M and N gene the bootstrap values of this subcluster decreased (to 78 and 41 respectively) and a subcluster containing HCoV-229E, HCoV-NL63 and PEDV becomes apparent. A phylogenetic analysis could not be performed for the ORF 3 and E gene because the region varied too much between the different coronavirus groups or because the region was too small for analysis, respectively. Bootscan analysis by the Simplot software version 2.5[29] found no signs of recombination (results not shown).

The presence of a single non-structural protein gene between the S and E gene is noteworthy since almost all coronaviruses have 2 or more ORFs in this region, with the exception of PEDV and OC43[30, 31]. Perhaps most remarkable is a large insert of 537 nucleotides in the 5' part of the S gene when compared to HCoV-229E. A Blast search found no similarity of this additional 179-amino acid domain of the spike protein to any coronavirus sequence or any other sequences deposited in GenBank.

Tables

TABLE 1 cDNA- AFLP oligonucleotides for virus discovery

| Oligo | Sequence |
|---|---|
| Top strand MSE adaptor | CTCGTAGACTGCGTACC (SEQ. ID. NO: 3) |
| Top strand for HinP1 adaptor | GACGATGAGTCCTGAC (SEQ. ID. NO: 4) |
| Bottom strand oligo for MSE adaptor | TAGGTACGCAGTC (SEQ. ID. NO: 5) |
| Bottom strand oligo for HinP1 adaptor | CGGTCAGGACTCAT (SEQ. ID. NO: 6) |
| HinPI standard primer | GACGATGAGTCCTGACCGC (SEQ. ID. NO: 7) |
| MseI standard primer | CTCGTAGACTGCGTACCTAA (SEQ. ID. NO: 8) |

TABLE 2

Oligonucleotide for PALM extension of the HCOV-NL63 Sequence

| Oligonucleotide name | Application | Sequence 5'-3' |
|---|---|---|
| JZH2R | 1st PCR | GCTATCATCACAATGGACNNNNNG (SEQ. ID. NO: 15) |

TABLE 3

Nucleotide- and corresponding deduced amino acid sequences

| Fragment | Sequence |
|---|---|
| 163-2 | GTATTGTTTTTGTTGCTTGTGCCCATGCTGCTGTTGATTCTTATGTGCAAAAGCTATGACTGTTTATAGCATTGATAAGTGTACTAGGATTATACCTGCAAGAGCTCGGGTTGAGTGTTATAGTGGCT (SEQ. ID. NO: 16) |

TABLE 3-continued

| Nucleotide- and corresponding deduced amino acid sequences | |
|---|---|
| Fragment | Sequence |
| 163-2 Translation | Replicase polyprotein 1a IVFVACAHAAVDSLCAKAMTVYSIDKCTRIIPARARVECYSG (SEQ. ID. NO: 17) |
| 163-4 | ATGGGTCTAGATATGGCTTGCAAAACTTACTACAGTTACCTACTTTTATTATGTTAGTAATGGTGGTAACAATTGCACTACGGCCGTTATGACCTATTCTAATTTTGGTATTTGTGCTGATGGTTCTTTGATTCCTGTTCGTCC (SEQ. ID. NO: 18) |
| 163-4 Translation | Spike protein GSRYGLQNLLQLPNFYYVSNGGNNCTTAVMTYSNFGICADGSLIPVR (SEQ. ID. NO: 19) |
| 163-9 (3'-UTR) | ATGATAAGGGTTTAGTCTTACACACAATGGTAGGCCAGTGATAGTAAAGTGTAAGTAATTTGCTATCATAT (SEQ. ID. NO: 20) |
| 163-10 | ATGTCAGTGATGCATATGCTAATTTGGTTCCATATTACCAACTTATTGGTAAACAAAAGATAACTACAATACAGGGTCCTCCTGGTAGTGGTAAGTCACATTGTTCCATTGGACTTGGATTGTACTACCCAGGT (SEQ. ID. NO: 21) |
| 163-10 Translation | Replicase polyprotein 1ab VSDAYANLVPYYQLIGKQKITTIQGPPGSGKSHCSIGLGLYYPG (SEQ. ID. NO: 22) |
| 163-11 | ATCTAAACTAAACAAAATGGCTAGTGTAAATTGGGCCGATGACAGAGCTGCTAGGAAGAAATTTCCTCCTCCTTCATTTTACATGCCTCTTTTGGTTAGTTCTGATAAGGCACCATATAGGGTCATTCCCAGGAATCTTGTCCCTATTGGTAAGGGTAATAAAGATGAGCAGATTGGTTATTGGAATGTTCAAGAGCGTTGGCGTAT (SEQ. ID. NO: 23) |
| 163-11 Translation | Nucleocapsid protein SKLNKMASVNWADDRAARKKFPPPSFYMPLLVSSDKAPYRVIPRNLVPIGKGNKDEQIGYWNVQERWR (SEQ. ID. NO: 24) |
| 163-14 | ACAAAAATTTGAATGAGGGTGTTCTTGAATCTTTTTCTGTTACACTTCTTGATAATCAAGAAGATAAGTTTTGGTGTGAAGATTTTTATGCTAGTATGTATGAAAATTCTACAATATTGCAAGCTGCTGGTTTATGTGTTGTTTGTGGTTCACAAACTGTACTTCGTTGTGGTGATTGTCTGCGTAAGCCTATGTTGTGCACTAAAT (SEQ. ID. NO: 25) |
| 163-14 Translation | Replicase polyprotein 1ab KNLNEGVLESFSVTLLDNQEDKFWCEDFYASMYENSTILQAAGLCVVCGSQTVLRCGDCLRKPMLCTK (SEQ. ID. NO: 26) |
| 163-15 | AGGGGGCAACGTGTTGATTTGCCTCCTAAAGTTCATTTTTATTACCTAGGTACTGGACCTCATAAGGACCT (SEQ. ID. NO: 27) |
| 163-15 Translation | Nucleocapsid protein RGQRVDLPPKVHFYYLGTGPHKD (SEQ. ID. NO: 28) |

TABLE 4

| Identification of cDNA-AFLP fragments | |
|---|---|
| Fragment | Identification best Blast hit |
| 163-2 | replicase polyprotein 1ab [Human coronavirus 229E] |
| 163-4 | spike protein [Human coronavirus 229E] |
| 163-9 | 3'UTR Human coronavirus 229E |
| 163-10 | replicase polyprotein 1ab [Human coronavirus 229E] |
| 163-11 | replicase polyprotein 1ab [Human coronavirus 229E] |
| 163-14 | replicase polyprotein 1ab [Human coronavirus 229E] |
| 163-15 | nucleocapsid protein [Human coronavirus 229E] |
| 163-18 | replicase polyprotein 1ab [Human coronavirus 229E] |

TABLE 5

Pairwise nucleotide sequence homologies between the virus of the present invention and different corona (like) viruses in percentages sequence identity (%)

| Fragment | BcoV | MHV | HcoV | PEDV | TGE | SARS | IBV |
|---|---|---|---|---|---|---|---|
| Replicase 1AB 163-2 | 59.6 | 61.2 | 76.7 | 70.5 | 64.3 | 65.8 | 64.3 |
| Spike gene 163-4 | 31.7 | 26.5 | 64.6 | 48.9 | 45.4 | 33.7 | 25.9 |
| 3'UTR 163-9 | 29.5 | 34 | 81.9 | 53.6 | 50 | 31.5 | 38 |
| Replicase 1AB 163-10 | 55.2 | 57.4 | 82 | 73.8 | 69.4 | 64.1 | 65.1 |
| Nucleocapsid 163-11 | 25.5 | 23.8 | 54.9 | 51.5 | 44.6 | 23.3 | 27.6 |
| Replicase 1AB 163-14 | 52.1 | 52.1 | 78.7 | 72.9 | 76.3 | 52.6 | 58.4 |
| Nucleocapsid 163-15 | 29.5 | 35.2 | 71.8 | 63.3 | 60.5 | 25.3 | 45 |
| Replicase 1AB 163-18 | 67.2 | 65.4 | 72.8 | 65.4 | 61.6 | 68.2 | 57 |

TABLE 6

Pairwise deduced amino acid sequence homologies between different corona (like) viruses in percentages sequence identity (%)

| Fragment | BCoV | MHV | HcoV | PEDV | TGE | SARS | IBV |
|---|---|---|---|---|---|---|---|
| Replicase 1AB 163-2 | 55.8 | 53.4 | 88.3 | 79 | 60.4 | 67.4 | 55.8 |
| Spike gene 163-4 | ND | ND | 56.2 | ND | ND | ND | ND |
| Replicase 1AB 163-10 | 51.1 | 53.3 | 93.3 | 86.6 | 80 | 57.7 | 55.5 |
| Nucleocapsid 163-11 | ND | ND | 48.4 | ND | ND | ND | ND |
| Replicase 1AB 163-14 | 50.7 | 50.7 | 86.9 | 78.2 | 78.2 | 46.3 | 47.8 |
| Nucleocapsid 163-15 | ND | ND | 82.6 | ND | ND | ND | ND |
| Nucleocapsid 163-18 | 63.8 | 63.8 | 77.7 | 69.4 | 69.4 | 58.3 | 55.5 |

ND = Not Determined

TABLE 7

| Oligos for specific detection of HcoV-163 | |
|---|---|
| Primer | Sequence |
| repSZ-RT | CCACTATAAC (SEQ. ID. NO: 9) |
| repSZ-1 | GTGATGCATATGCTAATTTG (SEQ. ID. NO: 10) |
| repSZ-2 | TTGGTAAACAAAAGATAACT (SEQ. ID. NO: 12) |
| repSZ-3 | CTCTTGCAGGTATAATCCTA (SEQ. ID. NO: 11) |
| repSZ-4 | TCAATGCTATAAACAGTCAT (SEQ. ID. NO: 13) |

TABLE 8

| Molecule Features | | | |
|---|---|---|---|
| Start | End | Name | Description |
| 287 | 12439 | 1a | ORF-1a |
| 4081 | 4459 | | Pfam 01661 |
| 9104 | 10012 | | 3Cl protease |
| 12433 | 12439 | | Ribosome slippery site |
| 12439 | 20475 | 1b | ORF-1b |
| 14166 | 14490 | | Pfam 00680 |
| 16162 | 16965 | | COG1112, Super family DNA and RNA helicase |
| 16237 | 16914 | | Pfam 01443 Viral helicase |
| 20472 | 24542 | 2 | ORF-2 S(pike)-gene |
| 21099 | 22619 | | S1 Pfam 01601 |
| 22625 | 24539 | | S2 Pfam 01601 |
| 24542 | 25219 | 3 | ORF-3 |
| 24551 | 25174 | | NS3b Pfam 03053 |
| 25200 | 25433 | 4 | ORF-4 Pfam 05780, Coronavirus NS4 E (envelope) protein |
| 25442 | 26122 | 5 | ORF-5 |
| 25442 | 26119 | | Matrix glycoprotein Pfam 01635 M-gene |
| 26133 | 27266 | 6 | ORF-6 |
| 26184 | 27256 | | Nucleocapsid Pfam 00937 N-gene |

Via a −1 frame shift at the ribosome slippery site the 1a ORF is extended to protein of 6729 amino acid residues referred to as 1ab. ORF 1a and 1ab encode two polyproteins that are proteolytically converted to 16 largely uncharacterized enzymes that are involved in RNA replication (for review see Snijder, E. J., P. J. Bredenbeek, J. C. Dobbe, V. Thiel, J. Ziebuhr, L. L. Poon, Y. Guan, M. Rozanov, W. J. Spaan, and A. E. Gorbalenya. 2003. Unique and Conserved Features of Genome and Proteome of SARS-coronavirus, an Early Split-off From the Coronavirus Group 2 Lineage. J. Mol. Biol. 331: 991-1004).

TABLE 9

| Proteins from HcoV-NL63 ORFs | | | |
|---|---|---|---|
| ORF | Number of AA | $M_w$ prediction | |
| 1a | 4060 | 451364 | Polyprotein |
| 1ab | 6729 | 752822 | Polyprotein |
| 2 | 1356 | 149841 | Spike |
| 3 | 225 | 25658 | |
| 4 | 77 | 9177 | Envelope |
| 5 | 226 | 25927 | Matrix |
| 6 | 377 | 42252 | Nucleocapsid |

The $M_w$ prediction does not take into account post-translational modification like glycosylation or cleavage of a signal sequence.

TABLE 10

| Amplification oligonucleotides for HCoV-NL65 S, M and N encoding regions | |
|---|---|
| Primer | Sequence |
| S1 | ACAAGTTTGTACAAAAAAGCAGGCTTC**AAACTTTTCTTGATTTTGCTTGTTTTGCCCC** (SEQ. ID. NO: 31) |
| S2 | ACCACTTTGTACAAGAAAGCTGGGTC**TTGAACGTGGACCTTTTCAAATTCG** (SEQ. ID. NO: 32) |
| M1 | ACAAGTTTGTACAAAAAAGCAGGCTTC**TCTAATAGTAGTGTGCCTCTTTTAGAGG** (SEQ. ID. NO: 33) |
| M2 | ACCACTTTGTACAAGAAAGCTGGGTC**GATTAAATGAAGCAACTTCTC** (SEQ. ID. NO: 34) |
| N1 | ACAAGTTTGTACAAAAAAGCAGGCTTC**GCTAGTGTAAATTGGGCCGATG** (SEQ. ID. NO: 35) |

TABLE 10-continued

| Amplification oligonucleotides for HCoV-NL65 S, M and N encoding regions | |
|---|---|
| Primer | Sequence |
| N2 | ACCACTTTGTACAAGAAAGCTGGGTC**ATGCAAAACCTCGTTGACAATTTCTATAATGGC** (SEQ. ID. NO: 36) |

The S, M and N complementary sequences are indicated in bold print. The remainder of the PCR primers is composed of either in-frame attB1 or attB2 sites

TABLE 11

| Overall full length genome DNA sequence identity | | | | | | | |
|---|---|---|---|---|---|---|---|
| | BCV | HC229E | IBV | SARS | TGV | HCoV-NL63 | HCoV-OC43 |
| BCV | 100 | 46 | 43 | 54 | 40 | 43 | 95 |
| HC229E | | 100 | 50 | 48 | 53 | 65 | 46 |
| IBV | | | 100 | 43 | 46 | 48 | 43 |
| SARS | | | | 100 | 40 | 43 | 53 |
| TGV | | | | | 100 | 55 | 40 |
| HCoV-NL63 | | | | | | 100 | 43 |
| OC43 | | | | | | | 100 |

Overall DNA sequence identity percentages of HCoV-NL63 compared to other coronaviruses. From the SimPlot graph (FIG. 7), comparing HCoV-NL63 (query) with SARS associated coronavirus and HCoV-229E, can be deduced that local sequence identity never exceeds 85%

TABLE 12

| Overall DNA sequence identity Spike encoding region | | | | |
|---|---|---|---|---|
| | OC43 | NL63 | 229E | SARS |
| OC43 | 100 | 46 | 40 | 44 |
| NL63 | | 100 | 59 | 38 |
| 229E | | | 100 | 41 |
| SARS | | | | 100 |

TABLE 13

| Overall DNA sequence identity in 5'UTR | | | | |
|---|---|---|---|---|
| | OC43 | NL63 | 229E | SARS |
| OC43 | 100 | 36 | 34 | 48 |
| NL63 | | 100 | 74 | 33 |
| 229E | | | 100 | 34 |
| SARS | | | | 100 |

BRIEF DESCRIPTION OF THE DRAWINGS

FIG. 1 cDNA-AFLP allows amplification of nucleic acids without any prior sequence information.

Figure 1:
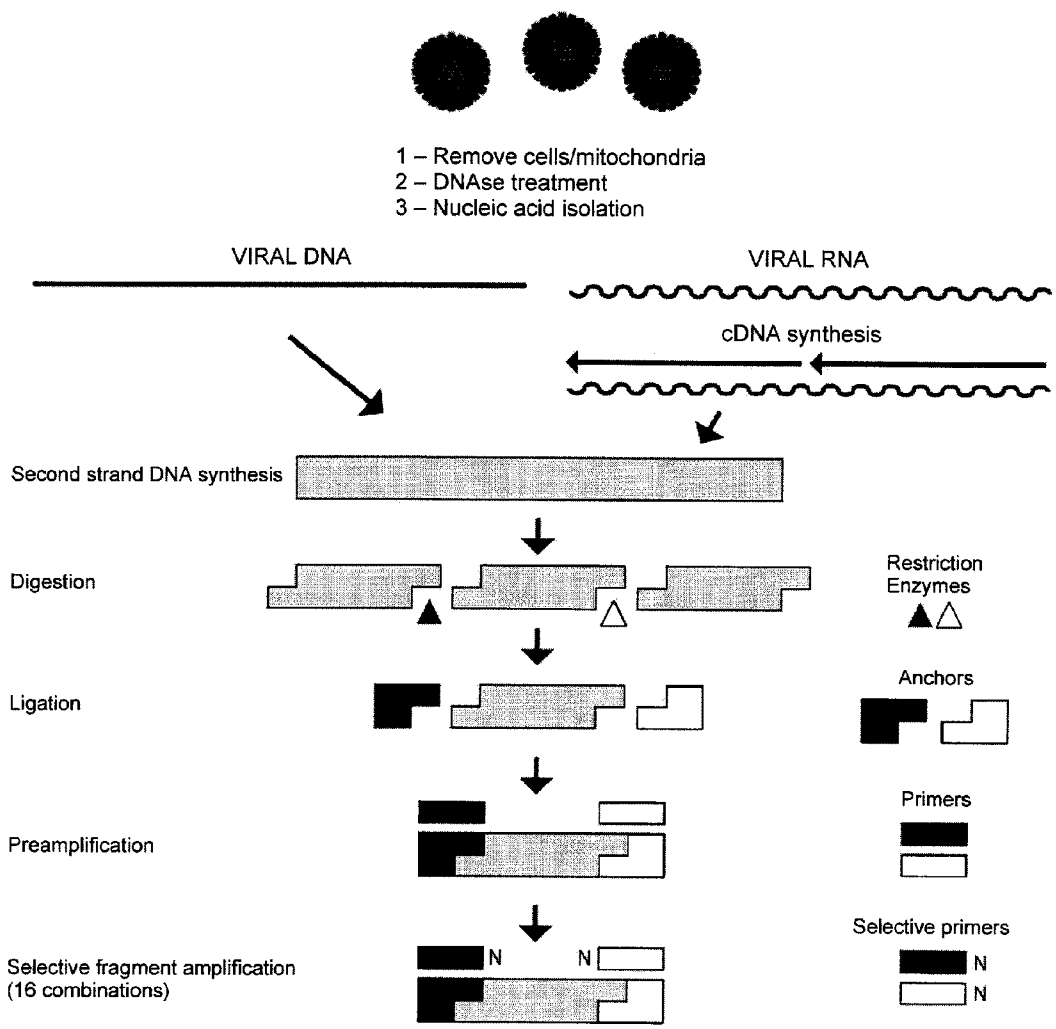
Figure 3:
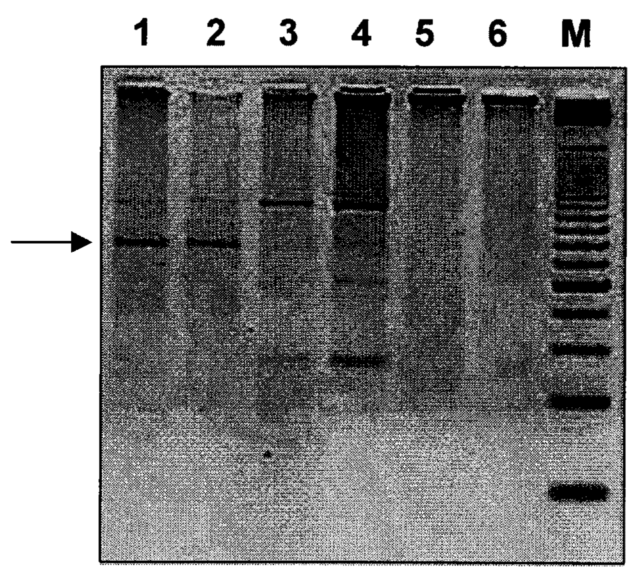
Figure 4:
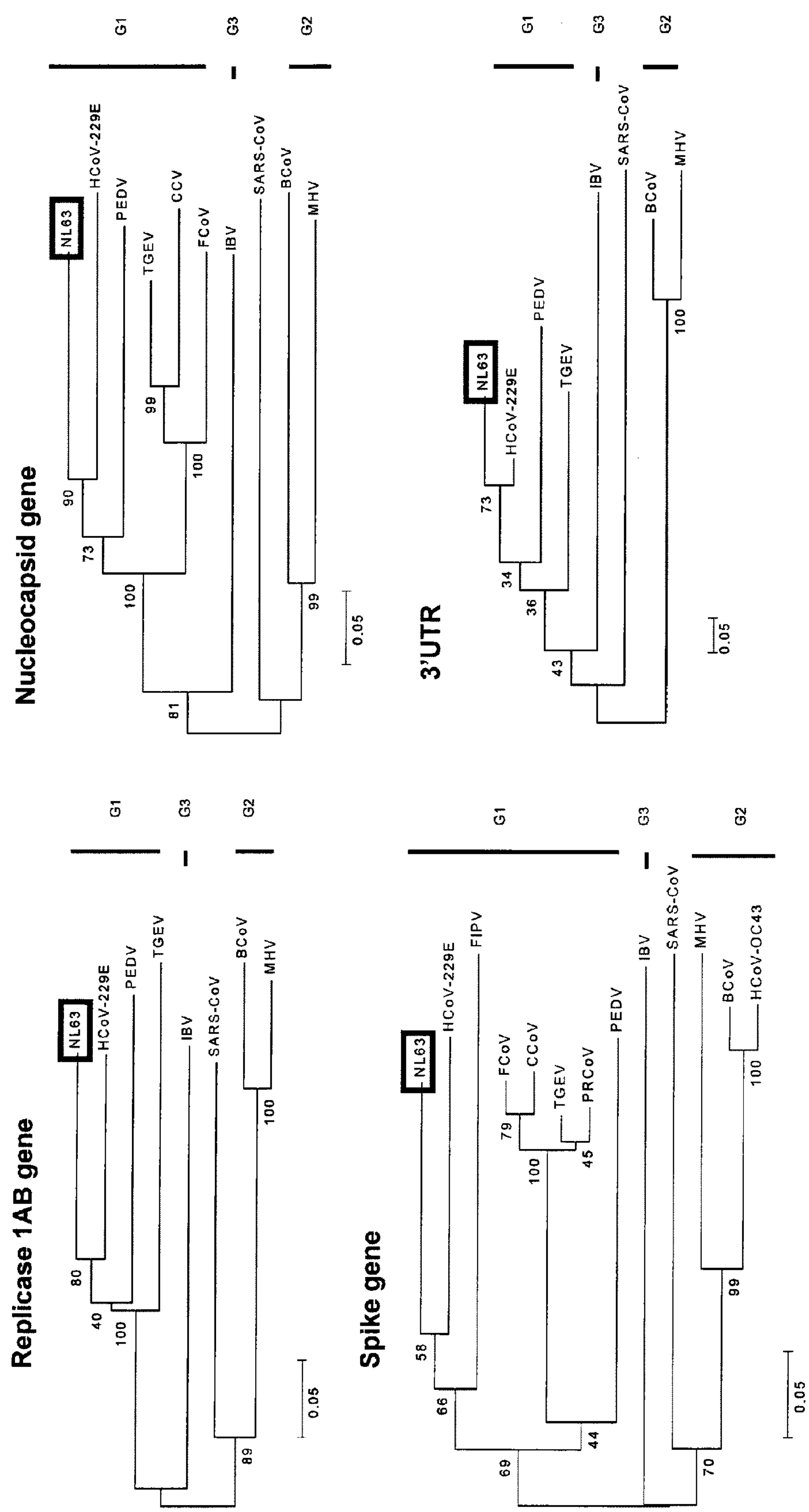
Figure 5:
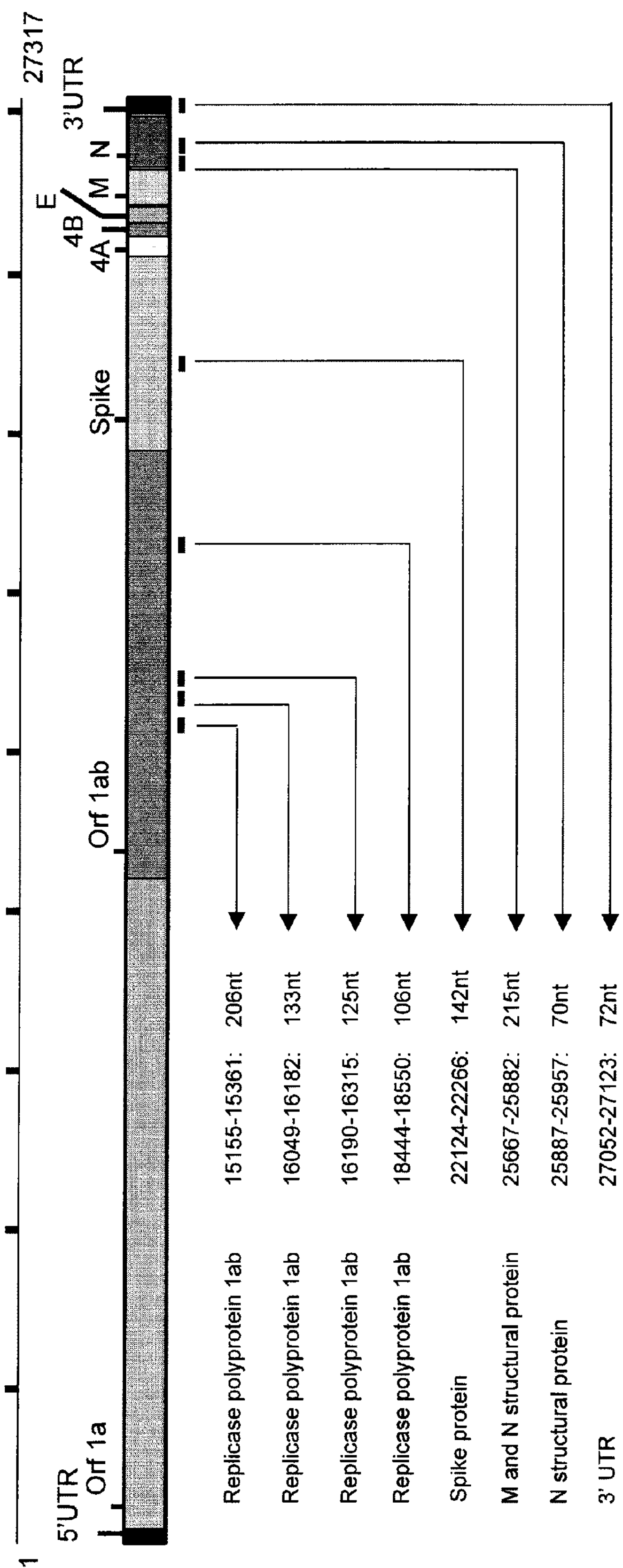
Figure 6:
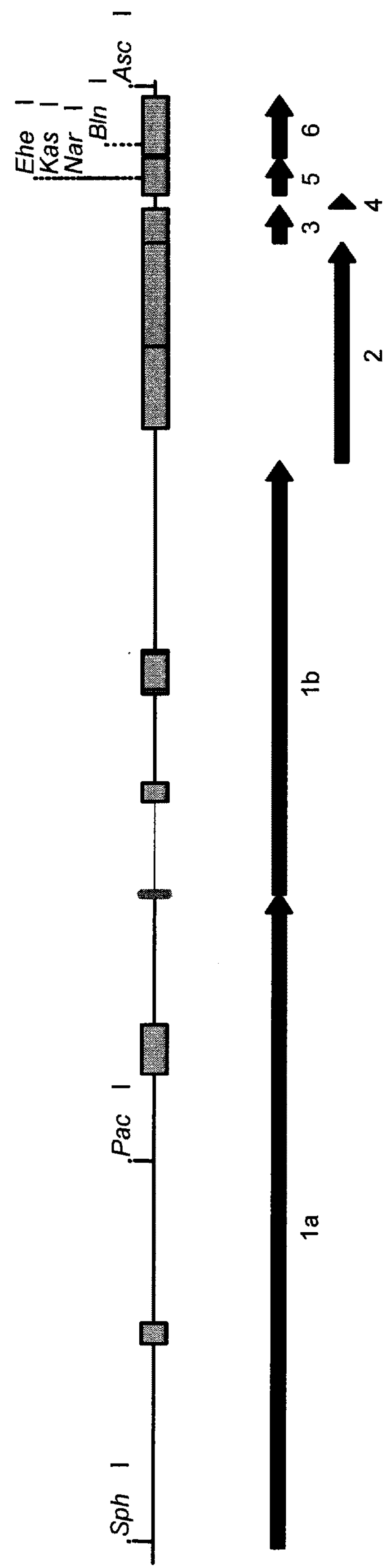
Figure 7:
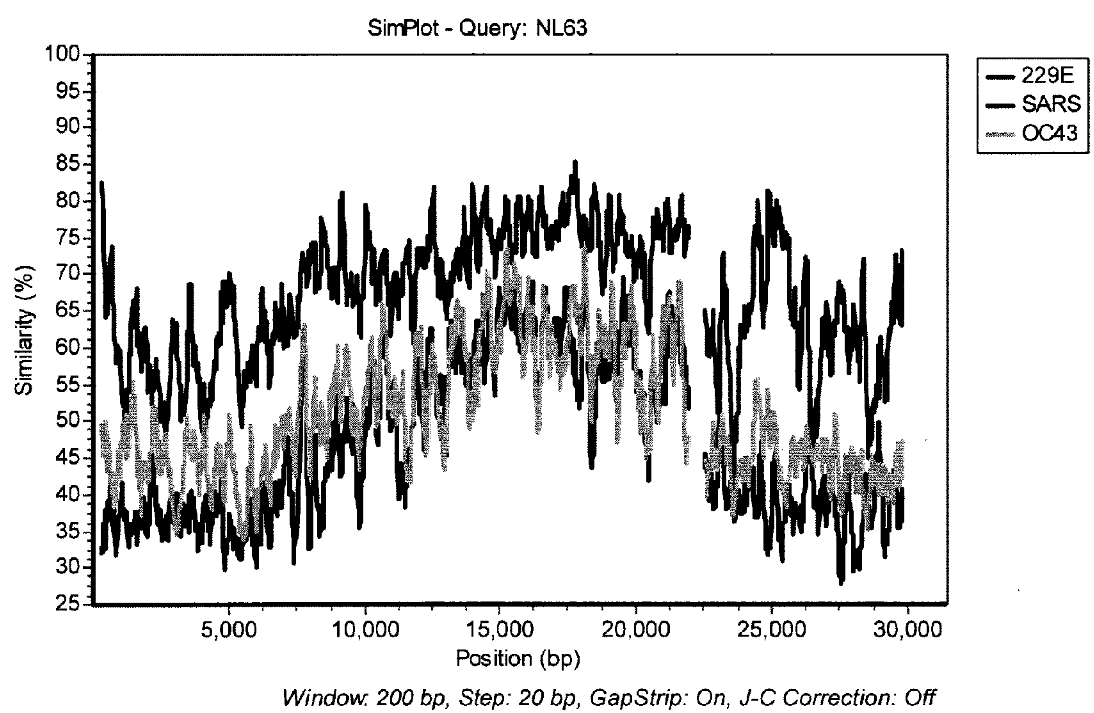
Figure 10:
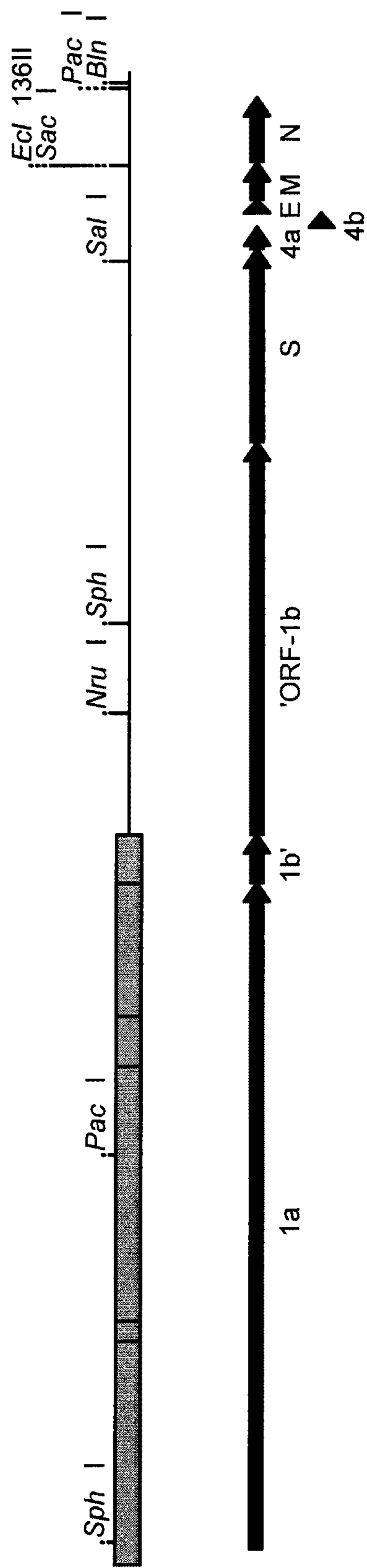

Culture supernatants from CPE-positive and uninfected cells are subjected to the cDNA-AFLP procedure. Amplification products derived from the CPE-positive culture which are not present in the uninfected control sample are cloned and sequenced.

FIG. 2

LLC-MK2 cells infected with HCoV-NL163.

Panel A and B are unstained cells while panel C and D are stained with haematoxilin eosin. The typical CPE of HCoV- NL163 is shown in panel A and C. The control uninfected LLC-MK cells are shown in panel B and D.

FIG. 3

VD-cDNA-AFLP PCR products visualized by Metaphor® agarose gel electrophoreses.

The PCR products of 1 (HinP I-G and Mse I-A) of 16 primer pair combinations used during the selective amplification step. Lanes 1 and 2: duplicate PCR product of virus culture NL163; lanes 5 and 6 control supernatant of LLC-MK2 cells and in lane 7 and 8 the negative PCR control. Lanes M: 25 bp molecular weight marker (InVitrogen). The arrow indicates a new coronavirus fragment that was excised out of gel and sequenced.

FIG. 4

Phylogenetic Analysis of the HCoV-163 Sequences.

G1, G2 and G3 denote the group 1, group 2 and group 3 coronavirus clusters. The Genbank accession number of the used sequences are: MHV (mouse hepatitis virus): AF201929; HCoV-229E: AF304460; PEDV (porcine epidemic diarrhea virus): AF353511; TGEV (transmissible gastroenteritis virus): AJ271965; SARS-CoV: AY278554; IBV (avian infectious bronchitis virus): NC__001451; BCoV (bovine coronavirus): NC__003045; FCoV (feline coronavirus): Y13921 and X80799; CCoV (canine coronavirus): AB105373 and A22732; PRCoV (porcine respiratory coronavirus): M94097; FIPV (feline infectious peritonitis virus): D32044. Position of the HCoV-163 fragments compared to HCoV-229E (AF304460): Replicase 1AB gene: 15155-15361, 16049-16182, 16190-16315, 18444-18550, Spike gene: 22124-22266; Nucleocapsid gene: 25667-25882 and 25887-25957; 3'UTR: 27052-27123. Branch lengths indicate the number of substitutions per sequence.

FIG. 5

Schematic representation of Coronavirus and the location of the 163-fragments listed in table 3.

FIG. 6

Restriction map of HCoV-NL63'

Complete 27553 nt cDNA derivative of the ssRNA genome. Open reading frames (ORF) are depicted as numbered black arrows and the identified (PFAM) domains within these ORFs are indicated as gray boxes.

FIG. 7

Simplot analysis HcoV NL63 and other human Coronaviruses

The gap in the comparison of HCoV NL63 to SARS, HCoV-OC43 and HCoV-229E is cause by a unique 537 in-frame insertion in the Spike protein encoding ORF (see elsewhere herein). Sigmaplot analysis is described in Lole, K. S., R. C. Bollinger, R. S. Paranjape, D. Gadkari, S. S. Kulkarni, N. G. Novak, R. Ingersoll, H. W. Sheppard, and S. C. Ray. 1999. Full-length human immunodeficiency virus type 1 genomes from subtype C-infected seroconverters in India, with evidence of intersubtype recombination. J. Virol. 73:152-160.

FIG. 8

Expression constructs for HCoV-NL63 Spike and Matrix protein Expression of a H is and StrepII tagged Spike fusion protein can be induced by addition of IPTG to the bacterial growth medium. Through attB1/B2-mediated recombination, the S gene insert can be transferred to other commercially available expression vectors, facilitating protein production in other hosts. Through an identical cloning procedure as for pGP7S, a Gateway compatible expression vector for HCoV-NL63 M-gene can be constructed. The plasmid directs IPTG inducible production of N and C-terminally affinity tagged Matrix fusion protein, allowing selective recovery of full-length fusion protein.

FIG. 9

Recombination site NL63-229E (SEQ ID NO: 38)

NL63-derived sequences are in underlined bold black print and the 229E derived sequences are in gray bold print.

FIG. 10

Restriction map cDNA Clone NL63/229E hybrid

The NL63 derived part is indicated as gray boxes and the 229E-derived region is indicated as a line. The junction between the two genomes is indicated by the succession of the two black arrows marked 1b' and 'ORF-1b indicating the hybrid 1b ORF.

A second chimeric genome was generated by a reciprocal recombination fusing nucleotide 19653 of HCoV-NL63 to nucleotide 20682 of HCoV-OC43 again creating a hybrid ORF 1b giving rise to a hybrid 1ab replicase polyprotein. Recombination occurred within the conserved sequence AATTATGG (SEQ. ID. NO: 37).

FIG. 11

Recombination site NL63/OC43 hybrid (SEQ ID NO: 39)

Figure 12:
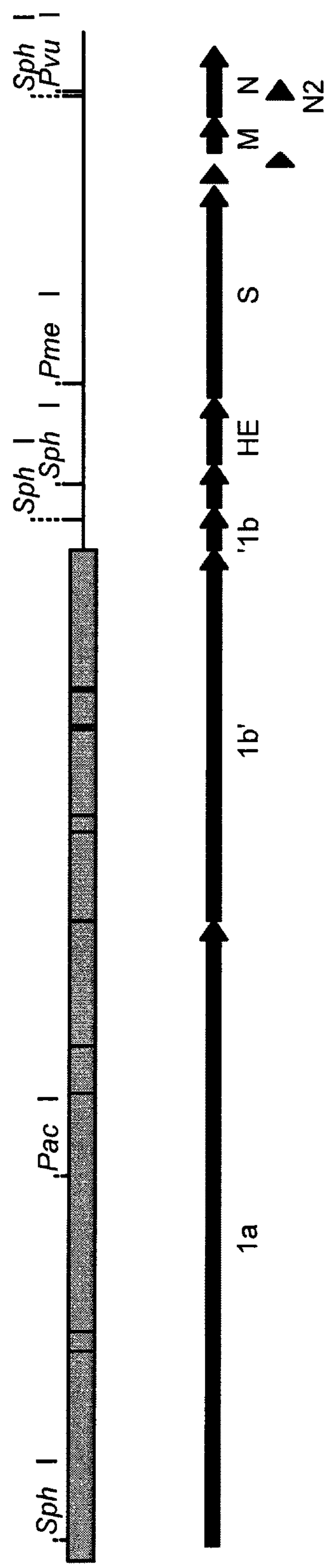
Figure 13:
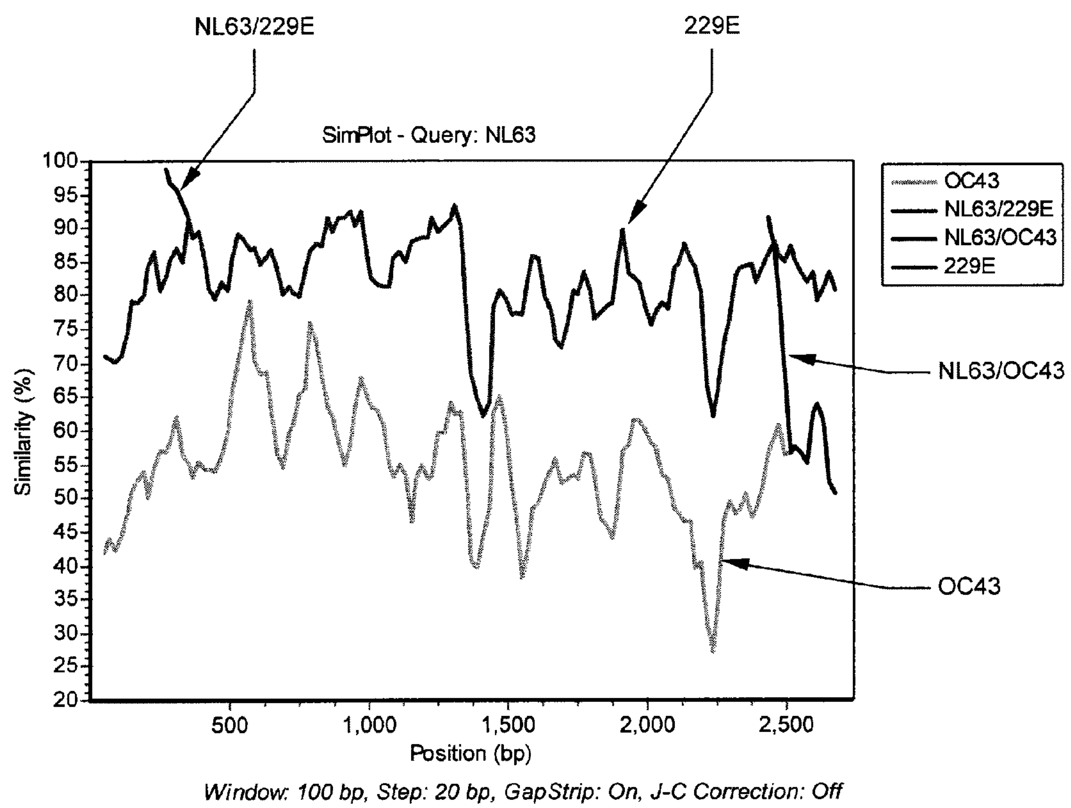
Figure 14:
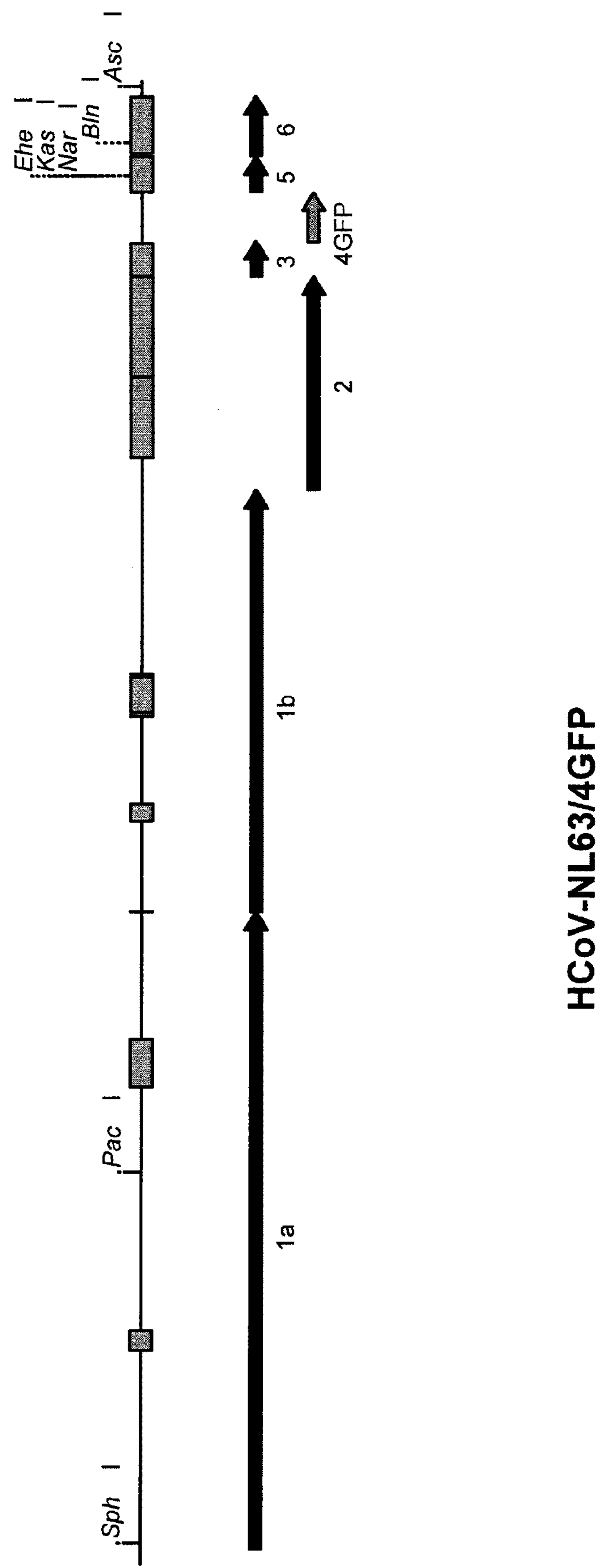
Figure 15:
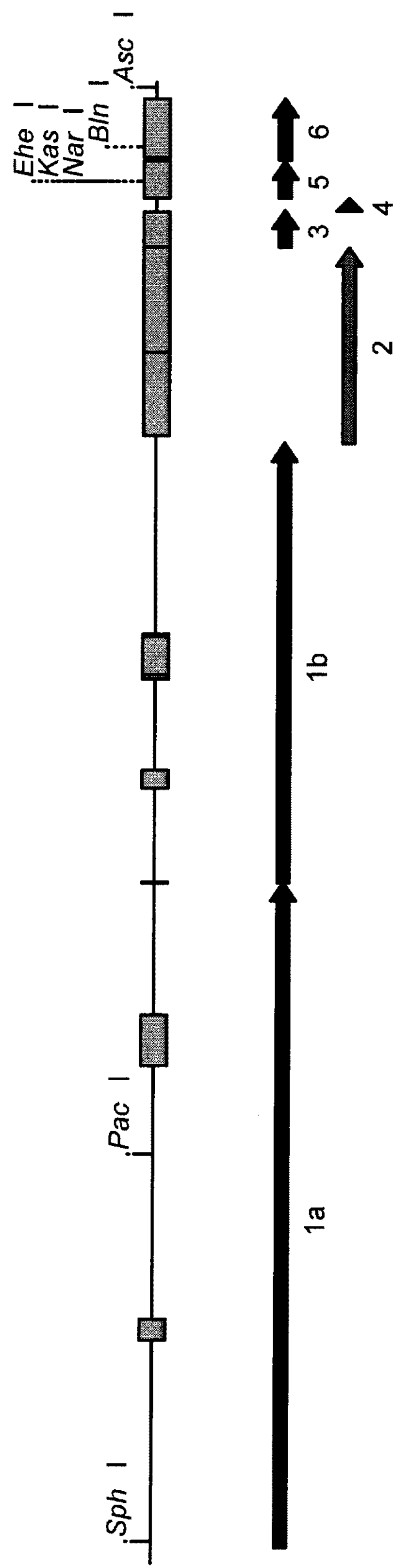

Again, NL63-derived region is in bold black underlined print and the OC43 derived sequences are in gray bold print. The resulting cDNA restriction map is depicted in FIG. 12

FIG. 12

Restriction map recombinant NL63/OC43 genome.

The NL63-derived part is indicated as gray boxes and the recombination site is depicted as the between the black arrows 1b' and '1b.

FIG. 13

Similarity plot deduced protein alignments of ORF1b from HCoV-NL63, HCoV-229E, HCoV-OC43 and the two hybrids NL63/229E and NL63/OC43.

FIG. 14

Green fluorescent protein expressing HcoV-NL63 derivative.

Functional equivalent NL63/4GFP carries an in-frame C-terminal fusion of the E protein (ORF4) with a human codon optimised Green Fluorescent Protein (EGFP, Stratagene). Infected cells appear fluorescent after excitation of the 4-EGFP fusion protein. HCoV-NL63 can be used to elucidate the process of viral; infection and the translation of the polycistronic sub-genomic messengers.

FIG. 15

Restriction map of functional derivative NL63D2052021011.

This deletion derivative of NL63 lacks most of the insertion at the N-terminal end of the Spike protein. By deleting nucleotides 20520-21011 the unique domain is removed while retaining the predicted secretory signal sequence (Nielsen, H., J. Engelbrecht, S. Brunak, and G. Von Heijne. 1997. Identification of prokaryotic and eukaryotic signal peptides and prediction of their cleavage sites. Protein Eng 10:1-6).

FIG. 16

Sequence variation in HCoV-NL63 from additional patient samples

Direct sequencing of both strands of RT-PCR products from 6 patient samples revealed the presence of polymorphisms in the ORF 1a region. REF (SEQ ID NO: 40); 223 B (SEQ ID NO: 41); 246_B (SEQ ID NO: 42); 248_B (SEQ ID NO: 43); 251_B (SEQ ID NO: 44); 466_B (SEQ ID NO: 45); 496_B (SEQ ID NO: 46)

FIG. 17

HCoV-NL63 specific and generic human Coronavirus detection probes. Coronavirus polymerases generate several sub-genomic RNAs. The frequency of S, E, M and N protein encoding cDNA clones in the sequencing library of HCoV-NL63 and SARS (Snijder, E. J., P. J. Bredenbeek, J. C. Dobbe, V. Thiel, J. Ziebuhr, L. L. Poon, Y. Guan, M. Rozanov, W. J.

Spaan, and A. E. Gorbalenya. 2003). Unique and conserved features of genome and proteome of SARS-coronavirus, an early split-off from the coronavirus group 2 lineage. J. Mol. Biol. 331:991-1004). Northern blot data demonstrate a high abundance of these sub-genomic RNAs in infected cells. Consequently, these genes are attractive targets for diagnostic tests.

Since the genomic and sub-genomic RNAs possess identical 3' ends, probes containing the N gene would hybridise to all of them (Table 8).

Through alignment of the full-length sequences of all human Coronaviruses a conserved region in ORF1b was identified, allowing their detection with a nested RT-PCR assay. Oligo NL63NF1 (SEQ ID NO: 47); Oligo NL63NR1 (SEQ ID NO: 48); Oligo NL63NF2 (SEQ ID NO: 49); Oligo NL63NR2 (SEQ ID NO: 50)

FIG. 18

Generic Coronavirus detection primers. Oligo COR1F (SEQ. ID. NO: 51); Oligo COR1R (Seq. ID. NO: 52), Oligo COR2F (SEQ. ID. NO: 53); Oligo COR2R (SEQ. ID. NO: 54)

FIG. 19

Nucleotide sequence an HcoV'_NL63 (SEQ. ID. NO: 55)

FIG. 20

ORF 1a, replicase enzyme complex of an HcoV_NL63 (SEQ. ID. NO: 56)

FIG. 21

ORF 1ab replicase polyprotein of an HcoV_NL63 (SEQ. ID. NO: 57). Adenosine diphosphate-ribose 1'-phosphate (SEQ ID NO: 58). 3CI$^{Pro}$ Coronavirus polyprotein processing endoprotease (SEQ ID NO: 59); RNA dependent RNA polymerase (pfam00680) (SEQ ID NO: 60); Exon 3' to 5' Exonuclease and helicase (SEQ ID NO: 61); XendoU (homolog of) polyU-specific endoribonuclease (SEQ ID NO: 62); 2'-0-MT 2:S-adenosvlmethionine-dependent ribose 2'-orthomethyltransferase (SEQ ID NO: 63)

FIG. 22 (SEQ ID NO: 64)

The spike protein (ORF3) contains an N-terminal secretory signal sequence of 16 AA (indicated on the first line of the continuous sequence listed below). (Nielsen, H., J. Engelbrecht, S. Brunak, and G. Von Heijne. 1997. Identification of prokaryotic and eukaryotic signal peptides and prediction of their cleavage sites. Protein Eng 10:1-6)

FIG. 23

ORF-4 Coronavirus_NS4 (SEQ ID NO: 65), Coronavirus non-structural protein 4. This family consists of several non-structural protein 4 (NS4) sequences or small membrane protein.

ORF-5 (SEQ ID NO: 66). This family consists of various coronavirus matrix proteins that are transmembrane glycoproteins. The M protein or E1 glycoprotein is implicated in virus assembly. The E1 viral membrane protein is required for formation of the viral envelope and is transported via the Golgi complex. The matrix protein is predicted to contain an N-terminal secretory signal sequence (indicated in the first part of the continuous sequence) (Nielsen, H., J. Engelbrecht, S. Brunak, and G. Von Heijne. 1997. Identification of prokaryotic and eukaryotic signal peptides and prediction of their cleavage sites. Protein Eng 10:1-6.)

ORF-6 Pfam 00937 (SEQ ID NO: 67), Coronavirus nucleocapsid protein. Structural protein forming complexes with the genomic RNA.

REFERENCE LIST

1. Bachem, C. W., R. S. van der Hoeven, S. M. de Bruijn, D. Vreugdenhil, M. Zabeau, and R. G. Visser. 1996. Visualization of differential gene expression using a novel method of RNA fingerprinting based on AFLP: analysis of gene expression during potato tuber development. Plant J. 9:745-753.
2. Bestebroer, T. M., A. I. M. Bartelds, A. M. van Loon, H. Boswijk, K. Bijlsma, E. C. J. Claas, J. A. F. W. Kleijne, C. Verweij, M. W. Verweij-Uijterwaal, A. G. Wermenbol, and J. de Jong., Virological NIVEL/RIVM-surveillance of respiratory virus infection in the season 1994/95. 245607002, 1-38. 1995. Bilthoven, RIVM. Virologische NIVEL/RIVM-surveillance van respiratoire virusinfecties in het seizoen 1994/95 RIVM. Ref Type: Report
3. Blondel, B., O. Akacem, R. Crainic, P. Couillin, and F. Horodniceanu. 1983. Detection by monoclonal antibodies of an antigenic determinant critical for poliovirus neutralization present on VP1 and on heat-inactivated virions. Virology 126:707-710.
4. Boom, R., C. J. Sol, M. M. Salimans, C. L. Jansen, P. M. Wertheim-van Dillen, and van der Noordaa J. 1990. Rapid and simple method for purification of nucleic acids. J. Clin. Microbiol. 28:495-503.
5. Kamur, S., Tamura, K., and Wei, M. Molecular Evolutionary Genetics Analysis (MEGA 2.0). 1993. Institute of Molecular Evolutionary Genetics, Pennsylvania State University, University Park. Ref Type: Computer Program
6. Kimura, M. 1980. A simple method for estimating evolutionary rates of base substitutions through comparative studies of nucleotide sequences. J. Mol. Evol. 16:111-120.
7. Kunkel, F. and G. Herrler. 1993. Structural and functional analysis of the surface protein of human coronavirus OC43. Virology 195:195-202.
8. Mounir, S., P. Labonte, and P. J. Talbot. 1993. Characterization of the nonstructural and spike proteins of the human respiratory coronavirus OC43: comparison with bovine enteric coronavirus. Adv. Exp. Med. Biol. 342:61-67.
9. Thompson, J. D., T. J. Gibson, F. Plewniak, F. Jeanmougin, and D. G. Higgins. 1997. The CLUSTAL X windows interface: flexible strategies for multiple sequence alignment aided by quality analysis tools. Nucleic Acids Res. 25:4876-4882.
10. Van Den Hoogen, B. G., J. C. de Jong, J. Groen, T. Kuiken, R. de Groot, R. A. Fouchier, and A. D. Osterhaus. 2001. A newly discovered human pneumovirus isolated from young children with respiratory tract disease. Nat. Med. 7:719-724.
11. Wu, C. N., Y. C. Lin, C. Fann, N. S. Liao, S. R. Shih, and M. S. Ho. 2001. Protection against lethal enterovirus 71 infection in newborn mice by passive immunization with subunit VP1 vaccines and inactivated virus. Vaccine 20:895-904.
13. Almeida, J. D. and D. A. Tyrrell, The morphology of three previously uncharacterized human respiratory viruses that grow in organ culture. J Gen Virol 1, 175-178 (1967).
14. Thiel, V., J. Herold, B. Schelle, and S. G. Siddell, Infectious RNA transcribed in vitro from a cDNA copy of the human coronavirus genome cloned in vaccinia virus. J Gen Virol 82, 1273-1281 (2001).
15. Hendley, J. O., H. B. Fishburne, and J. M. Gwaltney, Jr. Coronavirus infections in working adults. Eight-year study with 229 E and OC 43. Am Rev. Respir. Dis. 105, 805-811 (1972).
16. Mounir, S., P. Labonte, and P. J. Talbot, Characterization of the nonstructural and spike proteins of the human respiratory coronavirus OC43: comparison with bovine enteric coronavirus. Adv. Exp Med Biol 342, 61-67 (1993).

17. Kunkel, F. and G. Herrler, Structural and functional analysis of the surface protein of human coronavirus OC43. Virol. 195, 195-202 (1993).

18. Tyrrell, D. A. J. and M. L. Bynoe, Cultivation of novel type of common-cold virus in organ cultures. Br. Med. J 1, 1467-1470 (1965).

19. Bradburne, A. F., M. L. Bynoe, and D. A. Tyrrell, Effects of a "new" human respiratory virus in volunteers. Br. Med. J 3, 767-769 (1967).

20. Kapikian, A. Z. et al. Isolation from man of "avian infectious bronchitis virus-like" viruses (coronaviruses) similar to 229E virus, with some epidemiological observations. J. Infect. Dis. 119, 282-290 (1969).

21. Ksiazek, T. G. et al. A novel coronavirus associated with severe acute respiratory syndrome. N Engl J Med 2003. May 15.; 348. (20):1953.-66. 348, 1953-1966 (2003).

22. Stohlman, S. A. and D. R. Hinton, Viral induced demyelination. Brain Pathol. 11, 92-106 (2001).

23. Jubelt, B. and J. R. Berger, Does viral disease underlie ALS? Lessons from the AIDS pandemic. Neurology 57, 945-946 (2001).

24. Shingadia, D., A. Bose, and R. Booy, Could a herpesvirus be the cause of Kawasaki disease? Lancet Infect. Dis. 2, 310-313 (2002).

25. Bachem, C. W. et al. Visualization of differential gene expression using a novel method of RNA fingerprinting based on AFLP: analysis of gene expression during potato tuber development. Plant J 9, 745-753 (1996).

26. Hamparian, V. V. Diagnostic procedures for viral, rickettsial and chlamydial infection. Lennette, E. H. & Schmidt, N.J. (eds.), pp. 562 (American Public Health Association, Washington, D.C., 1979).

27. Marra, M. A. et al. The Genome sequence of the SARS-associated coronavirus. Science 2003. May 30.; 300. (5624.):1399.-404. 300, 1399-1404 (2003).

28. McIntosh, K. et al. Coronavirus infection in acute lower respiratory tract disease of infants. J. Infect. Dis. 130, 502-507 (1974).

29. Boivin, G. et al. Human metapneumovirus infections in hospitalized children. Emerg. Infect. Dis. 9, 634-640 (2003).

30. Rota, P. A. et al. Characterization of a novel coronavirus associated with severe acute respiratory syndrome. Science 300, 1394-1399 (2003).

31. Bestebroer, T. M. et al. Virological NIVEL/RIVM-surveillance of respiratory virus infection in the season 1994/95. 245607002, 1-38. 1995. Ref Type: Report 32. van den Hoogen, B. G. et al. A newly discovered human pneumovirus isolated from young children with respiratory tract disease. Nat. Med. 7, 719-724 (2001).

34. Earley, E. M. and K. M. Johnson. 1988. The lineage of Vero, Vero 76 and its clone C1008 in the United States., p. 26-29. In B. Simizu and T. Terasima (eds.), Vero cells: origin, properties and biomedical applications. Chiba Univ, Tokyo.

35. Kamur, S., K. Tamura, and M. Wei, Molecular Evolutionary Genetics Analysis (MEGA). (2.0). 1993. Institute of Molecular Evolutionary Genetics, Pennsylvania State University, University Park. Ref Type: Computer Program 36. Kimura, M. A simple method for estimating evolutionary rates of base substitutions through comparative studies of nucleotide sequences. J Mol. Evol. 16, 111-120 (1980).

37. Fouchier, R. A., T. M. Bestebroer, S. Herfst, K. L. Van Der, G. F. Rimmelzwaan, and A. D. Osterhaus. 2000. Detection of influenza A viruses from different species by PCR amplification of conserved sequences in the matrix gene. J. Clin. Microbiol. 38:4096-4101.

38. Nicaud, J. M., C. Madzak, B. P. van den, C. Gysler, P. Duboc, P. Niederberger, and C. Gaillardin. 2002. Protein expression and secretion in the yeast *Yarrowia lipolytica*. FEM. Yeast Res. 2:371-379.

39. Guy, J. S., Breslin, J. J., Breuhaus, B., Vivrette, S. & Smith, L. G. Characterization of a coronavirus isolated from a diarrheic foal. J Clin Microbiol. 38, 4523-4526 (2000).

40. Holmes, K. V. & Lai, M. M. C. Fields Virology. Fields, B. N., Knipe, D. M., Howley, P. M. & et al (eds.), pp. 1075-1093 (Lippincott-Raven Publishers, Philadelphia, 1996).

41. Hamre, D. & Procknow, J. J. A new virus isolated from the human respiratory tract. proc. soc. exp. biol. med. 121, 190-193 (1966).

42. McIntosh, K., Dees, J. H., Becker, W. B., Kapikian, A. Z. & Chanock, R. M. Recovery in tracheal organ cultures of novel viruses from patients with respiratory disease. Proc. Natl. Acad. Sci. U.S.A. 57, 933-940 (1967).

43. Peiris, J. S. et al. Clinical progression and viral load in a community outbreak of coronavirus-associated SARS pneumonia: a prospective study. lancet 361, 1767-1772 (2003).

44. Snijder, E. J. et al. Unique and conserved features of genome and proteome of SARS-coronavirus, an early split-off from the coronavirus group 2 lineage. J Mol Biol 331, 991-1004 (2003).

45. de Haan, C. A., Masters, P. S., Shen, X., Weiss, S. & Rottier, P. J. The group-specific murine coronavirus genes are not essential, but their deletion, by reverse genetics, is attenuating in the natural host. Virol. 296, 177-189 (2002).

46. Lai, M. M. & Cavanagh, D. The molecular biology of coronaviruses. Adv. Virus Res 48, 1-100 (1997).

47. Sawicki, S. G. & Sawicki, D. L. Coronaviruses use discontinuous extension for synthesis of subgenome-length negative strands. Adv. Exp Med Biol 380, 499-506 (1995).

48. van Marle, G. et al. Arterivirus discontinuous mRNA transcription is guided by base pairing between sense and antisense transcription-regulating sequences. Proc Natl Acad Sci U.S.A. 96, 12056-12061 (1999).

49. Chen, L. L., Ou, H. Y., Zhang, R. & Zhang, C. T. ZCURVE_CoV: a new system to recognize protein coding genes in coronavirus genomes, and its applications in analyzing SARS-CoV genomes. Biochem Biophys. Res Commun. 307, 382-388 (2003).

50. Liu, D. X. & Inglis, S. C. Internal entry of ribosomes on a tricistronic mRNA encoded by infectious bronchitis virus. J Virol 66, 6143-6154 (1992).

51. Thiel, V. & Siddell, S. G. Internal ribosome entry in the coding region of murine hepatitis virus mRNA 5. J Gen Virol 75 (Pt 11), 3041-3046 (1994).

52. Lole, K. S. et al. Full-length human immunodeficiency virus type 1 genomes from subtype C-infected seroconverters in India, with evidence of intersubtype recombination. J Virol 73, 152-160 (1999).

53. Vaughn, E. M., Halbur, P. G. & Paul, P. S. Sequence comparison of porcine respiratory coronavirus isolates reveals heterogeneity in the S, 3, and 3-1 genes. J Virol 69, 3176-3184 (1995).

54. Koren, G., S. King, S. Knowles, and E. Phillips. 2003. Ribavirin in the treatment of SARS: A new trick for an old drug? CMAJ. 168:1289-1292

55. Cinatl, J., B. Morgenstern, G. Bauer, P. Chandra, H. Rabenau, and H. W. Doerr. 2003. Glycyrrhizin, an active component of liquorice roots, and replication of SARS-associated coronavirus. Lancet 361:2045-2046.

56. Anand, K., J. Ziebuhr, P. Wadhwani, J. R. Mesters, and R. Hilgenfeld. 2003. Coronavirus main proteinase (3CLpro) structure: basis for design of anti-SARS drugs. Science 300:1763-1767.

57. Cinatl, J., B. Morgenstern, G. Bauer, P. Chandra, H. Rabenau, and H. W. Doerr. 2003. Treatment of SARS with human interferons. Lancet 362:293-294.

58. von Grotthuss, M., L. S. Wyrwicz, and L. Rychlewski. 2003. mRNA cap-1 methyltransferase in the SARS genome. Cell 113:701-702

59. Boivin, G., G. De Serres, S. Cote, R. Gilca, Y. Abed, L. Rochette, M. G. Bergeron, and P. Dery. 2003. Human metapneumovirus infections in hospitalized children. Emerg. Infect. Dis. 9:634-640.

The invention claimed is:

1. A method for determining whether an individual suffers from an HCoV-NL63 infection, said method comprising:

obtaining a biological sample from the individual, and detecting the presence of HCoV-NL63 virus sequences in said biological sample with a primer and/or probe capable of specifically detecting a HCoV-NL63 virus sequences.

2. The method according to claim 1, wherein said primer and/or probe is capable of specifically hybridizing to a sequence selected from the group consisting of SEQ ID NOS: 16, 18, 20, 21, 23, 25, 27 and 29.

3. The method according to claim 1, wherein said primer and/or probe is capable of specifically hybridizing to a nucleic acid encoding a proteinaceous molecule comprising a sequence selected from the group consisting of SEQ ID NOS: 17, 19, 22, 24, 26, 28 and 30.

4. The method according to claim 3, wherein the proteinaceous molecule comprises SEQ ID NO: 67.

5. A method for detecting an isolated or recombinant HCoV-NL63 virus comprising a nucleic acid sequence that is at least 90% homologous to a HC0V-NL63 nucleic acid sequence in a sample, the method comprising:

hybridizing and/or amplifying a HCoV-NL63 nucleic acid of said sample with a primer and/or probe capable of specifically hybridizing and/or amplifying said HCoV-NL63 nucleic acid, and detecting hybridized and/or amplified product.

6. The method according to claim 5, wherein said primer and/or probe is capable of specifically hybridizing to a sequence selected from the group consisting of SEQ ID NOS: 16, 18, 20, 21, 23, 25, 27 and 29.

7. The method according to claim 5, wherein said primer and/or probe is capable of specifically hybridizing to a nucleic acid encoding a proteinaceous molecule comprising a sequence selected from the group consisting of SEQ ID NOS: 17, 19, 22, 24, 26, 28 and 30.

8. The method according to claim 7, wherein the proteinaceous molecule comprises SEQ ID NO: 67.

9. The method according to claim 5, for diagnosing a HCoV-NL63 coronaviral genus infection.

* * * * *

SEQUENCE LISTING

```
<160> NUMBER OF SEQ ID NOS: 67

<210> SEQ ID NO 1
<211> LENGTH: 6
<212> TYPE: PRT
<213> ORGANISM: Artificial Sequence
<220> FEATURE:
<223> OTHER INFORMATION: Synthetic sequence Hexapeptide

<400> SEQUENCE: 1

Val Asn Ser Thr Leu Gln
1               5


<210> SEQ ID NO 2
<211> LENGTH: 6
<212> TYPE: PRT
<213> ORGANISM: Artificial Sequence
<220> FEATURE:
<223> OTHER INFORMATION: Synthetic sequence.  Hexapeptide

<400> SEQUENCE: 2

Tyr Asn Ser Thr Leu Gln
1               5


<210> SEQ ID NO 3
<211> LENGTH: 17
<212> TYPE: DNA
<213> ORGANISM: Artificial Sequence
<220> FEATURE:
<223> OTHER INFORMATION: Synthetic sequence.  Top strand oligo for MSE
      adaptor

<400> SEQUENCE: 3

ctcgtagact gcgtacc                                                 17


<210> SEQ ID NO 4
<211> LENGTH: 16
<212> TYPE: DNA
<213> ORGANISM: Artificial Sequence
<220> FEATURE:
<223> OTHER INFORMATION: Synthetic sequence.  Top strand oligo for HinP1
      adaptor

<400> SEQUENCE: 4

gacgatgagt cctgac                                                  16


<210> SEQ ID NO 5
<211> LENGTH: 13
<212> TYPE: DNA
<213> ORGANISM: Artificial Sequence
<220> FEATURE:
<223> OTHER INFORMATION: Synthetic sequence.  Bottom strand oligo for
      MSE adaptor

<400> SEQUENCE: 5

taggtacgca gtc                                                     13


<210> SEQ ID NO 6
```

```
<211> LENGTH: 14
<212> TYPE: DNA
<213> ORGANISM: Artificial Sequence
<220> FEATURE:
<223> OTHER INFORMATION: Synthetic sequence.  Bottom strand oligo for
      HinP1 adaptor

<400> SEQUENCE: 6

cggtcaggac tcat                                                     14


<210> SEQ ID NO 7
<211> LENGTH: 19
<212> TYPE: DNA
<213> ORGANISM: Artificial Sequence
<220> FEATURE:
<223> OTHER INFORMATION: Synthetic sequence.  HinP1 standard primer

<400> SEQUENCE: 7

gacgatgagt cctgaccgc                                                19


<210> SEQ ID NO 8
<211> LENGTH: 20
<212> TYPE: DNA
<213> ORGANISM: Artificial Sequence
<220> FEATURE:
<223> OTHER INFORMATION: Synthetic sequence.  MseI standard primer

<400> SEQUENCE: 8

ctcgtagact gcgtacctaa                                               20


<210> SEQ ID NO 9
<211> LENGTH: 10
<212> TYPE: DNA
<213> ORGANISM: Artificial Sequence
<220> FEATURE:
<223> OTHER INFORMATION: Synthetic sequence.  Primer repSZ-RT

<400> SEQUENCE: 9

ccactataac                                                          10


<210> SEQ ID NO 10
<211> LENGTH: 20
<212> TYPE: DNA
<213> ORGANISM: Artificial Sequence
<220> FEATURE:
<223> OTHER INFORMATION: Synthetic sequence.  Primer repSZ-1

<400> SEQUENCE: 10

gtgatgcata tgctaatttg                                               20


<210> SEQ ID NO 11
<211> LENGTH: 20
<212> TYPE: DNA
<213> ORGANISM: Artificial Sequence
<220> FEATURE:
<223> OTHER INFORMATION: Synthetic sequence.  Primer repSZ-3

<400> SEQUENCE: 11

ctcttgcagg tataatccta                                               20


<210> SEQ ID NO 12
<211> LENGTH: 20
<212> TYPE: DNA
<213> ORGANISM: Artificial Sequence
<220> FEATURE:
<223> OTHER INFORMATION: Synthetic sequence.  Primer repSZ-2
```

<400> SEQUENCE: 12
ttggtaaaca aaagataact 20

<210> SEQ ID NO 13
<211> LENGTH: 20
<212> TYPE: DNA
<213> ORGANISM: Artificial Sequence
<220> FEATURE:
<223> OTHER INFORMATION: Synthetic sequence. Primer repSZ-4

<400> SEQUENCE: 13
tcaatgctat aaacagtcat 20

<210> SEQ ID NO 14
<211> LENGTH: 12
<212> TYPE: RNA
<213> ORGANISM: Artificial Sequence
<220> FEATURE:
<223> OTHER INFORMATION: Synthetic sequence. Leader TRS

<400> SEQUENCE: 14
ucucaacuaa ac 12

<210> SEQ ID NO 15
<211> LENGTH: 24
<212> TYPE: DNA
<213> ORGANISM: Artificial Sequence
<220> FEATURE:
<223> OTHER INFORMATION: Synthetic sequence. Oligonucleotide JZH2R
<220> FEATURE:
<221> NAME/KEY: misc_feature
<222> LOCATION: (19)..(24)
<223> OTHER INFORMATION: “n” stands for any nucleic acid

<400> SEQUENCE: 15
gctatcatca caatggacnn nnng 24

<210> SEQ ID NO 16
<211> LENGTH: 129
<212> TYPE: DNA
<213> ORGANISM: Human Coronavirus 229E

<400> SEQUENCE: 16
gtattgtttt tgttgcttgt gcccatgctg ctgttgattc cttatgtgca aaagctatga 60
ctgtttatag cattgataag tgtactagga ttatacctgc aagagctcgg gttgagtgtt 120
atagtggct 129

<210> SEQ ID NO 17
<211> LENGTH: 42
<212> TYPE: PRT
<213> ORGANISM: Human Coronavirus 229E

<400> SEQUENCE: 17

Ile Val Phe Val Ala Cys Ala His Ala Ala Val Asp Ser Leu Cys Ala
1 5 10 15

Lys Ala Met Thr Val Tyr Ser Ile Asp Lys Cys Thr Arg Ile Ile Pro
20 25 30

Ala Arg Ala Arg Val Glu Cys Tyr Ser Gly
35 40

<210> SEQ ID NO 18
<211> LENGTH: 145
<212> TYPE: DNA

<213> ORGANISM: Human Coronavirus 229E

<400> SEQUENCE: 18

```
atgggtctag atatggcttg caaaacttac tacagttacc taacttttat tatgttagta     60

atggtggtaa caattgcact acggccgtta tgacctattc taattttggt atttgtgctg    120

atggttcttt gattcctgtt cgtcc                                         145
```

<210> SEQ ID NO 19
<211> LENGTH: 47
<212> TYPE: PRT
<213> ORGANISM: Human Coronavirus 229E

<400> SEQUENCE: 19

```
Gly Ser Arg Tyr Gly Leu Gln Asn Leu Leu Gln Leu Pro Asn Phe Tyr
1               5                   10                  15

Tyr Val Ser Asn Gly Gly Asn Asn Cys Thr Thr Ala Val Met Thr Tyr
            20                  25                  30

Ser Asn Phe Gly Ile Cys Ala Asp Gly Ser Leu Ile Pro Val Arg
        35                  40                  45
```

<210> SEQ ID NO 20
<211> LENGTH: 71
<212> TYPE: DNA
<213> ORGANISM: Human Coronavirus 229E

<400> SEQUENCE: 20

```
atgataaggg tttagtctta cacacaatgg taggccagtg atagtaaagt gtaagtaatt     60

tgctatcata t                                                          71
```

<210> SEQ ID NO 21
<211> LENGTH: 134
<212> TYPE: DNA
<213> ORGANISM: Human Coronavirus 229E

<400> SEQUENCE: 21

```
atgtcagtga tgcatatgct aatttggttc catattacca acttattggt aaacaaaaga     60

taactacaat acagggtcct cctggtagtg gtaagtcaca ttgttccatt ggacttggat    120

tgtactaccc aggt                                                      134
```

<210> SEQ ID NO 22
<211> LENGTH: 44
<212> TYPE: PRT
<213> ORGANISM: Human Coronavirus 229E

<400> SEQUENCE: 22

```
Val Ser Asp Ala Tyr Ala Asn Leu Val Pro Tyr Tyr Gln Leu Ile Gly
1               5                   10                  15

Lys Gln Lys Ile Thr Thr Ile Gln Gly Pro Pro Gly Ser Gly Lys Ser
            20                  25                  30

His Cys Ser Ile Gly Leu Gly Leu Tyr Tyr Pro Gly
        35                  40
```

<210> SEQ ID NO 23
<211> LENGTH: 207
<212> TYPE: DNA
<213> ORGANISM: Human Coronavirus 229E

<400> SEQUENCE: 23

```
atctaaacta aacaaaatgg ctagtgtaaa ttgggccgat gacagagctg ctaggaagaa     60
```

```
atttcctcct ccttcatttt acatgcctct tttggttagt tctgataagg caccatatag    120

ggtcattccc aggaatcttg tccctattgg taagggtaat aaagatgagc agattggtta    180

ttggaatgtt caagagcgtt ggcgtat                                         207


<210> SEQ ID NO 24
<211> LENGTH: 68
<212> TYPE: PRT
<213> ORGANISM: Human Coronavirus 229E

<400> SEQUENCE: 24

Ser Lys Leu Asn Lys Met Ala Ser Val Asn Trp Ala Asp Asp Arg Ala
1               5                   10                  15

Ala Arg Lys Lys Phe Pro Pro Pro Ser Phe Tyr Met Pro Leu Leu Val
            20                  25                  30

Ser Ser Asp Lys Ala Pro Tyr Arg Val Ile Pro Arg Asn Leu Val Pro
        35                  40                  45

Ile Gly Lys Gly Asn Lys Asp Glu Gln Ile Gly Tyr Trp Asn Val Gln
    50                  55                  60

Glu Arg Trp Arg
65


<210> SEQ ID NO 25
<211> LENGTH: 207
<212> TYPE: DNA
<213> ORGANISM: Human Coronavirus 229E

<400> SEQUENCE: 25

acaaaaattt gaatgagggt gttcttgaat ctttttctgt tacacttctt gataatcaag     60

aagataagtt ttggtgtgaa gatttttatg ctagtatgta tgaaaattct acaatattgc    120

aagctgctgg tttatgtgtt gtttgtggtt cacaaactgt acttcgttgt ggtgattgtc    180

tgcgtaagcc tatgttgtgc actaaat                                         207


<210> SEQ ID NO 26
<211> LENGTH: 68
<212> TYPE: PRT
<213> ORGANISM: Human Coronavirus 229E

<400> SEQUENCE: 26

Lys Asn Leu Asn Glu Gly Val Leu Glu Ser Phe Ser Val Thr Leu Leu
1               5                   10                  15

Asp Asn Gln Glu Asp Lys Phe Trp Cys Glu Asp Phe Tyr Ala Ser Met
            20                  25                  30

Tyr Glu Asn Ser Thr Ile Leu Gln Ala Ala Gly Leu Cys Val Val Cys
        35                  40                  45

Gly Ser Gln Thr Val Leu Arg Cys Gly Asp Cys Leu Arg Lys Pro Met
    50                  55                  60

Leu Cys Thr Lys
65


<210> SEQ ID NO 27
<211> LENGTH: 71
<212> TYPE: DNA
<213> ORGANISM: Human Coronavirus 229E

<400> SEQUENCE: 27

agggggcaac gtgttgattt gcctcctaaa gttcattttt attacctagg tactggacct     60
```

cataaggacc t 71

<210> SEQ ID NO 28
<211> LENGTH: 23
<212> TYPE: PRT
<213> ORGANISM: Human Coronavirus 229E

<400> SEQUENCE: 28

Arg Gly Gln Arg Val Asp Leu Pro Pro Lys Val His Phe Tyr Tyr Leu
1 5 10 15

Gly Thr Gly Pro His Lys Asp
20

<210> SEQ ID NO 29
<211> LENGTH: 107
<212> TYPE: DNA
<213> ORGANISM: Human Coronavirus 229E

<400> SEQUENCE: 29
tagtagttgt gttactcgtt gtaatatagg tggtgctgtt tgttcaaaac atgcaaattt 60
gtatcaaaaa tacgttgagg catataatac atttacacag gcaggtt 107

<210> SEQ ID NO 30
<211> LENGTH: 35
<212> TYPE: PRT
<213> ORGANISM: Human Coronavirus 229E

<400> SEQUENCE: 30

Ser Ser Cys Val Thr Arg Cys Asn Ile Gly Gly Ala Val Cys Ser Lys
1 5 10 15

His Ala Asn Leu Tyr Gln Lys Tyr Val Glu Ala Tyr Asn Thr Phe Thr
20 25 30

Gln Ala Gly
35

<210> SEQ ID NO 31
<211> LENGTH: 58
<212> TYPE: DNA
<213> ORGANISM: Artificial Sequence
<220> FEATURE:
<223> OTHER INFORMATION: Synthetic sequence. Primer S1

<400> SEQUENCE: 31
acaagtttgt acaaaaaagc aggcttcaaa cttttcttga ttttgcttgt tttgcccc 58

<210> SEQ ID NO 32
<211> LENGTH: 51
<212> TYPE: DNA
<213> ORGANISM: Artificial Sequence
<220> FEATURE:
<223> OTHER INFORMATION: Synthetic sequence. Primer S2

<400> SEQUENCE: 32
accactttgt acaagaaagc tgggtcttga acgtggacct tttcaaattc g 51

<210> SEQ ID NO 33
<211> LENGTH: 55
<212> TYPE: DNA
<213> ORGANISM: Artificial Sequence
<220> FEATURE:
<223> OTHER INFORMATION: Synthetic sequence. Primer M1

<400> SEQUENCE: 33

```
acaagtttgt acaaaaaagc aggcttctct aatagtagtg tgcctctttt agagg         55


<210> SEQ ID NO 34
<211> LENGTH: 47
<212> TYPE: DNA
<213> ORGANISM: Artificial Sequence
<220> FEATURE:
<223> OTHER INFORMATION: Synthetic sequence.  Primer M2

<400> SEQUENCE: 34

accactttgt acaagaaagc tgggtcgatt aaatgaagca acttctc                 47


<210> SEQ ID NO 35
<211> LENGTH: 49
<212> TYPE: DNA
<213> ORGANISM: Artificial Sequence
<220> FEATURE:
<223> OTHER INFORMATION: Synthetic sequence.  Primer N1

<400> SEQUENCE: 35

acaagtttgt acaaaaaagc aggcttcgct agtgtaaatt gggccgatg               49


<210> SEQ ID NO 36
<211> LENGTH: 59
<212> TYPE: DNA
<213> ORGANISM: Artificial Sequence
<220> FEATURE:
<223> OTHER INFORMATION: Synthetic sequence.  Primer N2

<400> SEQUENCE: 36

accactttgt acaagaaagc tgggtcatgc aaaacctcgt tgacaatttc tataatggc     59


<210> SEQ ID NO 37
<211> LENGTH: 8
<212> TYPE: DNA
<213> ORGANISM: Artificial Sequence
<220> FEATURE:
<223> OTHER INFORMATION: Synthetic sequence.  Conserved sequence

<400> SEQUENCE: 37

aattatgg                                                              8


<210> SEQ ID NO 38
<211> LENGTH: 69
<212> TYPE: DNA
<213> ORGANISM: Artificial Sequence
<220> FEATURE:
<223> OTHER INFORMATION: Synthetic sequence.  Recombination site NL63-
      229E

<400> SEQUENCE: 38

tcatcctaat tgttgtgact gttatgatga tatgtgtgtt atacattgtt caaattttaa    60

cacactctt                                                            69


<210> SEQ ID NO 39
<211> LENGTH: 60
<212> TYPE: DNA
<213> ORGANISM: Artificial Sequence
<220> FEATURE:
<223> OTHER INFORMATION: Synthetic sequence.  Recombination site
      NL63/OC43 hybrid

<400> SEQUENCE: 39

caacgtatgt gtttggaacc ttgtaattta tataattatg ggaagccagt tactttgcct    60
```

```
<210> SEQ ID NO 40
<211> LENGTH: 466
<212> TYPE: DNA
<213> ORGANISM: Artificial Sequence
<220> FEATURE:
<223> OTHER INFORMATION: Synthetic sequence.  Sequence REF

<400> SEQUENCE: 40

taataatgct gtctatgatg gtgctcgttt attttcttca gatttgtcta ctttagctgt     60

tacagctatt gttgtagtag gtggttgtgt aacatctaat gttccaacaa ttgttagtga    120

gaaaatttct gttatggata aacttgatac tggtgcacaa aaatttttcc aatttggtga    180

ttttgttatg aataacattg ttctgttttt aacttggttg cttagtatgt ttagtctttt    240

acgtacttct attatgaagc atgatattaa agttattgcc aaggctccta aacgtacagg    300

tgttattttg acacgtagtt ttaagtataa cattagatct gctttgtttg ttataaagca    360

gaagtggtgt gttattgtta ctttgtttaa gttcttatta ttattatatg ctatttatgc    420

acttgttttt atgattgtgc aatttagtcc ttttaatagt ctttta                   466


<210> SEQ ID NO 41
<211> LENGTH: 466
<212> TYPE: DNA
<213> ORGANISM: Artificial Sequence
<220> FEATURE:
<223> OTHER INFORMATION: Synthetic sequence.  Sequence 223B

<400> SEQUENCE: 41

taataatgct gtctatgatg gtgctcgttt atctgcttca gatttgtcta ctttagctgt     60

tacagctatt gttgtagtag gtggttgtgt aacatctaat gttccaccaa ttgttagtga    120

gaaaatttct gttatggata aacttgatac tggtgcacaa aaatttttcc aatttggtga    180

ttttgttatg aataacattg ttctgttttt aacttggttg cttagtatgt ttagtctttt    240

acgtacttct attatgaagc atgatattaa agttattgcc aaggctccta aacgtacagg    300

tgttattttg acacgtagtt ttaagtataa cattagatct gctttgtttg ttgtaaagca    360

gaagtggtgt gttattgtta ctttgtttaa gttcttattg ttattatatg ctatttatgc    420

acttgttttt atgattgtgc aatttagtcc ttttaatagt ctttta                   466


<210> SEQ ID NO 42
<211> LENGTH: 466
<212> TYPE: DNA
<213> ORGANISM: Artificial Sequence
<220> FEATURE:
<223> OTHER INFORMATION: Synthetic sequence.  Sequence 246B

<400> SEQUENCE: 42

taataatgct gtctatgatg gtgctcgttt attttcttca gatttgtcta ctttagctgt     60

tacagctatt gttgtagtag gtggttgtgt aacatctaat gttccaccaa ttgttagtga    120

gaaaatttct gttatggata aacttgatac tggtgcacaa aaatttttcc aatttggtga    180

ttttgttatg aataacattg ttctgttttt aacttggttg cttagtatgt ttagtctttt    240

acgtacttct attatgaagc atgatattaa agttattgcc aaggctccta aacgtacagg    300

tgttattttg acacgtagtt ttaagtataa cattagatct gctttgtttg ttataaagca    360

gaagtggtgt gttattgtta ctttgtttaa gttcttattg ttattatatg ctatttatgc    420

acttgttttt atgattgtgc aatttagtcc ttttaatagt ctttta                   466


<210> SEQ ID NO 43
```

<211> LENGTH: 466
<212> TYPE: DNA
<213> ORGANISM: Artificial Sequence
<220> FEATURE:
<223> OTHER INFORMATION: Synthetic sequence. Sequence 248B

<400> SEQUENCE: 43

```
taataatgct gtctatgatg gtgctcgttt atttgcttca gatttgtcta ctttagctgt     60

tacagctatt gttgtagtag gtggttgtgt aacatctaat gttccaccaa ttgttagtga    120

gaaaatttct gttatggata aacttgatac tggtgcacaa aaatttttcc aatttggtga    180

ttttgttatg aataacattg ttctgttttt aacttggttg cttagtatgt ttagtctttt    240

acgtacttct attatgaagc atgatattaa agttattgcc aaggctccta aacgtacagg    300

tgttattttg acacgtagtt ttaagtataa cattagatct gctttgtttg ttgtaaagca    360

gaagtggtgt gttattgtta ctttgtttaa gttcttattg ttattatatg ctatttatgc    420

acttgttttt atgattgtgc aatttagtcc ttttaatagt ctttta                   466
```

<210> SEQ ID NO 44
<211> LENGTH: 466
<212> TYPE: DNA
<213> ORGANISM: Artificial Sequence
<220> FEATURE:
<223> OTHER INFORMATION: Synthetic sequence. Sequence 251B

<400> SEQUENCE: 44

```
taataatgct gtctatgatg gtgctcgttt attttcttca gatttgtcta ctttagctgt     60

tacagctatt gttgtagtag gtggttgtgt aacatctaat gttccaccaa ttgttagtga    120

gaaaatttct gttatggata aacttgatac tggtgcacaa aaatttttcc aatttggtga    180

ttttgttatg aataacattg ttctgttttt aacttggttg cttagtatgt ttagtctttt    240

acgtacttct attatgaagc atgatattaa agttattgcc aaggctccta aacgtacagg    300

tgttattttg acacgtagtt ttaagtataa cattagatct gctttgtttg ttataaagca    360

gaagtggtgt gttattgtta ctttgtttaa gttcttatta ttattatatg ctatttatgc    420

acttgttttt atgattgtgc aatttagtcc ttttaatagt ctttta                   466
```

<210> SEQ ID NO 45
<211> LENGTH: 466
<212> TYPE: DNA
<213> ORGANISM: Artificial Sequence
<220> FEATURE:
<223> OTHER INFORMATION: Synthetic sequence. Sequence 466B

<400> SEQUENCE: 45

```
taataatgct gtctatgatg gtgctcgttt attttcttca gatttgtcta ctttagctgt     60

tacagctatt gttgtagtag gtggttgtgt aacatctaat gttccaacaa ttgttagtga    120

gaaaatttct gttatggata aacttgatac tggtgcacaa aaatttttcc aatttggtga    180

ttttgttatg aataacattg ttctgttttt aacttggttg cttagtatgt ttagtctttt    240

acgtacttct attatgaagc atgatattaa agttattgcc aaggctccta aacgtacagg    300

tgttattttg acacgtagtt ttaagtataa cattagatct gctttgtttg ttataaagca    360

gaagtggtgt gttattgtta ctttgtttaa gttcttatta ttattatatg ctatttatgc    420

acttgttttt atgattgtgc aatttagtcc ttttaatagt ctttta                   466
```

<210> SEQ ID NO 46
<211> LENGTH: 466

<212> TYPE: DNA
<213> ORGANISM: Artificial Sequence
<220> FEATURE:
<223> OTHER INFORMATION: Synthetic sequence. Sequence 496B

<400> SEQUENCE: 46
taataatgct gtctatgatg gtgctcgttt atttgcttca gatttgtcta ctttagctgt 60
tacagctatt gttgtagtag gtggttgtgt aacatctaat gttccatcaa ttgttagtga 120
gaaaatttct gttatggata aacttgatac tggtgcacaa aaatttttcc aatttggtga 180
ttttgttatg aataacattg ttctgttttt aacttggttg cttagtatgt ttagtctttt 240
acgtacttct attatgaagc atgatattaa agttattgcc aaggctccta aacgtacagg 300
tgttattttg acacgtagtt ttaagtataa cattagatct gctttgtttg ttataaagca 360
gaagtggtgt gttattgtta ctttgtttaa gttcttattg ttattatatg ctatttatgc 420
acttgttttt atgattgtgc aatttagtcc ttttaatagt ctttta 466

<210> SEQ ID NO 47
<211> LENGTH: 22
<212> TYPE: DNA
<213> ORGANISM: Artificial Sequence
<220> FEATURE:
<223> OTHER INFORMATION: Synthetic sequence. Oligo NL63NF1

<400> SEQUENCE: 47
gctagtgtaa attgggccga tg 22

<210> SEQ ID NO 48
<211> LENGTH: 24
<212> TYPE: DNA
<213> ORGANISM: Artificial Sequence
<220> FEATURE:
<223> OTHER INFORMATION: Synthetic sequence. Oligo NL63NR1

<400> SEQUENCE: 48
cttccaacga ggtttcttca actg 24

<210> SEQ ID NO 49
<211> LENGTH: 24
<212> TYPE: DNA
<213> ORGANISM: Artificial Sequence
<220> FEATURE:
<223> OTHER INFORMATION: Synthetic sequence. Oligo NL63NF2

<400> SEQUENCE: 49
tcctcctcct tcattttaca tgcc 24

<210> SEQ ID NO 50
<211> LENGTH: 25
<212> TYPE: DNA
<213> ORGANISM: Artificial Sequence
<220> FEATURE:
<223> OTHER INFORMATION: Synthetic sequence. Oligo NL63NR2

<400> SEQUENCE: 50
aactcaacaa cagagagctc tggag 25

<210> SEQ ID NO 51
<211> LENGTH: 26
<212> TYPE: DNA
<213> ORGANISM: Artificial Sequence
<220> FEATURE:
<223> OTHER INFORMATION: Synthetic sequence. Oligo COR1F
<220> FEATURE:

<221> NAME/KEY: misc_feature
<222> LOCATION: (18)..(18)
<223> OTHER INFORMATION: "n" stands for "i"

<400> SEQUENCE: 51
atgggwtggg aytatccnaa rtgtga 26

<210> SEQ ID NO 52
<211> LENGTH: 25
<212> TYPE: DNA
<213> ORGANISM: Artificial Sequence
<220> FEATURE:
<223> OTHER INFORMATION: Synthetic sequence. Oligo COR1R

<400> SEQUENCE: 52
gytgkgarca raaytcrtgw ggtcc 25

<210> SEQ ID NO 53
<211> LENGTH: 20
<212> TYPE: DNA
<213> ORGANISM: Artificial Sequence
<220> FEATURE:
<223> OTHER INFORMATION: Synthetic sequence. Oligo COR2F
<220> FEATURE:
<221> NAME/KEY: misc_feature
<222> LOCATION: (18)..(18)
<223> OTHER INFORMATION: "n" stands for "i"

<400> SEQUENCE: 53
tatkttaarc cwggtggnac 20

<210> SEQ ID NO 54
<211> LENGTH: 24
<212> TYPE: DNA
<213> ORGANISM: Artificial Sequence
<220> FEATURE:
<223> OTHER INFORMATION: Synthetic sequence. Oligo COR2R
<220> FEATURE:
<221> NAME/KEY: misc_feature
<222> LOCATION: (7)..(7)
<223> OTHER INFORMATION: "n" stands for unkown nucleic acid

<400> SEQUENCE: 54
catraanacr yyattytgrt aata 24

<210> SEQ ID NO 55
<211> LENGTH: 27553
<212> TYPE: DNA
<213> ORGANISM: Human coronavirus NL63

<400> SEQUENCE: 55
cttaaagaat ttttctatct atagatagag aattttctta tttagacttt gtgtctactc 60
ttctcaacta aacgaaattt ttctagtgct gtcatttgtt atggcagtcc tagtgtaatt 120
gaaatttcgt caagtttgta aactggttag gcaagtgttg tattttctgt gtctaagcac 180
tggtgattct gttcactagt gcatacattg atatttaagt ggtgttccgt cactgcttat 240
tgtggaagca acgttctgtc gttgtggaaa ccaataactg ctaaccatgt tttacaatca 300
agtgacactt gctgttgcaa gtgattcgga aatttcaggt tttggttttg ccattccttc 360
tgtagccgtt cgcacctata gcgaagccgc tgcacaaggt tttcaggcat gccgttttgt 420
tgcttttggc ttacaggatt gtgtaaccgg tattaatgat gatgattatg tcattgcatt 480
gactggtact aatcagctct gtgccaaaat tttacctttt tctgatagac cccttaattt 540
gcgaggttgg ctcatttttt ctaacagcaa ttatgttctt caggactttg atgttgtttt 600

```
tggccatggt gcaggaagtg tggtttttgt ggataagtac atgtgtggtt ttgatggtaa    660
acctgtgtta cctaaaaaca tgtgggaatt tagggattac tttaataata atactgatag    720
tattgttatt ggtggtgtca cttatcaact agcatgggat gttatacgta aagacctttc    780
ttatgaacag caaaatgttt tagccattga gagcattcat taccttggta ctacaggtca    840
tactttgaag tctggttgca aacttactaa tgctaagccg cctaaatatt cttctaaggt    900
tgttttgagt ggtgaatgga atgctgtgta tagggcgttt ggttcaccat ttattacaaa    960
tggtatgtca ttgctagata taattgttaa accagttttc tttaatgctt ttgttaaatg   1020
caattgtggt tctgagagtt ggagtgttgg tgcatgggat ggttacttat cttcttgttg   1080
tggcacacct gctaagaaac tttgtgttgt tcctggtaat gtcgttcctg gtgatgtgat   1140
catcacctca actagtgctg gttgtggtgt taaatactat gctggcttag ttgttaaaca   1200
tattactaac attactggtg tgtctttatg gcgtgttaca gctgttcatt ctgatggaat   1260
gtttgtggca tcatcttctt atgatgcact cttgcataga aattcattag accctttttg   1320
ctttgatgtt aacactttac tttctaatca attacgtcta gcttttcttg gtgcttctgt   1380
tacagaagat gttaaatttg ctgctagcac tggtgttatt gacattagtg ctggtatgtt   1440
tggtctttac gatgacatat tgacaaacaa taaaccttgg tttgtacgca aagcttctgg   1500
gctttttgat gcaatctggg atgcttttgt tgccgctatt aagcttgtac caactactac   1560
tggtgttttg gttaggtttg ttaagtctat tgcttcaact gttttaactg tctctaatgg   1620
tgttattatt atgtgtgcag atgttccaga tgcttttcaa tcagtttatc gcacatttac   1680
acaagctatt tgtgctgcat ttgatttttc tttagatgta tttaaaattg gtgatgttaa   1740
atttaaacga cttggtgatt atgttcttac tgaaaacgct cttgttcgtt tgactactga   1800
agttgttcgt ggtgttcgtg atgctcgcat aaagaaagcc atgtttacta aagtagttgt   1860
aggtcctaca actgaagtta agttttctgt tattgaactt gccactgtta atttgcgtct   1920
tgttgattgt gcacctgtag tttgccctaa aggtaagatt gttgttattg ctggacaagc   1980
tttttctat agtggtggtt tttatcgttt tatggttgat cctacaactg tattaaatga   2040
tcctgttttt actggtgatt tattctacac tattaagttt agtggtttta agcttgatgg   2100
ttttaaccat cagtttgtta ctgctagttc tgctacagat gccattattg ctgttgagct   2160
gttgttattg gattttaaaa ctgcagtttt tgtgtacaca tgtgtggttg atggctgtag   2220
tgtcattgtt agacgtgatg ctacattcgc tacacatgtg tgttttaagg actgttataa   2280
tgtttgggag caattctgca ttgataattg tggtgagcca tggtttttga ctgattataa   2340
tgctatcttg cagagtaata accctcaatg tgctattgtt caagcatcag agtctaaagt   2400
tttgcttgag aggtttttac ctaagtgtcc tgaaatactg ttgagtattg atgatggcca   2460
tttatggaat ctttttgttg aaaagtttaa ttttgttaca gattggttaa aaactcttaa   2520
gcttacactt acttctaatg gtcttttagg taattgtgcc aaacgtttta gacgtgtttt   2580
ggtaaaattg cttgatgtct ataatggttt tcttgaaact gtctgtagtg tcgcatacac   2640
tgctggtgtt tgcatcaaat attatgctgt taatgttcca tatgtagtta ttagtggttt   2700
tgtaagtcgt gtaattcgta gagaaaggtg tgacatgact ttccttgtg ttagttgtgt   2760
caccttttc tatgaatttt tagacacttg ttttggtgtt agtaaaccta atgccattga   2820
tgttgaacat ttagagctta aagaaactgt tttgttgaa cctaaggatg gtggtcaatt   2880
ttttgtttct ggtgattatc tttggtatgt tgtagatgac atttattatc cagcttcatg   2940
```

taatggtgta ttgcctgttg cttttacaaa attagctggt ggtaaaatat ctttttctga 3000
tgatgttata gttcatgatg ttgaacctac ccataaagtc aagctcatat ttgagtttga 3060
agatgatgtt gttaccagtc tttgtaagaa gagttttggt aagtccatta tttatacagg 3120
tgattgggaa ggtctacatg aagttcttac atctgcaatg aatgtcattg ggcaacatat 3180
taagttgcca caattttata tttatgatga agagggtggt tatgatgttt ctaaaccagt 3240
tatgatttca caatggccta ttagtaatga tagtaatggt tgtgttgttg aagcgagcac 3300
tgattttcat caattagaat gtattgttga tgactctgtt agagaagagg ttgatataat 3360
tgaacaacct tttgaagaag ttgaacatgt gctctcaatt aagcaacctt tttctttttc 3420
ttttagagat gaattgggtg ttcgtgtttt agatcaatct gataataatt gttggattag 3480
taccacactt gtacagttgc aacttacaaa gcttttggat gattctattg agatgcaatt 3540
gtttaaagtt ggtaaagttg attcaattgt ccaaaagtgt tatgagttgt ctcatttaat 3600
tagtggttca cttggtgata gtggtaaact tcttagtgaa cttcttaaag aaaaatatac 3660
atgttctata actttgaga tgtcttgtga ttgtggtaaa aagtttgatg atcaggttgg 3720
ttgtttgttt tggattatgc cttacacaaa actttttcaa aaaggtgagt gttgtatttg 3780
tcataaaatg cagacttata agcttgttag tatgaaaggt actggtgtgt ttgtacagga 3840
tccagcacct attgacattg atgctttccc tgtgaaacct atatgttcat ctgtatattt 3900
aggtgttaag ggttctggtc attatcaaac aaatttatac agttttaaca aagctattga 3960
tggttttggt gtctttgaca ttaaaaatag tagtgttaat actgtttgtt ttgttgatgt 4020
tgattttcat agtgtagaaa tagaagctgg tgaagttaaa ccttttgctg tatataaaaa 4080
tgttaaattt tatttaggtg atatttcaca ccttgtaaac tgtgtttctt ttgactttgt 4140
tgtcaatgct gctaatgaaa atctcttgca tggaggcggt gttgcacgtg ctattgatat 4200
tttgactgaa ggtcaacttc agtcactatc taaagattac attagtagta atggtccact 4260
taaggttgga gcaggtgtta tgttggagtg tgaaaaattc aacgtattta atgttgttgg 4320
tccgcgaact ggtaaacatg agcattcatt acttgttgaa gcttataatt ctattttatt 4380
tgaaaatggt attccactta tgcctcttct tagttgtggt atttttggtg taaggattga 4440
aaattctctt aaagctttgt ttagttgtga cattaataaa ccattgcaag tttttgttta 4500
ttcttcaaat gaagaacaag ctgttcttaa gtttttagat ggtttagatt taacaccagt 4560
cattgatgat gttgatgttg ttaaaccttt tagagttgaa ggtaattttt cattctttga 4620
ttgtggtgtc aatgccttgg atggtgatat ttacttatta tttactaact ctattttaat 4680
gttggataaa caaggacaat tattggacac aaaacttaat ggtattttgc aacaggcagc 4740
tcttgattat cttgctacag ttaaaactgt accagctggt aatttggtta aactttttgt 4800
tgagagttgt accatttata tgtgtgttgt accatcgata aatgatcttt cttttgataa 4860
aaatcttggt cgttgtgtgc gtaaacttaa tagattgaaa acttgtgtta ttgccaatgt 4920
tcctgctatt gatgttttga aaaagcttct ttcaagtttg actttaactg ttaaatttgt 4980
tgtagagagt aatgttatgg atgttaacga ctgttttaag aatgataatg tagttttgaa 5040
aattactgaa gatggtatta atgttaaaga tgttgttgtt gagtcttcta agtcacttgg 5100
taaacaattg ggtgttgtga gtgatggtgt tgactctttt gaaggtgttt tacctattaa 5160
tactgatact gtcttatctg tagctccaga agttgactgg gttgcttttt acggttttga 5220
aaaggcagca ctttttgctt ctttggatgt aaagccatat ggttacccta atgattttgt 5280
tggtggtttt agagttcttg ggaccaccga caataattgt tgggttaatg caacttgtat 5340

```
aattttacag tatcttaagc ctacttttaa atctaagggt ttaaatgttc tttggaacaa   5400
atttgttaca ggtgatgttg gaccttttgt tagttttatt tattttataa ctatgtcttc   5460
aaagggtcaa aagggtgatg ctgaagaggc attatctaaa ttgtcagagt atttgattag   5520
tgattctatt gttactcttg aacaatattc aacttgtgac atttgtaaaa gtactgtagt   5580
tgaagttaaa agtgctattg tctgtgctag tgtgcttaaa gatggttgtg atgttggttt   5640
ttgtccacac agacataaat tgcgttcacg tgttaagttt gttaatggac gtgttgttat   5700
taccaatgtt ggtgaaccta taatttcaca accttctaag ttgcttaatg gtattgctta   5760
tacaacattt tcaggttctt ttgataacgg tcactatgta gtttatgatg ctgctaataa   5820
tgctgtctat gatggtgctc gtttattttc ttcagatttg tctactttag ctgttacagc   5880
tattgttgta gtaggtggtt gtgtaacatc taatgttcca acaattgtta gtgagaaaat   5940
ttctgttatg gataaacttg atactggtgc acaaaaattt ttccaatttg gtgattttgt   6000
tatgaataac attgttctgt tttaacttg gttgcttagt atgtttagtc ttttacgtac   6060
ttctattatg aagcatgata ttaaagttat tgccaaggct cctaaacgta caggtgttat   6120
tttgacacgt agttttaagt ataacattag atctgctttg tttgttataa agcagaagtg   6180
gtgtgttatt gttactttgt ttaagttctt attattatta tatgctattt atgcacttgt   6240
ttttatgatt gtgcaattta gtccttttaa tagtctttta tgtggtgaca ttgtaagtgg   6300
ttatgaaaaa tccactttta ataaggatat ttattgtggt aattctatgg tttgtaagat   6360
gtgtttgttc agttatcaag agtttaatga tttggatcat actagtcttg tttggaagca   6420
cattcgtgat cctatattaa tcagtttaca accatttgtt atacttgtta ttttgttaat   6480
ttttggtaat atgtatttgc gttttggact tttatatttt gttgcacaat ttattagtac   6540
ttttggttct ttcttaggct ttcatcagaa acagtggttt ttacattttg tgccgtttga   6600
tgttttatgt aatgagtttt tagctacatt tattgtctgc aaaatcgttt tatttgttag   6660
acatattatt gttggctgta ataatgctga ctgtgtagct tgttctaaaa gtgctagact   6720
taaacgtgta ccacttcaaa ctattattaa tggtatgcat aaatcattct atgttaatgc   6780
taatggtggt acttgtttct gtaataaaca taacttcttt tgtgttaatt gtgattcttt   6840
tgggcctggt aatactttta ttaatggtga tattgcaaga gagcttggta atgttgttaa   6900
aacagctgtt caacccacag ctcctgcata tgttattatt gataaggtag attttgttaa   6960
tggattttat cgtctttata gtggtgacac tttttggcgg tatgactttg acattactga   7020
atctaagtat agttgtaaag aggttctgaa gaattgtaat gttttagaaa attttattgt   7080
ttacaataat agtggtagta acattacaca gattaaaaat gcttgtgttt atttttctca   7140
attgttgtgt gaacctataa agttggtaaa ttcagagttg ttgtcaactt tatctgttga   7200
ttttaatggt gttttgcata aggcatatgt tgatgttttg tgtaatagtt tttttaagga   7260
gttaactgct aacatgtcca tggctgaatg taaagctaca cttggtttga ctgtttctga   7320
tgatgatttt gtttcagctg ttgccaatgc acataggtat gacgttttgc tttcagattt   7380
gtcatttaat aatttttta tttcttatgc taaacctgaa gataagttgt ccgtttatga   7440
cattgcttgt tgtatgcgtg ccggttctaa ggttgttaac cataatgttt taattaaaga   7500
gtcaatacct attgtttggg gtgtcaagga ctttaatact ctttctcaag aaggtaagaa   7560
gtaccttgtt aaaacaacta aagcaaaggg tttgactttt ttattaactt ttaatgataa   7620
ccaagcaatt acacaagttc ctgctactag tatagttgca aaacagggtg ctggttttaa   7680
```

```
acgtacttat aattttctgt ggtatgtatg tttatttgtt gttgcattgt ttattggtgt   7740
ctcatttatt gattatacaa ccactgtaac tagctttcat ggttatgatt ttaagtacat   7800
tgagaatggt cagttgaagg tgtttgaagc acctttacac tgtgttcgta atgtttttga   7860
taattttaat caatggcatg aggctaagtt tggtgttgtt actactaata gtgataaatg   7920
tcctatagtt gttggtgttt cagagcgtat taatgttgtt cctggtgttc caacaaatgt   7980
atatttggta ggaaagactc ttgtttttac attacaggct gcttttggaa acacaggtgt   8040
ttgttatgac tttgatggtg ttaccactag tgataagtgt atttttaatt ctgcttgtac   8100
taggttggaa ggtttgggtg gtgacaatgt ttattgttac aacactgatc ttattgaagg   8160
ttctaaacct tatagtactt tacagcccaa tgcgtattat aagtatgatg ctaaaaatta   8220
tgtacgtttt ccagaaattt tagctagagg ttttggctta cgtactatta gaactttggc   8280
tacacgttat tgtagagttg gtgaatgccg tgactcacat aaaggtgttt gttttggttt   8340
tgataaatgg tatgttaatg atggacgtgt tgatgacggt tacatttgtg gtgatggtct   8400
tatagacctt cttgttaatg tactctcaat ctttagttca tcttttagcg ttgtggctat   8460
gtctggacat atgttgttta attttctttt tgcagcattt attacatttt tgtgcttttt   8520
agttactaaa tttaaacgtg tttttggtga tctttcttat ggtgttttta ctgttgtttg   8580
tgcaactttg attaataaca tttcttatgt tgttactcaa aatttatttt ttatgttgct   8640
ttatgctatt ttgtattttg tttttactag gacagtgcgt tatgcttgga tttggcatat   8700
tgcatacatt gttgcatact tcttgttaat accatggtgg cttctcacat ggtttagttt   8760
tgctgcattt ttagagcttt tacctaatgt ttttaagtta aaaatctcta ctcaattgtt   8820
tgaaggtgat aagtttatag gtacttttga gagtgctgct gcaggtacat ttgttcttga   8880
catgcgttct tatgaaaggc tgataaatac tatttcacct gagaaactta agaattatgc   8940
tgcaagttat aataaatata aatattatag tggtagtgct agtgaggctg attatcgttg   9000
tgcttgttat gctcatttag ccaaggctat gttagattat gcaaaagatc ataatgacat   9060
gttatattct ccacctacta ttagctacaa ttccacctta caatctggtc ttaagaagat   9120
ggcacaacca tctggttgtg ttgagagatg tgtggttcgc gtctgttatg gtagtactgt   9180
gcttaatgga gtttggttag gtgacactgt tacttgtcct agacatgtca tagcaccatc   9240
aaccactgtt cttattgatt atgatcatgc atatagtact atgcgtttgc ataatttttc   9300
agtgtctcat aatggtgtct tcttgggagt tgtcggtgtt acaatgcatg gttctgtgtt   9360
gcgtattaag gtttcacaat ctaatgtaca tacacctaaa catgttttta aaacgttgaa   9420
acctggtgat tcttttaata ttttagcatg ttatgaaggt attgcatctg gtgtttttgg   9480
tgttaattta cgtacaaact ttactattaa aggttctttt ataaatggag cttgtggttc   9540
tcctggttat aatgttagaa atgatggtac tgttgagttt tgttatttac accaaattga   9600
gttaggtagt ggtgctcatg ttggttctga ttttactggt agtgtttatg gtaattttga   9660
tgaccaacct agtttgcaag ttgagagtgc caaccttatg ctatcagata atgttgttgc   9720
ctttttgtat gctgctttgt tgaatggttg taggtggtgg ttgtgttcaa ctagagttaa   9780
tgttgatggt tttaatgaat gggctatggc taatggttat acaagtgttt ctagtgttga   9840
gtgctattct attttggcag caaaaactgg tgttagtgtt gaacaattgt tagcttccat   9900
tcaacatctt catgaaggtt ttggtggtaa aaacatactt ggttattcta gtttatgtga   9960
tgagttcaca ctagctgaag ttgtgaagca gatgtatggt gttaacttgc aaagtggtaa  10020
ggttattttt ggtttaaaaa caatgttttt atttagcgtt ttcttcacaa tgttttgggc  10080
```

-continued

```
agaactcttt atttatacaa acactatatg gataaaccct gtgatactta cacctatatt  10140
ttgtctactt ttgtttttgt cattagtttt aactatgttt cttaaacata agtttttgtt  10200
tttgcaagta tttttattac ctactgttat tgcaactgct ttatataatt gtgttttgga  10260
ttattacata gtaaaatttt tggctgacca ttttaactat aatgtttcag tattacaaat  10320
ggatgttcag ggtttagtta atgttttggt ctgtttattt gttgtatttt tacacacatg  10380
gcgcttttct aaagaacgtt ttacacattg gtttacatat gtgtgttctc ttatagcagt  10440
tgcttacact tatttttata gtggtgactt tttgagtttg cttgttatgt ttttatgtgc  10500
tatatctagt gattggtaca ttggtgccat tgtttttagg ttgtcacgtt tgattgtatt  10560
tttttcacct gaaagtgtat ttagtgtttt tggtgatgtg aaacttactt tagttgttta  10620
tttaatttgt ggttatttag tttgtactta ttggggcatt ttgtattggt tcaataggtt  10680
ttttaaatgt actatgggtg tttatgattt taaggtgagt gctgctgaat ttaaatacat  10740
ggttgctaat ggacttcatg caccacatgg acctttttgat gcactttggt tatcattcaa  10800
actacttggt attggtggtg accgttgtat aaaaatttca actgtccaat ccaaactgac  10860
tgatttgaag tgtactaatg ttgtgttatt gggttgtttg tctagtatga acattgcagc  10920
taattctagt gaatgggctt attgtgttga tttacacaat aagattaatc tttgtgatga  10980
ccctgaaaaa gctcaaagta tgttgttagc actccttgcg ttctttctaa gtaaacatag  11040
tgattttggt cttgatggcc ttattgattc ttattttgat aatagtagca cccttcagag  11100
tgttgcttca tcatttgtta gtatgccatc atatattgct tatgaaaatg ctagacaagc  11160
ttatgaggat gctattgcta atggatcttc ttctcaactt attaaacaat tgaagcgtgc  11220
catgaatatc gcaaagtctg aatttgatca tgagatatct gttcagaaga aaattaatag  11280
aatggctgaa caagctgcta ctcagatgta taaagaagca cgctctgtta atagaaaatc  11340
taaagttatt agtgctatgc actctttact ttttggaatg ttaagacgtt tggatatgtc  11400
tagtgttgaa actgttttga atttagcacg tgatggtgtt gtgccattgt cagttatacc  11460
tgcaacttca gcttctaaac taactattgt tagtccagat cttgaatctt attctaagat  11520
tgtttgtgat ggttctgttc attatgctgg agttgtttgg acacttaatg atgttaaaga  11580
caatgatggt agacctgttc atgttaaaga gattacaaag gaaaatgttg aaactttgac  11640
atggcctctt atccttaatt gtgaacgtgt tgttaaactt caaaataatg aaattatgcc  11700
tggtaaactt aagcaaaaac ctatgaaagc tgagggtgat ggtggtgttt taggtgatgg  11760
taatgccttg tataatactg agggtggtaa aacttttatg tacgcttata tttctaataa  11820
agctgacctt aaatttgtta agtgggagta tgagggtggt tgcaacacaa tcgagttaga  11880
ctctccttgt cgatttatgg tcgaaacacc taatggtcct caagtgaagt atttgtattt  11940
tgttaaaaat ttaaatacct tacgtagagg tgccgttctt ggttttatag gtgccacaat  12000
tcgtctacaa gctggtaaac aaactgaatt ggctgttaat tctggacttt taactgcttg  12060
tgctttttct gttgatccag caactactta cttggaagct gttaaacatg gtgcaaaacc  12120
tgtaagtaat tgtattaaga tgttatctaa tggtgctggt aatggtcaag ctataacaac  12180
tagtgtagat gctaacacca atcaagattc ttatggtgga gcgtctattt gtttgtattg  12240
tcgggcccac gttcctcacc ctagtatgga tggttactgt aagtttaagg gtaaatgtgt  12300
tcaggttcct attggttgtt tggatcctat taggttttgt ttagaaaata atgtgtgtaa  12360
tgtttgtggt tgttggttgg gacacgggtg tgcttgtgac cgtacaacta ttcaaagtgt  12420
```

```
tgacatttct tatttaaacg agcaaggggt tctagtgcag ctcgactaga accctgcaat  12480
ggcacggaca tcgataagtg tgttcgtgct tttgacattt ataataaaaa tgtttcattc  12540
ttgggtaagt gtttgaagat gaactgtgtt cgttttaaaa atgctgatct taaggatggt  12600
tattttgtta taaagaggtg tactaagtcg gttatggaac acgagcaatc catgtataac  12660
ctacttaact tttctggtgc tttggctgag catgatttct ttacttggaa agatggcaga  12720
gtcatttatg gtaatgttag tagacataat cttactaaat atactatgat ggacttggtc  12780
tatgctatgc gtaactttga tgaacaaaat tgtgatgttc taaaagaagt attagtttta  12840
actggttgtt gtgacaattc ttattttgat agtaagggtt ggtatgaccc agttgaaaat  12900
gaagatatac atagagttta tgcatctctt ggcaaaattg tagctagagc tatgcttaaa  12960
tgcgttgctc tatgcgatgc gatggttgct aaaggtgttg ttggtgtttt aacattagat  13020
aaccaagatc ttaatggtaa cttttatgat tttggtgatt ttgttgttag cttacctaat  13080
atgggtgttc cctgttgtac atcatattat tcttatatga tgcctattat gggtttaact  13140
aattgtttag ctagtgagtg ttttgtcaag agtgatattt ttggtagtga ttttaaaact  13200
tttgatttgc ttaagtatga tttcactgaa cataaagaaa atttattcaa taagtacttt  13260
aagcattgga gttttgatta tcatcctaat tgttgtgact gttatgatga tatgtgtgtt  13320
atacattgtg ctaattttaa tacactattt gccacaacta taccaggtac tgcttttggt  13380
ccactatgtc gtaaagtttt tatagatggt gttccacttg ttacaactgc tggttatcat  13440
tttaagcaat taggtttggt ttggaataaa gatgttaaca cacactcagt taggttgaca  13500
attactgaac ttttgcaatt tgtcaccgac ccttccttga taatagcttc ttccccagca  13560
ctcgttgatc aacgcactat ttgtttttct gttgcagcat tgagtactgg tttgacaaat  13620
caagttgtta agccaggtca ttttaatgaa gagttttata actttcttcg tttaagaggt  13680
ttctttgatg aaggttctga acttacatta aaacatttct tcttcgcaca gaatggtgat  13740
gctgctgtta aagattttga cttttaccgt tataataagc ctaccatttt agatatttgt  13800
caagctagag ttacatataa gatagtctct cgttattttg acatttatga aggtggctgt  13860
attaaggcat gtgaagttgt tgtaacaaat cttaataaga gtgctggttg gccattaaat  13920
aagtttggta aagctagttt gtattatgaa tctatatctt atgaagaaca ggatgctttg  13980
tttgctttga caaagcgtaa tgtcctccct actatgacac agctgaatct taagtatgct  14040
attagtggta aagaacgtgc tagaactgtt ggtggtgttt ctctgttgtc tacaatgacc  14100
acaagacaat accatcaaaa acatcttaaa tccattgtta atacacgcaa tgccactgtt  14160
gttattggta ctaccaaatt ttatggtggt tggaataata tgttgcgtac tttaattgat  14220
ggtgttgaaa accctatgct tatgggttgg gattatccca aatgtgatag agctttgcct  14280
aacatgatac gtatgatttc agccatggtg ttgggctcta agcatgttaa ttgttgtact  14340
gcaacagata ggttttatag gcttggtaat gagttggcac aagttttaac agaagttgtt  14400
tattctaatg gtggttttta ttttaagcca ggtggtacga cttctggtga cgctagtaca  14460
gcttatgcta attctatttt taacattttt caagccgtga gttctaacat taacaggttg  14520
cttagtgtcc catcagattc atgtaataat gttaatgtta gggatctaca acgacgtctg  14580
tatgataatt gttataggtt aactagtgtt gaagagtcat tcattgaaga ttattatggt  14640
tatcttagga aacatttttc aatgatgatt ctctctgatg acggtgttgt ctgttataac  14700
aaggattatg ctgagttagg ttatatagca gacattagtg cttttaaagc cactttgtat  14760
taccagaata atgtctttat gagtacttct aaatgttggg ttgaagaaga tttaactaag  14820
```

```
ggaccacatg agttttgttc ccagcatact atgcaaatag ttgacaaaga tggtacctat  14880
tatttgcctt acccagatcc tagtaggatc ttgtcagctg gtgtttttgt tgatgatgtt  14940
gttaagacag atgctgttgt tttgttagaa cgttatgtgt ctttagctat tgatgcatac  15000
cctctttcaa aacaccctaa ttccgaatat cgtaaggttt tttacgtatt acttgattgg  15060
gttaagcatc ttaacaaaaa tttgaatgag ggtgttcttg aatctttttc tgttacactt  15120
cttgataatc aagaagataa gttttggtgt gaagattttt atgctagtat gtatgaaaat  15180
tctacaatat tgcaagctgc tggtttatgt gttgtttgtg gttcacaaac tgtacttcgt  15240
tgtggtgatt gtctgcgtaa gcctatgttg tgcactaaat gcgcatatga tcatgtattt  15300
ggtaccgacc acaagtttat tttggctata acaccgtatg tatgtaatgc atcaggttgt  15360
ggtgttagtg atgtcaaaaa attgtatctt ggtggtttga attactattg tacaaatcat  15420
aaaccacagt tgtcttttcc attatgttca gctggtaata tatttggttt atataaaaat  15480
tcagcaactg gttccttaga tgttgaagtt tttaataggc ttgcaacgtc tgattggact  15540
gatgttaggg actataaact tgctaatgat gttaaagata cacttagact ctttgcggct  15600
gaaactatta aagctaaaga agagagtgtt aagtcttctt atgcttttgc aactcttaaa  15660
gaggttgttg gacctaaaga attgcttctt agttgggaaa gtggtaaagt taaaccacct  15720
ttgaatcgta attctgtttt cacttgtttt caaataagta aggactcaaa attccaaata  15780
ggtgagttca tctttgagaa ggttgaatat ggttctgata ctgttacgta taagtctact  15840
gtaactacta agttagttcc tggtatgatt tttgtcttaa catctcacaa tgtccaacct  15900
ttacgtgcac caactattgc aaaccaagag aagtattcta gcatttataa attgcaccct  15960
gcttttaatg tcagtgatgc atatgctaat ttggttccat attaccaact tattggtaaa  16020
caaaagataa ctacaataca gggtcctcct ggtagtggta agtcacattg ttccattgga  16080
cttggattgt actacccagg tgcgcgtatt gtttttgttg cttgtgccca tgctgctgtt  16140
gattccttat gtgcaaaagc tatgactgtt tatagcattg ataagtgtac taggattata  16200
cctgcaagag ctcgggttga gtgttatagt ggctttaaac caaataacac tagtgcacaa  16260
tacatattta gcactgttaa cgcattacct gagtgtaatg ctgatatcgt tgttgtagat  16320
gaagtttcaa tgtgtacaaa ttatgacctt tctgttatta accagcgttt atcatataaa  16380
catattgttt atgttggtga tccacaacaa cttcctgcac ctagagtaat gattactaaa  16440
ggtgttatgg agcctgttga ttataacgtt gttactcaac gtatgtgtgc tataggccct  16500
gatgtttttc ttcataaatg ttatagatgt cctgctgaaa tagtaataca gtttctgaac  16560
ttgtttatga gaacaagttt gtccctgtta aacctgctag taaacagtgt tttaaagtct  16620
tttttaaggg taatgtacaa ggttgacaat ggttctagta ttaacagaaa gcagcttgaa  16680
atagttaagc tgtttttagt taaaaatcca agttggagta aggctgtgtt tatttctcct  16740
tataatagtc agaattatgt tgctagtaga tttttaggac ttcaaattca aactgttgat  16800
tcttctcaag gtagtgagta tgattatgta atctatgcac aaacttctga cactgcacat  16860
gcttgcaatg taaaccgttt taatgttgct ataacacgtg ctaagaaggg tatattttgt  16920
gtaatgtgtg ataaaacttt gtttgattca cttaagtttt ttgagattaa acatgcagat  16980
ttacactcta gccaggtttg tggcttgttt aaaaattgta cacgcactcc tcttaattta  17040
ccaccaactc atgcacacac tttcttgtcg ttgtcagatc agtttaagac tacaggtgat  17100
ttagctgttc aaataggttc aaataacgtt tgtacttatg aacatgttat atcatttatg  17160
```

ggttttaggt ttgatattag tattcctggt agtcatagtt tgttttgtac acgtgacttt 17220
gctattcgta atgtgcgtgg ttggttgggt atggatgttg aaagtgctca tgtttgtggc 17280
gataacatag gtactaatgt tcctttacag gttggttttt caaatggtgt taattttgtt 17340
gtgcaaactg aaggttgtgt gtctaccaat tttggtgatg ttattaaacc tgtttgtgca 17400
aaatctccac caggtgaaca atttagacac cttattcctc ttttacgtaa aggacaacct 17460
tggttaattg ttcgtagacg cattgtgcaa atgatatctg attatttgtc caatttgtct 17520
gacattcttg tctttgtttt gtgggcaggt agtttggaat taactacaat gcgttacttt 17580
gtaaaaatag ggccaattaa atattgttat tgtggtaatt ttgccacttg ttataattca 17640
gttagtaatg aatattgttg ttttaaacat gcattgggtt gtgattatgt ttacaatccg 17700
tatgcttttg atatacaaca gtggggttat gttggttcct tgagccaaaa ccaccacaca 17760
ttctgtaaca ttcatagaaa cgagcatgat gcctctggtg atgctgttat gacacgttgt 17820
ttggcagtac atgattgttt tgtcaaaaat gttgattgga ctgtaacgta ccccctttatt 17880 gcaaatgaga aatttatcaa tggctgtggg cgtaatgtcc agggacatgt tgttcgtgca 17940
gccttgaaat tgtataaacc tagtgttatt catgacattg gtaatcctaa aggtgtacgt 18000
tgtgctgtta ctgatgccaa atggtactgt tatgacaagc aacctgttaa tagtaatgtc 18060
aagttgttgg attatgatta tgcaacccat ggtcaacttg atggtctttg tttattctgg 18120
aattgtaatg ttgatatgta tccagaattt tcaattgtgt gtcgttttga cacacgtact 18180
cgttctgttt ttaatttaga aggtgttaat ggtggttctc tttatgttaa caaacatgcg 18240
tttcatacac cagcatatga taaacgtgct tttgttaaat taaaacctat gccctttttt 18300
tactttgatg acagtgattg tgatgttgtg caagaacaag ttaattatgt accccttcgc 18360
gctagtagtt gtgttactcg ttgtaatata ggtggtgctg tttgttcaaa acatgcaaat 18420
ttgtatcaaa aatatgttga ggcatataat acatttacac aggcaggttt taacatttgg 18480
gtaccacata gttttgatgt ttataatttg tggcaaattt ttattgaaac taatttacaa 18540
agtcttgaaa atatagcatt taatgttgta aaaaaagggt gttttactgg tgttgatggt 18600
gagttacctg ttgcagttgt taacgacaaa gtttttgttc gctatggcga tgttgacaac 18660
ttggttttta caaataaaac aacattgcct actaatgttg cttttgaatt gtttgcaaaa 18720
cgaaaaatgg gtttaacacc accattgtct attctcaaaa atctcggtgt tgttgctaca 18780
tataaatttg ttttatggga ttatgaagct gaaagacctt ttacctcata tactaagagt 18840
gtatgtaaat acactgattt taatgaggat gtttgtgttt gttttgacaa tagtattcag 18900
ggttcgtatg agcgttttac gcttactacg aacgctgttt tattttctac tgttgtcatt 18960
aaaaatttaa cacctataaa gttgaatttt ggtatgttga atggtatgcc agtttcttct 19020
attaagggtg ataaaggtgt tgaaaaatta gttaattggt acatatatgt tcgtaaaaat 19080
ggtcaatttc aagatcacta tgatggtttt tacactcaag gtaggaattt atcagacttt 19140
acaccaagaa gtgatatgga gtatgatttt cttaacatgg atatgggtgt ttttattaat 19200
aaatatggtc ttgaggattt taattttgaa catgttgtat atggtgatgt ttcaaaaact 19260
acattaggag gtcttcattt gttgatatca cagtttaggc ttagtaaaat gggtgttttg 19320
aaagctgatg attttgtcac tgcttctgac acaactttga ggtgctgtac tgttacttat 19380
cttaatgaac ttagttcaaa agttgtttgt acttatatgg atttgttgtt ggacgacttt 19440
gttactatac taaagagttt agatcttggt gtaatatcta aagttcatga agttattata 19500
gataataaac cttataggtg gatgttgtgg tgtaaagata accacttgtc cactttttat 19560

```
ccacagttgc agtctgctga atggaagtgt ggttatgcta tgccacaaat ttataagctt  19620
caacgtatgt gtttggaacc ttgtaattta tataattatg gtgctggtat taagttgcct  19680
agtggtataa tgttaaatgt tgttaaatac actcagcttt gtcaatacct aaatagcact  19740
acaatgtgcg tacctcataa tatgcgtgtt ttgcactatg gtgctggttc tgacaaaggt  19800
gtggcacctg gtacaactgt tttaaaacgt tggctaccac ccgatgcaat aatcattgat  19860
aatgatatca atgattatgt tagtgatgca gattttagca ttacaggtga ttgtgctact  19920
gtttatcttg aagataagtt tgacttactt atttctgata tgtatgatgg tagaattaaa  19980
ttttgtgatg gtgaaaatgt ctctaaagat gggtttttta cttatcttaa tggtgttatt  20040
agagaaaaat tagctattgg tggtagtgtt gccattaaga ttacagaata tagttggaat  20100
aagtatcttt atgaattaat acaaagattt gctttttgga ctttgttttg cacgtctgtt  20160
aatacatcct cttcagaagc ttttcttatt ggtattaatt atttaggtga ctttattcaa  20220
ggtcctttta tagctggtaa cactgttcat gctaattata tattttggcg taattctact  20280
attatgtctt tgtcatacaa ttcagtttta gatttaagta agtttgaatg taaacataaa  20340
gccactgttg ttgttacact taaagatagt gatgtaaatg atatggtttt gagtttgatt  20400
aagagtggta ggttgttgtt acgcaataat ggtcgttttg gtggttttag taatcattta  20460
gtctcaacta aatgaaactt ttcttgattt tgcttgtttt gcccctggcc tcttgctttt  20520
tcacatgtaa tagtaatgct aatctctcta tgttacaatt aggtgttcct gacaattctt  20580
caactattgt tacgggttta ttgccaactc attggttttg tgctaatcag agtacatctg  20640
tttactcagc caatggtttc ttttatattg atgttggtaa tcaccgtagt gcttttgcgc  20700
tccatactgg ttattatgat gctaatcagt attatattta tgttactaat gaaataggct  20760
taaatgcttc tgttactctt aagatttgta agtttagtag aaacactact tttgattttt  20820
taagtaatgc ttctagttct tttgactgta tagttaattt gttatttaca gaacagttag  20880
gtgcgccttt gggcataact atatctggtg aaactgtgcg tctgcattta tataatgtaa  20940
ctcgtacttt ttatgtgcca gcagcttata aacttactaa acttagtgtt aaatgttact  21000
ttaactattc ctgtgttttt agtgttgtca acgccaccgt tactgtgaat gtcaccacac  21060
ataatggccg tgtagttaac tacactgttt gtgatgattg taatggttat actgataaca  21120
tattttctgt tcaacaggat ggccgcattc ctaatggttt cccttttaat aattggtttt  21180
tgttaactaa tggttccaca ctagtggacg gggtctctag actttatcaa ccactccgtt  21240
taacttgttt atggcctgta cctggtctta aatcttcaac tggttttgtt tattttaatg  21300
ccactggttc tgatgttaat tgtaacggct atcaacataa ttctgttgtt gatgttatgc  21360
gttacaatct taacttcagt gctaattctt tggacaatct caagagtggt gttatagttt  21420
ttaaaacttt acagtacgat gttttgtttt attgtagtaa ttcttcctca ggtgttcttg  21480
acaccacaat accttttggc ccgtcctctc aaccttatta ctgttttata aacagcacta  21540
tcaacactac tcatgttagc acttttgtgg gtattttacc acccactgtg cgtgaaattg  21600
ttgttgctag aactggccag ttttatatta atggttttaa gtatttcgat ttgggtttca  21660
tagaagctgt caattttaat gtcacgactg ctagcgccac agatttttgg acggttgcat  21720
ttgctacttt tgttgatgtt ttggttaatg ttagtgcaac taacattcaa aacttacttt  21780
attgcgattc tccatttgaa aagttgcagt gtgagcactt gcagtttgga ttgcaggatg  21840
gtttttattc tgcaaatttt cttgatgata atgttttgcc tgagacttat gttgcactcc  21900
```

```
ccatttatta tcaacacacg gacataaatt ttactgcaac tgcatctttt ggtggttctt  21960
gttatgtttg taaaccacac caggttaata tatctcttaa tggtaacact tcagtgtgtg  22020
ttagaacatc tcatttttca attaggtata tttataaccg cgttaagagt ggttcaccag  22080
gtgactcttc atggcacatt tatttaaaga gtggcacttg tccattttct ttttctaagt  22140
taaataattt tcaaaagttc aagactattt gtttctcaac cgtcgaagtg cctggtagtt  22200
gtaattttcc gcttgaagcc acctggcatt acacttctta tactattgtt ggtgctttgt  22260
atgttacttg gtctgaaggt aattctatta ctggtgtacc ttatcctgtc tctggtattc  22320
gtgagtttag taatttagtt ttaaataatt gtaccaaata taatatttat gattatgttg  22380
gtactggaat tatacgttct tcaaaccagt cacttgctgg tggtattaca tatgtttcta  22440
actctggtaa tttacttggt tttaaaaatg tttccactgg taacattttt attgtgacac  22500
catgtaacca accagaccaa gtagctgttt atcaacaaag cattattggt gccatgaccg  22560
ctgttaatga gtctagatat ggcttgcaaa acttactaca gttacctaac ttttattatg  22620
ttagtaatgg tggtaacaat tgcactacgg ccgttatgac ttattctaat tttggtattt  22680
gtgctgatgg ttctttgatt cctgttcgtc cgcgtaattc tagtgataat ggtatttcag  22740
ccataatcac tgctaattta tccattcctt ctaactggac tacttcagtt caagttgagt  22800
acctccaaat tactagtact ccaatagttg ttgattgtgc tacttatgtg tgtaatggta  22860
accctcgctg taagaatcta cttaagcagt atacttctgc ttgtaaaact attgaagatg  22920
ccttacgact tagtgctcat ttggaaacta atgatgttag tagtatgcta actttcgata  22980
gcaatgcttt tagtttggct aatgttacta gttttggaga ttataacctt tctagtgttt  23040
tacctcagag aaacattcgt tcaagccgta tagcaggacg tagtgctttg gaagatttgt  23100
tgtttagcaa agttgttaca tctggtttgg gtactgttga tgttgactat aagtcttgta  23160
ctaaaggtct ttctattgct gaccttgctt gtgctcagta ctacaatggc ataatggttt  23220
tgccaggtgt tgctgatgct gaacgtatgg ccatgtacac aggttctctt ataggtggca  23280
tggtgctcgg aggtcttaca tcagcagccg ccatacottt ttctttggca ctgcaagcac  23340
gacttaacta tgttgcttta caaactgatg tgcttcaaga aaatcagaaa attttggctg  23400
catcatttaa taaggctatt aataatattg ttgcttcttt tagtagcgtt aatgatgcta  23460
ttacacaaac tgcagaggct atacatactg ttactattgc acttaataag attcaggatg  23520
ttgttaatca acagggtagt gctcttaacc atctcacttc acaattgaga cataattttc  23580
aggccatttc taattcaatt caggctattt atgaccggct tgattcaatt caagccgatc  23640
aacaagttga cagattaatt actggacggc ttgcagcttt gaatgcattt gtttcccaag  23700
ttttgaataa atatactgaa gttcgtggtt caagacgctt agcacagcag aagattaatg  23760
aatgtgtcaa gtcacaatct aatagatatg gtttttgtgg caatggcact cacatctttt  23820
caatcgtcaa ctctgctcca gatggtttgc tttttcttca tactgttttg ctgccaactg  23880
attacaagaa tgtaaaggcg tggtctggta tctgtgttga tggcatttat ggctatgttc  23940
tgcgtcaacc taacttggtt ctttattctg ataatggtgt ctttcgtgta acttccaggg  24000
tcatgtttca acctcgctta cctgttttgt ctgattttgt gcaaatatat aattgtaatg  24060
ttacttttgt taacatatct cgtgttgagt tacatactgt catacctgac tacgttgatg  24120
ttaataaaac attacaagag tttgcacaaa acttaccaaa gtatgttaag cctaattttg  24180
acttgactcc ttttaattta acatatctta atttgagttc tgagttgaag caactcgaag  24240
ctaaaactgc tagtcttttt caaactactg ttgaattaca aggtcttatt gatcagatta  24300
```

```
acagtacata tgttgatttg aagttgctta ataggtttga aaattatatc aaatggcctt  24360
ggtgggtttg gctcattatt tctgttgttt ttgttgtatt gttgagtctt cttgtgtttt  24420
gttgtctttc tacaggttgt tgtggttgtt gcaattgttt aacttcatca atgcgaggct  24480
gttgtgattg tggttcaact aaacttcctt attacgaatt tgaaaaggtc cacgttcaat  24540
aatgcctttt ggtggcctat ttcaacttac tcttgaaagt actattaata agagtgtggc  24600
taatctcaaa ttaccacctc atgatgttac tgtcttgcgt gacaatctta aacctgttac  24660
tacacttagt actattactg cttatttgtt agttagtttg tttgtcactt actttgcttt  24720
attcaaacct cttactgcta gaggtcgtgt tgcttgtttt gttttaaaac tattgacact  24780
atttgtctat gtgcctttat tggttctttt tggtatgtat cttgacagtt ttataatttt  24840
ttctacgctg ttgtttcgat tcatacatgt tggctattat gcctatctct ataaaaattt  24900
ttcatttgtt ttgttcaatg ttactaaact atgcttcgtt tcaggcaagt gttggtatct  24960
tgaacaatca ttttatgaaa atcgttttgc tgctatttat ggtggtgacc actatgtcgt  25020
tttaggtggt gaaactatta cttttgtttc ttttgatgac ctttatgttg ctattagagg  25080
ttcttgtgaa aagaacctac aacttatgcg taaggttgac ttgtataatg gtgctgtcat  25140
ttacattttt gccgaagagc ctgttgttgg tatagtctac tcttctcaac tatacgaaga  25200
tgttccttcg attaattgat gacaatggta ttgtcctcaa ttccatttta tggctccttg  25260
ttatgatatt tttctttgtg ttggcaatga cctttattaa actgattcaa ttgtgtttta  25320
cttgtcatta tttttttagt aggacattat atcaaccagt ttataaaatt tttcttgctt  25380
accaagatta tatgcaaata gcacctgttc cagctgaagt actaaatgtc taaactaaac  25440
gatgtctaat agtagtgtgc ctcttttaga ggtttatgtc catttacgta actggaactt  25500
tagttggaat ttaattctaa cgctttttat agttgtgttg cagtatgggc attataagta  25560
tagcagactt ctttatggtt taaagatgtc tgttttatgg tgtttatggc cacttgttct  25620
agctttgtct atttttgact gttttgtcaa ttttaatgtg gactgggtct tttttggttt  25680
tagtattctt atgtctatta ttacactttg tttatgggtt atgtattttg ttaatagttt  25740
cagactttgg cgccgtgtta aaactttttg ggcttttaat cctgaaacta atgcaatcat  25800
ctctctccag gtttacggac ataattatta cttaccggtg atggctgcac ctacaggtgt  25860
tacattaaca cttcttagtg gtgtacttct tgttgatggc cataagattg ctactcgtgt  25920
tcaagtgggt cagttgccta aatatgtaat agttgctacg cctagtacca caattgtttg  25980
tgaccgtgtt ggtcgctctg ttaatgaaac aagccagact ggttgggcat tctacgtccg  26040
tgctaaacat ggtgattttt ctggtgttgc ctctcaggag ggtgttttgt cagaaagaga  26100
gaagttgctt catttaatct aaactaaaca aaatggctag tgtaaattgg gccgatgaca  26160
gagctgctag gaagaaattt cctcctcctt cattttacat gcctcttttg gttagttctg  26220
ataaggcacc atatagggtc attcccagga atcttgtccc tattggtaag ggtaataaag  26280
atgagcagat tggttattgg aatgttcaag agcgttggcg tatgcgcagg gggcaacgtg  26340
ttgatttgcc tcctaaagtt catttttatt acctaggtac tggacctcat aaggacctta  26400
aattcagaca acgttctgat ggtgttgttt gggttgctaa ggaaggtgct aaaactgtta  26460
ataccagtct tggtaatcgc aaacgtaatc agaaaccttt ggaaccaaag ttctctattg  26520
ctttgcctcc agagctctct gttgttgagt ttgaggatcg ctctaataac tcatctcgtg  26580
ctagcagtcg ttcttcaact cgtaacaact cacgagactc ttctcgtagc acttcaagac  26640
```

```
aacagtctcg cactcgttct gattctaacc agtcttcttc agatcttgtt gctgctgtta  26700

ctttggcctt aaagaactta ggttttgata accagtcgaa gtcacctagt tcttctggta  26760

cttccactcc taagaaacct aataagcctc tttctcaacc cagggctgat aagccttctc  26820

agttgaagaa acctcgttgg aagcgtgttc ctaccagaga ggaaaatgtt attcagtgct  26880

ttggtcctcg tgattttaat cacaatatgg gggattcaga tcttgttcag aatggtgttg  26940

atgccaaagg ttttccacag cttgctgaat tgattcctaa tcaggctgcg ttattctttg  27000

atagtgaggt tagcactgat gaagtgggtg ataatgttca gattacctac acctacaaaa  27060

tgcttgtagc taaggataat aagaaccttc ctaagttcat tgagcagatt agtgctttta  27120

ctaaacccag ttctatcaaa gaaatgcagt cacaatcatc tcatgttgct cagaacacag  27180

tacttaatgc ttctattcca gaatctaaac cattggctga tgatgattca gccattatag  27240

aaattgtcaa cgaggttttg cattaaattg ttttgtaatt ccagttgaat gtttattatt  27300

attagttgca accccatgcg tttagcgcat gataagggtt tagtcttaca cacaatggta  27360

ggccagtgat agtaaagtgt aagtaatttg ctatcatatt aacatgtcta gaggaaagtc  27420

agaacttttt ctgtttgtgt tgttggagta cttaaagatc gcataggcgc gccaacaatg  27480

gaagagccaa caacatatct aaaaatgttt tgtctggtac ttgttaatga tattgttttt  27540

gatatggata cac                                                     27553
```

<210> SEQ ID NO 56
<211> LENGTH: 4060
<212> TYPE: PRT
<213> ORGANISM: Human coronavirus
<220> FEATURE:
<221> NAME/KEY: MISC_FEATURE
<222> LOCATION: (1)..(4060)
<223> OTHER INFORMATION: ORF 1a, replicase enzyme complex

<400> SEQUENCE: 56

```
Met Phe Tyr Asn Gln Val Thr Leu Ala Val Ala Ser Asp Ser Glu Ile
1               5                   10                  15

Ser Gly Phe Gly Phe Ala Ile Pro Ser Val Ala Val Arg Thr Tyr Ser
            20                  25                  30

Glu Ala Ala Ala Gln Gly Phe Gln Ala Cys Arg Phe Val Ala Phe Gly
        35                  40                  45

Leu Gln Asp Cys Val Thr Gly Ile Asn Asp Asp Asp Tyr Val Ile Ala
    50                  55                  60

Leu Thr Gly Thr Asn Gln Leu Cys Ala Lys Ile Leu Pro Phe Ser Asp
65                  70                  75                  80

Arg Pro Leu Asn Leu Arg Gly Trp Leu Ile Phe Ser Asn Ser Asn Tyr
                85                  90                  95

Val Leu Gln Asp Phe Asp Val Val Phe Gly His Gly Ala Gly Ser Val
            100                 105                 110

Val Phe Val Asp Lys Tyr Met Cys Gly Phe Asp Gly Lys Pro Val Leu
        115                 120                 125

Pro Lys Asn Met Trp Glu Phe Arg Asp Tyr Phe Asn Asn Asn Thr Asp
    130                 135                 140

Ser Ile Val Ile Gly Gly Val Thr Tyr Gln Leu Ala Trp Asp Val Ile
145                 150                 155                 160

Arg Lys Asp Leu Ser Tyr Glu Gln Gln Asn Val Leu Ala Ile Glu Ser
                165                 170                 175

Ile His Tyr Leu Gly Thr Thr Gly His Thr Leu Lys Ser Gly Cys Lys
            180                 185                 190
```

```
Leu Thr Asn Ala Lys Pro Pro Lys Tyr Ser Ser Lys Val Val Leu Ser
        195                 200                 205

Gly Glu Trp Asn Ala Val Tyr Arg Ala Phe Gly Ser Pro Phe Ile Thr
    210                 215                 220

Asn Gly Met Ser Leu Leu Asp Ile Ile Val Lys Pro Val Phe Phe Asn
225                 230                 235                 240

Ala Phe Val Lys Cys Asn Cys Gly Ser Glu Ser Trp Ser Val Gly Ala
                245                 250                 255

Trp Asp Gly Tyr Leu Ser Ser Cys Cys Gly Thr Pro Ala Lys Lys Leu
            260                 265                 270

Cys Val Val Pro Gly Asn Val Val Pro Gly Asp Val Ile Ile Thr Ser
        275                 280                 285

Thr Ser Ala Gly Cys Gly Val Lys Tyr Tyr Ala Gly Leu Val Val Lys
    290                 295                 300

His Ile Thr Asn Ile Thr Gly Val Ser Leu Trp Arg Val Thr Ala Val
305                 310                 315                 320

His Ser Asp Gly Met Phe Val Ala Ser Ser Ser Tyr Asp Ala Leu Leu
                325                 330                 335

His Arg Asn Ser Leu Asp Pro Phe Cys Phe Asp Val Asn Thr Leu Leu
            340                 345                 350

Ser Asn Gln Leu Arg Leu Ala Phe Leu Gly Ala Ser Val Thr Glu Asp
        355                 360                 365

Val Lys Phe Ala Ala Ser Thr Gly Val Ile Asp Ile Ser Ala Gly Met
    370                 375                 380

Phe Gly Leu Tyr Asp Asp Ile Leu Thr Asn Asn Lys Pro Trp Phe Val
385                 390                 395                 400

Arg Lys Ala Ser Gly Leu Phe Asp Ala Ile Trp Asp Ala Phe Val Ala
                405                 410                 415

Ala Ile Lys Leu Val Pro Thr Thr Thr Gly Val Leu Val Arg Phe Val
            420                 425                 430

Lys Ser Ile Ala Ser Thr Val Leu Thr Val Ser Asn Gly Val Ile Ile
        435                 440                 445

Met Cys Ala Asp Val Pro Asp Ala Phe Gln Ser Val Tyr Arg Thr Phe
    450                 455                 460

Thr Gln Ala Ile Cys Ala Ala Phe Asp Phe Ser Leu Asp Val Phe Lys
465                 470                 475                 480

Ile Gly Asp Val Lys Phe Lys Arg Leu Gly Asp Tyr Val Leu Thr Glu
                485                 490                 495

Asn Ala Leu Val Arg Leu Thr Thr Glu Val Val Arg Gly Val Arg Asp
            500                 505                 510

Ala Arg Ile Lys Lys Ala Met Phe Thr Lys Val Val Val Gly Pro Thr
        515                 520                 525

Thr Glu Val Lys Phe Ser Val Ile Glu Leu Ala Thr Val Asn Leu Arg
    530                 535                 540

Leu Val Asp Cys Ala Pro Val Val Cys Pro Lys Gly Lys Ile Val Val
545                 550                 555                 560

Ile Ala Gly Gln Ala Phe Phe Tyr Ser Gly Gly Phe Tyr Arg Phe Met
                565                 570                 575

Val Asp Pro Thr Thr Val Leu Asn Asp Pro Val Phe Thr Gly Asp Leu
            580                 585                 590

Phe Tyr Thr Ile Lys Phe Ser Gly Phe Lys Leu Asp Gly Phe Asn His
        595                 600                 605
```

```
Gln Phe Val Thr Ala Ser Ser Ala Thr Asp Ala Ile Ile Ala Val Glu
    610                 615                 620

Leu Leu Leu Leu Asp Phe Lys Thr Ala Val Phe Val Tyr Thr Cys Val
625                 630                 635                 640

Val Asp Gly Cys Ser Val Ile Val Arg Arg Asp Ala Thr Phe Ala Thr
                645                 650                 655

His Val Cys Phe Lys Asp Cys Tyr Asn Val Trp Glu Gln Phe Cys Ile
            660                 665                 670

Asp Asn Cys Gly Glu Pro Trp Phe Leu Thr Asp Tyr Asn Ala Ile Leu
        675                 680                 685

Gln Ser Asn Asn Pro Gln Cys Ala Ile Val Gln Ala Ser Glu Ser Lys
    690                 695                 700

Val Leu Leu Glu Arg Phe Leu Pro Lys Cys Pro Glu Ile Leu Leu Ser
705                 710                 715                 720

Ile Asp Asp Gly His Leu Trp Asn Leu Phe Val Glu Lys Phe Asn Phe
                725                 730                 735

Val Thr Asp Trp Leu Lys Thr Leu Lys Leu Thr Leu Thr Ser Asn Gly
            740                 745                 750

Leu Leu Gly Asn Cys Ala Lys Arg Phe Arg Arg Val Leu Val Lys Leu
        755                 760                 765

Leu Asp Val Tyr Asn Gly Phe Leu Glu Thr Val Cys Ser Val Ala Tyr
    770                 775                 780

Thr Ala Gly Val Cys Ile Lys Tyr Tyr Ala Val Asn Val Pro Tyr Val
785                 790                 795                 800

Val Ile Ser Gly Phe Val Ser Arg Val Ile Arg Arg Glu Arg Cys Asp
                805                 810                 815

Met Thr Phe Pro Cys Val Ser Cys Val Thr Phe Phe Tyr Glu Phe Leu
            820                 825                 830

Asp Thr Cys Phe Gly Val Ser Lys Pro Asn Ala Ile Asp Val Glu His
        835                 840                 845

Leu Glu Leu Lys Glu Thr Val Phe Val Glu Pro Lys Asp Gly Gly Gln
    850                 855                 860

Phe Phe Val Ser Gly Asp Tyr Leu Trp Tyr Val Val Asp Asp Ile Tyr
865                 870                 875                 880

Tyr Pro Ala Ser Cys Asn Gly Val Leu Pro Val Ala Phe Thr Lys Leu
                885                 890                 895

Ala Gly Gly Lys Ile Ser Phe Ser Asp Asp Val Ile Val His Asp Val
            900                 905                 910

Glu Pro Thr His Lys Val Lys Leu Ile Phe Glu Phe Glu Asp Asp Val
        915                 920                 925

Val Thr Ser Leu Cys Lys Lys Ser Phe Gly Lys Ser Ile Ile Tyr Thr
    930                 935                 940

Gly Asp Trp Glu Gly Leu His Glu Val Leu Thr Ser Ala Met Asn Val
945                 950                 955                 960

Ile Gly Gln His Ile Lys Leu Pro Gln Phe Tyr Ile Tyr Asp Glu Glu
                965                 970                 975

Gly Gly Tyr Asp Val Ser Lys Pro Val Met Ile Ser Gln Trp Pro Ile
            980                 985                 990

Ser Asn Asp Ser Asn Gly Cys Val  Val Glu Ala Ser Thr  Asp Phe His
        995                 1000                 1005

Gln Leu  Glu Cys Ile Val Asp  Asp Ser Val Arg Glu  Glu Val Asp
    1010                 1015                 1020

Ile Ile  Glu Gln Pro Phe Glu  Glu Val Glu His Val  Leu Ser Ile
```

```
    1025                1030                1035

Lys Gln  Pro Phe Ser Phe Ser  Phe Arg Asp Glu Leu  Gly Val Arg
    1040                1045                1050

Val Leu  Asp Gln Ser Asp Asn  Asn Cys Trp Ile Ser  Thr Thr Leu
    1055                1060                1065

Val Gln  Leu Gln Leu Thr Lys  Leu Leu Asp Asp Ser  Ile Glu Met
    1070                1075                1080

Gln Leu  Phe Lys Val Gly Lys  Val Asp Ser Ile Val  Gln Lys Cys
    1085                1090                1095

Tyr Glu  Leu Ser His Leu Ile  Ser Gly Ser Leu Gly  Asp Ser Gly
    1100                1105                1110

Lys Leu  Leu Ser Glu Leu Leu  Lys Glu Lys Tyr Thr  Cys Ser Ile
    1115                1120                1125

Thr Phe  Glu Met Ser Cys Asp  Cys Gly Lys Lys Phe  Asp Asp Gln
    1130                1135                1140

Val Gly  Cys Leu Phe Trp Ile  Met Pro Tyr Thr Lys  Leu Phe Gln
    1145                1150                1155

Lys Gly  Glu Cys Cys Ile Cys  His Lys Met Gln Thr  Tyr Lys Leu
    1160                1165                1170

Val Ser  Met Lys Gly Thr Gly  Val Phe Val Gln Asp  Pro Ala Pro
    1175                1180                1185

Ile Asp  Ile Asp Ala Phe Pro  Val Lys Pro Ile Cys  Ser Ser Val
    1190                1195                1200

Tyr Leu  Gly Val Lys Gly Ser  Gly His Tyr Gln Thr  Asn Leu Tyr
    1205                1210                1215

Ser Phe  Asn Lys Ala Ile Asp  Gly Phe Gly Val Phe  Asp Ile Lys
    1220                1225                1230

Asn Ser  Ser Val Asn Thr Val  Cys Phe Val Asp Val  Asp Phe His
    1235                1240                1245

Ser Val  Glu Ile Glu Ala Gly  Glu Val Lys Pro Phe  Ala Val Tyr
    1250                1255                1260

Lys Asn  Val Lys Phe Tyr Leu  Gly Asp Ile Ser His  Leu Val Asn
    1265                1270                1275

Cys Val  Ser Phe Asp Phe Val  Val Asn Ala Ala Asn  Glu Asn Leu
    1280                1285                1290

Leu His  Gly Gly Gly Val Ala  Arg Ala Ile Asp Ile  Leu Thr Glu
    1295                1300                1305

Gly Gln  Leu Gln Ser Leu Ser  Lys Asp Tyr Ile Ser  Ser Asn Gly
    1310                1315                1320

Pro Leu  Lys Val Gly Ala Gly  Val Met Leu Glu Cys  Glu Lys Phe
    1325                1330                1335

Asn Val  Phe Asn Val Val Gly  Pro Arg Thr Gly Lys  His Glu His
    1340                1345                1350

Ser Leu  Leu Val Glu Ala Tyr  Asn Ser Ile Leu Phe  Glu Asn Gly
    1355                1360                1365

Ile Pro  Leu Met Pro Leu Leu  Ser Cys Gly Ile Phe  Gly Val Arg
    1370                1375                1380

Ile Glu  Asn Ser Leu Lys Ala  Leu Phe Ser Cys Asp  Ile Asn Lys
    1385                1390                1395

Pro Leu  Gln Val Phe Val Tyr  Ser Ser Asn Glu Glu  Gln Ala Val
    1400                1405                1410

Leu Lys  Phe Leu Asp Gly Leu  Asp Leu Thr Pro Val  Ile Asp Asp
    1415                1420                1425
```

```
Val Asp Val Val Lys Pro Phe Arg Val Glu Gly Asn Phe Ser Phe
    1430                1435                1440

Phe Asp Cys Gly Val Asn Ala Leu Asp Gly Asp Ile Tyr Leu Leu
    1445                1450                1455

Phe Thr Asn Ser Ile Leu Met Leu Asp Lys Gln Gly Gln Leu Leu
    1460                1465                1470

Asp Thr Lys Leu Asn Gly Ile Leu Gln Gln Ala Ala Leu Asp Tyr
    1475                1480                1485

Leu Ala Thr Val Lys Thr Val Pro Ala Gly Asn Leu Val Lys Leu
    1490                1495                1500

Phe Val Glu Ser Cys Thr Ile Tyr Met Cys Val Val Pro Ser Ile
    1505                1510                1515

Asn Asp Leu Ser Phe Asp Lys Asn Leu Gly Arg Cys Val Arg Lys
    1520                1525                1530

Leu Asn Arg Leu Lys Thr Cys Val Ile Ala Asn Val Pro Ala Ile
    1535                1540                1545

Asp Val Leu Lys Lys Leu Leu Ser Ser Leu Thr Leu Thr Val Lys
    1550                1555                1560

Phe Val Val Glu Ser Asn Val Met Asp Val Asn Asp Cys Phe Lys
    1565                1570                1575

Asn Asp Asn Val Val Leu Lys Ile Thr Glu Asp Gly Ile Asn Val
    1580                1585                1590

Lys Asp Val Val Val Glu Ser Ser Lys Ser Leu Gly Lys Gln Leu
    1595                1600                1605

Gly Val Val Ser Asp Gly Val Asp Ser Phe Glu Gly Val Leu Pro
    1610                1615                1620

Ile Asn Thr Asp Thr Val Leu Ser Val Ala Pro Glu Val Asp Trp
    1625                1630                1635

Val Ala Phe Tyr Gly Phe Glu Lys Ala Ala Leu Phe Ala Ser Leu
    1640                1645                1650

Asp Val Lys Pro Tyr Gly Tyr Pro Asn Asp Phe Val Gly Gly Phe
    1655                1660                1665

Arg Val Leu Gly Thr Thr Asp Asn Asn Cys Trp Val Asn Ala Thr
    1670                1675                1680

Cys Ile Ile Leu Gln Tyr Leu Lys Pro Thr Phe Lys Ser Lys Gly
    1685                1690                1695

Leu Asn Val Leu Trp Asn Lys Phe Val Thr Gly Asp Val Gly Pro
    1700                1705                1710

Phe Val Ser Phe Ile Tyr Phe Ile Thr Met Ser Ser Lys Gly Gln
    1715                1720                1725

Lys Gly Asp Ala Glu Glu Ala Leu Ser Lys Leu Ser Glu Tyr Leu
    1730                1735                1740

Ile Ser Asp Ser Ile Val Thr Leu Glu Gln Tyr Ser Thr Cys Asp
    1745                1750                1755

Ile Cys Lys Ser Thr Val Val Glu Val Lys Ser Ala Ile Val Cys
    1760                1765                1770

Ala Ser Val Leu Lys Asp Gly Cys Asp Val Gly Phe Cys Pro His
    1775                1780                1785

Arg His Lys Leu Arg Ser Arg Val Lys Phe Val Asn Gly Arg Val
    1790                1795                1800

Val Ile Thr Asn Val Gly Glu Pro Ile Ile Ser Gln Pro Ser Lys
    1805                1810                1815
```

```
Leu Leu  Asn Gly Ile Ala Tyr  Thr Thr Phe Ser Gly  Ser Phe Asp
    1820                 1825                 1830

Asn Gly  His Tyr Val Val Tyr  Asp Ala Ala Asn Asn  Ala Val Tyr
    1835                 1840                 1845

Asp Gly  Ala Arg Leu Phe Ser  Ser Asp Leu Ser Thr  Leu Ala Val
    1850                 1855                 1860

Thr Ala  Ile Val Val Val Gly  Gly Cys Val Thr Ser  Asn Val Pro
    1865                 1870                 1875

Thr Ile  Val Ser Glu Lys Ile  Ser Val Met Asp Lys  Leu Asp Thr
    1880                 1885                 1890

Gly Ala  Gln Lys Phe Phe Gln  Phe Gly Asp Phe Val  Met Asn Asn
    1895                 1900                 1905

Ile Val  Leu Phe Leu Thr Trp  Leu Leu Ser Met Phe  Ser Leu Leu
    1910                 1915                 1920

Arg Thr  Ser Ile Met Lys His  Asp Ile Lys Val Ile  Ala Lys Ala
    1925                 1930                 1935

Pro Lys  Arg Thr Gly Val Ile  Leu Thr Arg Ser Phe  Lys Tyr Asn
    1940                 1945                 1950

Ile Arg  Ser Ala Leu Phe Val  Ile Lys Gln Lys Trp  Cys Val Ile
    1955                 1960                 1965

Val Thr  Leu Phe Lys Phe Leu  Leu Leu Leu Tyr Ala  Ile Tyr Ala
    1970                 1975                 1980

Leu Val  Phe Met Ile Val Gln  Phe Ser Pro Phe Asn  Ser Leu Leu
    1985                 1990                 1995

Cys Gly  Asp Ile Val Ser Gly  Tyr Glu Lys Ser Thr  Phe Asn Lys
    2000                 2005                 2010

Asp Ile  Tyr Cys Gly Asn Ser  Met Val Cys Lys Met  Cys Leu Phe
    2015                 2020                 2025

Ser Tyr  Gln Glu Phe Asn Asp  Leu Asp His Thr Ser  Leu Val Trp
    2030                 2035                 2040

Lys His  Ile Arg Asp Pro Ile  Leu Ile Ser Leu Gln  Pro Phe Val
    2045                 2050                 2055

Ile Leu  Val Ile Leu Leu Ile  Phe Gly Asn Met Tyr  Leu Arg Phe
    2060                 2065                 2070

Gly Leu  Leu Tyr Phe Val Ala  Gln Phe Ile Ser Thr  Phe Gly Ser
    2075                 2080                 2085

Phe Leu  Gly Phe His Gln Lys  Gln Trp Phe Leu His  Phe Val Pro
    2090                 2095                 2100

Phe Asp  Val Leu Cys Asn Glu  Phe Leu Ala Thr Phe  Ile Val Cys
    2105                 2110                 2115

Lys Ile  Val Leu Phe Val Arg  His Ile Ile Val Gly  Cys Asn Asn
    2120                 2125                 2130

Ala Asp  Cys Val Ala Cys Ser  Lys Ser Ala Arg Leu  Lys Arg Val
    2135                 2140                 2145

Pro Leu  Gln Thr Ile Ile Asn  Gly Met His Lys Ser  Phe Tyr Val
    2150                 2155                 2160

Asn Ala  Asn Gly Gly Thr Cys  Phe Cys Asn Lys His  Asn Phe Phe
    2165                 2170                 2175

Cys Val  Asn Cys Asp Ser Phe  Gly Pro Gly Asn Thr  Phe Ile Asn
    2180                 2185                 2190

Gly Asp  Ile Ala Arg Glu Leu  Gly Asn Val Val Lys  Thr Ala Val
    2195                 2200                 2205

Gln Pro  Thr Ala Pro Ala Tyr  Val Ile Ile Asp Lys  Val Asp Phe
```

```
    2210                2215                2220

Val Asn  Gly Phe Tyr Arg Leu  Tyr Ser Gly Asp Thr  Phe Trp Arg
    2225                2230                2235

Tyr Asp  Phe Asp Ile Thr Glu  Ser Lys Tyr Ser Cys  Lys Glu Val
    2240                2245                2250

Leu Lys  Asn Cys Asn Val Leu  Glu Asn Phe Ile Val  Tyr Asn Asn
    2255                2260                2265

Ser Gly  Ser Asn Ile Thr Gln  Ile Lys Asn Ala Cys  Val Tyr Phe
    2270                2275                2280

Ser Gln  Leu Leu Cys Glu Pro  Ile Lys Leu Val Asn  Ser Glu Leu
    2285                2290                2295

Leu Ser  Thr Leu Ser Val Asp  Phe Asn Gly Val Leu  His Lys Ala
    2300                2305                2310

Tyr Val  Asp Val Leu Cys Asn  Ser Phe Phe Lys Glu  Leu Thr Ala
    2315                2320                2325

Asn Met  Ser Met Ala Glu Cys  Lys Ala Thr Leu Gly  Leu Thr Val
    2330                2335                2340

Ser Asp  Asp Asp Phe Val Ser  Ala Val Ala Asn Ala  His Arg Tyr
    2345                2350                2355

Asp Val  Leu Leu Ser Asp Leu  Ser Phe Asn Asn Phe  Phe Ile Ser
    2360                2365                2370

Tyr Ala  Lys Pro Glu Asp Lys  Leu Ser Val Tyr Asp  Ile Ala Cys
    2375                2380                2385

Cys Met  Arg Ala Gly Ser Lys  Val Val Asn His Asn  Val Leu Ile
    2390                2395                2400

Lys Glu  Ser Ile Pro Ile Val  Trp Gly Val Lys Asp  Phe Asn Thr
    2405                2410                2415

Leu Ser  Gln Glu Gly Lys Lys  Tyr Leu Val Lys Thr  Thr Lys Ala
    2420                2425                2430

Lys Gly  Leu Thr Phe Leu Leu  Thr Phe Asn Asp Asn  Gln Ala Ile
    2435                2440                2445

Thr Gln  Val Pro Ala Thr Ser  Ile Val Ala Lys Gln  Gly Ala Gly
    2450                2455                2460

Phe Lys  Arg Thr Tyr Asn Phe  Leu Trp Tyr Val Cys  Leu Phe Val
    2465                2470                2475

Val Ala  Leu Phe Ile Gly Val  Ser Phe Ile Asp Tyr  Thr Thr Thr
    2480                2485                2490

Val Thr  Ser Phe His Gly Tyr  Asp Phe Lys Tyr Ile  Glu Asn Gly
    2495                2500                2505

Gln Leu  Lys Val Phe Glu Ala  Pro Leu His Cys Val  Arg Asn Val
    2510                2515                2520

Phe Asp  Asn Phe Asn Gln Trp  His Glu Ala Lys Phe  Gly Val Val
    2525                2530                2535

Thr Thr  Asn Ser Asp Lys Cys  Pro Ile Val Val Gly  Val Ser Glu
    2540                2545                2550

Arg Ile  Asn Val Val Pro Gly  Val Pro Thr Asn Val  Tyr Leu Val
    2555                2560                2565

Gly Lys  Thr Leu Val Phe Thr  Leu Gln Ala Ala Phe  Gly Asn Thr
    2570                2575                2580

Gly Val  Cys Tyr Asp Phe Asp  Gly Val Thr Thr Ser  Asp Lys Cys
    2585                2590                2595

Ile Phe  Asn Ser Ala Cys Thr  Arg Leu Glu Gly Leu  Gly Gly Asp
    2600                2605                2610
```

```
Asn Val  Tyr Cys Tyr Asn Thr  Asp Leu Ile Glu Gly  Ser Lys Pro
    2615                 2620                 2625

Tyr Ser  Thr Leu Gln Pro Asn  Ala Tyr Tyr Lys Tyr  Asp Ala Lys
    2630                 2635                 2640

Asn Tyr  Val Arg Phe Pro Glu  Ile Leu Ala Arg Gly  Phe Gly Leu
    2645                 2650                 2655

Arg Thr  Ile Arg Thr Leu Ala  Thr Arg Tyr Cys Arg  Val Gly Glu
    2660                 2665                 2670

Cys Arg  Asp Ser His Lys Gly  Val Cys Phe Gly Phe  Asp Lys Trp
    2675                 2680                 2685

Tyr Val  Asn Asp Gly Arg Val  Asp Asp Gly Tyr Ile  Cys Gly Asp
    2690                 2695                 2700

Gly Leu  Ile Asp Leu Leu Val  Asn Val Leu Ser Ile  Phe Ser Ser
    2705                 2710                 2715

Ser Phe  Ser Val Val Ala Met  Ser Gly His Met Leu  Phe Asn Phe
    2720                 2725                 2730

Leu Phe  Ala Ala Phe Ile Thr  Phe Leu Cys Phe Leu  Val Thr Lys
    2735                 2740                 2745

Phe Lys  Arg Val Phe Gly Asp  Leu Ser Tyr Gly Val  Phe Thr Val
    2750                 2755                 2760

Val Cys  Ala Thr Leu Ile Asn  Asn Ile Ser Tyr Val  Val Thr Gln
    2765                 2770                 2775

Asn Leu  Phe Phe Met Leu Leu  Tyr Ala Ile Leu Tyr  Phe Val Phe
    2780                 2785                 2790

Thr Arg  Thr Val Arg Tyr Ala  Trp Ile Trp His Ile  Ala Tyr Ile
    2795                 2800                 2805

Val Ala  Tyr Phe Leu Leu Ile  Pro Trp Trp Leu Leu  Thr Trp Phe
    2810                 2815                 2820

Ser Phe  Ala Ala Phe Leu Glu  Leu Leu Pro Asn Val  Phe Lys Leu
    2825                 2830                 2835

Lys Ile  Ser Thr Gln Leu Phe  Glu Gly Asp Lys Phe  Ile Gly Thr
    2840                 2845                 2850

Phe Glu  Ser Ala Ala Ala Gly  Thr Phe Val Leu Asp  Met Arg Ser
    2855                 2860                 2865

Tyr Glu  Arg Leu Ile Asn Thr  Ile Ser Pro Glu Lys  Leu Lys Asn
    2870                 2875                 2880

Tyr Ala  Ala Ser Tyr Asn Lys  Tyr Lys Tyr Tyr Ser  Gly Ser Ala
    2885                 2890                 2895

Ser Glu  Ala Asp Tyr Arg Cys  Ala Cys Tyr Ala His  Leu Ala Lys
    2900                 2905                 2910

Ala Met  Leu Asp Tyr Ala Lys  Asp His Asn Asp Met  Leu Tyr Ser
    2915                 2920                 2925

Pro Pro  Thr Ile Ser Tyr Asn  Ser Thr Leu Gln Ser  Gly Leu Lys
    2930                 2935                 2940

Lys Met  Ala Gln Pro Ser Gly  Cys Val Glu Arg Cys  Val Val Arg
    2945                 2950                 2955

Val Cys  Tyr Gly Ser Thr Val  Leu Asn Gly Val Trp  Leu Gly Asp
    2960                 2965                 2970

Thr Val  Thr Cys Pro Arg His  Val Ile Ala Pro Ser  Thr Thr Val
    2975                 2980                 2985

Leu Ile  Asp Tyr Asp His Ala  Tyr Ser Thr Met Arg  Leu His Asn
    2990                 2995                 3000
```

```
Phe Ser  Val Ser His Asn Gly  Val Phe Leu Gly Val  Val Gly Val
    3005                 3010                 3015

Thr Met  His Gly Ser Val Leu  Arg Ile Lys Val Ser  Gln Ser Asn
    3020                 3025                 3030

Val His  Thr Pro Lys His Val  Phe Lys Thr Leu Lys  Pro Gly Asp
    3035                 3040                 3045

Ser Phe  Asn Ile Leu Ala Cys  Tyr Glu Gly Ile Ala  Ser Gly Val
    3050                 3055                 3060

Phe Gly  Val Asn Leu Arg Thr  Asn Phe Thr Ile Lys  Gly Ser Phe
    3065                 3070                 3075

Ile Asn  Gly Ala Cys Gly Ser  Pro Gly Tyr Asn Val  Arg Asn Asp
    3080                 3085                 3090

Gly Thr  Val Glu Phe Cys Tyr  Leu His Gln Ile Glu  Leu Gly Ser
    3095                 3100                 3105

Gly Ala  His Val Gly Ser Asp  Phe Thr Gly Ser Val  Tyr Gly Asn
    3110                 3115                 3120

Phe Asp  Asp Gln Pro Ser Leu  Gln Val Glu Ser Ala  Asn Leu Met
    3125                 3130                 3135

Leu Ser  Asp Asn Val Val Ala  Phe Leu Tyr Ala Ala  Leu Leu Asn
    3140                 3145                 3150

Gly Cys  Arg Trp Trp Leu Cys  Ser Thr Arg Val Asn  Val Asp Gly
    3155                 3160                 3165

Phe Asn  Glu Trp Ala Met Ala  Asn Gly Tyr Thr Ser  Val Ser Ser
    3170                 3175                 3180

Val Glu  Cys Tyr Ser Ile Leu  Ala Ala Lys Thr Gly  Val Ser Val
    3185                 3190                 3195

Glu Gln  Leu Leu Ala Ser Ile  Gln His Leu His Glu  Gly Phe Gly
    3200                 3205                 3210

Gly Lys  Asn Ile Leu Gly Tyr  Ser Ser Leu Cys Asp  Glu Phe Thr
    3215                 3220                 3225

Leu Ala  Glu Val Val Lys Gln  Met Tyr Gly Val Asn  Leu Gln Ser
    3230                 3235                 3240

Gly Lys  Val Ile Phe Gly Leu  Lys Thr Met Phe Leu  Phe Ser Val
    3245                 3250                 3255

Phe Phe  Thr Met Phe Trp Ala  Glu Leu Phe Ile Tyr  Thr Asn Thr
    3260                 3265                 3270

Ile Trp  Ile Asn Pro Val Ile  Leu Thr Pro Ile Phe  Cys Leu Leu
    3275                 3280                 3285

Leu Phe  Leu Ser Leu Val Leu  Thr Met Phe Leu Lys  His Lys Phe
    3290                 3295                 3300

Leu Phe  Leu Gln Val Phe Leu  Leu Pro Thr Val Ile  Ala Thr Ala
    3305                 3310                 3315

Leu Tyr  Asn Cys Val Leu Asp  Tyr Tyr Ile Val Lys  Phe Leu Ala
    3320                 3325                 3330

Asp His  Phe Asn Tyr Asn Val  Ser Val Leu Gln Met  Asp Val Gln
    3335                 3340                 3345

Gly Leu  Val Asn Val Leu Val  Cys Leu Phe Val Val  Phe Leu His
    3350                 3355                 3360

Thr Trp  Arg Phe Ser Lys Glu  Arg Phe Thr His Trp  Phe Thr Tyr
    3365                 3370                 3375

Val Cys  Ser Leu Ile Ala Val  Ala Tyr Thr Tyr Phe  Tyr Ser Gly
    3380                 3385                 3390

Asp Phe  Leu Ser Leu Leu Val  Met Phe Leu Cys Ala  Ile Ser Ser
```

```
    3395                3400                3405

Asp Trp  Tyr Ile Gly Ala Ile  Val Phe Arg Leu Ser  Arg Leu Ile
    3410                3415                3420

Val Phe  Phe Ser Pro Glu Ser  Val Phe Ser Val Phe  Gly Asp Val
    3425                3430                3435

Lys Leu  Thr Leu Val Val Tyr  Leu Ile Cys Gly Tyr  Leu Val Cys
    3440                3445                3450

Thr Tyr  Trp Gly Ile Leu Tyr  Trp Phe Asn Arg Phe  Phe Lys Cys
    3455                3460                3465

Thr Met  Gly Val Tyr Asp Phe  Lys Val Ser Ala Ala  Glu Phe Lys
    3470                3475                3480

Tyr Met  Val Ala Asn Gly Leu  His Ala Pro His Gly  Pro Phe Asp
    3485                3490                3495

Ala Leu  Trp Leu Ser Phe Lys  Leu Leu Gly Ile Gly  Gly Asp Arg
    3500                3505                3510

Cys Ile  Lys Ile Ser Thr Val  Gln Ser Lys Leu Thr  Asp Leu Lys
    3515                3520                3525

Cys Thr  Asn Val Val Leu Leu  Gly Cys Leu Ser Ser  Met Asn Ile
    3530                3535                3540

Ala Ala  Asn Ser Ser Glu Trp  Ala Tyr Cys Val Asp  Leu His Asn
    3545                3550                3555

Lys Ile  Asn Leu Cys Asp Asp  Pro Glu Lys Ala Gln  Ser Met Leu
    3560                3565                3570

Leu Ala  Leu Leu Ala Phe Phe  Leu Ser Lys His Ser  Asp Phe Gly
    3575                3580                3585

Leu Asp  Gly Leu Ile Asp Ser  Tyr Phe Asp Asn Ser  Ser Thr Leu
    3590                3595                3600

Gln Ser  Val Ala Ser Ser Phe  Val Ser Met Pro Ser  Tyr Ile Ala
    3605                3610                3615

Tyr Glu  Asn Ala Arg Gln Ala  Tyr Glu Asp Ala Ile  Ala Asn Gly
    3620                3625                3630

Ser Ser  Ser Gln Leu Ile Lys  Gln Leu Lys Arg Ala  Met Asn Ile
    3635                3640                3645

Ala Lys  Ser Glu Phe Asp His  Glu Ile Ser Val Gln  Lys Lys Ile
    3650                3655                3660

Asn Arg  Met Ala Glu Gln Ala  Ala Thr Gln Met Tyr  Lys Glu Ala
    3665                3670                3675

Arg Ser  Val Asn Arg Lys Ser  Lys Val Ile Ser Ala  Met His Ser
    3680                3685                3690

Leu Leu  Phe Gly Met Leu Arg  Arg Leu Asp Met Ser  Ser Val Glu
    3695                3700                3705

Thr Val  Leu Asn Leu Ala Arg  Asp Gly Val Val Pro  Leu Ser Val
    3710                3715                3720

Ile Pro  Ala Thr Ser Ala Ser  Lys Leu Thr Ile Val  Ser Pro Asp
    3725                3730                3735

Leu Glu  Ser Tyr Ser Lys Ile  Val Cys Asp Gly Ser  Val His Tyr
    3740                3745                3750

Ala Gly  Val Val Trp Thr Leu  Asn Asp Val Lys Asp  Asn Asp Gly
    3755                3760                3765

Arg Pro  Val His Val Lys Glu  Ile Thr Lys Glu Asn  Val Glu Thr
    3770                3775                3780

Leu Thr  Trp Pro Leu Ile Leu  Asn Cys Glu Arg Val  Val Lys Leu
    3785                3790                3795
```

```
Gln Asn  Asn Glu Ile Met Pro  Gly Lys Leu Lys Gln  Lys Pro Met
    3800                 3805                 3810

Lys Ala  Glu Gly Asp Gly Gly  Val Leu Gly Asp Gly  Asn Ala Leu
    3815                 3820                 3825

Tyr Asn  Thr Glu Gly Gly Lys  Thr Phe Met Tyr Ala  Tyr Ile Ser
    3830                 3835                 3840

Asn Lys  Ala Asp Leu Lys Phe  Val Lys Trp Glu Tyr  Glu Gly Gly
    3845                 3850                 3855

Cys Asn  Thr Ile Glu Leu Asp  Ser Pro Cys Arg Phe  Met Val Glu
    3860                 3865                 3870

Thr Pro  Asn Gly Pro Gln Val  Lys Tyr Leu Tyr Phe  Val Lys Asn
    3875                 3880                 3885

Leu Asn  Thr Leu Arg Arg Gly  Ala Val Leu Gly Phe  Ile Gly Ala
    3890                 3895                 3900

Thr Ile  Arg Leu Gln Ala Gly  Lys Gln Thr Glu Leu  Ala Val Asn
    3905                 3910                 3915

Ser Gly  Leu Leu Thr Ala Cys  Ala Phe Ser Val Asp  Pro Ala Thr
    3920                 3925                 3930

Thr Tyr  Leu Glu Ala Val Lys  His Gly Ala Lys Pro  Val Ser Asn
    3935                 3940                 3945

Cys Ile  Lys Met Leu Ser Asn  Gly Ala Gly Asn Gly  Gln Ala Ile
    3950                 3955                 3960

Thr Thr  Ser Val Asp Ala Asn  Thr Asn Gln Asp Ser  Tyr Gly Gly
    3965                 3970                 3975

Ala Ser  Ile Cys Leu Tyr Cys  Arg Ala His Val Pro  His Pro Ser
    3980                 3985                 3990

Met Asp  Gly Tyr Cys Lys Phe  Lys Gly Lys Cys Val  Gln Val Pro
    3995                 4000                 4005

Ile Gly  Cys Leu Asp Pro Ile  Arg Phe Cys Leu Glu  Asn Asn Val
    4010                 4015                 4020

Cys Asn  Val Cys Gly Cys Trp  Leu Gly His Gly Cys  Ala Cys Asp
    4025                 4030                 4035

Arg Thr  Thr Ile Gln Ser Val  Asp Ile Ser Tyr Leu  Asn Glu Gln
    4040                 4045                 4050

Gly Val  Leu Val Gln Leu Asp
    4055                 4060
```

<210> SEQ ID NO 57
<211> LENGTH: 6738
<212> TYPE: PRT
<213> ORGANISM: Human coronavirus
<220> FEATURE:
<221> NAME/KEY: MISC_FEATURE
<222> LOCATION: (1)..(6738)
<223> OTHER INFORMATION: ORF 1ab replicase polyprotein

<400> SEQUENCE: 57

```
Met Phe Tyr Asn Gln Val Thr Leu Ala Val Ala Ser Asp Ser Glu Ile
1               5                   10                  15

Ser Gly Phe Gly Phe Ala Ile Pro Ser Val Ala Val Arg Thr Tyr Ser
            20                  25                  30

Glu Ala Ala Ala Gln Gly Phe Gln Ala Cys Arg Phe Val Ala Phe Gly
        35                  40                  45

Leu Gln Asp Cys Val Thr Gly Ile Asn Asp Asp Asp Tyr Val Ile Ala
    50                  55                  60
```

```
Leu Thr Gly Thr Asn Gln Leu Cys Ala Lys Ile Leu Pro Phe Ser Asp
65                  70                  75                  80

Arg Pro Leu Asn Leu Arg Gly Trp Leu Ile Phe Ser Asn Ser Asn Tyr
                85                  90                  95

Val Leu Gln Asp Phe Asp Val Val Phe Gly His Gly Ala Gly Ser Val
            100                 105                 110

Val Phe Val Asp Lys Tyr Met Cys Gly Phe Asp Gly Lys Pro Val Leu
        115                 120                 125

Pro Lys Asn Met Trp Glu Phe Arg Asp Tyr Phe Asn Asn Asn Thr Asp
    130                 135                 140

Ser Ile Val Ile Gly Gly Val Thr Tyr Gln Leu Ala Trp Asp Val Ile
145                 150                 155                 160

Arg Lys Asp Leu Ser Tyr Glu Gln Gln Asn Val Leu Ala Ile Glu Ser
                165                 170                 175

Ile His Tyr Leu Gly Thr Thr Gly His Thr Leu Lys Ser Gly Cys Lys
            180                 185                 190

Leu Thr Asn Ala Lys Pro Pro Lys Tyr Ser Ser Lys Val Val Leu Ser
        195                 200                 205

Gly Glu Trp Asn Ala Val Tyr Arg Ala Phe Gly Ser Pro Phe Ile Thr
    210                 215                 220

Asn Gly Met Ser Leu Leu Asp Ile Ile Val Lys Pro Val Phe Phe Asn
225                 230                 235                 240

Ala Phe Val Lys Cys Asn Cys Gly Ser Glu Ser Trp Ser Val Gly Ala
                245                 250                 255

Trp Asp Gly Tyr Leu Ser Ser Cys Cys Gly Thr Pro Ala Lys Lys Leu
            260                 265                 270

Cys Val Val Pro Gly Asn Val Val Pro Gly Asp Val Ile Ile Thr Ser
        275                 280                 285

Thr Ser Ala Gly Cys Gly Val Lys Tyr Tyr Ala Gly Leu Val Val Lys
    290                 295                 300

His Ile Thr Asn Ile Thr Gly Val Ser Leu Trp Arg Val Thr Ala Val
305                 310                 315                 320

His Ser Asp Gly Met Phe Val Ala Ser Ser Ser Tyr Asp Ala Leu Leu
                325                 330                 335

His Arg Asn Ser Leu Asp Pro Phe Cys Phe Asp Val Asn Thr Leu Leu
            340                 345                 350

Ser Asn Gln Leu Arg Leu Ala Phe Leu Gly Ala Ser Val Thr Glu Asp
        355                 360                 365

Val Lys Phe Ala Ala Ser Thr Gly Val Ile Asp Ile Ser Ala Gly Met
    370                 375                 380

Phe Gly Leu Tyr Asp Asp Ile Leu Thr Asn Asn Lys Pro Trp Phe Val
385                 390                 395                 400

Arg Lys Ala Ser Gly Leu Phe Asp Ala Ile Trp Asp Ala Phe Val Ala
                405                 410                 415

Ala Ile Lys Leu Val Pro Thr Thr Thr Gly Val Leu Val Arg Phe Val
            420                 425                 430

Lys Ser Ile Ala Ser Thr Val Leu Thr Val Ser Asn Gly Val Ile Ile
        435                 440                 445

Met Cys Ala Asp Val Pro Asp Ala Phe Gln Ser Val Tyr Arg Thr Phe
    450                 455                 460

Thr Gln Ala Ile Cys Ala Ala Phe Asp Phe Ser Leu Asp Val Phe Lys
465                 470                 475                 480

Ile Gly Asp Val Lys Phe Lys Arg Leu Gly Asp Tyr Val Leu Thr Glu
```

```
                485                 490                 495

Asn Ala Leu Val Arg Leu Thr Thr Glu Val Val Arg Gly Val Arg Asp
            500                 505                 510

Ala Arg Ile Lys Lys Ala Met Phe Thr Lys Val Val Val Gly Pro Thr
        515                 520                 525

Thr Glu Val Lys Phe Ser Val Ile Glu Leu Ala Thr Val Asn Leu Arg
    530                 535                 540

Leu Val Asp Cys Ala Pro Val Val Cys Pro Lys Gly Lys Ile Val Val
545                 550                 555                 560

Ile Ala Gly Gln Ala Phe Phe Tyr Ser Gly Gly Phe Tyr Arg Phe Met
                565                 570                 575

Val Asp Pro Thr Thr Val Leu Asn Asp Pro Val Phe Thr Gly Asp Leu
            580                 585                 590

Phe Tyr Thr Ile Lys Phe Ser Gly Phe Lys Leu Asp Gly Phe Asn His
        595                 600                 605

Gln Phe Val Thr Ala Ser Ser Ala Thr Asp Ala Ile Ile Ala Val Glu
    610                 615                 620

Leu Leu Leu Leu Asp Phe Lys Thr Ala Val Phe Val Tyr Thr Cys Val
625                 630                 635                 640

Val Asp Gly Cys Ser Val Ile Val Arg Arg Asp Ala Thr Phe Ala Thr
                645                 650                 655

His Val Cys Phe Lys Asp Cys Tyr Asn Val Trp Glu Gln Phe Cys Ile
            660                 665                 670

Asp Asn Cys Gly Glu Pro Trp Phe Leu Thr Asp Tyr Asn Ala Ile Leu
        675                 680                 685

Gln Ser Asn Asn Pro Gln Cys Ala Ile Val Gln Ala Ser Glu Ser Lys
    690                 695                 700

Val Leu Leu Glu Arg Phe Leu Pro Lys Cys Pro Glu Ile Leu Leu Ser
705                 710                 715                 720

Ile Asp Asp Gly His Leu Trp Asn Leu Phe Val Glu Lys Phe Asn Phe
                725                 730                 735

Val Thr Asp Trp Leu Lys Thr Leu Lys Leu Thr Leu Thr Ser Asn Gly
            740                 745                 750

Leu Leu Gly Asn Cys Ala Lys Arg Phe Arg Arg Val Leu Val Lys Leu
        755                 760                 765

Leu Asp Val Tyr Asn Gly Phe Leu Glu Thr Val Cys Ser Val Ala Tyr
    770                 775                 780

Thr Ala Gly Val Cys Ile Lys Tyr Tyr Ala Val Asn Val Pro Tyr Val
785                 790                 795                 800

Val Ile Ser Gly Phe Val Ser Arg Val Ile Arg Arg Glu Arg Cys Asp
                805                 810                 815

Met Thr Phe Pro Cys Val Ser Cys Val Thr Phe Phe Tyr Glu Phe Leu
            820                 825                 830

Asp Thr Cys Phe Gly Val Ser Lys Pro Asn Ala Ile Asp Val Glu His
        835                 840                 845

Leu Glu Leu Lys Glu Thr Val Phe Val Glu Pro Lys Asp Gly Gly Gln
    850                 855                 860

Phe Phe Val Ser Gly Asp Tyr Leu Trp Tyr Val Val Asp Asp Ile Tyr
865                 870                 875                 880

Tyr Pro Ala Ser Cys Asn Gly Val Leu Pro Val Ala Phe Thr Lys Leu
                885                 890                 895

Ala Gly Gly Lys Ile Ser Phe Ser Asp Asp Val Ile Val His Asp Val
            900                 905                 910
```

```
Glu Pro Thr His Lys Val Lys Leu Ile Phe Glu Phe Glu Asp Asp Val
        915                 920                 925

Val Thr Ser Leu Cys Lys Lys Ser Phe Gly Lys Ser Ile Ile Tyr Thr
    930                 935                 940

Gly Asp Trp Glu Gly Leu His Glu Val Leu Thr Ser Ala Met Asn Val
945                 950                 955                 960

Ile Gly Gln His Ile Lys Leu Pro Gln Phe Tyr Ile Tyr Asp Glu Glu
                965                 970                 975

Gly Gly Tyr Asp Val Ser Lys Pro Val Met Ile Ser Gln Trp Pro Ile
            980                 985                 990

Ser Asn Asp Ser Asn Gly Cys Val  Val Glu Ala Ser Thr  Asp Phe His
        995                 1000                1005

Gln Leu  Glu Cys Ile Val Asp  Asp Ser Val Arg Glu  Glu Val Asp
    1010                1015                1020

Ile Ile  Glu Gln Pro Phe Glu  Glu Val Glu His Val  Leu Ser Ile
    1025                1030                1035

Lys Gln  Pro Phe Ser Phe Ser  Phe Arg Asp Glu Leu  Gly Val Arg
    1040                1045                1050

Val Leu  Asp Gln Ser Asp Asn  Asn Cys Trp Ile Ser  Thr Thr Leu
    1055                1060                1065

Val Gln  Leu Gln Leu Thr Lys  Leu Leu Asp Asp Ser  Ile Glu Met
    1070                1075                1080

Gln Leu  Phe Lys Val Gly Lys  Val Asp Ser Ile Val  Gln Lys Cys
    1085                1090                1095

Tyr Glu  Leu Ser His Leu Ile  Ser Gly Ser Leu Gly  Asp Ser Gly
    1100                1105                1110

Lys Leu  Leu Ser Glu Leu Leu  Lys Glu Lys Tyr Thr  Cys Ser Ile
    1115                1120                1125

Thr Phe  Glu Met Ser Cys Asp  Cys Gly Lys Lys Phe  Asp Asp Gln
    1130                1135                1140

Val Gly  Cys Leu Phe Trp Ile  Met Pro Tyr Thr Lys  Leu Phe Gln
    1145                1150                1155

Lys Gly  Glu Cys Cys Ile Cys  His Lys Met Gln Thr  Tyr Lys Leu
    1160                1165                1170

Val Ser  Met Lys Gly Thr Gly  Val Phe Val Gln Asp  Pro Ala Pro
    1175                1180                1185

Ile Asp  Ile Asp Ala Phe Pro  Val Lys Pro Ile Cys  Ser Ser Val
    1190                1195                1200

Tyr Leu  Gly Val Lys Gly Ser  Gly His Tyr Gln Thr  Asn Leu Tyr
    1205                1210                1215

Ser Phe  Asn Lys Ala Ile Asp  Gly Phe Gly Val Phe  Asp Ile Lys
    1220                1225                1230

Asn Ser  Ser Val Asn Thr Val  Cys Phe Val Asp Val  Asp Phe His
    1235                1240                1245

Ser Val  Glu Ile Glu Ala Gly  Glu Val Lys Pro Phe  Ala Val Tyr
    1250                1255                1260

Lys Asn  Val Lys Phe Tyr Leu  Gly Asp Ile Ser His  Leu Val Asn
    1265                1270                1275

Cys Val  Ser Phe Asp Phe Val  Val Asn Ala Ala Asn  Glu Asn Leu
    1280                1285                1290

Leu His  Gly Gly Gly Val Ala  Arg Ala Ile Asp Ile  Leu Thr Glu
    1295                1300                1305
```

```
Gly Gln  Leu Gln Ser Leu Ser  Lys Asp Tyr Ile Ser  Ser Asn Gly
    1310                 1315                 1320

Pro Leu  Lys Val Gly Ala Gly  Val Met Leu Glu Cys  Glu Lys Phe
    1325                 1330                 1335

Asn Val  Phe Asn Val Val Gly  Pro Arg Thr Gly Lys  His Glu His
    1340                 1345                 1350

Ser Leu  Leu Val Glu Ala Tyr  Asn Ser Ile Leu Phe  Glu Asn Gly
    1355                 1360                 1365

Ile Pro  Leu Met Pro Leu Leu  Ser Cys Gly Ile Phe  Gly Val Arg
    1370                 1375                 1380

Ile Glu  Asn Ser Leu Lys Ala  Leu Phe Ser Cys Asp  Ile Asn Lys
    1385                 1390                 1395

Pro Leu  Gln Val Phe Val Tyr  Ser Ser Asn Glu Glu  Gln Ala Val
    1400                 1405                 1410

Leu Lys  Phe Leu Asp Gly Leu  Asp Leu Thr Pro Val  Ile Asp Asp
    1415                 1420                 1425

Val Asp  Val Val Lys Pro Phe  Arg Val Glu Gly Asn  Phe Ser Phe
    1430                 1435                 1440

Phe Asp  Cys Gly Val Asn Ala  Leu Asp Gly Asp Ile  Tyr Leu Leu
    1445                 1450                 1455

Phe Thr  Asn Ser Ile Leu Met  Leu Asp Lys Gln Gly  Gln Leu Leu
    1460                 1465                 1470

Asp Thr  Lys Leu Asn Gly Ile  Leu Gln Gln Ala Ala  Leu Asp Tyr
    1475                 1480                 1485

Leu Ala  Thr Val Lys Thr Val  Pro Ala Gly Asn Leu  Val Lys Leu
    1490                 1495                 1500

Phe Val  Glu Ser Cys Thr Ile  Tyr Met Cys Val Val  Pro Ser Ile
    1505                 1510                 1515

Asn Asp  Leu Ser Phe Asp Lys  Asn Leu Gly Arg Cys  Val Arg Lys
    1520                 1525                 1530

Leu Asn  Arg Leu Lys Thr Cys  Val Ile Ala Asn Val  Pro Ala Ile
    1535                 1540                 1545

Asp Val  Leu Lys Lys Leu Leu  Ser Ser Leu Thr Leu  Thr Val Lys
    1550                 1555                 1560

Phe Val  Val Glu Ser Asn Val  Met Asp Val Asn Asp  Cys Phe Lys
    1565                 1570                 1575

Asn Asp  Asn Val Val Leu Lys  Ile Thr Glu Asp Gly  Ile Asn Val
    1580                 1585                 1590

Lys Asp  Val Val Val Glu Ser  Ser Lys Ser Leu Gly  Lys Gln Leu
    1595                 1600                 1605

Gly Val  Val Ser Asp Gly Val  Asp Ser Phe Glu Gly  Val Leu Pro
    1610                 1615                 1620

Ile Asn  Thr Asp Thr Val Leu  Ser Val Ala Pro Glu  Val Asp Trp
    1625                 1630                 1635

Val Ala  Phe Tyr Gly Phe Glu  Lys Ala Ala Leu Phe  Ala Ser Leu
    1640                 1645                 1650

Asp Val  Lys Pro Tyr Gly Tyr  Pro Asn Asp Phe Val  Gly Gly Phe
    1655                 1660                 1665

Arg Val  Leu Gly Thr Thr Asp  Asn Asn Cys Trp Val  Asn Ala Thr
    1670                 1675                 1680

Cys Ile  Ile Leu Gln Tyr Leu  Lys Pro Thr Phe Lys  Ser Lys Gly
    1685                 1690                 1695

Leu Asn  Val Leu Trp Asn Lys  Phe Val Thr Gly Asp  Val Gly Pro
```

```
    1700                1705                1710

Phe Val  Ser Phe Ile Tyr Phe  Ile Thr Met Ser Ser  Lys Gly Gln
    1715                1720                1725

Lys Gly  Asp Ala Glu Glu Ala  Leu Ser Lys Leu Ser  Glu Tyr Leu
    1730                1735                1740

Ile Ser  Asp Ser Ile Val Thr  Leu Glu Gln Tyr Ser  Thr Cys Asp
    1745                1750                1755

Ile Cys  Lys Ser Thr Val Val  Glu Val Lys Ser Ala  Ile Val Cys
    1760                1765                1770

Ala Ser  Val Leu Lys Asp Gly  Cys Asp Val Gly Phe  Cys Pro His
    1775                1780                1785

Arg His  Lys Leu Arg Ser Arg  Val Lys Phe Val Asn  Gly Arg Val
    1790                1795                1800

Val Ile  Thr Asn Val Gly Glu  Pro Ile Ile Ser Gln  Pro Ser Lys
    1805                1810                1815

Leu Leu  Asn Gly Ile Ala Tyr  Thr Thr Phe Ser Gly  Ser Phe Asp
    1820                1825                1830

Asn Gly  His Tyr Val Val Tyr  Asp Ala Ala Asn Asn  Ala Val Tyr
    1835                1840                1845

Asp Gly  Ala Arg Leu Phe Ser  Ser Asp Leu Ser Thr  Leu Ala Val
    1850                1855                1860

Thr Ala  Ile Val Val Val Gly  Gly Cys Val Thr Ser  Asn Val Pro
    1865                1870                1875

Thr Ile  Val Ser Glu Lys Ile  Ser Val Met Asp Lys  Leu Asp Thr
    1880                1885                1890

Gly Ala  Gln Lys Phe Phe Gln  Phe Gly Asp Phe Val  Met Asn Asn
    1895                1900                1905

Ile Val  Leu Phe Leu Thr Trp  Leu Leu Ser Met Phe  Ser Leu Leu
    1910                1915                1920

Arg Thr  Ser Ile Met Lys His  Asp Ile Lys Val Ile  Ala Lys Ala
    1925                1930                1935

Pro Lys  Arg Thr Gly Val Ile  Leu Thr Arg Ser Phe  Lys Tyr Asn
    1940                1945                1950

Ile Arg  Ser Ala Leu Phe Val  Ile Lys Gln Lys Trp  Cys Val Ile
    1955                1960                1965

Val Thr  Leu Phe Lys Phe Leu  Leu Leu Leu Tyr Ala  Ile Tyr Ala
    1970                1975                1980

Leu Val  Phe Met Ile Val Gln  Phe Ser Pro Phe Asn  Ser Leu Leu
    1985                1990                1995

Cys Gly  Asp Ile Val Ser Gly  Tyr Glu Lys Ser Thr  Phe Asn Lys
    2000                2005                2010

Asp Ile  Tyr Cys Gly Asn Ser  Met Val Cys Lys Met  Cys Leu Phe
    2015                2020                2025

Ser Tyr  Gln Glu Phe Asn Asp  Leu Asp His Thr Ser  Leu Val Trp
    2030                2035                2040

Lys His  Ile Arg Asp Pro Ile  Leu Ile Ser Leu Gln  Pro Phe Val
    2045                2050                2055

Ile Leu  Val Ile Leu Leu Ile  Phe Gly Asn Met Tyr  Leu Arg Phe
    2060                2065                2070

Gly Leu  Leu Tyr Phe Val Ala  Gln Phe Ile Ser Thr  Phe Gly Ser
    2075                2080                2085

Phe Leu  Gly Phe His Gln Lys  Gln Trp Phe Leu His  Phe Val Pro
    2090                2095                2100
```

```
Phe Asp  Val Leu Cys Asn Glu  Phe Leu Ala Thr Phe  Ile Val Cys
    2105                 2110                 2115

Lys Ile  Val Leu Phe Val Arg  His Ile Ile Val Gly  Cys Asn Asn
    2120                 2125                 2130

Ala Asp  Cys Val Ala Cys Ser  Lys Ser Ala Arg Leu  Lys Arg Val
    2135                 2140                 2145

Pro Leu  Gln Thr Ile Ile Asn  Gly Met His Lys Ser  Phe Tyr Val
    2150                 2155                 2160

Asn Ala  Asn Gly Gly Thr Cys  Phe Cys Asn Lys His  Asn Phe Phe
    2165                 2170                 2175

Cys Val  Asn Cys Asp Ser Phe  Gly Pro Gly Asn Thr  Phe Ile Asn
    2180                 2185                 2190

Gly Asp  Ile Ala Arg Glu Leu  Gly Asn Val Val Lys  Thr Ala Val
    2195                 2200                 2205

Gln Pro  Thr Ala Pro Ala Tyr  Val Ile Ile Asp Lys  Val Asp Phe
    2210                 2215                 2220

Val Asn  Gly Phe Tyr Arg Leu  Tyr Ser Gly Asp Thr  Phe Trp Arg
    2225                 2230                 2235

Tyr Asp  Phe Asp Ile Thr Glu  Ser Lys Tyr Ser Cys  Lys Glu Val
    2240                 2245                 2250

Leu Lys  Asn Cys Asn Val Leu  Glu Asn Phe Ile Val  Tyr Asn Asn
    2255                 2260                 2265

Ser Gly  Ser Asn Ile Thr Gln  Ile Lys Asn Ala Cys  Val Tyr Phe
    2270                 2275                 2280

Ser Gln  Leu Leu Cys Glu Pro  Ile Lys Leu Val Asn  Ser Glu Leu
    2285                 2290                 2295

Leu Ser  Thr Leu Ser Val Asp  Phe Asn Gly Val Leu  His Lys Ala
    2300                 2305                 2310

Tyr Val  Asp Val Leu Cys Asn  Ser Phe Phe Lys Glu  Leu Thr Ala
    2315                 2320                 2325

Asn Met  Ser Met Ala Glu Cys  Lys Ala Thr Leu Gly  Leu Thr Val
    2330                 2335                 2340

Ser Asp  Asp Asp Phe Val Ser  Ala Val Ala Asn Ala  His Arg Tyr
    2345                 2350                 2355

Asp Val  Leu Leu Ser Asp Leu  Ser Phe Asn Asn Phe  Phe Ile Ser
    2360                 2365                 2370

Tyr Ala  Lys Pro Glu Asp Lys  Leu Ser Val Tyr Asp  Ile Ala Cys
    2375                 2380                 2385

Cys Met  Arg Ala Gly Ser Lys  Val Val Asn His Asn  Val Leu Ile
    2390                 2395                 2400

Lys Glu  Ser Ile Pro Ile Val  Trp Gly Val Lys Asp  Phe Asn Thr
    2405                 2410                 2415

Leu Ser  Gln Glu Gly Lys Lys  Tyr Leu Val Lys Thr  Thr Lys Ala
    2420                 2425                 2430

Lys Gly  Leu Thr Phe Leu Leu  Thr Phe Asn Asp Asn  Gln Ala Ile
    2435                 2440                 2445

Thr Gln  Val Pro Ala Thr Ser  Ile Val Ala Lys Gln  Gly Ala Gly
    2450                 2455                 2460

Phe Lys  Arg Thr Tyr Asn Phe  Leu Trp Tyr Val Cys  Leu Phe Val
    2465                 2470                 2475

Val Ala  Leu Phe Ile Gly Val  Ser Phe Ile Asp Tyr  Thr Thr Thr
    2480                 2485                 2490
```

-continued

```
Val Thr  Ser Phe His Gly Tyr  Asp Phe Lys Tyr Ile  Glu Asn Gly
    2495                 2500                 2505

Gln Leu  Lys Val Phe Glu Ala  Pro Leu His Cys Val  Arg Asn Val
    2510                 2515                 2520

Phe Asp  Asn Phe Asn Gln Trp  His Glu Ala Lys Phe  Gly Val Val
    2525                 2530                 2535

Thr Thr  Asn Ser Asp Lys Cys  Pro Ile Val Val Gly  Val Ser Glu
    2540                 2545                 2550

Arg Ile  Asn Val Val Pro Gly  Val Pro Thr Asn Val  Tyr Leu Val
    2555                 2560                 2565

Gly Lys  Thr Leu Val Phe Thr  Leu Gln Ala Ala Phe  Gly Asn Thr
    2570                 2575                 2580

Gly Val  Cys Tyr Asp Phe Asp  Gly Val Thr Thr Ser  Asp Lys Cys
    2585                 2590                 2595

Ile Phe  Asn Ser Ala Cys Thr  Arg Leu Glu Gly Leu  Gly Gly Asp
    2600                 2605                 2610

Asn Val  Tyr Cys Tyr Asn Thr  Asp Leu Ile Glu Gly  Ser Lys Pro
    2615                 2620                 2625

Tyr Ser  Thr Leu Gln Pro Asn  Ala Tyr Tyr Lys Tyr  Asp Ala Lys
    2630                 2635                 2640

Asn Tyr  Val Arg Phe Pro Glu  Ile Leu Ala Arg Gly  Phe Gly Leu
    2645                 2650                 2655

Arg Thr  Ile Arg Thr Leu Ala  Thr Arg Tyr Cys Arg  Val Gly Glu
    2660                 2665                 2670

Cys Arg  Asp Ser His Lys Gly  Val Cys Phe Gly Phe  Asp Lys Trp
    2675                 2680                 2685

Tyr Val  Asn Asp Gly Arg Val  Asp Asp Gly Tyr Ile  Cys Gly Asp
    2690                 2695                 2700

Gly Leu  Ile Asp Leu Leu Val  Asn Val Leu Ser Ile  Phe Ser Ser
    2705                 2710                 2715

Ser Phe  Ser Val Val Ala Met  Ser Gly His Met Leu  Phe Asn Phe
    2720                 2725                 2730

Leu Phe  Ala Ala Phe Ile Thr  Phe Leu Cys Phe Leu  Val Thr Lys
    2735                 2740                 2745

Phe Lys  Arg Val Phe Gly Asp  Leu Ser Tyr Gly Val  Phe Thr Val
    2750                 2755                 2760

Val Cys  Ala Thr Leu Ile Asn  Asn Ile Ser Tyr Val  Val Thr Gln
    2765                 2770                 2775

Asn Leu  Phe Phe Met Leu Leu  Tyr Ala Ile Leu Tyr  Phe Val Phe
    2780                 2785                 2790

Thr Arg  Thr Val Arg Tyr Ala  Trp Ile Trp His Ile  Ala Tyr Ile
    2795                 2800                 2805

Val Ala  Tyr Phe Leu Leu Ile  Pro Trp Trp Leu Leu  Thr Trp Phe
    2810                 2815                 2820

Ser Phe  Ala Ala Phe Leu Glu  Leu Leu Pro Asn Val  Phe Lys Leu
    2825                 2830                 2835

Lys Ile  Ser Thr Gln Leu Phe  Glu Gly Asp Lys Phe  Ile Gly Thr
    2840                 2845                 2850

Phe Glu  Ser Ala Ala Ala Gly  Thr Phe Val Leu Asp  Met Arg Ser
    2855                 2860                 2865

Tyr Glu  Arg Leu Ile Asn Thr  Ile Ser Pro Glu Lys  Leu Lys Asn
    2870                 2875                 2880

Tyr Ala  Ala Ser Tyr Asn Lys  Tyr Lys Tyr Tyr Ser  Gly Ser Ala
```

-continued

```
    2885                2890                2895

Ser Glu  Ala Asp Tyr Arg Cys  Ala Cys Tyr Ala His  Leu Ala Lys
    2900                2905                2910

Ala Met  Leu Asp Tyr Ala Lys  Asp His Asn Asp Met  Leu Tyr Ser
    2915                2920                2925

Pro Pro  Thr Ile Ser Tyr Asn  Ser Thr Leu Gln Ser  Gly Leu Lys
    2930                2935                2940

Lys Met  Ala Gln Pro Ser Gly  Cys Val Glu Arg Cys  Val Val Arg
    2945                2950                2955

Val Cys  Tyr Gly Ser Thr Val  Leu Asn Gly Val Trp  Leu Gly Asp
    2960                2965                2970

Thr Val  Thr Cys Pro Arg His  Val Ile Ala Pro Ser  Thr Thr Val
    2975                2980                2985

Leu Ile  Asp Tyr Asp His Ala  Tyr Ser Thr Met Arg  Leu His Asn
    2990                2995                3000

Phe Ser  Val Ser His Asn Gly  Val Phe Leu Gly Val  Val Gly Val
    3005                3010                3015

Thr Met  His Gly Ser Val Leu  Arg Ile Lys Val Ser  Gln Ser Asn
    3020                3025                3030

Val His  Thr Pro Lys His Val  Phe Lys Thr Leu Lys  Pro Gly Asp
    3035                3040                3045

Ser Phe  Asn Ile Leu Ala Cys  Tyr Glu Gly Ile Ala  Ser Gly Val
    3050                3055                3060

Phe Gly  Val Asn Leu Arg Thr  Asn Phe Thr Ile Lys  Gly Ser Phe
    3065                3070                3075

Ile Asn  Gly Ala Cys Gly Ser  Pro Gly Tyr Asn Val  Arg Asn Asp
    3080                3085                3090

Gly Thr  Val Glu Phe Cys Tyr  Leu His Gln Ile Glu  Leu Gly Ser
    3095                3100                3105

Gly Ala  His Val Gly Ser Asp  Phe Thr Gly Ser Val  Tyr Gly Asn
    3110                3115                3120

Phe Asp  Asp Gln Pro Ser Leu  Gln Val Glu Ser Ala  Asn Leu Met
    3125                3130                3135

Leu Ser  Asp Asn Val Val Ala  Phe Leu Tyr Ala Ala  Leu Leu Asn
    3140                3145                3150

Gly Cys  Arg Trp Trp Leu Cys  Ser Thr Arg Val Asn  Val Asp Gly
    3155                3160                3165

Phe Asn  Glu Trp Ala Met Ala  Asn Gly Tyr Thr Ser  Val Ser Ser
    3170                3175                3180

Val Glu  Cys Tyr Ser Ile Leu  Ala Ala Lys Thr Gly  Val Ser Val
    3185                3190                3195

Glu Gln  Leu Leu Ala Ser Ile  Gln His Leu His Glu  Gly Phe Gly
    3200                3205                3210

Gly Lys  Asn Ile Leu Gly Tyr  Ser Ser Leu Cys Asp  Glu Phe Thr
    3215                3220                3225

Leu Ala  Glu Val Val Lys Gln  Met Tyr Gly Val Asn  Leu Gln Ser
    3230                3235                3240

Gly Lys  Val Ile Phe Gly Leu  Lys Thr Met Phe Leu  Phe Ser Val
    3245                3250                3255

Phe Phe  Thr Met Phe Trp Ala  Glu Leu Phe Ile Tyr  Thr Asn Thr
    3260                3265                3270

Ile Trp  Ile Asn Pro Val Ile  Leu Thr Pro Ile Phe  Cys Leu Leu
    3275                3280                3285
```

```
Leu Phe  Leu Ser Leu Val Leu  Thr Met Phe Leu Lys  His Lys Phe
    3290                 3295                 3300

Leu Phe  Leu Gln Val Phe Leu  Leu Pro Thr Val Ile  Ala Thr Ala
    3305                 3310                 3315

Leu Tyr  Asn Cys Val Leu Asp  Tyr Tyr Ile Val Lys  Phe Leu Ala
    3320                 3325                 3330

Asp His  Phe Asn Tyr Asn Val  Ser Val Leu Gln Met  Asp Val Gln
    3335                 3340                 3345

Gly Leu  Val Asn Val Leu Val  Cys Leu Phe Val Val  Phe Leu His
    3350                 3355                 3360

Thr Trp  Arg Phe Ser Lys Glu  Arg Phe Thr His Trp  Phe Thr Tyr
    3365                 3370                 3375

Val Cys  Ser Leu Ile Ala Val  Ala Tyr Thr Tyr Phe  Tyr Ser Gly
    3380                 3385                 3390

Asp Phe  Leu Ser Leu Leu Val  Met Phe Leu Cys Ala  Ile Ser Ser
    3395                 3400                 3405

Asp Trp  Tyr Ile Gly Ala Ile  Val Phe Arg Leu Ser  Arg Leu Ile
    3410                 3415                 3420

Val Phe  Phe Ser Pro Glu Ser  Val Phe Ser Val Phe  Gly Asp Val
    3425                 3430                 3435

Lys Leu  Thr Leu Val Val Tyr  Leu Ile Cys Gly Tyr  Leu Val Cys
    3440                 3445                 3450

Thr Tyr  Trp Gly Ile Leu Tyr  Trp Phe Asn Arg Phe  Phe Lys Cys
    3455                 3460                 3465

Thr Met  Gly Val Tyr Asp Phe  Lys Val Ser Ala Ala  Glu Phe Lys
    3470                 3475                 3480

Tyr Met  Val Ala Asn Gly Leu  His Ala Pro His Gly  Pro Phe Asp
    3485                 3490                 3495

Ala Leu  Trp Leu Ser Phe Lys  Leu Leu Gly Ile Gly  Gly Asp Arg
    3500                 3505                 3510

Cys Ile  Lys Ile Ser Thr Val  Gln Ser Lys Leu Thr  Asp Leu Lys
    3515                 3520                 3525

Cys Thr  Asn Val Val Leu Leu  Gly Cys Leu Ser Ser  Met Asn Ile
    3530                 3535                 3540

Ala Ala  Asn Ser Ser Glu Trp  Ala Tyr Cys Val Asp  Leu His Asn
    3545                 3550                 3555

Lys Ile  Asn Leu Cys Asp Asp  Pro Glu Lys Ala Gln  Ser Met Leu
    3560                 3565                 3570

Leu Ala  Leu Leu Ala Phe Phe  Leu Ser Lys His Ser  Asp Phe Gly
    3575                 3580                 3585

Leu Asp  Gly Leu Ile Asp Ser  Tyr Phe Asp Asn Ser  Ser Thr Leu
    3590                 3595                 3600

Gln Ser  Val Ala Ser Ser Phe  Val Ser Met Pro Ser  Tyr Ile Ala
    3605                 3610                 3615

Tyr Glu  Asn Ala Arg Gln Ala  Tyr Glu Asp Ala Ile  Ala Asn Gly
    3620                 3625                 3630

Ser Ser  Ser Gln Leu Ile Lys  Gln Leu Lys Arg Ala  Met Asn Ile
    3635                 3640                 3645

Ala Lys  Ser Glu Phe Asp His  Glu Ile Ser Val Gln  Lys Lys Ile
    3650                 3655                 3660

Asn Arg  Met Ala Glu Gln Ala  Ala Thr Gln Met Tyr  Lys Glu Ala
    3665                 3670                 3675
```

```
Arg Ser  Val Asn Arg Lys Ser  Lys Val Ile Ser Ala  Met His Ser
    3680                 3685                 3690

Leu Leu  Phe Gly Met Leu Arg  Arg Leu Asp Met Ser  Ser Val Glu
    3695                 3700                 3705

Thr Val  Leu Asn Leu Ala Arg  Asp Gly Val Val Pro  Leu Ser Val
    3710                 3715                 3720

Ile Pro  Ala Thr Ser Ala Ser  Lys Leu Thr Ile Val  Ser Pro Asp
    3725                 3730                 3735

Leu Glu  Ser Tyr Ser Lys Ile  Val Cys Asp Gly Ser  Val His Tyr
    3740                 3745                 3750

Ala Gly  Val Val Trp Thr Leu  Asn Asp Val Lys Asp  Asn Asp Gly
    3755                 3760                 3765

Arg Pro  Val His Val Lys Glu  Ile Thr Lys Glu Asn  Val Glu Thr
    3770                 3775                 3780

Leu Thr  Trp Pro Leu Ile Leu  Asn Cys Glu Arg Val  Val Lys Leu
    3785                 3790                 3795

Gln Asn  Asn Glu Ile Met Pro  Gly Lys Leu Lys Gln  Lys Pro Met
    3800                 3805                 3810

Lys Ala  Glu Gly Asp Gly Gly  Val Leu Gly Asp Gly  Asn Ala Leu
    3815                 3820                 3825

Tyr Asn  Thr Glu Gly Gly Lys  Thr Phe Met Tyr Ala  Tyr Ile Ser
    3830                 3835                 3840

Asn Lys  Ala Asp Leu Lys Phe  Val Lys Trp Glu Tyr  Glu Gly Gly
    3845                 3850                 3855

Cys Asn  Thr Ile Glu Leu Asp  Ser Pro Cys Arg Phe  Met Val Glu
    3860                 3865                 3870

Thr Pro  Asn Gly Pro Gln Val  Lys Tyr Leu Tyr Phe  Val Lys Asn
    3875                 3880                 3885

Leu Asn  Thr Leu Arg Arg Gly  Ala Val Leu Gly Phe  Ile Gly Ala
    3890                 3895                 3900

Thr Ile  Arg Leu Gln Ala Gly  Lys Gln Thr Glu Leu  Ala Val Asn
    3905                 3910                 3915

Ser Gly  Leu Leu Thr Ala Cys  Ala Phe Ser Val Asp  Pro Ala Thr
    3920                 3925                 3930

Thr Tyr  Leu Glu Ala Val Lys  His Gly Ala Lys Pro  Val Ser Asn
    3935                 3940                 3945

Cys Ile  Lys Met Leu Ser Asn  Gly Ala Gly Asn Gly  Gln Ala Ile
    3950                 3955                 3960

Thr Thr  Ser Val Asp Ala Asn  Thr Asn Gln Asp Ser  Tyr Gly Gly
    3965                 3970                 3975

Ala Ser  Ile Cys Leu Tyr Cys  Arg Ala His Val Pro  His Pro Ser
    3980                 3985                 3990

Met Asp  Gly Tyr Cys Lys Phe  Lys Gly Lys Cys Val  Gln Val Pro
    3995                 4000                 4005

Ile Gly  Cys Leu Asp Pro Ile  Arg Phe Cys Leu Glu  Asn Asn Val
    4010                 4015                 4020

Cys Asn  Val Cys Gly Cys Trp  Leu Gly His Gly Cys  Ala Cys Asp
    4025                 4030                 4035

Arg Thr  Thr Ile Gln Ser Val  Asp Ile Ser Tyr Leu  Asn Glu Gln
    4040                 4045                 4050

Gly Val  Leu Val Gln Leu Asp  Arg Ala Arg Gly Ser  Ser Ala Ala
    4055                 4060                 4065

Arg Leu  Glu Pro Cys Asn Gly  Thr Asp Ile Asp Lys  Cys Val Arg
```

```
    4070                4075                4080

Ala Phe  Asp Ile Tyr Asn Lys  Asn Val Ser Phe Leu  Gly Lys Cys
    4085                4090                4095

Leu Lys  Met Asn Cys Val Arg  Phe Lys Asn Ala Asp  Leu Lys Asp
    4100                4105                4110

Gly Tyr  Phe Val Ile Lys Arg  Cys Thr Lys Ser Val  Met Glu His
    4115                4120                4125

Glu Gln  Ser Met Tyr Asn Leu  Leu Asn Phe Ser Gly  Ala Leu Ala
    4130                4135                4140

Glu His  Asp Phe Phe Thr Trp  Lys Asp Gly Arg Val  Ile Tyr Gly
    4145                4150                4155

Asn Val  Ser Arg His Asn Leu  Thr Lys Tyr Thr Met  Met Asp Leu
    4160                4165                4170

Val Tyr  Ala Met Arg Asn Phe  Asp Glu Gln Asn Cys  Asp Val Leu
    4175                4180                4185

Lys Glu  Val Leu Val Leu Thr  Gly Cys Cys Asp Asn  Ser Tyr Phe
    4190                4195                4200

Asp Ser  Lys Gly Trp Tyr Asp  Pro Val Glu Asn Glu  Asp Ile His
    4205                4210                4215

Arg Val  Tyr Ala Ser Leu Gly  Lys Ile Val Ala Arg  Ala Met Leu
    4220                4225                4230

Lys Cys  Val Ala Leu Cys Asp  Ala Met Val Ala Lys  Gly Val Val
    4235                4240                4245

Gly Val  Leu Thr Leu Asp Asn  Gln Asp Leu Asn Gly  Asn Phe Tyr
    4250                4255                4260

Asp Phe  Gly Asp Phe Val Val  Ser Leu Pro Asn Met  Gly Val Pro
    4265                4270                4275

Cys Cys  Thr Ser Tyr Tyr Ser  Tyr Met Met Pro Ile  Met Gly Leu
    4280                4285                4290

Thr Asn  Cys Leu Ala Ser Glu  Cys Phe Val Lys Ser  Asp Ile Phe
    4295                4300                4305

Gly Ser  Asp Phe Lys Thr Phe  Asp Leu Leu Lys Tyr  Asp Phe Thr
    4310                4315                4320

Glu His  Lys Glu Asn Leu Phe  Asn Lys Tyr Phe Lys  His Trp Ser
    4325                4330                4335

Phe Asp  Tyr His Pro Asn Cys  Cys Asp Cys Tyr Asp  Asp Met Cys
    4340                4345                4350

Val Ile  His Cys Ala Asn Phe  Asn Thr Leu Phe Ala  Thr Thr Ile
    4355                4360                4365

Pro Gly  Thr Ala Phe Gly Pro  Leu Cys Arg Lys Val  Phe Ile Asp
    4370                4375                4380

Gly Val  Pro Leu Val Thr Thr  Ala Gly Tyr His Phe  Lys Gln Leu
    4385                4390                4395

Gly Leu  Val Trp Asn Lys Asp  Val Asn Thr His Ser  Val Arg Leu
    4400                4405                4410

Thr Ile  Thr Glu Leu Leu Gln  Phe Val Thr Asp Pro  Ser Leu Ile
    4415                4420                4425

Ile Ala  Ser Ser Pro Ala Leu  Val Asp Gln Arg Thr  Ile Cys Phe
    4430                4435                4440

Ser Val  Ala Ala Leu Ser Thr  Gly Leu Thr Asn Gln  Val Val Lys
    4445                4450                4455

Pro Gly  His Phe Asn Glu Glu  Phe Tyr Asn Phe Leu  Arg Leu Arg
    4460                4465                4470
```

```
Gly Phe  Phe Asp Glu Gly Ser  Glu Leu Thr Leu Lys  His Phe Phe
    4475                 4480                 4485

Phe Ala  Gln Asn Gly Asp Ala  Ala Val Lys Asp Phe  Asp Phe Tyr
    4490                 4495                 4500

Arg Tyr  Asn Lys Pro Thr Ile  Leu Asp Ile Cys Gln  Ala Arg Val
    4505                 4510                 4515

Thr Tyr  Lys Ile Val Ser Arg  Tyr Phe Asp Ile Tyr  Glu Gly Gly
    4520                 4525                 4530

Cys Ile  Lys Ala Cys Glu Val  Val Val Thr Asn Leu  Asn Lys Ser
    4535                 4540                 4545

Ala Gly  Trp Pro Leu Asn Lys  Phe Gly Lys Ala Ser  Leu Tyr Tyr
    4550                 4555                 4560

Glu Ser  Ile Ser Tyr Glu Glu  Gln Asp Ala Leu Phe  Ala Leu Thr
    4565                 4570                 4575

Lys Arg  Asn Val Leu Pro Thr  Met Thr Gln Leu Asn  Leu Lys Tyr
    4580                 4585                 4590

Ala Ile  Ser Gly Lys Glu Arg  Ala Arg Thr Val Gly  Gly Val Ser
    4595                 4600                 4605

Leu Leu  Ser Thr Met Thr Thr  Arg Gln Tyr His Gln  Lys His Leu
    4610                 4615                 4620

Lys Ser  Ile Val Asn Thr Arg  Asn Ala Thr Val Val  Ile Gly Thr
    4625                 4630                 4635

Thr Lys  Phe Tyr Gly Gly Trp  Asn Asn Met Leu Arg  Thr Leu Ile
    4640                 4645                 4650

Asp Gly  Val Glu Asn Pro Met  Leu Met Gly Trp Asp  Tyr Pro Lys
    4655                 4660                 4665

Cys Asp  Arg Ala Leu Pro Asn  Met Ile Arg Met Ile  Ser Ala Met
    4670                 4675                 4680

Val Leu  Gly Ser Lys His Val  Asn Cys Cys Thr Ala  Thr Asp Arg
    4685                 4690                 4695

Phe Tyr  Arg Leu Gly Asn Glu  Leu Ala Gln Val Leu  Thr Glu Val
    4700                 4705                 4710

Val Tyr  Ser Asn Gly Gly Phe  Tyr Phe Lys Pro Gly  Gly Thr Thr
    4715                 4720                 4725

Ser Gly  Asp Ala Ser Thr Ala  Tyr Ala Asn Ser Ile  Phe Asn Ile
    4730                 4735                 4740

Phe Gln  Ala Val Ser Ser Asn  Ile Asn Arg Leu Leu  Ser Val Pro
    4745                 4750                 4755

Ser Asp  Ser Cys Asn Asn Val  Asn Val Arg Asp Leu  Gln Arg Arg
    4760                 4765                 4770

Leu Tyr  Asp Asn Cys Tyr Arg  Leu Thr Ser Val Glu  Glu Ser Phe
    4775                 4780                 4785

Ile Glu  Asp Tyr Tyr Gly Tyr  Leu Arg Lys His Phe  Ser Met Met
    4790                 4795                 4800

Ile Leu  Ser Asp Asp Gly Val  Val Cys Tyr Asn Lys  Asp Tyr Ala
    4805                 4810                 4815

Glu Leu  Gly Tyr Ile Ala Asp  Ile Ser Ala Phe Lys  Ala Thr Leu
    4820                 4825                 4830

Tyr Tyr  Gln Asn Asn Val Phe  Met Ser Thr Ser Lys  Cys Trp Val
    4835                 4840                 4845

Glu Glu  Asp Leu Thr Lys Gly  Pro His Glu Phe Cys  Ser Gln His
    4850                 4855                 4860
```

```
Thr Met  Gln Ile Val Asp Lys  Asp Gly Thr Tyr Tyr  Leu Pro Tyr
    4865                 4870                 4875

Pro Asp  Pro Ser Arg Ile Leu  Ser Ala Gly Val Phe  Val Asp Asp
    4880                 4885                 4890

Val Val  Lys Thr Asp Ala Val  Val Leu Leu Glu Arg  Tyr Val Ser
    4895                 4900                 4905

Leu Ala  Ile Asp Ala Tyr Pro  Leu Ser Lys His Pro  Asn Ser Glu
    4910                 4915                 4920

Tyr Arg  Lys Val Phe Tyr Val  Leu Leu Asp Trp Val  Lys His Leu
    4925                 4930                 4935

Asn Lys  Asn Leu Asn Glu Gly  Val Leu Glu Ser Phe  Ser Val Thr
    4940                 4945                 4950

Leu Leu  Asp Asn Gln Glu Asp  Lys Phe Trp Cys Glu  Asp Phe Tyr
    4955                 4960                 4965

Ala Ser  Met Tyr Glu Asn Ser  Thr Ile Leu Gln Ala  Ala Gly Leu
    4970                 4975                 4980

Cys Val  Val Cys Gly Ser Gln  Thr Val Leu Arg Cys  Gly Asp Cys
    4985                 4990                 4995

Leu Arg  Lys Pro Met Leu Cys  Thr Lys Cys Ala Tyr  Asp His Val
    5000                 5005                 5010

Phe Gly  Thr Asp His Lys Phe  Ile Leu Ala Ile Thr  Pro Tyr Val
    5015                 5020                 5025

Cys Asn  Ala Ser Gly Cys Gly  Val Ser Asp Val Lys  Lys Leu Tyr
    5030                 5035                 5040

Leu Gly  Gly Leu Asn Tyr Tyr  Cys Thr Asn His Lys  Pro Gln Leu
    5045                 5050                 5055

Ser Phe  Pro Leu Cys Ser Ala  Gly Asn Ile Phe Gly  Leu Tyr Lys
    5060                 5065                 5070

Asn Ser  Ala Thr Gly Ser Leu  Asp Val Glu Val Phe  Asn Arg Leu
    5075                 5080                 5085

Ala Thr  Ser Asp Trp Thr Asp  Val Arg Asp Tyr Lys  Leu Ala Asn
    5090                 5095                 5100

Asp Val  Lys Asp Thr Leu Arg  Leu Phe Ala Ala Glu  Thr Ile Lys
    5105                 5110                 5115

Ala Lys  Glu Glu Ser Val Lys  Ser Ser Tyr Ala Phe  Ala Thr Leu
    5120                 5125                 5130

Lys Glu  Val Val Gly Pro Lys  Glu Leu Leu Leu Ser  Trp Glu Ser
    5135                 5140                 5145

Gly Lys  Val Lys Pro Pro Leu  Asn Arg Asn Ser Val  Phe Thr Cys
    5150                 5155                 5160

Phe Gln  Ile Ser Lys Asp Ser  Lys Phe Gln Ile Gly  Glu Phe Ile
    5165                 5170                 5175

Phe Glu  Lys Val Glu Tyr Gly  Ser Asp Thr Val Thr  Tyr Lys Ser
    5180                 5185                 5190

Thr Val  Thr Thr Lys Leu Val  Pro Gly Met Ile Phe  Val Leu Thr
    5195                 5200                 5205

Ser His  Asn Val Gln Pro Leu  Arg Ala Pro Thr Ile  Ala Asn Gln
    5210                 5215                 5220

Glu Lys  Tyr Ser Ser Ile Tyr  Lys Leu His Pro Ala  Phe Asn Val
    5225                 5230                 5235

Ser Asp  Ala Tyr Ala Asn Leu  Val Pro Tyr Tyr Gln  Leu Ile Gly
    5240                 5245                 5250

Lys Gln  Lys Ile Thr Thr Ile  Gln Gly Pro Pro Gly  Ser Gly Lys
```

```
    5255                5260                5265

Ser His  Cys Ser Ile Gly Leu  Gly Leu Tyr Tyr Pro  Gly Ala Arg
    5270                5275                5280

Ile Val  Phe Val Ala Cys Ala  His Ala Ala Val Asp  Ser Leu Cys
    5285                5290                5295

Ala Lys  Ala Met Thr Val Tyr  Ser Ile Asp Lys Cys  Thr Arg Ile
    5300                5305                5310

Ile Pro  Ala Arg Ala Arg Val  Glu Cys Tyr Ser Gly  Phe Lys Pro
    5315                5320                5325

Asn Asn  Thr Ser Ala Gln Tyr  Ile Phe Ser Thr Val  Asn Ala Leu
    5330                5335                5340

Pro Glu  Cys Asn Ala Asp Ile  Val Val Val Asp Glu  Val Ser Met
    5345                5350                5355

Cys Thr  Asn Tyr Asp Leu Ser  Val Ile Asn Gln Arg  Leu Ser Tyr
    5360                5365                5370

Lys His  Ile Val Tyr Val Gly  Asp Pro Gln Gln Leu  Pro Ala Pro
    5375                5380                5385

Arg Val  Met Ile Thr Lys Gly  Val Met Glu Pro Val  Asp Tyr Asn
    5390                5395                5400

Val Val  Thr Gln Arg Met Cys  Ala Ile Gly Pro Asp  Val Phe Leu
    5405                5410                5415

His Lys  Cys Tyr Arg Cys Pro  Ala Glu Ile Val Ile  Gln Phe Leu
    5420                5425                5430

Asn Leu  Phe Met Arg Thr Ser  Leu Ser Leu Leu Asn  Leu Leu Val
    5435                5440                5445

Asn Ser  Val Leu Lys Ser Phe  Leu Arg Val Met Tyr  Lys Val Asp
    5450                5455                5460

Asn Gly  Ser Ser Ile Asn Arg  Lys Gln Leu Glu Ile  Val Lys Leu
    5465                5470                5475

Phe Leu  Val Lys Asn Pro Ser  Trp Ser Lys Ala Val  Phe Ile Ser
    5480                5485                5490

Pro Tyr  Asn Ser Gln Asn Tyr  Val Ala Ser Arg Phe  Leu Gly Leu
    5495                5500                5505

Gln Ile  Gln Thr Val Asp Ser  Ser Gln Gly Ser Glu  Tyr Asp Tyr
    5510                5515                5520

Val Ile  Tyr Ala Gln Thr Ser  Asp Thr Ala His Ala  Cys Asn Val
    5525                5530                5535

Asn Arg  Phe Asn Val Ala Ile  Thr Arg Ala Lys Lys  Gly Ile Phe
    5540                5545                5550

Cys Val  Met Cys Asp Lys Thr  Leu Phe Asp Ser Leu  Lys Phe Phe
    5555                5560                5565

Glu Ile  Lys His Ala Asp Leu  His Ser Ser Gln Val  Cys Gly Leu
    5570                5575                5580

Phe Lys  Asn Cys Thr Arg Thr  Pro Leu Asn Leu Pro  Pro Thr His
    5585                5590                5595

Ala His  Thr Phe Leu Ser Leu  Ser Asp Gln Phe Lys  Thr Thr Gly
    5600                5605                5610

Asp Leu  Ala Val Gln Ile Gly  Ser Asn Asn Val Cys  Thr Tyr Glu
    5615                5620                5625

His Val  Ile Ser Phe Met Gly  Phe Arg Phe Asp Ile  Ser Ile Pro
    5630                5635                5640

Gly Ser  His Ser Leu Phe Cys  Thr Arg Asp Phe Ala  Ile Arg Asn
    5645                5650                5655
```

```
Val Arg Gly Trp Leu Gly Met Asp Val Glu Ser Ala His Val Cys
    5660                5665                5670

Gly Asp Asn Ile Gly Thr Asn Val Pro Leu Gln Val Gly Phe Ser
    5675                5680                5685

Asn Gly Val Asn Phe Val Val Gln Thr Glu Gly Cys Val Ser Thr
    5690                5695                5700

Asn Phe Gly Asp Val Ile Lys Pro Val Cys Ala Lys Ser Pro Pro
    5705                5710                5715

Gly Glu Gln Phe Arg His Leu Ile Pro Leu Leu Arg Lys Gly Gln
    5720                5725                5730

Pro Trp Leu Ile Val Arg Arg Arg Ile Val Gln Met Ile Ser Asp
    5735                5740                5745

Tyr Leu Ser Asn Leu Ser Asp Ile Leu Val Phe Val Leu Trp Ala
    5750                5755                5760

Gly Ser Leu Glu Leu Thr Thr Met Arg Tyr Phe Val Lys Ile Gly
    5765                5770                5775

Pro Ile Lys Tyr Cys Tyr Cys Gly Asn Phe Ala Thr Cys Tyr Asn
    5780                5785                5790

Ser Val Ser Asn Glu Tyr Cys Cys Phe Lys His Ala Leu Gly Cys
    5795                5800                5805

Asp Tyr Val Tyr Asn Pro Tyr Ala Phe Asp Ile Gln Gln Trp Gly
    5810                5815                5820

Tyr Val Gly Ser Leu Ser Gln Asn His His Thr Phe Cys Asn Ile
    5825                5830                5835

His Arg Asn Glu His Asp Ala Ser Gly Asp Ala Val Met Thr Arg
    5840                5845                5850

Cys Leu Ala Val His Asp Cys Phe Val Lys Asn Val Asp Trp Thr
    5855                5860                5865

Val Thr Tyr Pro Phe Ile Ala Asn Glu Lys Phe Ile Asn Gly Cys
    5870                5875                5880

Gly Arg Asn Val Gln Gly His Val Val Arg Ala Ala Leu Lys Leu
    5885                5890                5895

Tyr Lys Pro Ser Val Ile His Asp Ile Gly Asn Pro Lys Gly Val
    5900                5905                5910

Arg Cys Ala Val Thr Asp Ala Lys Trp Tyr Cys Tyr Asp Lys Gln
    5915                5920                5925

Pro Val Asn Ser Asn Val Lys Leu Leu Asp Tyr Asp Tyr Ala Thr
    5930                5935                5940

His Gly Gln Leu Asp Gly Leu Cys Leu Phe Trp Asn Cys Asn Val
    5945                5950                5955

Asp Met Tyr Pro Glu Phe Ser Ile Val Cys Arg Phe Asp Thr Arg
    5960                5965                5970

Thr Arg Ser Val Phe Asn Leu Glu Gly Val Asn Gly Gly Ser Leu
    5975                5980                5985

Tyr Val Asn Lys His Ala Phe His Thr Pro Ala Tyr Asp Lys Arg
    5990                5995                6000

Ala Phe Val Lys Leu Lys Pro Met Pro Phe Phe Tyr Phe Asp Asp
    6005                6010                6015

Ser Asp Cys Asp Val Val Gln Glu Gln Val Asn Tyr Val Pro Leu
    6020                6025                6030

Arg Ala Ser Ser Cys Val Thr Arg Cys Asn Ile Gly Gly Ala Val
    6035                6040                6045
```

```
Cys Ser Lys His Ala Asn Leu Tyr Gln Lys Tyr Val Glu Ala Tyr
    6050                6055                6060

Asn Thr Phe Thr Gln Ala Gly Phe Asn Ile Trp Val Pro His Ser
    6065                6070                6075

Phe Asp Val Tyr Asn Leu Trp Gln Ile Phe Ile Glu Thr Asn Leu
    6080                6085                6090

Gln Ser Leu Glu Asn Ile Ala Phe Asn Val Val Lys Lys Gly Cys
    6095                6100                6105

Phe Thr Gly Val Asp Gly Glu Leu Pro Val Ala Val Val Asn Asp
    6110                6115                6120

Lys Val Phe Val Arg Tyr Gly Asp Val Asp Asn Leu Val Phe Thr
    6125                6130                6135

Asn Lys Thr Thr Leu Pro Thr Asn Val Ala Phe Glu Leu Phe Ala
    6140                6145                6150

Lys Arg Lys Met Gly Leu Thr Pro Pro Leu Ser Ile Leu Lys Asn
    6155                6160                6165

Leu Gly Val Val Ala Thr Tyr Lys Phe Val Leu Trp Asp Tyr Glu
    6170                6175                6180

Ala Glu Arg Pro Phe Thr Ser Tyr Thr Lys Ser Val Cys Lys Tyr
    6185                6190                6195

Thr Asp Phe Asn Glu Asp Val Cys Val Cys Phe Asp Asn Ser Ile
    6200                6205                6210

Gln Gly Ser Tyr Glu Arg Phe Thr Leu Thr Thr Asn Ala Val Leu
    6215                6220                6225

Phe Ser Thr Val Val Ile Lys Asn Leu Thr Pro Ile Lys Leu Asn
    6230                6235                6240

Phe Gly Met Leu Asn Gly Met Pro Val Ser Ser Ile Lys Gly Asp
    6245                6250                6255

Lys Gly Val Glu Lys Leu Val Asn Trp Tyr Ile Tyr Val Arg Lys
    6260                6265                6270

Asn Gly Gln Phe Gln Asp His Tyr Asp Gly Phe Tyr Thr Gln Gly
    6275                6280                6285

Arg Asn Leu Ser Asp Phe Thr Pro Arg Ser Asp Met Glu Tyr Asp
    6290                6295                6300

Phe Leu Asn Met Asp Met Gly Val Phe Ile Asn Lys Tyr Gly Leu
    6305                6310                6315

Glu Asp Phe Asn Phe Glu His Val Val Tyr Gly Asp Val Ser Lys
    6320                6325                6330

Thr Thr Leu Gly Gly Leu His Leu Leu Ile Ser Gln Phe Arg Leu
    6335                6340                6345

Ser Lys Met Gly Val Leu Lys Ala Asp Asp Phe Val Thr Ala Ser
    6350                6355                6360

Asp Thr Thr Leu Arg Cys Cys Thr Val Thr Tyr Leu Asn Glu Leu
    6365                6370                6375

Ser Ser Lys Val Val Cys Thr Tyr Met Asp Leu Leu Leu Asp Asp
    6380                6385                6390

Phe Val Thr Ile Leu Lys Ser Leu Asp Leu Gly Val Ile Ser Lys
    6395                6400                6405

Val His Glu Val Ile Ile Asp Asn Lys Pro Tyr Arg Trp Met Leu
    6410                6415                6420

Trp Cys Lys Asp Asn His Leu Ser Thr Phe Tyr Pro Gln Leu Gln
    6425                6430                6435

Ser Ala Glu Trp Lys Cys Gly Tyr Ala Met Pro Gln Ile Tyr Lys
```

```
    6440                6445                6450

Leu Gln  Arg Met Cys Leu Glu  Pro Cys Asn Leu Tyr  Asn Tyr Gly
    6455                6460                6465

Ala Gly  Ile Lys Leu Pro Ser  Gly Ile Met Leu Asn  Val Val Lys
    6470                6475                6480

Tyr Thr  Gln Leu Cys Gln Tyr  Leu Asn Ser Thr Thr  Met Cys Val
    6485                6490                6495

Pro His  Asn Met Arg Val Leu  His Tyr Gly Ala Gly  Ser Asp Lys
    6500                6505                6510

Gly Val  Ala Pro Gly Thr Thr  Val Leu Lys Arg Trp  Leu Pro Pro
    6515                6520                6525

Asp Ala  Ile Ile Ile Asp Asn  Asp Ile Asn Asp Tyr  Val Ser Asp
    6530                6535                6540

Ala Asp  Phe Ser Ile Thr Gly  Asp Cys Ala Thr Val  Tyr Leu Glu
    6545                6550                6555

Asp Lys  Phe Asp Leu Leu Ile  Ser Asp Met Tyr Asp  Gly Arg Ile
    6560                6565                6570

Lys Phe  Cys Asp Gly Glu Asn  Val Ser Lys Asp Gly  Phe Phe Thr
    6575                6580                6585

Tyr Leu  Asn Gly Val Ile Arg  Glu Lys Leu Ala Ile  Gly Gly Ser
    6590                6595                6600

Val Ala  Ile Lys Ile Thr Glu  Tyr Ser Trp Asn Lys  Tyr Leu Tyr
    6605                6610                6615

Glu Leu  Ile Gln Arg Phe Ala  Phe Trp Thr Leu Phe  Cys Thr Ser
    6620                6625                6630

Val Asn  Thr Ser Ser Ser Glu  Ala Phe Leu Ile Gly  Ile Asn Tyr
    6635                6640                6645

Leu Gly  Asp Phe Ile Gln Gly  Pro Phe Ile Ala Gly  Asn Thr Val
    6650                6655                6660

His Ala  Asn Tyr Ile Phe Trp  Arg Asn Ser Thr Ile  Met Ser Leu
    6665                6670                6675

Ser Tyr  Asn Ser Val Leu Asp  Leu Ser Lys Phe Glu  Cys Lys His
    6680                6685                6690

Lys Ala  Thr Val Val Val Thr  Leu Lys Asp Ser Asp  Val Asn Asp
    6695                6700                6705

Met Val  Leu Ser Leu Ile Lys  Ser Gly Arg Leu Leu  Leu Arg Asn
    6710                6715                6720

Asn Gly  Arg Phe Gly Gly Phe  Ser Asn His Leu Val  Ser Thr Lys
    6725                6730                6735
```

```
<210> SEQ ID NO 58
<211> LENGTH: 2250
<212> TYPE: PRT
<213> ORGANISM: Human coronavirus
<220> FEATURE:
<221> NAME/KEY: MISC_FEATURE
<222> LOCATION: (1)..(2250)
<223> OTHER INFORMATION: Adenosine diphosphate-ribose 1'-phosphatase

<400> SEQUENCE: 58

Ser Asn Asn Pro Gln Cys Ala Ile Val Gln Ala Ser Glu Ser Lys Val
1               5                   10                  15

Leu Leu Glu Arg Phe Leu Pro Lys Cys Pro Glu Ile Leu Leu Ser Ile
            20                  25                  30

Asp Asp Gly His Leu Trp Asn Leu Phe Val Glu Lys Phe Asn Phe Val
        35                  40                  45
```

-continued

```
Thr Asp Trp Leu Lys Thr Leu Lys Leu Thr Leu Thr Ser Asn Gly Leu
    50                  55                  60

Leu Gly Asn Cys Ala Lys Arg Phe Arg Arg Val Leu Val Lys Leu Leu
65                  70                  75                  80

Asp Val Tyr Asn Gly Phe Leu Glu Thr Val Cys Ser Val Ala Tyr Thr
                85                  90                  95

Ala Gly Val Cys Ile Lys Tyr Tyr Ala Val Asn Val Pro Tyr Val Val
            100                 105                 110

Ile Ser Gly Phe Val Ser Arg Val Ile Arg Arg Glu Arg Cys Asp Met
        115                 120                 125

Thr Phe Pro Cys Val Ser Cys Val Thr Phe Phe Tyr Glu Phe Leu Asp
    130                 135                 140

Thr Cys Phe Gly Val Ser Lys Pro Asn Ala Ile Asp Val Glu His Leu
145                 150                 155                 160

Glu Leu Lys Glu Thr Val Phe Val Glu Pro Lys Asp Gly Gly Gln Phe
                165                 170                 175

Phe Val Ser Gly Asp Tyr Leu Trp Tyr Val Val Asp Asp Ile Tyr Tyr
            180                 185                 190

Pro Ala Ser Cys Asn Gly Val Leu Pro Val Ala Phe Thr Lys Leu Ala
        195                 200                 205

Gly Gly Lys Ile Ser Phe Ser Asp Asp Val Ile Val His Asp Val Glu
    210                 215                 220

Pro Thr His Lys Val Lys Leu Ile Phe Glu Phe Glu Asp Asp Val Val
225                 230                 235                 240

Thr Ser Leu Cys Lys Lys Ser Phe Gly Lys Ser Ile Ile Tyr Thr Gly
                245                 250                 255

Asp Trp Glu Gly Leu His Glu Val Leu Thr Ser Ala Met Asn Val Ile
            260                 265                 270

Gly Gln His Ile Lys Leu Pro Gln Phe Tyr Ile Tyr Asp Glu Glu Gly
        275                 280                 285

Gly Tyr Asp Val Ser Lys Pro Val Met Ile Ser Gln Trp Pro Ile Ser
    290                 295                 300

Asn Asp Ser Asn Gly Cys Val Val Glu Ala Ser Thr Asp Phe His Gln
305                 310                 315                 320

Leu Glu Cys Ile Val Asp Asp Ser Val Arg Glu Glu Val Asp Ile Ile
                325                 330                 335

Glu Gln Pro Phe Glu Glu Val Glu His Val Leu Ser Ile Lys Gln Pro
            340                 345                 350

Phe Ser Phe Ser Phe Arg Asp Glu Leu Gly Val Arg Val Leu Asp Gln
        355                 360                 365

Ser Asp Asn Asn Cys Trp Ile Ser Thr Thr Leu Val Gln Leu Gln Leu
    370                 375                 380

Thr Lys Leu Leu Asp Asp Ser Ile Glu Met Gln Leu Phe Lys Val Gly
385                 390                 395                 400

Lys Val Asp Ser Ile Val Gln Lys Cys Tyr Glu Leu Ser His Leu Ile
                405                 410                 415

Ser Gly Ser Leu Gly Asp Ser Gly Lys Leu Leu Ser Glu Leu Leu Lys
            420                 425                 430

Glu Lys Tyr Thr Cys Ser Ile Thr Phe Glu Met Ser Cys Asp Cys Gly
        435                 440                 445

Lys Lys Phe Asp Asp Gln Val Gly Cys Leu Phe Trp Ile Met Pro Tyr
    450                 455                 460
```

```
Thr Lys Leu Phe Gln Lys Gly Glu Cys Cys Ile Cys His Lys Met Gln
465                 470                 475                 480

Thr Tyr Lys Leu Val Ser Met Lys Gly Thr Gly Val Phe Val Gln Asp
                485                 490                 495

Pro Ala Pro Ile Asp Ile Asp Ala Phe Pro Val Lys Pro Ile Cys Ser
            500                 505                 510

Ser Val Tyr Leu Gly Val Lys Gly Ser Gly His Tyr Gln Thr Asn Leu
        515                 520                 525

Tyr Ser Phe Asn Lys Ala Ile Asp Gly Phe Gly Val Phe Asp Ile Lys
    530                 535                 540

Asn Ser Ser Val Asn Thr Val Cys Phe Val Asp Val Asp Phe His Ser
545                 550                 555                 560

Val Glu Ile Glu Ala Gly Glu Val Lys Pro Phe Ala Val Tyr Lys Asn
                565                 570                 575

Val Lys Phe Tyr Leu Gly Asp Ile Ser His Leu Val Asn Cys Val Ser
            580                 585                 590

Phe Asp Phe Val Val Asn Ala Ala Asn Glu Asn Leu Leu His Gly Gly
        595                 600                 605

Gly Val Ala Arg Ala Ile Asp Ile Leu Thr Glu Gly Gln Leu Gln Ser
    610                 615                 620

Leu Ser Lys Asp Tyr Ile Ser Ser Asn Gly Pro Leu Lys Val Gly Ala
625                 630                 635                 640

Gly Val Met Leu Glu Cys Glu Lys Phe Asn Val Phe Asn Val Val Gly
                645                 650                 655

Pro Arg Thr Gly Lys His Glu His Ser Leu Leu Val Glu Ala Tyr Asn
            660                 665                 670

Ser Ile Leu Phe Glu Asn Gly Ile Pro Leu Met Pro Leu Leu Ser Cys
        675                 680                 685

Gly Ile Phe Gly Val Arg Ile Glu Asn Ser Leu Lys Ala Leu Phe Ser
    690                 695                 700

Cys Asp Ile Asn Lys Pro Leu Gln Val Phe Val Tyr Ser Ser Asn Glu
705                 710                 715                 720

Glu Gln Ala Val Leu Lys Phe Leu Asp Gly Leu Asp Leu Thr Pro Val
                725                 730                 735

Ile Asp Asp Val Asp Val Val Lys Pro Phe Arg Val Glu Gly Asn Phe
            740                 745                 750

Ser Phe Phe Asp Cys Gly Val Asn Ala Leu Asp Gly Asp Ile Tyr Leu
        755                 760                 765

Leu Phe Thr Asn Ser Ile Leu Met Leu Asp Lys Gln Gly Gln Leu Leu
    770                 775                 780

Asp Thr Lys Leu Asn Gly Ile Leu Gln Gln Ala Ala Leu Asp Tyr Leu
785                 790                 795                 800

Ala Thr Val Lys Thr Val Pro Ala Gly Asn Leu Val Lys Leu Phe Val
                805                 810                 815

Glu Ser Cys Thr Ile Tyr Met Cys Val Val Pro Ser Ile Asn Asp Leu
            820                 825                 830

Ser Phe Asp Lys Asn Leu Gly Arg Cys Val Arg Lys Leu Asn Arg Leu
        835                 840                 845

Lys Thr Cys Val Ile Ala Asn Val Pro Ala Ile Asp Val Leu Lys Lys
    850                 855                 860

Leu Leu Ser Ser Leu Thr Leu Thr Val Lys Phe Val Val Glu Ser Asn
865                 870                 875                 880

Val Met Asp Val Asn Asp Cys Phe Lys Asn Asp Asn Val Val Leu Lys
```

```
                885                 890                 895

Ile Thr Glu Asp Gly Ile Asn Val Lys Asp Val Val Val Glu Ser Ser
            900                 905                 910

Lys Ser Leu Gly Lys Gln Leu Gly Val Val Ser Asp Gly Val Asp Ser
        915                 920                 925

Phe Glu Gly Val Leu Pro Ile Asn Thr Asp Thr Val Leu Ser Val Ala
    930                 935                 940

Pro Glu Val Asp Trp Val Ala Phe Tyr Gly Phe Glu Lys Ala Ala Leu
945                 950                 955                 960

Phe Ala Ser Leu Asp Val Lys Pro Tyr Gly Tyr Pro Asn Asp Phe Val
                965                 970                 975

Gly Gly Phe Arg Val Leu Gly Thr Thr Asp Asn Asn Cys Trp Val Asn
            980                 985                 990

Ala Thr Cys Ile Ile Leu Gln Tyr  Leu Lys Pro Thr Phe  Lys Ser Lys
        995                 1000                1005

Gly Leu  Asn Val Leu Trp Asn  Lys Phe Val Thr Gly  Asp Val Gly
    1010                1015                1020

Pro Phe  Val Ser Phe Ile Tyr  Phe Ile Thr Met Ser  Ser Lys Gly
    1025                1030                1035

Gln Lys  Gly Asp Ala Glu Glu  Ala Leu Ser Lys Leu  Ser Glu Tyr
    1040                1045                1050

Leu Ile  Ser Asp Ser Ile Val  Thr Leu Glu Gln Tyr  Ser Thr Cys
    1055                1060                1065

Asp Ile  Cys Lys Ser Thr Val  Val Glu Val Lys Ser  Ala Ile Val
    1070                1075                1080

Cys Ala  Ser Val Leu Lys Asp  Gly Cys Asp Val Gly  Phe Cys Pro
    1085                1090                1095

His Arg  His Lys Leu Arg Ser  Arg Val Lys Phe Val  Asn Gly Arg
    1100                1105                1110

Val Val  Ile Thr Asn Val Gly  Glu Pro Ile Ile Ser  Gln Pro Ser
    1115                1120                1125

Lys Leu  Leu Asn Gly Ile Ala  Tyr Thr Thr Phe Ser  Gly Ser Phe
    1130                1135                1140

Asp Asn  Gly His Tyr Val Val  Tyr Asp Ala Ala Asn  Asn Ala Val
    1145                1150                1155

Tyr Asp  Gly Ala Arg Leu Phe  Ser Ser Asp Leu Ser  Thr Leu Ala
    1160                1165                1170

Val Thr  Ala Ile Val Val Val  Gly Gly Cys Val Thr  Ser Asn Val
    1175                1180                1185

Pro Thr  Ile Val Ser Glu Lys  Ile Ser Val Met Asp  Lys Leu Asp
    1190                1195                1200

Thr Gly  Ala Gln Lys Phe Phe  Gln Phe Gly Asp Phe  Val Met Asn
    1205                1210                1215

Asn Ile  Val Leu Phe Leu Thr  Trp Leu Leu Ser Met  Phe Ser Leu
    1220                1225                1230

Leu Arg  Thr Ser Ile Met Lys  His Asp Ile Lys Val  Ile Ala Lys
    1235                1240                1245

Ala Pro  Lys Arg Thr Gly Val  Ile Leu Thr Arg Ser  Phe Lys Tyr
    1250                1255                1260

Asn Ile  Arg Ser Ala Leu Phe  Val Ile Lys Gln Lys  Trp Cys Val
    1265                1270                1275

Ile Val  Thr Leu Phe Lys Phe  Leu Leu Leu Leu Tyr  Ala Ile Tyr
    1280                1285                1290
```

```
Ala Leu  Val Phe Met Ile Val  Gln Phe Ser Pro Phe  Asn Ser Leu
    1295                 1300                 1305

Leu Cys  Gly Asp Ile Val Ser  Gly Tyr Glu Lys Ser  Thr Phe Asn
    1310                 1315                 1320

Lys Asp  Ile Tyr Cys Gly Asn  Ser Met Val Cys Lys  Met Cys Leu
    1325                 1330                 1335

Phe Ser  Tyr Gln Glu Phe Asn  Asp Leu Asp His Thr  Ser Leu Val
    1340                 1345                 1350

Trp Lys  His Ile Arg Asp Pro  Ile Leu Ile Ser Leu  Gln Pro Phe
    1355                 1360                 1365

Val Ile  Leu Val Ile Leu Leu  Ile Phe Gly Asn Met  Tyr Leu Arg
    1370                 1375                 1380

Phe Gly  Leu Leu Tyr Phe Val  Ala Gln Phe Ile Ser  Thr Phe Gly
    1385                 1390                 1395

Ser Phe  Leu Gly Phe His Gln  Lys Gln Trp Phe Leu  His Phe Val
    1400                 1405                 1410

Pro Phe  Asp Val Leu Cys Asn  Glu Phe Leu Ala Thr  Phe Ile Val
    1415                 1420                 1425

Cys Lys  Ile Val Leu Phe Val  Arg His Ile Ile Val  Gly Cys Asn
    1430                 1435                 1440

Asn Ala  Asp Cys Val Ala Cys  Ser Lys Ser Ala Arg  Leu Lys Arg
    1445                 1450                 1455

Val Pro  Leu Gln Thr Ile Ile  Asn Gly Met His Lys  Ser Phe Tyr
    1460                 1465                 1470

Val Asn  Ala Asn Gly Gly Thr  Cys Phe Cys Asn Lys  His Asn Phe
    1475                 1480                 1485

Phe Cys  Val Asn Cys Asp Ser  Phe Gly Pro Gly Asn  Thr Phe Ile
    1490                 1495                 1500

Asn Gly  Asp Ile Ala Arg Glu  Leu Gly Asn Val Val  Lys Thr Ala
    1505                 1510                 1515

Val Gln  Pro Thr Ala Pro Ala  Tyr Val Ile Ile Asp  Lys Val Asp
    1520                 1525                 1530

Phe Val  Asn Gly Phe Tyr Arg  Leu Tyr Ser Gly Asp  Thr Phe Trp
    1535                 1540                 1545

Arg Tyr  Asp Phe Asp Ile Thr  Glu Ser Lys Tyr Ser  Cys Lys Glu
    1550                 1555                 1560

Val Leu  Lys Asn Cys Asn Val  Leu Glu Asn Phe Ile  Val Tyr Asn
    1565                 1570                 1575

Asn Ser  Gly Ser Asn Ile Thr  Gln Ile Lys Asn Ala  Cys Val Tyr
    1580                 1585                 1590

Phe Ser  Gln Leu Leu Cys Glu  Pro Ile Lys Leu Val  Asn Ser Glu
    1595                 1600                 1605

Leu Leu  Ser Thr Leu Ser Val  Asp Phe Asn Gly Val  Leu His Lys
    1610                 1615                 1620

Ala Tyr  Val Asp Val Leu Cys  Asn Ser Phe Phe Lys  Glu Leu Thr
    1625                 1630                 1635

Ala Asn  Met Ser Met Ala Glu  Cys Lys Ala Thr Leu  Gly Leu Thr
    1640                 1645                 1650

Val Ser  Asp Asp Asp Phe Val  Ser Ala Val Ala Asn  Ala His Arg
    1655                 1660                 1665

Tyr Asp  Val Leu Leu Ser Asp  Leu Ser Phe Asn Asn  Phe Phe Ile
    1670                 1675                 1680
```

```
Ser Tyr  Ala Lys Pro Glu Asp  Lys Leu Ser Val Tyr  Asp Ile Ala
    1685                 1690                 1695

Cys Cys  Met Arg Ala Gly Ser  Lys Val Val Asn His  Asn Val Leu
    1700                 1705                 1710

Ile Lys  Glu Ser Ile Pro Ile  Val Trp Gly Val Lys  Asp Phe Asn
    1715                 1720                 1725

Thr Leu  Ser Gln Glu Gly Lys  Lys Tyr Leu Val Lys  Thr Thr Lys
    1730                 1735                 1740

Ala Lys  Gly Leu Thr Phe Leu  Leu Thr Phe Asn Asp  Asn Gln Ala
    1745                 1750                 1755

Ile Thr  Gln Val Pro Ala Thr  Ser Ile Val Ala Lys  Gln Gly Ala
    1760                 1765                 1770

Gly Phe  Lys Arg Thr Tyr Asn  Phe Leu Trp Tyr Val  Cys Leu Phe
    1775                 1780                 1785

Val Val  Ala Leu Phe Ile Gly  Val Ser Phe Ile Asp  Tyr Thr Thr
    1790                 1795                 1800

Thr Val  Thr Ser Phe His Gly  Tyr Asp Phe Lys Tyr  Ile Glu Asn
    1805                 1810                 1815

Gly Gln  Leu Lys Val Phe Glu  Ala Pro Leu His Cys  Val Arg Asn
    1820                 1825                 1830

Val Phe  Asp Asn Phe Asn Gln  Trp His Glu Ala Lys  Phe Gly Val
    1835                 1840                 1845

Val Thr  Thr Asn Ser Asp Lys  Cys Pro Ile Val Val  Gly Val Ser
    1850                 1855                 1860

Glu Arg  Ile Asn Val Val Pro  Gly Val Pro Thr Asn  Val Tyr Leu
    1865                 1870                 1875

Val Gly  Lys Thr Leu Val Phe  Thr Leu Gln Ala Ala  Phe Gly Asn
    1880                 1885                 1890

Thr Gly  Val Cys Tyr Asp Phe  Asp Gly Val Thr Thr  Ser Asp Lys
    1895                 1900                 1905

Cys Ile  Phe Asn Ser Ala Cys  Thr Arg Leu Glu Gly  Leu Gly Gly
    1910                 1915                 1920

Asp Asn  Val Tyr Cys Tyr Asn  Thr Asp Leu Ile Glu  Gly Ser Lys
    1925                 1930                 1935

Pro Tyr  Ser Thr Leu Gln Pro  Asn Ala Tyr Tyr Lys  Tyr Asp Ala
    1940                 1945                 1950

Lys Asn  Tyr Val Arg Phe Pro  Glu Ile Leu Ala Arg  Gly Phe Gly
    1955                 1960                 1965

Leu Arg  Thr Ile Arg Thr Leu  Ala Thr Arg Tyr Cys  Arg Val Gly
    1970                 1975                 1980

Glu Cys  Arg Asp Ser His Lys  Gly Val Cys Phe Gly  Phe Asp Lys
    1985                 1990                 1995

Trp Tyr  Val Asn Asp Gly Arg  Val Asp Asp Gly Tyr  Ile Cys Gly
    2000                 2005                 2010

Asp Gly  Leu Ile Asp Leu Leu  Val Asn Val Leu Ser  Ile Phe Ser
    2015                 2020                 2025

Ser Ser  Phe Ser Val Val Ala  Met Ser Gly His Met  Leu Phe Asn
    2030                 2035                 2040

Phe Leu  Phe Ala Ala Phe Ile  Thr Phe Leu Cys Phe  Leu Val Thr
    2045                 2050                 2055

Lys Phe  Lys Arg Val Phe Gly  Asp Leu Ser Tyr Gly  Val Phe Thr
    2060                 2065                 2070

Val Val  Cys Ala Thr Leu Ile  Asn Asn Ile Ser Tyr  Val Val Thr
```

```
    2075                2080                2085

Gln Asn  Leu Phe Phe Met Leu  Leu Tyr Ala Ile Leu  Tyr Phe Val
    2090                2095                2100

Phe Thr  Arg Thr Val Arg Tyr  Ala Trp Ile Trp His  Ile Ala Tyr
    2105                2110                2115

Ile Val  Ala Tyr Phe Leu Leu  Ile Pro Trp Trp Leu  Leu Thr Trp
    2120                2125                2130

Phe Ser  Phe Ala Ala Phe Leu  Glu Leu Leu Pro Asn  Val Phe Lys
    2135                2140                2145

Leu Lys  Ile Ser Thr Gln Leu  Phe Glu Gly Asp Lys  Phe Ile Gly
    2150                2155                2160

Thr Phe  Glu Ser Ala Ala Ala  Gly Thr Phe Val Leu  Asp Met Arg
    2165                2170                2175

Ser Tyr  Glu Arg Leu Ile Asn  Thr Ile Ser Pro Glu  Lys Leu Lys
    2180                2185                2190

Asn Tyr  Ala Ala Ser Tyr Asn  Lys Tyr Lys Tyr Tyr  Ser Gly Ser
    2195                2200                2205

Ala Ser  Glu Ala Asp Tyr Arg  Cys Ala Cys Tyr Ala  His Leu Ala
    2210                2215                2220

Lys Ala  Met Leu Asp Tyr Ala  Lys Asp His Asn Asp  Met Leu Tyr
    2225                2230                2235

Ser Pro  Pro Thr Ile Ser Tyr  Asn Ser Thr Leu Gln
    2240                2245                2250


<210> SEQ ID NO 59
<211> LENGTH: 361
<212> TYPE: PRT
<213> ORGANISM: Human coronavirus
<220> FEATURE:
<221> NAME/KEY: MISC_FEATURE
<222> LOCATION: (1)..(361)
<223> OTHER INFORMATION: 3CI pro Coronavirus polyprotein processing
      endoprotease

<400> SEQUENCE: 59

Ser Gly Leu Lys Lys Met Ala Gln Pro Ser Gly Cys Val Glu Arg Cys
1               5                   10                  15

Val Val Arg Val Cys Tyr Gly Ser Thr Val Leu Asn Gly Val Trp Leu
            20                  25                  30

Gly Asp Thr Val Thr Cys Pro Arg His Val Ile Ala Pro Ser Thr Thr
        35                  40                  45

Val Leu Ile Asp Tyr Asp His Ala Tyr Ser Thr Met Arg Leu His Asn
    50                  55                  60

Phe Ser Val Ser His Asn Gly Val Phe Leu Gly Val Val Gly Val Thr
65                  70                  75                  80

Met His Gly Ser Val Leu Arg Ile Lys Val Ser Gln Ser Asn Val His
                85                  90                  95

Thr Pro Lys His Val Phe Lys Thr Leu Lys Pro Gly Asp Ser Phe Asn
            100                 105                 110

Ile Leu Ala Cys Tyr Glu Gly Ile Ala Ser Gly Val Phe Gly Val Asn
        115                 120                 125

Leu Arg Thr Asn Phe Thr Ile Lys Gly Ser Phe Ile Asn Gly Ala Cys
    130                 135                 140

Gly Ser Pro Gly Tyr Asn Val Arg Asn Asp Gly Thr Val Glu Phe Cys
145                 150                 155                 160

Tyr Leu His Gln Ile Glu Leu Gly Ser Gly Ala His Val Gly Ser Asp
```

```
                165                 170                 175

Phe Thr Gly Ser Val Tyr Gly Asn Phe Asp Asp Gln Pro Ser Leu Gln
            180                 185                 190

Val Glu Ser Ala Asn Leu Met Leu Ser Asp Asn Val Val Ala Phe Leu
        195                 200                 205

Tyr Ala Ala Leu Leu Asn Gly Cys Arg Trp Trp Leu Cys Ser Thr Arg
    210                 215                 220

Val Asn Val Asp Gly Phe Asn Glu Trp Ala Met Ala Asn Gly Tyr Thr
225                 230                 235                 240

Ser Val Ser Ser Val Glu Cys Tyr Ser Ile Leu Ala Ala Lys Thr Gly
                245                 250                 255

Val Ser Val Glu Gln Leu Leu Ala Ser Ile Gln His Leu His Glu Gly
            260                 265                 270

Phe Gly Gly Lys Asn Ile Leu Gly Tyr Ser Ser Leu Cys Asp Glu Phe
        275                 280                 285

Thr Leu Ala Glu Val Val Lys Gln Met Tyr Gly Val Asn Leu Gln Ser
    290                 295                 300

Gly Lys Val Ile Phe Gly Leu Lys Thr Met Phe Leu Phe Ser Val Phe
305                 310                 315                 320

Phe Thr Met Phe Trp Ala Glu Leu Phe Ile Tyr Thr Asn Thr Ile Trp
                325                 330                 335

Ile Asn Pro Val Ile Leu Thr Pro Ile Phe Cys Leu Leu Leu Phe Leu
            340                 345                 350

Ser Leu Val Leu Thr Met Phe Leu Lys
        355                 360


<210> SEQ ID NO 60
<211> LENGTH: 1071
<212> TYPE: PRT
<213> ORGANISM: Human coronavirus
<220> FEATURE:
<221> NAME/KEY: MISC_FEATURE
<222> LOCATION: (1)..(1071)
<223> OTHER INFORMATION: RNA dependant RNA polymerase (pfam00680)

<400> SEQUENCE: 60

Ala Gly Lys Gln Thr Glu Leu Ala Val Asn Ser Gly Leu Leu Thr Ala
1               5                   10                  15

Cys Ala Phe Ser Val Asp Pro Ala Thr Thr Tyr Leu Glu Ala Val Lys
            20                  25                  30

His Gly Ala Lys Pro Val Ser Asn Cys Ile Lys Met Leu Ser Asn Gly
        35                  40                  45

Ala Gly Asn Gly Gln Ala Ile Thr Thr Ser Val Asp Ala Asn Thr Asn
    50                  55                  60

Gln Asp Ser Tyr Gly Gly Ala Ser Ile Cys Leu Tyr Cys Arg Ala His
65                  70                  75                  80

Val Pro His Pro Ser Met Asp Gly Tyr Cys Lys Phe Lys Gly Lys Cys
                85                  90                  95

Val Gln Val Pro Ile Gly Cys Leu Asp Pro Ile Arg Phe Cys Leu Glu
            100                 105                 110

Asn Asn Val Cys Asn Val Cys Gly Cys Trp Leu Gly His Gly Cys Ala
        115                 120                 125

Cys Asp Arg Thr Thr Ile Gln Ser Val Asp Ile Ser Tyr Leu Asn Glu
    130                 135                 140

Gln Gly Val Leu Val Gln Leu Asp Arg Ala Arg Gly Ser Ser Ala Ala
145                 150                 155                 160
```

```
Arg Leu Glu Pro Cys Asn Gly Thr Asp Ile Asp Lys Cys Val Arg Ala
                165                 170                 175

Phe Asp Ile Tyr Asn Lys Asn Val Ser Phe Leu Gly Lys Cys Leu Lys
            180                 185                 190

Met Asn Cys Val Arg Phe Lys Asn Ala Asp Leu Lys Asp Gly Tyr Phe
        195                 200                 205

Val Ile Lys Arg Cys Thr Lys Ser Val Met Glu His Glu Gln Ser Met
    210                 215                 220

Tyr Asn Leu Leu Asn Phe Ser Gly Ala Leu Ala Glu His Asp Phe Phe
225                 230                 235                 240

Thr Trp Lys Asp Gly Arg Val Ile Tyr Gly Asn Val Ser Arg His Asn
                245                 250                 255

Leu Thr Lys Tyr Thr Met Met Asp Leu Val Tyr Ala Met Arg Asn Phe
            260                 265                 270

Asp Glu Gln Asn Cys Asp Val Leu Lys Glu Val Leu Val Leu Thr Gly
        275                 280                 285

Cys Cys Asp Asn Ser Tyr Phe Asp Ser Lys Gly Trp Tyr Asp Pro Val
    290                 295                 300

Glu Asn Glu Asp Ile His Arg Val Tyr Ala Ser Leu Gly Lys Ile Val
305                 310                 315                 320

Ala Arg Ala Met Leu Lys Cys Val Ala Leu Cys Asp Ala Met Val Ala
                325                 330                 335

Lys Gly Val Val Gly Val Leu Thr Leu Asp Asn Gln Asp Leu Asn Gly
            340                 345                 350

Asn Phe Tyr Asp Phe Gly Asp Phe Val Val Ser Leu Pro Asn Met Gly
        355                 360                 365

Val Pro Cys Cys Thr Ser Tyr Tyr Ser Tyr Met Met Pro Ile Met Gly
    370                 375                 380

Leu Thr Asn Cys Leu Ala Ser Glu Cys Phe Val Lys Ser Asp Ile Phe
385                 390                 395                 400

Gly Ser Asp Phe Lys Thr Phe Asp Leu Leu Lys Tyr Asp Phe Thr Glu
                405                 410                 415

His Lys Glu Asn Leu Phe Asn Lys Tyr Phe Lys His Trp Ser Phe Asp
            420                 425                 430

Tyr His Pro Asn Cys Cys Asp Cys Tyr Asp Asp Met Cys Val Ile His
        435                 440                 445

Cys Ala Asn Phe Asn Thr Leu Phe Ala Thr Thr Ile Pro Gly Thr Ala
    450                 455                 460

Phe Gly Pro Leu Cys Arg Lys Val Phe Ile Asp Gly Val Pro Leu Val
465                 470                 475                 480

Thr Thr Ala Gly Tyr His Phe Lys Gln Leu Gly Leu Val Trp Asn Lys
                485                 490                 495

Asp Val Asn Thr His Ser Val Arg Leu Thr Ile Thr Glu Leu Leu Gln
            500                 505                 510

Phe Val Thr Asp Pro Ser Leu Ile Ile Ala Ser Ser Pro Ala Leu Val
        515                 520                 525

Asp Gln Arg Thr Ile Cys Phe Ser Val Ala Ala Leu Ser Thr Gly Leu
    530                 535                 540

Thr Asn Gln Val Val Lys Pro Gly His Phe Asn Glu Glu Phe Tyr Asn
545                 550                 555                 560

Phe Leu Arg Leu Arg Gly Phe Phe Asp Glu Gly Ser Glu Leu Thr Leu
                565                 570                 575
```

```
Lys His Phe Phe Phe Ala Gln Asn Gly Asp Ala Ala Val Lys Asp Phe
            580                 585                 590

Asp Phe Tyr Arg Tyr Asn Lys Pro Thr Ile Leu Asp Ile Cys Gln Ala
        595                 600                 605

Arg Val Thr Tyr Lys Ile Val Ser Arg Tyr Phe Asp Ile Tyr Glu Gly
    610                 615                 620

Gly Cys Ile Lys Ala Cys Glu Val Val Val Thr Asn Leu Asn Lys Ser
625                 630                 635                 640

Ala Gly Trp Pro Leu Asn Lys Phe Gly Lys Ala Ser Leu Tyr Tyr Glu
                645                 650                 655

Ser Ile Ser Tyr Glu Glu Gln Asp Ala Leu Phe Ala Leu Thr Lys Arg
            660                 665                 670

Asn Val Leu Pro Thr Met Thr Gln Leu Asn Leu Lys Tyr Ala Ile Ser
        675                 680                 685

Gly Lys Glu Arg Ala Arg Thr Val Gly Gly Val Ser Leu Leu Ser Thr
    690                 695                 700

Met Thr Thr Arg Gln Tyr His Gln Lys His Leu Lys Ser Ile Val Asn
705                 710                 715                 720

Thr Arg Asn Ala Thr Val Val Ile Gly Thr Thr Lys Phe Tyr Gly Gly
                725                 730                 735

Trp Asn Asn Met Leu Arg Thr Leu Ile Asp Gly Val Glu Asn Pro Met
            740                 745                 750

Leu Met Gly Trp Asp Tyr Pro Lys Cys Asp Arg Ala Leu Pro Asn Met
        755                 760                 765

Ile Arg Met Ile Ser Ala Met Val Leu Gly Ser Lys His Val Asn Cys
    770                 775                 780

Cys Thr Ala Thr Asp Arg Phe Tyr Arg Leu Gly Asn Glu Leu Ala Gln
785                 790                 795                 800

Val Leu Thr Glu Val Val Tyr Ser Asn Gly Gly Phe Tyr Phe Lys Pro
                805                 810                 815

Gly Gly Thr Thr Ser Gly Asp Ala Ser Thr Ala Tyr Ala Asn Ser Ile
            820                 825                 830

Phe Asn Ile Phe Gln Ala Val Ser Ser Asn Ile Asn Arg Leu Leu Ser
        835                 840                 845

Val Pro Ser Asp Ser Cys Asn Asn Val Asn Val Arg Asp Leu Gln Arg
    850                 855                 860

Arg Leu Tyr Asp Asn Cys Tyr Arg Leu Thr Ser Val Glu Glu Ser Phe
865                 870                 875                 880

Ile Glu Asp Tyr Tyr Gly Tyr Leu Arg Lys His Phe Ser Met Met Ile
                885                 890                 895

Leu Ser Asp Asp Gly Val Val Cys Tyr Asn Lys Asp Tyr Ala Glu Leu
            900                 905                 910

Gly Tyr Ile Ala Asp Ile Ser Ala Phe Lys Ala Thr Leu Tyr Tyr Gln
        915                 920                 925

Asn Asn Val Phe Met Ser Thr Ser Lys Cys Trp Val Glu Glu Asp Leu
    930                 935                 940

Thr Lys Gly Pro His Glu Phe Cys Ser Gln His Thr Met Gln Ile Val
945                 950                 955                 960

Asp Lys Asp Gly Thr Tyr Tyr Leu Pro Tyr Pro Asp Pro Ser Arg Ile
                965                 970                 975

Leu Ser Ala Gly Val Phe Val Asp Asp Val Val Lys Thr Asp Ala Val
            980                 985                 990

Val Leu Leu Glu Arg Tyr Val Ser  Leu Ala Ile Asp Ala  Tyr Pro Leu
```

```
        995                 1000                1005

Ser Lys  His Pro Asn Ser Glu  Tyr Arg Lys Val Phe  Tyr Val Leu
    1010                1015                1020

Leu Asp  Trp Val Lys His Leu  Asn Lys Asn Leu Asn  Glu Gly Val
    1025                1030                1035

Leu Glu  Ser Phe Ser Val Thr  Leu Leu Asp Asn Gln  Glu Asp Lys
    1040                1045                1050

Phe Trp  Cys Glu Asp Phe Tyr  Ala Ser Met Tyr Glu  Asn Ser Thr
    1055                1060                1065

Ile Leu  Gln
    1070


<210> SEQ ID NO 61
<211> LENGTH: 1115
<212> TYPE: PRT
<213> ORGANISM: Human coronavirus
<220> FEATURE:
<221> NAME/KEY: MISC_FEATURE
<222> LOCATION: (1)..(1115)
<223> OTHER INFORMATION: ExoN 3' to 5' Exonuclease and helicase

<400> SEQUENCE: 61

Ala Ala Gly Leu Cys Val Val Cys Gly Ser Gln Thr Val Leu Arg Cys
1               5                   10                  15

Gly Asp Cys Leu Arg Lys Pro Met Leu Cys Thr Lys Cys Ala Tyr Asp
            20                  25                  30

His Val Phe Gly Thr Asp His Lys Phe Ile Leu Ala Ile Thr Pro Tyr
        35                  40                  45

Val Cys Asn Ala Ser Gly Cys Gly Val Ser Asp Val Lys Lys Leu Tyr
    50                  55                  60

Leu Gly Gly Leu Asn Tyr Tyr Cys Thr Asn His Lys Pro Gln Leu Ser
65                  70                  75                  80

Phe Pro Leu Cys Ser Ala Gly Asn Ile Phe Gly Leu Tyr Lys Asn Ser
                85                  90                  95

Ala Thr Gly Ser Leu Asp Val Glu Val Phe Asn Arg Leu Ala Thr Ser
            100                 105                 110

Asp Trp Thr Asp Val Arg Asp Tyr Lys Leu Ala Asn Asp Val Lys Asp
        115                 120                 125

Thr Leu Arg Leu Phe Ala Ala Glu Thr Ile Lys Ala Lys Glu Glu Ser
    130                 135                 140

Val Lys Ser Ser Tyr Ala Phe Ala Thr Leu Lys Glu Val Val Gly Pro
145                 150                 155                 160

Lys Glu Leu Leu Leu Ser Trp Glu Ser Gly Lys Val Lys Pro Pro Leu
                165                 170                 175

Asn Arg Asn Ser Val Phe Thr Cys Phe Gln Ile Ser Lys Asp Ser Lys
            180                 185                 190

Phe Gln Ile Gly Glu Phe Ile Phe Glu Lys Val Glu Tyr Gly Ser Asp
        195                 200                 205

Thr Val Thr Tyr Lys Ser Thr Val Thr Thr Lys Leu Val Pro Gly Met
    210                 215                 220

Ile Phe Val Leu Thr Ser His Asn Val Gln Pro Leu Arg Ala Pro Thr
225                 230                 235                 240

Ile Ala Asn Gln Glu Lys Tyr Ser Ser Ile Tyr Lys Leu His Pro Ala
                245                 250                 255

Phe Asn Val Ser Asp Ala Tyr Ala Asn Leu Val Pro Tyr Tyr Gln Leu
            260                 265                 270
```

```
Ile Gly Lys Gln Lys Ile Thr Thr Ile Gln Gly Pro Pro Gly Ser Gly
        275                 280                 285

Lys Ser His Cys Ser Ile Gly Leu Gly Leu Tyr Tyr Pro Gly Ala Arg
    290                 295                 300

Ile Val Phe Val Ala Cys Ala His Ala Ala Val Asp Ser Leu Cys Ala
305                 310                 315                 320

Lys Ala Met Thr Val Tyr Ser Ile Asp Lys Cys Thr Arg Ile Ile Pro
                325                 330                 335

Ala Arg Ala Arg Val Glu Cys Tyr Ser Gly Phe Lys Pro Asn Asn Thr
            340                 345                 350

Ser Ala Gln Tyr Ile Phe Ser Thr Val Asn Ala Leu Pro Glu Cys Asn
        355                 360                 365

Ala Asp Ile Val Val Val Asp Glu Val Ser Met Cys Thr Asn Tyr Asp
    370                 375                 380

Leu Ser Val Ile Asn Gln Arg Leu Ser Tyr Lys His Ile Val Tyr Val
385                 390                 395                 400

Gly Asp Pro Gln Gln Leu Pro Ala Pro Arg Val Met Ile Thr Lys Gly
                405                 410                 415

Val Met Glu Pro Val Asp Tyr Asn Val Val Thr Gln Arg Met Cys Ala
            420                 425                 430

Ile Gly Pro Asp Val Phe Leu His Lys Cys Tyr Arg Cys Pro Ala Glu
        435                 440                 445

Ile Val Ile Gln Phe Leu Asn Leu Phe Met Arg Thr Ser Leu Ser Leu
    450                 455                 460

Leu Asn Leu Leu Val Asn Ser Val Leu Lys Ser Phe Leu Arg Val Met
465                 470                 475                 480

Tyr Lys Val Asp Asn Gly Ser Ser Ile Asn Arg Lys Gln Leu Glu Ile
                485                 490                 495

Val Lys Leu Phe Leu Val Lys Asn Pro Ser Trp Ser Lys Ala Val Phe
            500                 505                 510

Ile Ser Pro Tyr Asn Ser Gln Asn Tyr Val Ala Ser Arg Phe Leu Gly
        515                 520                 525

Leu Gln Ile Gln Thr Val Asp Ser Ser Gln Gly Ser Glu Tyr Asp Tyr
    530                 535                 540

Val Ile Tyr Ala Gln Thr Ser Asp Thr Ala His Ala Cys Asn Val Asn
545                 550                 555                 560

Arg Phe Asn Val Ala Ile Thr Arg Ala Lys Lys Gly Ile Phe Cys Val
                565                 570                 575

Met Cys Asp Lys Thr Leu Phe Asp Ser Leu Lys Phe Phe Glu Ile Lys
            580                 585                 590

His Ala Asp Leu His Ser Ser Gln Val Cys Gly Leu Phe Lys Asn Cys
        595                 600                 605

Thr Arg Thr Pro Leu Asn Leu Pro Pro Thr His Ala His Thr Phe Leu
    610                 615                 620

Ser Leu Ser Asp Gln Phe Lys Thr Thr Gly Asp Leu Ala Val Gln Ile
625                 630                 635                 640

Gly Ser Asn Asn Val Cys Thr Tyr Glu His Val Ile Ser Phe Met Gly
                645                 650                 655

Phe Arg Phe Asp Ile Ser Ile Pro Gly Ser His Ser Leu Phe Cys Thr
            660                 665                 670

Arg Asp Phe Ala Ile Arg Asn Val Arg Gly Trp Leu Gly Met Asp Val
        675                 680                 685
```

```
Glu Ser Ala His Val Cys Gly Asp Asn Ile Gly Thr Asn Val Pro Leu
    690                 695                 700

Gln Val Gly Phe Ser Asn Gly Val Asn Phe Val Val Gln Thr Glu Gly
705                 710                 715                 720

Cys Val Ser Thr Asn Phe Gly Asp Val Ile Lys Pro Val Cys Ala Lys
                725                 730                 735

Ser Pro Pro Gly Glu Gln Phe Arg His Leu Ile Pro Leu Leu Arg Lys
            740                 745                 750

Gly Gln Pro Trp Leu Ile Val Arg Arg Arg Ile Val Gln Met Ile Ser
        755                 760                 765

Asp Tyr Leu Ser Asn Leu Ser Asp Ile Leu Val Phe Val Leu Trp Ala
    770                 775                 780

Gly Ser Leu Glu Leu Thr Thr Met Arg Tyr Phe Val Lys Ile Gly Pro
785                 790                 795                 800

Ile Lys Tyr Cys Tyr Cys Gly Asn Phe Ala Thr Cys Tyr Asn Ser Val
                805                 810                 815

Ser Asn Glu Tyr Cys Cys Phe Lys His Ala Leu Gly Cys Asp Tyr Val
            820                 825                 830

Tyr Asn Pro Tyr Ala Phe Asp Ile Gln Gln Trp Gly Tyr Val Gly Ser
        835                 840                 845

Leu Ser Gln Asn His His Thr Phe Cys Asn Ile His Arg Asn Glu His
    850                 855                 860

Asp Ala Ser Gly Asp Ala Val Met Thr Arg Cys Leu Ala Val His Asp
865                 870                 875                 880

Cys Phe Val Lys Asn Val Asp Trp Thr Val Thr Tyr Pro Phe Ile Ala
                885                 890                 895

Asn Glu Lys Phe Ile Asn Gly Cys Gly Arg Asn Val Gln Gly His Val
            900                 905                 910

Val Arg Ala Ala Leu Lys Leu Tyr Lys Pro Ser Val Ile His Asp Ile
        915                 920                 925

Gly Asn Pro Lys Gly Val Arg Cys Ala Val Thr Asp Ala Lys Trp Tyr
    930                 935                 940

Cys Tyr Asp Lys Gln Pro Val Asn Ser Asn Val Lys Leu Leu Asp Tyr
945                 950                 955                 960

Asp Tyr Ala Thr His Gly Gln Leu Asp Gly Leu Cys Leu Phe Trp Asn
                965                 970                 975

Cys Asn Val Asp Met Tyr Pro Glu Phe Ser Ile Val Cys Arg Phe Asp
            980                 985                 990

Thr Arg Thr Arg Ser Val Phe Asn  Leu Glu Gly Val Asn  Gly Gly Ser
        995                 1000                1005

Leu Tyr  Val Asn Lys His Ala  Phe His Thr Pro Ala  Tyr Asp Lys
    1010                 1015                 1020

Arg Ala  Phe Val Lys Leu Lys  Pro Met Pro Phe Phe  Tyr Phe Asp
    1025                 1030                 1035

Asp Ser  Asp Cys Asp Val Val  Gln Glu Gln Val Asn  Tyr Val Pro
    1040                 1045                 1050

Leu Arg  Ala Ser Ser Cys Val  Thr Arg Cys Asn Ile  Gly Gly Ala
    1055                 1060                 1065

Val Cys  Ser Lys His Ala Asn  Leu Tyr Gln Lys Tyr  Val Glu Ala
    1070                 1075                 1080

Tyr Asn  Thr Phe Thr Gln Ala  Gly Phe Asn Ile Trp  Val Pro His
    1085                 1090                 1095

Ser Phe  Asp Val Tyr Asn Leu  Trp Gln Ile Phe Ile  Glu Thr Asn
```

```
    1100                1105                1110

Leu Gln
    1115


<210> SEQ ID NO 62
<211> LENGTH: 344
<212> TYPE: PRT
<213> ORGANISM: Human coronavirus
<220> FEATURE:
<221> NAME/KEY: MISC_FEATURE
<222> LOCATION: (1)..(344)
<223> OTHER INFORMATION: XendoU (homolog of) polyU-specific
      endoribonuclease

<400> SEQUENCE: 62

Ser Leu Glu Asn Ile Ala Phe Asn Val Val Lys Lys Gly Cys Phe Thr
1               5                   10                  15

Gly Val Asp Gly Glu Leu Pro Val Ala Val Val Asn Asp Lys Val Phe
            20                  25                  30

Val Arg Tyr Gly Asp Val Asp Asn Leu Val Phe Thr Asn Lys Thr Thr
        35                  40                  45

Leu Pro Thr Asn Val Ala Phe Glu Leu Phe Ala Lys Arg Lys Met Gly
    50                  55                  60

Leu Thr Pro Pro Leu Ser Ile Leu Lys Asn Leu Gly Val Val Ala Thr
65                  70                  75                  80

Tyr Lys Phe Val Leu Trp Asp Tyr Glu Ala Glu Arg Pro Phe Thr Ser
                85                  90                  95

Tyr Thr Lys Ser Val Cys Lys Tyr Thr Asp Phe Asn Glu Asp Val Cys
            100                 105                 110

Val Cys Phe Asp Asn Ser Ile Gln Gly Ser Tyr Glu Arg Phe Thr Leu
        115                 120                 125

Thr Thr Asn Ala Val Leu Phe Ser Thr Val Val Ile Lys Asn Leu Thr
    130                 135                 140

Pro Ile Lys Leu Asn Phe Gly Met Leu Asn Gly Met Pro Val Ser Ser
145                 150                 155                 160

Ile Lys Gly Asp Lys Gly Val Glu Lys Leu Val Asn Trp Tyr Ile Tyr
                165                 170                 175

Val Arg Lys Asn Gly Gln Phe Gln Asp His Tyr Asp Gly Phe Tyr Thr
            180                 185                 190

Gln Gly Arg Asn Leu Ser Asp Phe Thr Pro Arg Ser Asp Met Glu Tyr
        195                 200                 205

Asp Phe Leu Asn Met Asp Met Gly Val Phe Ile Asn Lys Tyr Gly Leu
    210                 215                 220

Glu Asp Phe Asn Phe Glu His Val Val Tyr Gly Asp Val Ser Lys Thr
225                 230                 235                 240

Thr Leu Gly Gly Leu His Leu Leu Ile Ser Gln Phe Arg Leu Ser Lys
                245                 250                 255

Met Gly Val Leu Lys Ala Asp Asp Phe Val Thr Ala Ser Asp Thr Thr
            260                 265                 270

Leu Arg Cys Cys Thr Val Thr Tyr Leu Asn Glu Leu Ser Ser Lys Val
        275                 280                 285

Val Cys Thr Tyr Met Asp Leu Leu Leu Asp Asp Phe Val Thr Ile Leu
    290                 295                 300

Lys Ser Leu Asp Leu Gly Val Ile Ser Lys Val His Glu Val Ile Ile
305                 310                 315                 320

Asp Asn Lys Pro Tyr Arg Trp Met Leu Trp Cys Lys Asp Asn His Leu
```

```
                325                 330                 335

Ser Thr Phe Tyr Pro Gln Leu Gln
            340


<210> SEQ ID NO 63
<211> LENGTH: 300
<212> TYPE: PRT
<213> ORGANISM: Human coronavirus
<220> FEATURE:
<221> NAME/KEY: MISC_FEATURE
<222> LOCATION: (1)..(300)
<223> OTHER INFORMATION: 2'-O-MT 2: S-adenosylmethionine-dependant
      ribose 2'-orthomethyltransferase

<400> SEQUENCE: 63

Ser Ala Glu Trp Lys Cys Gly Tyr Ala Met Pro Gln Ile Tyr Lys Leu
1               5                   10                  15

Gln Arg Met Cys Leu Glu Pro Cys Asn Leu Tyr Asn Tyr Gly Ala Gly
            20                  25                  30

Ile Lys Leu Pro Ser Gly Ile Met Leu Asn Val Val Lys Tyr Thr Gln
        35                  40                  45

Leu Cys Gln Tyr Leu Asn Ser Thr Thr Met Cys Val Pro His Asn Met
    50                  55                  60

Arg Val Leu His Tyr Gly Ala Gly Ser Asp Lys Gly Val Ala Pro Gly
65                  70                  75                  80

Thr Thr Val Leu Lys Arg Trp Leu Pro Pro Asp Ala Ile Ile Ile Asp
                85                  90                  95

Asn Asp Ile Asn Asp Tyr Val Ser Asp Ala Asp Phe Ser Ile Thr Gly
            100                 105                 110

Asp Cys Ala Thr Val Tyr Leu Glu Asp Lys Phe Asp Leu Leu Ile Ser
        115                 120                 125

Asp Met Tyr Asp Gly Arg Ile Lys Phe Cys Asp Gly Glu Asn Val Ser
    130                 135                 140

Lys Asp Gly Phe Phe Thr Tyr Leu Asn Gly Val Ile Arg Glu Lys Leu
145                 150                 155                 160

Ala Ile Gly Gly Ser Val Ala Ile Lys Ile Thr Glu Tyr Ser Trp Asn
                165                 170                 175

Lys Tyr Leu Tyr Glu Leu Ile Gln Arg Phe Ala Phe Trp Thr Leu Phe
            180                 185                 190

Cys Thr Ser Val Asn Thr Ser Ser Ser Glu Ala Phe Leu Ile Gly Ile
        195                 200                 205

Asn Tyr Leu Gly Asp Phe Ile Gln Gly Pro Phe Ile Ala Gly Asn Thr
    210                 215                 220

Val His Ala Asn Tyr Ile Phe Trp Arg Asn Ser Thr Ile Met Ser Leu
225                 230                 235                 240

Ser Tyr Asn Ser Val Leu Asp Leu Ser Lys Phe Glu Cys Lys His Lys
                245                 250                 255

Ala Thr Val Val Val Thr Leu Lys Asp Ser Asp Val Asn Asp Met Val
            260                 265                 270

Leu Ser Leu Ile Lys Ser Gly Arg Leu Leu Leu Arg Asn Asn Gly Arg
        275                 280                 285

Phe Gly Gly Phe Ser Asn His Leu Val Ser Thr Lys
    290                 295                 300


<210> SEQ ID NO 64
<211> LENGTH: 1356
<212> TYPE: PRT
```

<213> ORGANISM: Human coronavirus
<220> FEATURE:
<221> NAME/KEY: MISC_FEATURE
<222> LOCATION: (1)..(1356)
<223> OTHER INFORMATION: ORF-2 Spike protein/S-gene

<400> SEQUENCE: 64

```
Met Lys Leu Phe Leu Ile Leu Leu Val Leu Pro Leu Ala Ser Cys Phe
1               5                   10                  15

Phe Thr Cys Asn Ser Asn Ala Asn Leu Ser Met Leu Gln Leu Gly Val
            20                  25                  30

Pro Asp Asn Ser Ser Thr Ile Val Thr Gly Leu Leu Pro Thr His Trp
        35                  40                  45

Phe Cys Ala Asn Gln Ser Thr Ser Val Tyr Ser Ala Asn Gly Phe Phe
    50                  55                  60

Tyr Ile Asp Val Gly Asn His Arg Ser Ala Phe Ala Leu His Thr Gly
65                  70                  75                  80

Tyr Tyr Asp Ala Asn Gln Tyr Tyr Ile Tyr Val Thr Asn Glu Ile Gly
                85                  90                  95

Leu Asn Ala Ser Val Thr Leu Lys Ile Cys Lys Phe Ser Arg Asn Thr
            100                 105                 110

Thr Phe Asp Phe Leu Ser Asn Ala Ser Ser Ser Phe Asp Cys Ile Val
        115                 120                 125

Asn Leu Leu Phe Thr Glu Gln Leu Gly Ala Pro Leu Gly Ile Thr Ile
    130                 135                 140

Ser Gly Glu Thr Val Arg Leu His Leu Tyr Asn Val Thr Arg Thr Phe
145                 150                 155                 160

Tyr Val Pro Ala Ala Tyr Lys Leu Thr Lys Leu Ser Val Lys Cys Tyr
                165                 170                 175

Phe Asn Tyr Ser Cys Val Phe Ser Val Val Asn Ala Thr Val Thr Val
            180                 185                 190

Asn Val Thr Thr His Asn Gly Arg Val Val Asn Tyr Thr Val Cys Asp
        195                 200                 205

Asp Cys Asn Gly Tyr Thr Asp Asn Ile Phe Ser Val Gln Gln Asp Gly
    210                 215                 220

Arg Ile Pro Asn Gly Phe Pro Phe Asn Asn Trp Phe Leu Leu Thr Asn
225                 230                 235                 240

Gly Ser Thr Leu Val Asp Gly Val Ser Arg Leu Tyr Gln Pro Leu Arg
                245                 250                 255

Leu Thr Cys Leu Trp Pro Val Pro Gly Leu Lys Ser Ser Thr Gly Phe
            260                 265                 270

Val Tyr Phe Asn Ala Thr Gly Ser Asp Val Asn Cys Asn Gly Tyr Gln
        275                 280                 285

His Asn Ser Val Val Asp Val Met Arg Tyr Asn Leu Asn Phe Ser Ala
    290                 295                 300

Asn Ser Leu Asp Asn Leu Lys Ser Gly Val Ile Val Phe Lys Thr Leu
305                 310                 315                 320

Gln Tyr Asp Val Leu Phe Tyr Cys Ser Asn Ser Ser Ser Gly Val Leu
                325                 330                 335

Asp Thr Thr Ile Pro Phe Gly Pro Ser Ser Gln Pro Tyr Tyr Cys Phe
            340                 345                 350

Ile Asn Ser Thr Ile Asn Thr Thr His Val Ser Thr Phe Val Gly Ile
        355                 360                 365

Leu Pro Pro Thr Val Arg Glu Ile Val Val Ala Arg Thr Gly Gln Phe
    370                 375                 380
```

```
Tyr Ile Asn Gly Phe Lys Tyr Phe Asp Leu Gly Phe Ile Glu Ala Val
385                 390                 395                 400

Asn Phe Asn Val Thr Thr Ala Ser Ala Thr Asp Phe Trp Thr Val Ala
                405                 410                 415

Phe Ala Thr Phe Val Asp Val Leu Val Asn Val Ser Ala Thr Asn Ile
            420                 425                 430

Gln Asn Leu Leu Tyr Cys Asp Ser Pro Phe Glu Lys Leu Gln Cys Glu
        435                 440                 445

His Leu Gln Phe Gly Leu Gln Asp Gly Phe Tyr Ser Ala Asn Phe Leu
    450                 455                 460

Asp Asp Asn Val Leu Pro Glu Thr Tyr Val Ala Leu Pro Ile Tyr Tyr
465                 470                 475                 480

Gln His Thr Asp Ile Asn Phe Thr Ala Thr Ala Ser Phe Gly Gly Ser
                485                 490                 495

Cys Tyr Val Cys Lys Pro His Gln Val Asn Ile Ser Leu Asn Gly Asn
            500                 505                 510

Thr Ser Val Cys Val Arg Thr Ser His Phe Ser Ile Arg Tyr Ile Tyr
        515                 520                 525

Asn Arg Val Lys Ser Gly Ser Pro Gly Asp Ser Ser Trp His Ile Tyr
    530                 535                 540

Leu Lys Ser Gly Thr Cys Pro Phe Ser Phe Ser Lys Leu Asn Asn Phe
545                 550                 555                 560

Gln Lys Phe Lys Thr Ile Cys Phe Ser Thr Val Glu Val Pro Gly Ser
                565                 570                 575

Cys Asn Phe Pro Leu Glu Ala Thr Trp His Tyr Thr Ser Tyr Thr Ile
            580                 585                 590

Val Gly Ala Leu Tyr Val Thr Trp Ser Glu Gly Asn Ser Ile Thr Gly
        595                 600                 605

Val Pro Tyr Pro Val Ser Gly Ile Arg Glu Phe Ser Asn Leu Val Leu
    610                 615                 620

Asn Asn Cys Thr Lys Tyr Asn Ile Tyr Asp Tyr Val Gly Thr Gly Ile
625                 630                 635                 640

Ile Arg Ser Ser Asn Gln Ser Leu Ala Gly Gly Ile Thr Tyr Val Ser
                645                 650                 655

Asn Ser Gly Asn Leu Leu Gly Phe Lys Asn Val Ser Thr Gly Asn Ile
            660                 665                 670

Phe Ile Val Thr Pro Cys Asn Gln Pro Asp Gln Val Ala Val Tyr Gln
        675                 680                 685

Gln Ser Ile Ile Gly Ala Met Thr Ala Val Asn Glu Ser Arg Tyr Gly
    690                 695                 700

Leu Gln Asn Leu Leu Gln Leu Pro Asn Phe Tyr Tyr Val Ser Asn Gly
705                 710                 715                 720

Gly Asn Asn Cys Thr Thr Ala Val Met Thr Tyr Ser Asn Phe Gly Ile
                725                 730                 735

Cys Ala Asp Gly Ser Leu Ile Pro Val Arg Pro Arg Asn Ser Ser Asp
            740                 745                 750

Asn Gly Ile Ser Ala Ile Ile Thr Ala Asn Leu Ser Ile Pro Ser Asn
        755                 760                 765

Trp Thr Thr Ser Val Gln Val Glu Tyr Leu Gln Ile Thr Ser Thr Pro
    770                 775                 780

Ile Val Val Asp Cys Ala Thr Tyr Val Cys Asn Gly Asn Pro Arg Cys
785                 790                 795                 800
```

```
Lys Asn Leu Leu Lys Gln Tyr Thr Ser Ala Cys Lys Thr Ile Glu Asp
            805                 810                 815

Ala Leu Arg Leu Ser Ala His Leu Glu Thr Asn Asp Val Ser Ser Met
            820                 825                 830

Leu Thr Phe Asp Ser Asn Ala Phe Ser Leu Ala Asn Val Thr Ser Phe
        835                 840                 845

Gly Asp Tyr Asn Leu Ser Ser Val Leu Pro Gln Arg Asn Ile Arg Ser
    850                 855                 860

Ser Arg Ile Ala Gly Arg Ser Ala Leu Glu Asp Leu Leu Phe Ser Lys
865                 870                 875                 880

Val Val Thr Ser Gly Leu Gly Thr Val Asp Val Asp Tyr Lys Ser Cys
            885                 890                 895

Thr Lys Gly Leu Ser Ile Ala Asp Leu Ala Cys Ala Gln Tyr Tyr Asn
            900                 905                 910

Gly Ile Met Val Leu Pro Gly Val Ala Asp Ala Glu Arg Met Ala Met
        915                 920                 925

Tyr Thr Gly Ser Leu Ile Gly Gly Met Val Leu Gly Gly Leu Thr Ser
    930                 935                 940

Ala Ala Ala Ile Pro Phe Ser Leu Ala Leu Gln Ala Arg Leu Asn Tyr
945                 950                 955                 960

Val Ala Leu Gln Thr Asp Val Leu Gln Glu Asn Gln Lys Ile Leu Ala
            965                 970                 975

Ala Ser Phe Asn Lys Ala Ile Asn Asn Ile Val Ala Ser Phe Ser Ser
            980                 985                 990

Val Asn Asp Ala Ile Thr Gln Thr  Ala Glu Ala Ile His  Thr Val Thr
        995                 1000                1005

Ile Ala  Leu Asn Lys Ile Gln  Asp Val Val Asn Gln  Gln Gly Ser
    1010                 1015                 1020

Ala Leu  Asn His Leu Thr Ser  Gln Leu Arg His Asn  Phe Gln Ala
    1025                 1030                 1035

Ile Ser  Asn Ser Ile Gln Ala  Ile Tyr Asp Arg Leu  Asp Ser Ile
    1040                 1045                 1050

Gln Ala  Asp Gln Gln Val Asp  Arg Leu Ile Thr Gly  Arg Leu Ala
    1055                 1060                 1065

Ala Leu  Asn Ala Phe Val Ser  Gln Val Leu Asn Lys  Tyr Thr Glu
    1070                 1075                 1080

Val Arg  Gly Ser Arg Arg Leu  Ala Gln Gln Lys Ile  Asn Glu Cys
    1085                 1090                 1095

Val Lys  Ser Gln Ser Asn Arg  Tyr Gly Phe Cys Gly  Asn Gly Thr
    1100                 1105                 1110

His Ile  Phe Ser Ile Val Asn  Ser Ala Pro Asp Gly  Leu Leu Phe
    1115                 1120                 1125

Leu His  Thr Val Leu Leu Pro  Thr Asp Tyr Lys Asn  Val Lys Ala
    1130                 1135                 1140

Trp Ser  Gly Ile Cys Val Asp  Gly Ile Tyr Gly Tyr  Val Leu Arg
    1145                 1150                 1155

Gln Pro  Asn Leu Val Leu Tyr  Ser Asp Asn Gly Val  Phe Arg Val
    1160                 1165                 1170

Thr Ser  Arg Val Met Phe Gln  Pro Arg Leu Pro Val  Leu Ser Asp
    1175                 1180                 1185

Phe Val  Gln Ile Tyr Asn Cys  Asn Val Thr Phe Val  Asn Ile Ser
    1190                 1195                 1200

Arg Val  Glu Leu His Thr Val  Ile Pro Asp Tyr Val  Asp Val Asn
```

```
    1205                1210                1215

Lys Thr  Leu Gln Glu Phe Ala  Gln Asn Leu Pro Lys  Tyr Val Lys
    1220                1225                1230

Pro Asn  Phe Asp Leu Thr Pro  Phe Asn Leu Thr Tyr  Leu Asn Leu
    1235                1240                1245

Ser Ser  Glu Leu Lys Gln Leu  Glu Ala Lys Thr Ala  Ser Leu Phe
    1250                1255                1260

Gln Thr  Thr Val Glu Leu Gln  Gly Leu Ile Asp Gln  Ile Asn Ser
    1265                1270                1275

Thr Tyr  Val Asp Leu Lys Leu  Leu Asn Arg Phe Glu  Asn Tyr Ile
    1280                1285                1290

Lys Trp  Pro Trp Trp Val Trp  Leu Ile Ile Ser Val  Val Phe Val
    1295                1300                1305

Val Leu  Leu Ser Leu Leu Val  Phe Cys Cys Leu Ser  Thr Gly Cys
    1310                1315                1320

Cys Gly  Cys Cys Asn Cys Leu  Thr Ser Ser Met Arg  Gly Cys Cys
    1325                1330                1335

Asp Cys  Gly Ser Thr Lys Leu  Pro Tyr Tyr Glu Phe  Glu Lys Val
    1340                1345                1350

His Val  Gln
    1355


<210> SEQ ID NO 65
<211> LENGTH: 77
<212> TYPE: PRT
<213> ORGANISM: Human coronavirus
<220> FEATURE:
<221> NAME/KEY: MISC_FEATURE
<222> LOCATION: (1)..(77)
<223> OTHER INFORMATION: ORF-4 Corona virus envelope protein/E-gene

<400> SEQUENCE: 65

Met Phe Leu Arg Leu Ile Asp Asp Asn Gly Ile Val Leu Asn Ser Ile
1               5                   10                  15

Leu Trp Leu Leu Val Met Ile Phe Phe Phe Val Leu Ala Met Thr Phe
            20                  25                  30

Ile Lys Leu Ile Gln Leu Cys Phe Thr Cys His Tyr Phe Phe Ser Arg
        35                  40                  45

Thr Leu Tyr Gln Pro Val Tyr Lys Ile Phe Leu Ala Tyr Gln Asp Tyr
    50                  55                  60

Met Gln Ile Ala Pro Val Pro Ala Glu Val Leu Asn Val
65                  70                  75


<210> SEQ ID NO 66
<211> LENGTH: 226
<212> TYPE: PRT
<213> ORGANISM: Human coronavirus
<220> FEATURE:
<221> NAME/KEY: MISC_FEATURE
<222> LOCATION: (1)..(226)
<223> OTHER INFORMATION: ORF-5 pfam01635, Corona_M, Coronavirus M
      matrix/glycoprotein

<400> SEQUENCE: 66

Met Ser Asn Ser Ser Val Pro Leu Leu Glu Val Tyr Val His Leu Arg
1               5                   10                  15

Asn Trp Asn Phe Ser Trp Asn Leu Ile Leu Thr Leu Phe Ile Val Val
            20                  25                  30

Leu Gln Tyr Gly His Tyr Lys Tyr Ser Arg Leu Leu Tyr Gly Leu Lys
```

```
        35                  40                  45

Met Ser Val Leu Trp Cys Leu Trp Pro Leu Val Leu Ala Leu Ser Ile
    50                  55                  60

Phe Asp Cys Phe Val Asn Phe Asn Val Asp Trp Val Phe Phe Gly Phe
65                  70                  75                  80

Ser Ile Leu Met Ser Ile Ile Thr Leu Cys Leu Trp Val Met Tyr Phe
                85                  90                  95

Val Asn Ser Phe Arg Leu Trp Arg Arg Val Lys Thr Phe Trp Ala Phe
            100                 105                 110

Asn Pro Glu Thr Asn Ala Ile Ile Ser Leu Gln Val Tyr Gly His Asn
        115                 120                 125

Tyr Tyr Leu Pro Val Met Ala Ala Pro Thr Gly Val Thr Leu Thr Leu
    130                 135                 140

Leu Ser Gly Val Leu Leu Val Asp Gly His Lys Ile Ala Thr Arg Val
145                 150                 155                 160

Gln Val Gly Gln Leu Pro Lys Tyr Val Ile Val Ala Thr Pro Ser Thr
                165                 170                 175

Thr Ile Val Cys Asp Arg Val Gly Arg Ser Val Asn Glu Thr Ser Gln
            180                 185                 190

Thr Gly Trp Ala Phe Tyr Val Arg Ala Lys His Gly Asp Phe Ser Gly
        195                 200                 205

Val Ala Ser Gln Glu Gly Val Leu Ser Glu Arg Glu Lys Leu Leu His
    210                 215                 220

Leu Ile
225


<210> SEQ ID NO 67
<211> LENGTH: 377
<212> TYPE: PRT
<213> ORGANISM: Human coronavirus
<220> FEATURE:
<221> NAME/KEY: MISC_FEATURE
<222> LOCATION: (1)..(377)
<223> OTHER INFORMATION: ORF-6 Pfam 00937, Coronavirus nucleocapsid
      protein

<400> SEQUENCE: 67

Met Ala Ser Val Asn Trp Ala Asp Asp Arg Ala Ala Arg Lys Lys Phe
1               5                   10                  15

Pro Pro Pro Ser Phe Tyr Met Pro Leu Leu Val Ser Ser Asp Lys Ala
            20                  25                  30

Pro Tyr Arg Val Ile Pro Arg Asn Leu Val Pro Ile Gly Lys Gly Asn
        35                  40                  45

Lys Asp Glu Gln Ile Gly Tyr Trp Asn Val Gln Glu Arg Trp Arg Met
    50                  55                  60

Arg Arg Gly Gln Arg Val Asp Leu Pro Pro Lys Val His Phe Tyr Tyr
65                  70                  75                  80

Leu Gly Thr Gly Pro His Lys Asp Leu Lys Phe Arg Gln Arg Ser Asp
                85                  90                  95

Gly Val Val Trp Val Ala Lys Glu Gly Ala Lys Thr Val Asn Thr Ser
            100                 105                 110

Leu Gly Asn Arg Lys Arg Asn Gln Lys Pro Leu Glu Pro Lys Phe Ser
        115                 120                 125

Ile Ala Leu Pro Pro Glu Leu Ser Val Val Glu Phe Glu Asp Arg Ser
    130                 135                 140

Asn Asn Ser Ser Arg Ala Ser Ser Arg Ser Ser Thr Arg Asn Asn Ser
```

```
145                 150                 155                 160

Arg Asp Ser Ser Arg Ser Thr Ser Arg Gln Gln Ser Arg Thr Arg Ser
                165                 170                 175

Asp Ser Asn Gln Ser Ser Ser Asp Leu Val Ala Ala Val Thr Leu Ala
            180                 185                 190

Leu Lys Asn Leu Gly Phe Asp Asn Gln Ser Lys Ser Pro Ser Ser Ser
        195                 200                 205

Gly Thr Ser Thr Pro Lys Lys Pro Asn Lys Pro Leu Ser Gln Pro Arg
    210                 215                 220

Ala Asp Lys Pro Ser Gln Leu Lys Lys Pro Arg Trp Lys Arg Val Pro
225                 230                 235                 240

Thr Arg Glu Glu Asn Val Ile Gln Cys Phe Gly Pro Arg Asp Phe Asn
                245                 250                 255

His Asn Met Gly Asp Ser Asp Leu Val Gln Asn Gly Val Asp Ala Lys
            260                 265                 270

Gly Phe Pro Gln Leu Ala Glu Leu Ile Pro Asn Gln Ala Ala Leu Phe
        275                 280                 285

Phe Asp Ser Glu Val Ser Thr Asp Glu Val Gly Asp Asn Val Gln Ile
    290                 295                 300

Thr Tyr Thr Tyr Lys Met Leu Val Ala Lys Asp Asn Lys Asn Leu Pro
305                 310                 315                 320

Lys Phe Ile Glu Gln Ile Ser Ala Phe Thr Lys Pro Ser Ser Ile Lys
                325                 330                 335

Glu Met Gln Ser Gln Ser Ser His Val Ala Gln Asn Thr Val Leu Asn
            340                 345                 350

Ala Ser Ile Pro Glu Ser Lys Pro Leu Ala Asp Asp Asp Ser Ala Ile
        355                 360                 365

Ile Glu Ile Val Asn Glu Val Leu His
    370                 375
```